(12) United States Patent
Proud

(10) Patent No.: US 10,004,451 B1
(45) Date of Patent: Jun. 26, 2018

(54) USER MONITORING SYSTEM

(71) Applicant: Fitbit, Inc., San Francisco, CA (US)

(72) Inventor: James Proud, San Francisco, CA (US)

(73) Assignee: FITBIT, INC., San Francisco, CA (US)

( * ) Notice: Subject to any disclaimer, the term of this patent is extended or adjusted under 35 U.S.C. 154(b) by 0 days. days.

(21) Appl. No.: 15/276,797

(22) Filed: Sep. 27, 2016

Related U.S. Application Data

(63) Continuation-in-part of application No. 15/276,788, filed on Sep. 26, 2016, which is a continuation-in-part of application No. 15/276,772, filed on Sep. 26, 2016, which is a continuation-in-part of application No. 15/242,545, filed on Aug. 21, 2016, now Pat. No. 9,576,236, which is a continuation of application No. 15/242,543, filed on Aug. 21, 2016, now Pat. No. 9,655,558, which is a continuation of application No. 15/242,542, filed on Aug. 21, 2016, now Pat. No.
(Continued)

(51) Int. Cl.
| | |
|---|---|
| *A61B 5/00* | (2006.01) |
| *A61B 5/113* | (2006.01) |
| *A61M 21/02* | (2006.01) |
| *A61M 21/00* | (2006.01) |

(52) U.S. Cl.
CPC ......... *A61B 5/4806* (2013.01); *A61B 5/0022* (2013.01); *A61B 5/113* (2013.01); *A61B 5/749* (2013.01); *A61M 21/02* (2013.01); *A61B 2560/0252* (2013.01); *A61B 2560/0257* (2013.01); *A61B 2562/0204* (2013.01); *A61B 2562/0257* (2013.01); *A61M 2021/0027* (2013.01)

(58) Field of Classification Search
None
See application file for complete search history.

(56) References Cited

U.S. PATENT DOCUMENTS

| | | | |
|---|---|---|---|
| 3,127,363 | A | 3/1964 | Nitzsche et al. |
| 3,715,334 | A | 2/1973 | Karstedt |
| (Continued) | | | |

FOREIGN PATENT DOCUMENTS

| | | |
|---|---|---|
| DE | 3839900 | 5/1990 |
| EP | 0183553 | 6/1986 |
| (Continued) | | |

OTHER PUBLICATIONS

Davida, G.I., et al., "On enabling secure applications through off-line biometric identification", Proceedings of the IEEE Symposium on Security and Privacy (May 1998).
(Continued)

*Primary Examiner* — Kristy A Haupt
(74) *Attorney, Agent, or Firm* — Hogan Lovells US LLP

(57) ABSTRACT

A user monitoring device system includes a user monitoring device with one or more microphones, a transmitter and sensors to determine light, sound temperature and humidity near the user, the transmitter serving as a communication system. A motion detection apparatus detects a user's movement information. The motion detection apparatus and the monitoring system assist to determine at least one of: user sleep information and sleep behavior information, or user respiration information. A cloud based system is in communication with the monitoring device and the motion detection apparatus. The cloud based system includes a user database.

23 Claims, 62 Drawing Sheets

Related U.S. Application Data 9,569,720, which is a continuation of application No. 15/242,541, filed on Aug. 21, 2016, now Pat. No. 9,569,719, which is a continuation of application No. 15/242,540, filed on Aug. 21, 2016, now Pat. No. 9,756,403, which is a continuation of application No. 15/218,082, filed on Jul. 25, 2016, now Pat. No. 9,542,685, which is a continuation of application No. 15/218,080, filed on Jul. 25, 2016, now Pat. No. 9,582,749, which is a continuation of application No. 15/201,589, filed on Jul. 4, 2016, which is a continuation of application No. 15/195,016, filed on Jun. 28, 2016, which is a continuation-in-part of application No. 15/180,026, filed on Jun. 12, 2016, now Pat. No. 9,723,898, which is a continuation of application No. 15/177,324, filed on Jun. 8, 2016, which is a continuation of application No. 15/133,921, filed on Apr. 20, 2016, now abandoned, which is a continuation of application No. 15/131,330, filed on Apr. 18, 2016, now Pat. No. 9,427,190, which is a continuation of application No. 15/098,070, filed on Apr. 13, 2016, now abandoned, which is a continuation of application No. 15/097,840, filed on Apr. 13, 2016, which is a continuation-in-part of application No. 15/058,986, filed on Mar. 2, 2016, which is a continuation-in-part of application No. 15/058,869, filed on Mar. 2, 2016, which is a continuation-in-part of application No. 15/058,809, filed on Mar. 2, 2016, which is a continuation-in-part of application No. 15/058,728, filed on Mar. 2, 2016, which is a continuation-in-part of application No. 14/729,608, filed on Jun. 3, 2015, which is a continuation-in-part of application No. 14/725,973, filed on May 29, 2015, which is a continuation of application No. 14/604,569, filed on Jan. 23, 2015, which is a continuation-in-part of application No. 14/604,566, filed on Jan. 23, 2015, now Pat. No. 9,610,030, which is a continuation of application No. 14/588,853, filed on Jan. 2, 2015, which is a continuation-in-part of application No. 14/588,848, filed on Jan. 2, 2015, which is a continuation of application No. 14/495,656, filed on Sep. 24, 2014, now Pat. No. 9,380,941, which is a continuation-in-part of application No. 14/495,332, filed on Sep. 24, 2014, now Pat. No. 9,320,435, which is a continuation-in-part of application No. 14/180,152, filed on Feb. 13, 2014, now Pat. No. 9,582,748, which is a continuation-in-part of application No. 14/180,109, filed on Feb. 13, 2014, now abandoned, which is a continuation of application No. 14/052,376, filed on Oct. 11, 2013, now Pat. No. 9,553,486, which is a continuation of application No. 14/051,093, filed on Oct. 10, 2013, now Pat. No. 9,662,015, which is a continuation of application No. 14/049,822, filed on Oct. 9, 2013, now Pat. No. 9,501,735, which is a continuation of application No. 14/049,690, filed on Oct. 9, 2013, now Pat. No. 9,704,209, which is a continuation-in-part of application No. 14/048,731, filed on Oct. 8, 2013, now Pat. No. 9,427,189, which is a continuation of application No. 14/039,802, filed on Sep. 27, 2013, now Pat. No. 9,361,572, which is a continuation of application No. 14/039,145, filed on Sep. 27, 2013, now Pat. No. 9,445,651, which is a continuation-in-part of application No. 14/038,990, filed on Sep. 27, 2013, now Pat. No. 9,424,508, which is a continuation-in-part of application No. 14/037,974, filed on Sep. 26, 2013, now Pat. No. 9,634,921, which is a continuation of application No. 14/037,870, filed on Sep. 26, 2013, now Pat. No. 9,436,903, which is a continuation of application No. 14/037,825, filed on Sep. 26, 2013, now Pat. No. 9,530,089, which is a continuation-in-part of application No. 14/037,747, filed on Sep. 26, 2013, now Pat. No. 9,420,857, which is a continuation of application No. 14/037,717, filed on Sep. 26, 2013, now Pat. No. 9,055,791, which is a continuation of application No. 14/037,643, filed on Sep. 26, 2013, now Pat. No. 9,462,856, which is a continuation of application No. 14/037,594, filed on Sep. 26, 2013, now Pat. No. 9,427,053, which is a continuation-in-part of application No. 14/037,536, filed on Sep. 26, 2013, now Pat. No. 9,414,651, which is a continuation of application No. 14/036,382, filed on Sep. 25, 2013, now Pat. No. 9,367,793, which is a continuation of application No. 14/036,287, filed on Sep. 25, 2013, now Pat. No. 9,420,856, which is a continuation-in-part of application No. 14/036,111, filed on Sep. 25, 2013, now Pat. No. 9,427,160, which is a continuation-in-part of application No. 14/023,876, filed on Sep. 11, 2013, now Pat. No. 9,159,223, which is a continuation of application No. 13/966,641, filed on Aug. 14, 2013, now Pat. No. 9,406,220, which is a continuation of application No. 13/966,623, filed on Aug. 14, 2013, now Pat. No. 9,345,403, which is a continuation of application No. 13/967,120, filed on Aug. 14, 2013, now Pat. No. 9,526,422, which is a continuation of application No. 13/967,109, filed on Aug. 14, 2013, now Pat. No. 9,398,854, which is a continuation-in-part of application No. 13/967,094, filed on Aug. 14, 2013, now abandoned, which is a continuation-in-part of application No. 13/961,599, filed on Aug. 7, 2013, now Pat. No. 9,149,189, which is a continuation-in-part of application No. 13/961,511, filed on Aug. 7, 2013, now Pat. No. 9,204,798, which is a continuation-in-part of application No. 13/960,491, filed on Aug. 6, 2013, now Pat. No. 9,345,404, which is a continuation-in-part of application No. 13/960,451, filed on Aug. 6, 2013, now Pat. No. 9,848,776, which is a continuation-in-part of application No. 13/960,436, filed on Aug. 6, 2013, now Pat. No. 9,339,188, which is a continuation-in-part of application No. 13/960,407, filed on Aug. 6, 2013, now Pat. No. 9,392,939, which is a continuation-in-part of application No. 13/960,075, filed on Aug. 6, 2013, now Pat. No. 9,357,922, which is a continuation-in-part of application No. 13/959,085, filed on Aug. 5, 2013, now Pat. No. 9,532,716, which is a continuation-in-part of application No. 13/959,022, filed on Aug. 5, 2013, which is a continuation of application No. 13/956,815, filed on Aug. 1, 2013, now Pat. No. 9,298,882, which is a continuation of application No. 13/956,674, filed on Aug. 1, 2013, now Pat. No. 9,432,091, which is a continuation-in-part of application No. 13/956,564, filed on Aug. 1, 2013, now Pat. No. 9,737,214, which is a continuation of application No. 13/955,892, filed on Jul. 31, 2013, which is a continuation of application No. 13/955,845, filed on Jul. 31, 2013, now Pat. No. 9,330,561, which is a continuation of application No. 13/955,810, filed on Jul. 31, 2013, now Pat. No. 9,320,434, which is a continuation-in-part of application No. 13/955,777, filed on Jul. 31, 2013, now Pat. No. 9,430,938, which is a continuation of application No. 13/923,937, filed on Jun. 21, 2013, which is a continuation of application No. 13/923,909, filed on Jun. 21, 2013, now Pat. No. 9,407,097, which is a continuation of application No. 13/923,809, filed on Jun. 21, 2013, now Pat. No. 9,425,627, which is a continuation of application No. 13/923,750, filed on Jun. 21, 2013, now Pat. No. 9,438,044, which is a continuation of application No. 13/923,637, filed on Jun. 21, 2013, now Pat. No. 8,810,430, which is a continuation of application No. 13/923,614, filed on Jun. 21, 2013, now Pat. No. 8,850,421, which is a continuation of application No. 13/923,560, filed on Jun. 21, 2013, now Pat. No. 8,803,366, which is a continuation of application No. 13/923,543, filed on Jun. 21, 2013.

(56) References Cited

U.S. PATENT DOCUMENTS

| | | |
|---|---|---|
| 3,775,452 A | 11/1973 | Karstedt |
| 3,813,364 A | 5/1974 | Selin et al. |
| 3,814,730 A | 6/1974 | Karstedt |
| 4,394,317 A | 7/1983 | McAfee et al. |
| 4,603,152 A | 7/1986 | Laurin et al. |
| 4,780,556 A | 10/1988 | Hata et al. |
| 5,057,151 A | 10/1991 | Schuster et al. |
| 5,187,657 A | 2/1993 | Forbes |
| 5,319,363 A | 6/1994 | Welch et al. |
| 5,348,008 A | 9/1994 | Bornn et al. |
| 5,564,429 A | 10/1996 | Bornn et al. |
| 5,576,054 A | 11/1996 | Brown |
| 5,735,887 A | 4/1998 | Barreras, Sr. et al. |
| 5,910,544 A | 8/1999 | Ozawa et al. |
| 5,971,941 A | 10/1999 | Simons et al. |
| 6,038,315 A | 3/2000 | Strait et al. |
| 6,120,467 A | 9/2000 | Schallhorn |
| 6,200,289 B1 | 3/2001 | Hochman et al. |
| 6,221,012 B1 | 4/2001 | Maschke et al. |
| 6,323,846 B1 | 11/2001 | Westerman et al. |
| 6,416,471 B1 | 7/2002 | Kumar et al. |
| 6,440,067 B1 | 8/2002 | DeLuca et al. |
| 6,454,708 B1 | 9/2002 | Ferguson et al. |
| 6,570,557 B1 | 5/2003 | Westerman et al. |
| 6,580,356 B1 | 6/2003 | Alt et al. |
| 6,661,372 B1 | 12/2003 | Girerd et al. |
| 6,677,932 B1 | 1/2004 | Westerman |
| 6,893,396 B2 | 5/2005 | Schulze et al. |
| 7,099,850 B1 | 8/2006 | Mann, II et al. |
| 7,113,932 B2 | 9/2006 | Tayebnejad et al. |
| 7,248,894 B2 | 7/2007 | Fujida et al. |
| 7,314,451 B2 | 1/2008 | Halperin et al. |
| 7,502,643 B2 | 3/2009 | Farringdon et al. |
| 7,614,008 B2 | 11/2009 | Ording |
| 7,616,110 B2 | 11/2009 | Crump et al. |
| 7,633,076 B2 | 12/2009 | Huppi et al. |
| 7,653,883 B2 | 1/2010 | Hotelling et al. |
| 7,657,849 B2 | 2/2010 | Chaudhri et al. |
| 7,663,607 B2 | 2/2010 | Hotelling et al. |
| 7,689,508 B2 | 3/2010 | Davis et al. |
| 7,720,855 B2 | 5/2010 | Brown |
| 7,733,224 B2 | 6/2010 | Tran |
| 7,844,914 B2 | 11/2010 | Andre et al. |
| 7,957,762 B2 | 6/2011 | Herz et al. |
| 7,959,567 B2 | 6/2011 | Stivoric et al. |
| 8,006,002 B2 | 8/2011 | Kalayjian et al. |
| 8,028,905 B2 | 10/2011 | Holberg |
| 8,033,996 B2 | 10/2011 | Behar |
| 8,044,363 B2 | 10/2011 | Ales et al. |
| 8,126,729 B2 | 2/2012 | Dicks et al. |
| 8,126,735 B2 | 2/2012 | Dicks et al. |
| 8,157,731 B2 | 4/2012 | Teller et al. |
| 8,180,591 B2 | 5/2012 | Yuen et al. |
| 8,204,786 B2 | 6/2012 | LeBoeuf et al. |
| 8,239,784 B2 | 8/2012 | Hotelling et al. |
| 8,251,903 B2 | 8/2012 | LeBoeuf et al. |
| 8,279,180 B2 | 10/2012 | Hotelling et al. |
| 8,328,718 B2 | 12/2012 | Tran |
| 8,352,211 B2 | 1/2013 | Vock et al. |
| 8,369,936 B2 | 2/2013 | Farringdon et al. |
| 8,378,811 B2 | 2/2013 | Crump et al. |
| 8,381,135 B2 | 2/2013 | Hotelling et al. |
| 8,389,627 B2 | 3/2013 | Rubinsztajn et al. |
| 8,390,463 B2 | 3/2013 | Munthe-Kaas et al. |
| 8,398,538 B2 | 3/2013 | Dothie |
| 8,398,546 B2 | 3/2013 | Pacione et al. |
| 8,452,654 B1 | 5/2013 | Wooters et al. |
| 8,479,122 B2 | 7/2013 | Hotelling et al. |
| 8,508,356 B2 | 8/2013 | Shuster et al. |
| 8,587,426 B2 | 11/2013 | Bloem |
| 8,663,106 B2 | 3/2014 | Stivoric et al. |
| 8,882,684 B2 | 11/2014 | Halperin |
| 9,047,600 B2 | 6/2015 | Zhou et al. |
| 9,159,223 B2 | 10/2015 | Proud |
| 9,177,307 B2 | 11/2015 | Ross et al. |
| 9,204,806 B2 | 12/2015 | Stivoric |
| 9,326,364 B2 | 4/2016 | Maeda |
| 9,345,433 B1 | 5/2016 | Shinozuka |
| 9,360,351 B2 | 6/2016 | Van Thienen |
| 9,424,508 B2 | 8/2016 | Proud |
| 9,427,053 B2 | 8/2016 | Proud |
| 2002/0015024 A1 | 2/2002 | Westerman et al. |
| 2002/0109600 A1 | 8/2002 | Mault et al. |
| 2003/0023467 A1 | 1/2003 | Moldovan |
| 2003/0121033 A1 | 6/2003 | Peev et al. |
| 2003/0143113 A2 | 7/2003 | Yuzhakov |
| 2004/0039254 A1* | 2/2004 | Stivoric .............. A61B 5/0205 600/300 |
| 2004/0122685 A1 | 6/2004 | Bunce |
| 2004/0172290 A1 | 9/2004 | Leven |
| 2005/0113650 A1 | 5/2005 | Pacione et al. |
| 2005/0115561 A1 | 6/2005 | Stahmann et al. |
| 2005/0190059 A1 | 9/2005 | Wehrenberg |
| 2005/0245839 A1 | 11/2005 | Stivoric et al. |
| 2005/0250538 A1 | 11/2005 | Narasimhan et al. |
| 2006/0017692 A1 | 1/2006 | Wehrenberg et al. |
| 2006/0026536 A1 | 2/2006 | Hotelling et al. |
| 2006/0030891 A1 | 2/2006 | Saltzstein et al. |
| 2006/0033724 A1 | 2/2006 | Chaudhri et al. |
| 2006/0066449 A1 | 3/2006 | Johnson |
| 2006/0098772 A1 | 5/2006 | Reho et al. |
| 2006/0136270 A1 | 6/2006 | Morgan et al. |
| 2006/0159645 A1 | 6/2006 | Miller et al. |
| 2006/0197753 A1 | 9/2006 | Hotelling |
| 2006/0208065 A1 | 9/2006 | Mendelovich et al. |
| 2007/0021979 A1 | 1/2007 | Cosentino et al. |
| 2007/0033069 A1 | 2/2007 | Rao et al. |
| 2007/0149862 A1 | 6/2007 | Pipke |
| 2007/0174633 A1 | 7/2007 | Draper et al. |
| 2007/0255564 A1 | 11/2007 | Yee et al. |
| 2008/0012701 A1 | 1/2008 | Kass et al. |
| 2008/0076969 A1 | 3/2008 | Kraft et al. |
| 2008/0146890 A1* | 6/2008 | LeBoeuf .............. A61B 5/0059 600/300 |
| 2008/0275309 A1 | 11/2008 | Stivoric et al. |
| 2009/0023428 A1 | 1/2009 | Behzad et al. |
| 2009/0112247 A1 | 4/2009 | Freeman et al. |
| 2009/0119760 A1 | 5/2009 | Hung et al. |
| 2009/0182208 A1 | 7/2009 | Cho et al. |
| 2009/0203972 A1 | 8/2009 | Heneghan et al. |
| 2009/0240120 A1 | 9/2009 | Mensinger et al. |
| 2009/0255122 A1 | 10/2009 | Azrielant |
| 2009/0318773 A1 | 12/2009 | Jung et al. |
| 2010/0141042 A1 | 6/2010 | Kesler et al. |
| 2010/0153269 A1 | 6/2010 | McCabe |
| 2010/0191570 A1 | 7/2010 | Michaud et al. |
| 2010/0205091 A1 | 8/2010 | Grazino et al. |
| 2010/0234695 A1 | 9/2010 | Morris |
| 2010/0277003 A1 | 11/2010 | Von Novak et al. |
| 2011/0055132 A1 | 3/2011 | Mahdian et al. |
| 2011/0068935 A1 | 3/2011 | Riley et al. |
| 2011/0201306 A1 | 8/2011 | Ali Al-Harbi et al. |

(56) References Cited

U.S. PATENT DOCUMENTS

| | | | |
|---|---|---|---|
| 2012/0016793 A1 | 1/2012 | Peters et al. |
| 2012/0068820 A1 | 3/2012 | Mollicone et al. |
| 2012/0133079 A1 | 5/2012 | Sykes et al. |
| 2012/0146795 A1 | 6/2012 | Margon et al. |
| 2012/0149996 A1 | 6/2012 | Stivoric et al. |
| 2012/0170521 A1 | 7/2012 | Vogedes et al. |
| 2012/0184876 A1 | 7/2012 | Freeman et al. |
| 2012/0194419 A1 | 8/2012 | Osterhout et al. |
| 2012/0196832 A1 | 8/2012 | Luria |
| 2012/0205373 A1 | 8/2012 | Caldwell |
| 2012/0225719 A1 | 9/2012 | Nowozin et al. |
| 2012/0226639 A1 | 9/2012 | Burdick et al. |
| 2012/0229270 A1 | 9/2012 | Morley et al. |
| 2012/0242501 A1 | 9/2012 | Tran et al. |
| 2012/0253485 A1 | 10/2012 | Weast et al. |
| 2012/0253489 A1 | 10/2012 | Dugan |
| 2012/0271712 A1 | 10/2012 | Katzin et al. |
| 2012/0290327 A1 | 11/2012 | Hanlon et al. |
| 2012/0290950 A1 | 11/2012 | Rapaport et al. |
| 2012/0330109 A1 | 12/2012 | Tran |
| 2013/0022659 A1 | 1/2013 | Roberts |
| 2013/0030711 A1 | 1/2013 | Korhonen |
| 2013/0030934 A1 | 1/2013 | Bakshi et al. |
| 2013/0102937 A1 | 4/2013 | Ehrenreich et al. |
| 2013/0127980 A1 | 5/2013 | Haddick et al. |
| 2013/0144190 A1 | 6/2013 | Bruce et al. |
| 2013/0175732 A1 | 7/2013 | Lust et al. |
| 2013/0326790 A1 | 12/2013 | Cauwels et al. |
| 2013/0338446 A1 | 12/2013 | Van Vugt et al. |
| 2014/0045547 A1* | 2/2014 | Singamsetty ......... G06F 1/1643 455/552.1 |
| 2014/0236922 A1 | 8/2014 | Boyer et al. |
| 2014/0266939 A1 | 9/2014 | Baringer et al. |

FOREIGN PATENT DOCUMENTS

| | | |
|---|---|---|
| EP | 0369255 | 5/1990 |
| EP | 0477681 | 4/1992 |
| EP | 0567253 | 10/1993 |
| EP | 0640663 | 3/1995 |
| EP | 0654497 | 5/1995 |
| EP | 1094091 | 4/2001 |
| EP | 1113042 | 7/2001 |
| EP | 1133936 | 9/2001 |
| EP | 1172414 | 1/2002 |
| EP | 1217042 | 6/2002 |
| EP | 1367534 | 12/2003 |
| EP | 1371004 | 12/2003 |
| EP | 1555297 | 7/2005 |
| EP | 1595676 | 11/2005 |
| EP | 1785454 | 5/2007 |
| EP | 1792944 | 6/2007 |
| EP | 1883798 | 2/2008 |
| EP | 2052352 | 4/2009 |
| EP | 2063555 | 5/2009 |
| EP | 2071423 | 6/2009 |
| EP | 2428774 | 3/2012 |
| EP | 2582116 | 4/2013 |
| EP | 2614945 | 7/2013 |
| GB | 1278798 | 6/1972 |
| GB | 1381933 | 1/1975 |
| GB | 2460890 | 12/2009 |
| WO | 9500992 | 1/1995 |
| WO | 1987004449 | 7/1997 |
| WO | 1999056922 | 11/1999 |
| WO | 02063555 | 8/2002 |
| WO | 2002063555 | 8/2002 |
| WO | 2006127726 | 11/2006 |
| WO | 2008050951 | 5/2008 |
| WO | 2012170305 | 12/2012 |
| WO | 2013076676 | 5/2013 |
| WO | 2013081447 | 6/2013 |

OTHER PUBLICATIONS

Juels, A., et al., "A Fuzzy Vault Scheme", Proceedings of the 2002 IEEE Symposium on Information Theory (Jun. 2002).

Juels, A., et al., "A fuzzy commitment scheme", Proc. 5th ACM Conference on Comp. and Commun. Security, pp. 28-36.

Yang, S., et al., "Secure fuzzy vault fingerprint verification system", Asilomar Conf. on Signals, Systems and Comp., vol. 1, pp. 577-581 (Nov. 2004).

Uludag, U., et al., "Fuzzy fingerprint vault", Proc. Workshop: Biometrics: Challenges arising from theory to practice, pp. 13-16 (Aug. 2004).

* cited by examiner

FRONT

BACK

USER MONITORING SYSTEM

CROSS-REFERENCE TO RELATED APPLICATIONS

This application claims the priority benefit of all of the following: This application also is related to and claims the benefit of which is a Continuation-in-Part of U.S. patent application Ser. No. 15/276,788, filed on Sep. 26, 2016, which is continuation in part of U.S. patent application Ser. No. 15/276,772, filed on Sep. 26, 2016, which is continuation in part of U.S. patent application Ser. No. 15/242,545, filed on Aug. 21, 2016, which is a Continuation of U.S. patent application Ser. No. 15/242,543, filed on Aug. 21, 2016, which is a Continuation of U.S. patent application Ser. No. 15/242,542, filed on Aug. 21, 2016, which is a Continuation of U.S. patent application Ser. No. 15/242,541, filed on Aug. 21, 2016, which is a Continuation of U.S. patent application Ser. No. 15/242,540, filed on Aug. 21, 2016, which is a Continuation of U.S. patent application Ser. No. 15/218,082, filed on Jul. 25, 2016, which is a Continuation of U.S. patent application Ser. No. 15/218,080, filed on Jul. 25, 2016, which is a Continuation of U.S. patent application Ser. No. 15/201,589, filed on Jul. 4, 2016, which is a Continuation of U.S. patent application Ser. No. 15/195,016, filed on Jun. 28, 2016, which is a Continuation-in-Part of U.S. patent application Ser. No. 15/180,026, filed on Jun. 12, 2016, which is a Continuation of U.S. patent application Ser. No. 15/177,324, filed on Jun. 8, 2016, which is a Continuation of U.S. patent application Ser. No. 15/133,921, filed Apr. 20, 2016, which is a Continuation of U.S. patent application Ser. No. 15/131,330, filed Apr. 18, 2016, which is a Continuation of U.S. patent application Ser. No. 15/098,070, filed Apr. 13, 2016, which is a Continuation of U.S. patent application Ser. No. 15/097,840, filed Apr. 13, 2016, which is a Continuation-in-Part of U.S. patent application Ser. No. 15/058,986, filed Mar. 2, 2016, which is a Continuation-in-Part of U.S. patent application Ser. No. 15/058,869, filed Mar. 2, 2016, which is a Continuation-in-Part of U.S. patent application Ser. No. 15/058,809, filed Mar. 2, 2016, which is a Continuation-in-Part of U.S. patent application Ser. No. 15/058,728, filed Mar. 2, 2016, which is a Continuation-in-Part of U.S. patent application Ser. No. 14/729,608, filed Jun. 6, 2015, which is a Continuation-in-Part of U.S. patent application Ser. No. 14/725,973, filed May 29, 2015, which is a U.S. Provisional Patent Application No. 62/118,384, filed Feb. 19, 2015, which is a Continuation of U.S. application Ser. No. 14/604,569, filed Jan. 23, 2015, which is a Continuation-in-Part of U.S. application Ser. No. 14/604,566, filed Jan. 23, 2015, which is a Continuation of U.S. application Ser. No. 14/588,853, filed Jan. 2, 2015, which is a Continuation-in-Part of U.S. application Ser. No. 14/588,848, filed Jan. 2, 2015, which is a Continuation of U.S. application Ser. No. 14/495,656, filed Sep. 24, 2014, which is a Continuation-in-Part of U.S. application Ser. No. 14/495,332, filed Sep. 24, 2014, now U.S. Pat. No. 9,320,435, issued Apr. 26, 2016 which is a U.S. Provisional Patent Application No. 62/027,885, filed Jul. 23, 2014, which is a Continuation-in-Part of U.S. application Ser. No. 14/180,152, filed Feb. 13, 2014, which is a Continuation-in-Part of U.S. application Ser. No. 14/180,109, filed Feb. 13, 2014, which is a Continuation of U.S. application Ser. No. 14/052,376, filed Oct. 11, 2013, which is a Continuation of U.S. application Ser. No. 14/051,093, filed Oct. 10, 2013, which is a Continuation of U.S. application Ser. No. 14/049,822, filed Oct. 9, 2013, which is a Continuation of U.S. application Ser. No. 14/049,690, filed Oct. 9, 2013, which is a Continuation-in-Part of U.S. application Ser. No. 14/048,731, filed Oct. 8, 2013, which is a Continuation of U.S. application Ser. No. 14/039,802, filed Sep. 27, 2013, which is a Continuation of U.S. patent application Ser. No. 14/039,145, filed Sep. 27, 2013, which is a Continuation-in-Part of U.S. application Ser. No. 14/038,990, filed Sep. 27, 2013, which is a Continuation of U.S. application Ser. No. 14/037,974, filed Sep. 26, 2013, now abandoned, which is a Continuation of U.S. application Ser. No. 14/037,870, filed Sep. 26, 2013, which is a Continuation of U.S. application Ser. No. 14/037,825, filed Sep. 26, 2013, which is a Continuation of U.S. application Ser. No. 14/037,747, filed Sep. 26, 2013, which is a Continuation of U.S. application Ser. No. 14/037,717, filed Sep. 26, 2013, now U.S. Pat. No. 9,055,791, issued Jun. 16, 2015, which is a Continuation of U.S. application Ser. No. 14/037,643, filed Sep. 26, 2013, which is a Continuation of U.S. application Ser. No. 14/037,594, filed Sep. 26, 2013, which is a Continuation-in-Part of U.S. application Ser. No. 14/037,536, filed Sep. 26, 2013, which is a Continuation of U.S. application Ser. No. 14/036,382, filed Sep. 25, 2013, which is a Continuation of U.S. application Ser. No. 14/036,287, filed Sep. 25, 2013, which is a Continuation-in-Part of U.S. application Ser. No. 14/036,111, filed Sep. 25, 2013, which is a Continuation-in-Part of U.S. application Ser. No. 14/023,876, filed Sep. 11, 2013, now U.S. Pat. No. 9,159,223, issued Oct. 13, 2015, which is a Continuation of U.S. application Ser. No. 13/966,641, filed Aug. 14, 2013, which is a Continuation of U.S. application Ser. No. 13/966,623, filed Aug. 14, 2013, which is a Continuation of U.S. application Ser. No. 13/967,120, filed Aug. 14, 2013, which is Continuation of U.S. application Ser. No. 13/967,109, filed Aug. 14, 2013, which is a Continuation-in-Part of U.S. application Ser. No. 13/967,094, filed Aug. 14, 2013, which is a Continuation-in-Part of U.S. application Ser. No. 13/961,599, filed Aug. 7, 2013, now U.S. Pat. No. 9,149,189, issued Oct. 6, 2015, which is a Continuation-in-Part of U.S. application Ser. No. 13/961,511, filed Aug. 7, 2013, now U.S. Pat. No. 9,204,798, issued Dec. 8, 2015, which is a Continuation-in-Part of U.S. application Ser. No. 13/960,491, filed Aug. 6, 2013, which is a Continuation-in-Part of U.S. application Ser. No. 13/960,451, filed Aug. 6, 2013, which is a Continuation-in-Part of U.S. application Ser. No. 13/960,436, filed Aug. 6, 2013, which is a Continuation-in-Part of U.S. application Ser. No. 13/960,407, filed Aug. 6, 2013, which is a Continuation-in-Part of U.S. application Ser. No. 13/960,075, filed Aug. 6, 2013, which is a Continuation-in-Part of U.S. application Ser. No. 13/959,085, filed Aug. 5, 2013, which is a Continuation-in-Part of U.S. application Ser. No. 13/959,022, filed Aug. 5, 2013, which is a Continuation of U.S. application Ser. No. 13/956,815, filed Aug. 1, 2013, now U.S. Pat. No. 9,298,882, issued Mar. 29, 2016, which is a Continuation of U.S. application Ser. No. 13/956,674, filed Aug. 1, 2013, which is a Continuation-in-Part of U.S. application Ser. No. 13/956,564, filed Aug. 1, 2013, which is a Continuation of U.S. application Ser. No. 13/955,892, filed Jul. 31, 2013, which is a Continuation of U.S. application Ser. No. 13/955,845, filed Jul. 31, 2013, which is a Continuation of U.S. application Ser. No. 13/955,810, filed Jul. 31, 2013, now U.S. Pat. No. 9,320,434, issued Apr. 26, 2016, which is a Continuation-in-Part of U.S. application Ser. No. 13/955,777, filed Jul. 31, 2013, which is a Continuation of U.S. application Ser. No. 13/923,937, filed Jun. 21, 2013, which is a Continuation of U.S. patent application Ser. No. 13/923,909, filed Jun. 21, 2013, which is a Continuation of U.S. application Ser. No. 13/923,809, filed Jun. 21, 2013, which is a Continuation of U.S. application Ser.

No. 13/923,750, filed Jun. 21, 2013, which is a Continuation of U.S. application Ser. No. 13/923,637, filed Jun. 21, 2013, now U.S. Pat. No. 8,810,430, issued on Aug. 19, 2014, which is a Continuation of U.S. patent application Ser. No. 13/923,614, filed Jun. 21, 2013, now U.S. Pat. No. 8,850,421, issued on Sep. 30, 2014, which is a Continuation of U.S. application Ser. No. 13/923,560, filed Jun. 21, 2013, now U.S. Pat. No. 8,803,366, issued Aug. 12, 2014, which is a Continuation of U.S. application Ser. No. 13/923,543, filed Jun. 21, 2013. All of the above applications are fully incorporated herein by reference.

BACKGROUND

Field of the Invention

The present invention relates generally to monitoring systems, and more particularly to monitoring systems that include a plurality of sensors.

Description of the Related Art

Systems have been provided for monitoring physiological parameters of individuals such as temperature, blood pressure, heart rate, heart activity, and the like.

Vital signs of some individual's have been monitored and/or measured on a substantially continuous basis to enable physicians, nurses and other health care providers to detect sudden changes in a patient's condition and evaluate a patient's condition over an extended period of time.

There is a need for improved monitoring systems.

SUMMARY

An object of the present invention is to provide an improved user monitoring device system.

Another object of the present invention is to provide a user monitoring system that includes a user monitoring device with one or more microphones, and sensors to determine light, sound temperature and humidity near a monitored user.

A further object of the present invention is to provide a user monitoring system that includes a user monitoring device with one or more microphones, and sensors to determine light, sound temperature and humidity near a monitored user as well as a proximity sensor.

A further object of the present invention is to provide a user monitoring system that includes a user monitoring device with one or more microphones, and sensors to determine light, sound temperature and humidity near a monitored user as well as a proximity sensor.

Still another object of the present invention is to provide a user monitoring system that includes a user monitoring device with one or more microphones, and sensors to determine light, sound temperature and humidity near a monitored user, and a barometric pressure sensor.

Another object of the present invention is to provide a user monitoring system that includes a user monitoring device with one or more microphones, and sensors to determine light, sound temperature and humidity near a monitored user, as well as a barometric pressure sensor to detect changes in pressure in a vicinity of the monitored user.

A further other object of the present invention is to provide a user monitoring system that includes a user monitoring device with one or more microphones, and sensors to determine light, sound temperature and humidity near a monitored user, as well as a motion detection apparatus at the monitoring device.

Still another object of the present invention is to provide a user monitoring system that includes a user monitoring device with one or more microphones, and sensors to determine light, sound temperature and humidity near a monitored user, as well as a gas sensor at the monitoring device.

These and other objects of the present invention are achieved in a user monitoring device system that includes a user monitoring device with one or more microphones, a transmitter and sensors to determine light, sound temperature and humidity near the user, the transmitter serving as a communication system. A motion detection apparatus detects a user's movement information. The motion detection apparatus and the monitoring system assist to determine at least one of: user sleep information and sleep behavior information, or user respiration information. A cloud based system is in communication with the monitoring device and the motion detection apparatus. The cloud based system includes a user database.

In another embodiment of the present invention a user monitoring device system includes a user monitoring device with one or more microphones, a transmitter and sensors to determine light, sound temperature and humidity near the user, the transmitter serving as a communication system. A motion detection apparatus detects a user's movement information. The motion detection apparatus and the monitoring system assist to determine at least one of: user sleep information and sleep behavior information, or user respiration information. A cloud based system is in communication with the monitoring device and the motion detection apparatus. The cloud based system includes a user database. A voice recognition system is at the cloud based system or at the monitoring device.

BRIEF DESCRIPTION OF THE DRAWINGS

FIG. 12($b$) is another embodiment of a control logic that can be used with the FIG. 4 embodiment.

FIG. 27($b$) illustrates a schematic diagram of the proximity sensing unit sensing when the LED is inactive under the condition that no object is close by to the proximity sensor of the electronic apparatus.

FIG. 27($c$) illustrates a schematic diagram of the proximity sensing unit sensing when the LED is active and emits lights under the condition that an object is located in the detection range of the proximity sensor.

FIG. 27($d$) illustrates a schematic diagram of the proximity sensing unit sensing when the LED is inactive under the condition that an object is located in the detection range of the proximity sensor.

FIG. 27($e$) illustrates a schematic diagram of the proximity sensing unit sensing when the LED is active and emits lights under the condition that an object is located out of the detection range of the proximity sensor.

FIG. 27($f$) illustrates a schematic diagram of the proximity sensing unit sensing when the LED is inactive under the condition that an object is located out of the detection range of the proximity sensor.

DETAILED DESCRIPTION

Figure 1A:
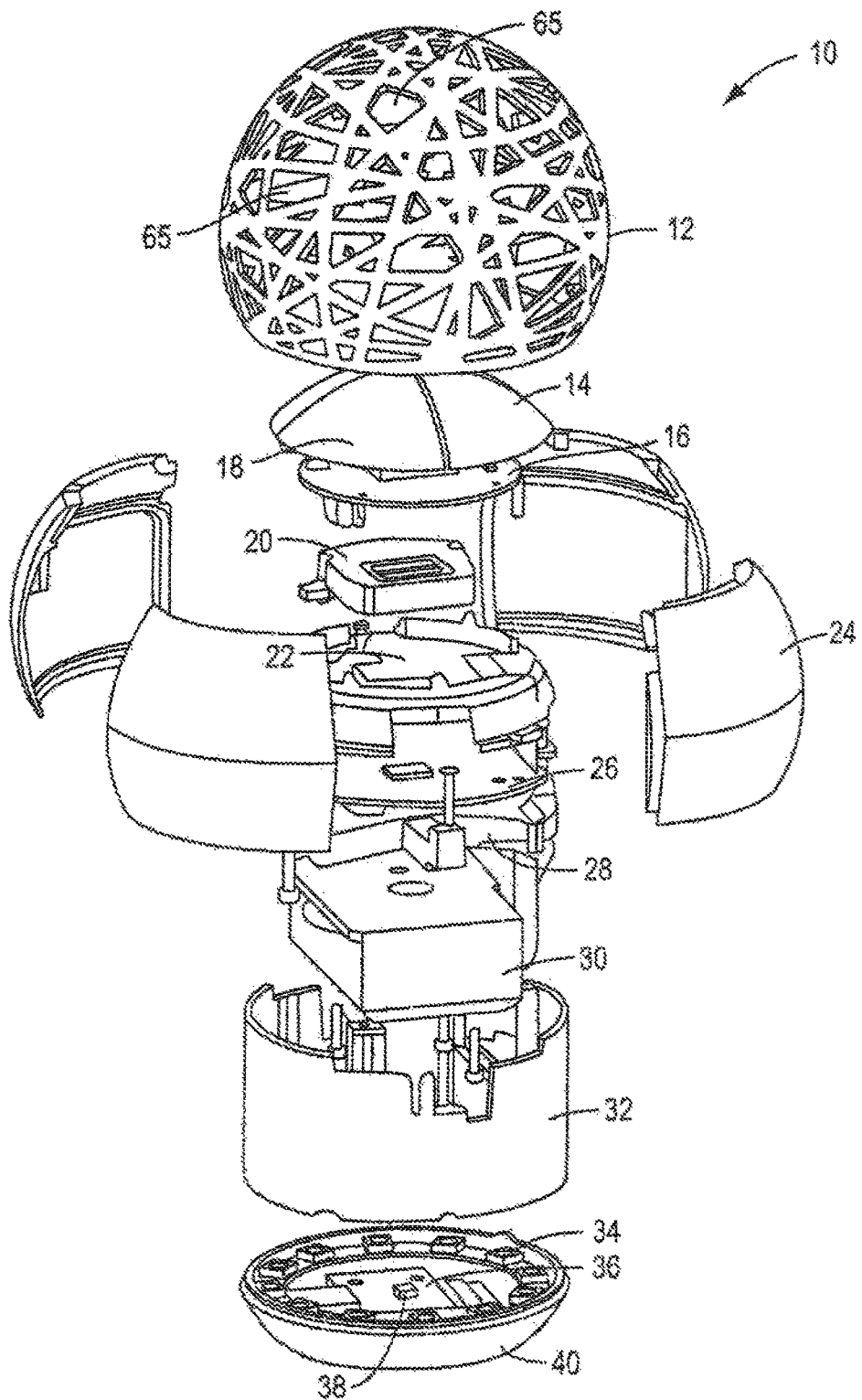
FIG. 1(a) is an exploded view of one embodiment of a user monitoring device of the present invention.

As used herein, the term engine refers to software, firmware, hardware, or other component that can be used to effectuate a purpose. The engine will typically include software instructions that are stored in non-volatile memory (also referred to as secondary memory) and a processor with instructions to execute the software. When the software instructions are executed, at least a subset of the software instructions can be loaded into memory (also referred to as primary memory) by a processor. The processor then executes the software instructions in memory. The processor may be a shared processor, a dedicated processor, or a combination of shared or dedicated processors. A typical program will include calls to hardware components (such as I/O devices), which typically requires the execution of drivers. The drivers may or may not be considered part of the engine, but the distinction is not critical.

As used herein, the term database is used broadly to include any known or convenient means for storing data, whether centralized or distributed, relational or otherwise.

As used herein a mobile device includes, but is not limited to, a cell phone, such as Apple's iPhone®, other portable electronic devices, such as Apple's iPod Touches®, Apple's iPads®, and mobile devices based on Google's Android® operating system, and any other portable electronic device that includes software, firmware, hardware, or a combination thereof that is capable of at least receiving a wireless signal, decoding if needed, and exchanging information with a server. Typical components of mobile device may include but are not limited to persistent memories like flash ROM, random access memory like SRAM, a camera, a battery, LCD driver, a display, a cellular antenna, a speaker, a BLUETOOTH® circuit, and WIFI circuitry, where the persistent memory may contain programs, applications, and/or an operating system for the mobile device. For purposes of this application, a mobile device is also defined to include a fob, and its equivalents.

As used herein, the term "computer" is a general purpose device that can be programmed to carry out a finite set of arithmetic or logical operations. Since a sequence of operations can be readily changed, the computer can solve more than one kind of problem. A computer can include of at least one processing element, typically a central processing unit (CPU) and some form of memory. The processing element carries out arithmetic and logic operations, and a sequencing and control unit that can change the order of operations based on stored information. Peripheral devices allow information to be retrieved from an external source, and the result of operations saved and retrieved. Computer also includes a graphic display medium.

As used herein, the term "internet" is a global system of interconnected computer networks that use the standard Network Systems protocol suite (TCP/IP) to serve billions of users worldwide. It is a network of networks that consists of millions of private, public, academic, business, and government networks, of local to global scope, that are linked by a broad array of electronic, wireless and optical networking technologies. The internet carries an extensive range of information resources and services, such as the inter-linked hypertext documents of the World Wide Web (WWW) and the infrastructure to support email. The communications infrastructure of the internet consists of its hardware components and a system of software layers that control various aspects of the architecture.

As used herein, the term "extranet" is a computer network that allows controlled access from the outside. An extranet can be an extension of an organization's intranet that is extended to users outside the organization in isolation from all other internet users. An extranet can be an intranet mapped onto the public internet or some other transmission system not accessible to the general public, but managed by more than one company's administrator(s). Examples of extranet-style networks include but are not limited to:

LANs or WANs belonging to multiple organizations and interconnected and accessed using remote dial-up LANs or WANs belonging to multiple organizations and interconnected and accessed using dedicated lines Virtual private network (VPN) that is comprised of LANs or WANs belonging to multiple organizations, and that extends usage to remote users using special "tunneling" software that creates a secure, usually encrypted network connection over public lines, sometimes via an ISP.

As used herein, the term "Intranet" is a network that is owned by a single organization that controls its security policies and network management. Examples of intranets include but are not limited to:

A LAN

A Wide-area network (WAN) that is comprised of a LAN that extends usage to remote employees with dial-up access A WAN that is comprised of interconnected LANs using dedicated communication lines A Virtual private network (VPN) that is comprised of a LAN or WAN that extends usage to remote employees or networks using special "tunneling" software that creates a secure, usually encrypted connection over public lines, sometimes via an Internet Service Provider (ISP).

For purposes of the present invention, the Internet, extranets and intranets collectively are referred to as ("Network Systems").

As used herein "Cloud Application" refers to cloud application services or "software as a service" (SaaS) which deliver software over the Network Systems eliminating the need to install and run the application on a device.

As used herein "Cloud Platform" refers to a cloud platform services or "platform as a service" (PaaS) which deliver a computing platform and/or solution stack as a service, and facilitates the deployment of applications without the cost and complexity of obtaining and managing the underlying hardware and software layers.

As used herein "Cloud System" refers to cloud infrastructure services or "infrastructure as a service" (IAAS) which deliver computer infrastructure as a service with raw block storage and networking.

As used herein "Server" refers to server layers that consist of computer hardware and/or software products specifically designed for the delivery of cloud services.

As used herein, the term "user monitoring" includes: (i) cardiac monitoring, which generally refers to continuous electrocardiography with assessment of the user's condition relative to their cardiac rhythm. A small monitor worn by an ambulatory user for this purpose is known as a Holter monitor. Cardiac monitoring can also involve cardiac output monitoring via an invasive Swan-Ganz catheter (ii) Hemodynamic monitoring, which monitors the blood pressure and blood flow within the circulatory system. Blood pressure can be measured either invasively through an inserted blood pressure transducer assembly, or noninvasively with an inflatable blood pressure cuff. (iii) Respiratory monitoring, such as: pulse oximetry which involves measurement of the saturated percentage of oxygen in the blood, referred to as SpO2, and measured by an infrared finger cuff, capnography, which involves CO2 measurements, referred to as EtCO2 or end-tidal carbon dioxide concentration. The respiratory rate monitored as such is called AWRR or airway respiratory rate), (iv) respiratory rate monitoring through a thoracic transducer belt, an ECG channel or via capnography, (v) Neurological monitoring, such as of intracranial pressure. Special user monitors can incorporate the monitoring of brain waves electroencephalography, gas anesthetic concentrations, bispectral index (BIS), and the like, (vi) blood glucose monitoring using glucose sensors. (vii) childbirth monitoring with sensors that monitor various aspects of childbirth. (viii) body temperature monitoring which in one embodiment is through an adhesive pad containing a thermoelectric transducer. (ix) stress monitoring that can utilize sensors to provide warnings when stress levels signs are rising before a human can notice it and provide alerts and suggestions. (x) epilepsy monitoring. (xi) toxicity monitoring, (xii) general lifestyle parameters, (xiii) sleep, including but not limited to: sleep patterns, type of sleep, sleep disorders, movement during sleep, waking up, falling asleep, problems with sleep, habits during, before and after sleep, time of sleep, length sleep in terms of the amount of time for each sleep, body activities during sleep, brain patterns during sleep and the like (xiv) body gesture, movement and motion (xv) body habits, (xvi) and the like.

In various embodiments, the present invention provides systems and methods for monitoring and reporting human physiological information, life activities data of the individual, generate data indicative of one or more contextual parameters of the individual, monitor the degree to which an individual has followed a routine and the like, along with providing feedback to the individual.

In certain embodiments, the suggested routine may include a plurality of categories, including but not limited to, body movement/motion/gesture, habits, health parameters, activity level, mind centering, sleep, daily activities, exercise and the like.

In general, according to the present invention, data relating to any or all of the above is collected and transmitted, either subsequently or in real-time, to a site, the cloud and the like that can be remote from the individual, where it is analyzed, stored, utilized, and the like via Network System. Contextual parameters as used herein means parameters relating any of the above, including the environment, surroundings and location of the individual, air quality, sound quality, ambient temperature, global positioning and the like, as well as anything relative to the categories mentioned above.

In various embodiments, the present invention provides a user monitoring device 10. As illustrated in FIG. 1(a) monitoring device 10 can include an outer shell 12, a protective cover 14, a top circuit board 16, a microphone 18, a speaker module 20, a circuit board support structure 22, a protective quadrant 24, a middle circuit board 26, a particular air duct 28, a particulate sensor 30, a center support structure 32, a light emitter 34, a bottom circuit board 36, a temperature sensor 38, FIG. 1(b) and a base 40.

Figure 1B:
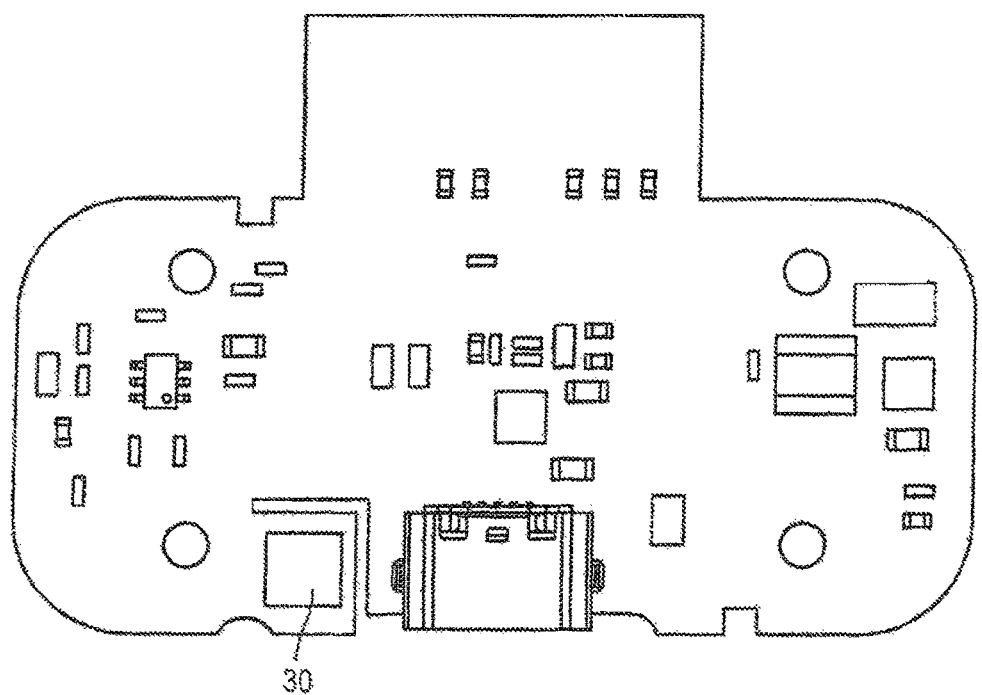
FIG. 1(b) illustrates one embodiment of a bottom board of the FIG. 1(a) user monitoring device with a temperature and humidity sensor.
Figure 1C:
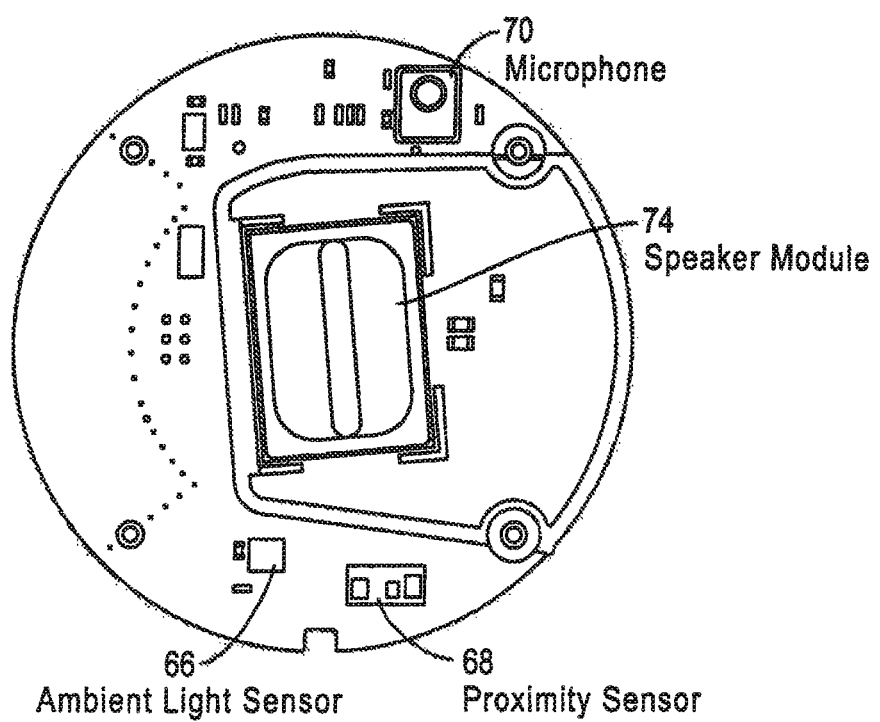
FIG. 1(c) illustrates one embodiment of a top board of the FIG. 1(a) user monitoring device with an ambient light sensor, a proximity sensor, a speak module and a microphone.
Figure 1D:
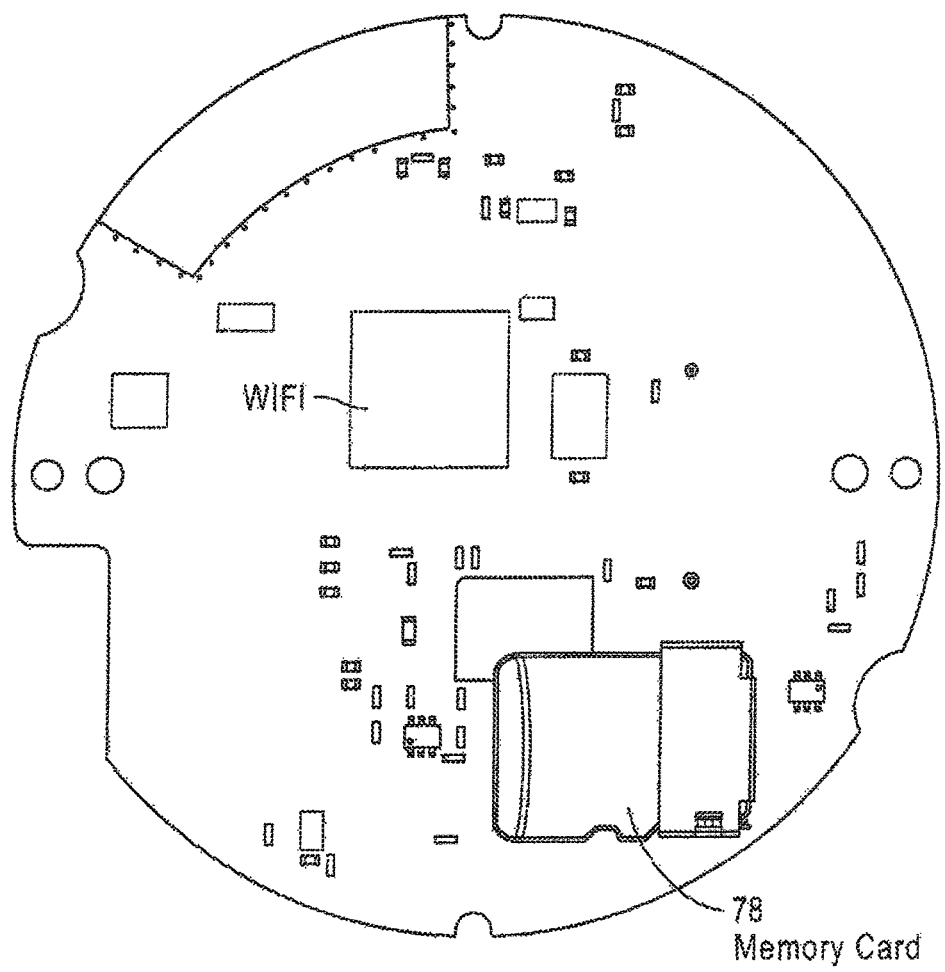
FIG. 1(d) illustrates one embodiment of a middle board of the FIG. 1(a) user monitoring device.
Figure 1E:
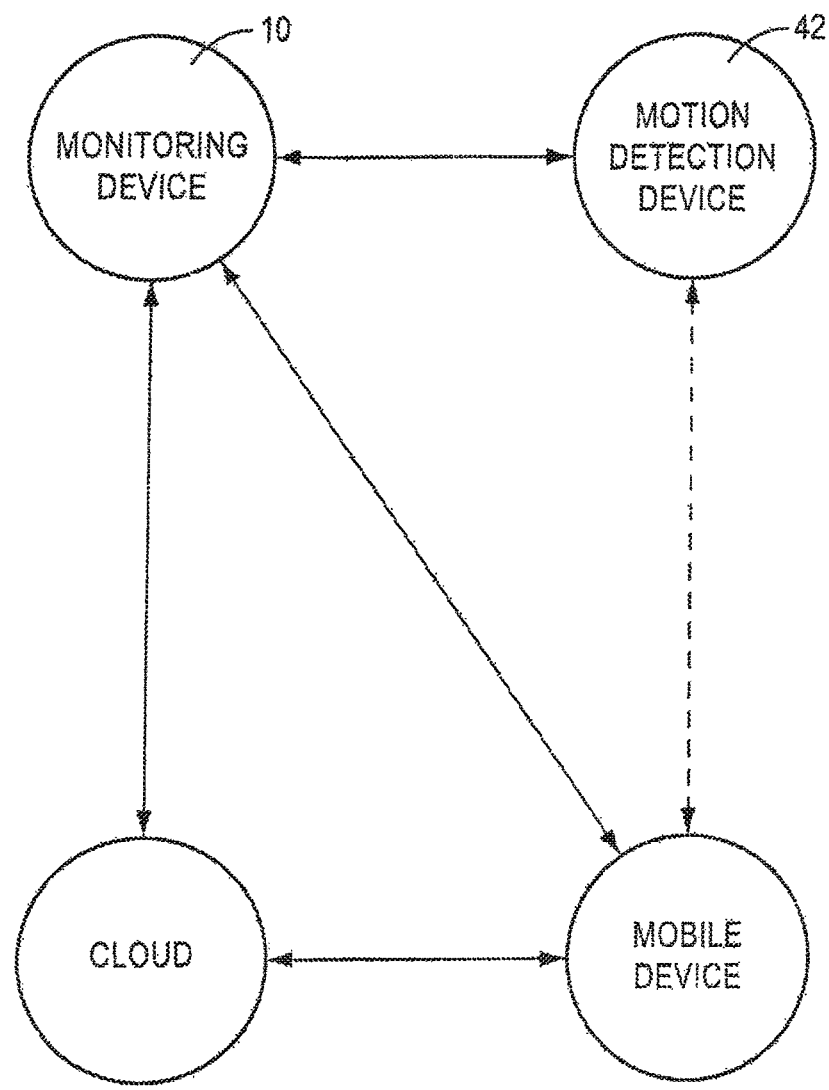
FIG. 1(e) illustrates the communication between the cloud, client or mobile device, monitoring device 10 and motion detection device 42.

FIG. 1(e) illustrates the communication between the cloud, client or mobile device, monitoring device 10 and motion detection device 42.

Figure 2A:
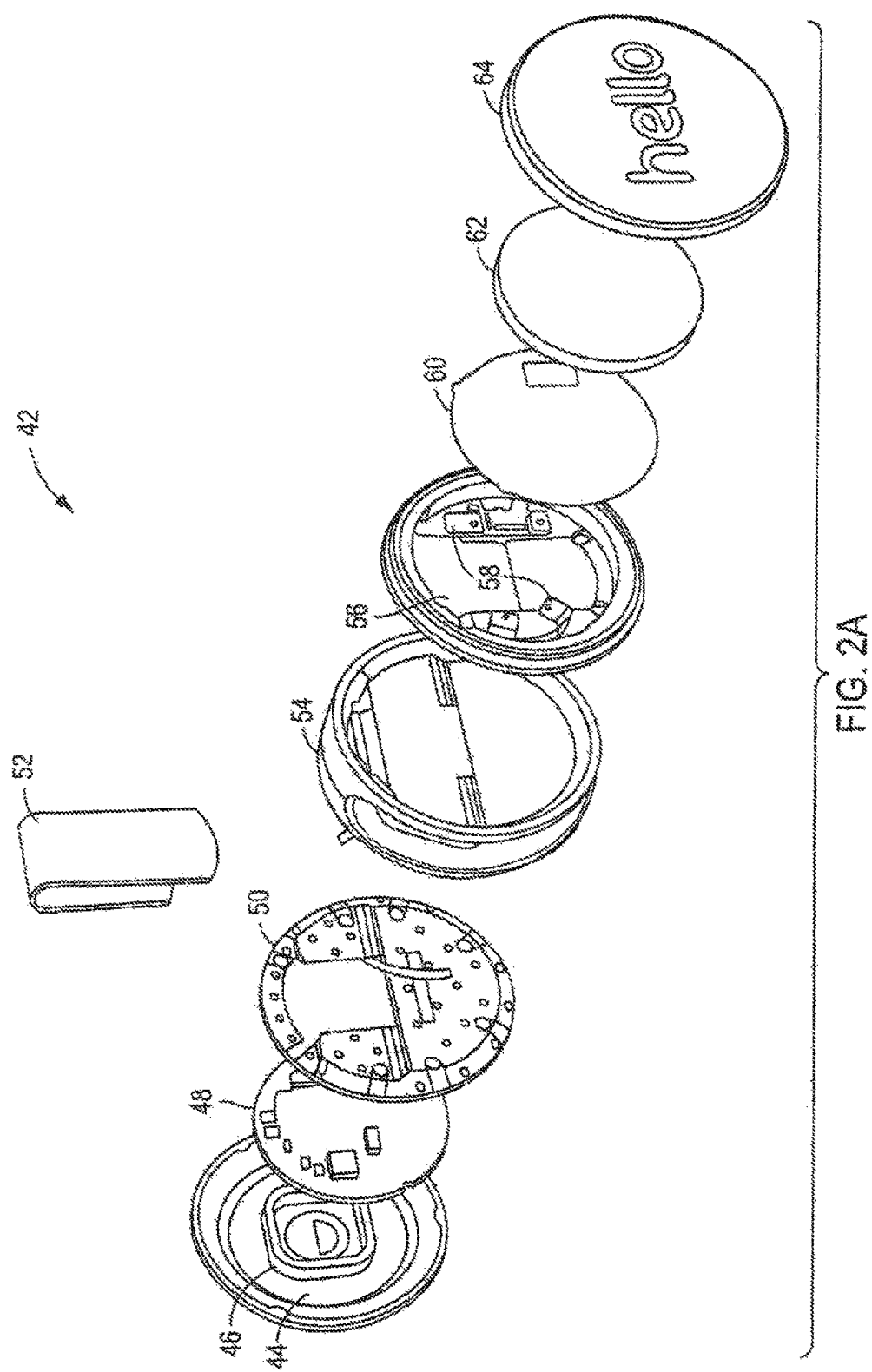
FIG. 2(a) is an exploded view of one embodiment of a motion/movement/gesture detective device of the present invention.

FIG. 2(a) illustrates one embodiment of a detection device, (hereafter motion/movement/gesture detective device 42). In one embodiment motion/movement/gesture/ detection device 42 includes a front shell 44, an emitter gasket 46, a circuit board 48, a front support structure 50, spring steel 52, an elastomeric foot 54, a rear support structure 56, a battery terminal 58, and a terminal insulting film 60, a coin cell battery 62 and a back shell 64.

The monitor device 10 can include a plurality of ports, generally denoted as 65, that: (i) allow light to be transmitted from an interior of the monitor device to the user for visual feedback, (ii) a port 65 for the proximity sensor 68, and (iii) one or more ports 65 that allows for the introduction of air. In one embodiment the ports 65 for the introduction for air are located at a bottom portion of monitor device 10.

As illustrated in FIGS. 1(b), 1(c) and 1(d) in one embodiment the monitor device10 includes four different printed circuit boards (PCBs). In one embodiment a top PCB includes an ambient light sensor 66, a proximity sensor 70, a microphone 72 and speaker module 74. These are utilized for user interaction and also to pick up the most data. There are no sensors on the middle PCB. In one embodiment the bottom PCB has one temperature/humidity sensor 76 as the USB for wall charging. A battery pact is optional. Air ducting inside the monitor device 10 is provided to direct particulates, including but not limited to dust, towards the particulate sensor 30.

In one embodiment the monitor device 10 includes one or more of a housing with a plurality of ports 65, and one or more of the following elements: proximity sensor; temperature sensor/humidity sensor; particulate sensor 30; light sensor 66; microphone 70; speaker 74; two RF transmitters 76 (BLE/ANT+WIFI); a memory card 78; and LED's 80.

In one embodiment the monitor device 10 lights up to indicate either that the user is alarmed, that something is wrong, or if everything is ok. This provides quick feedback to the user.

Figure 2B:
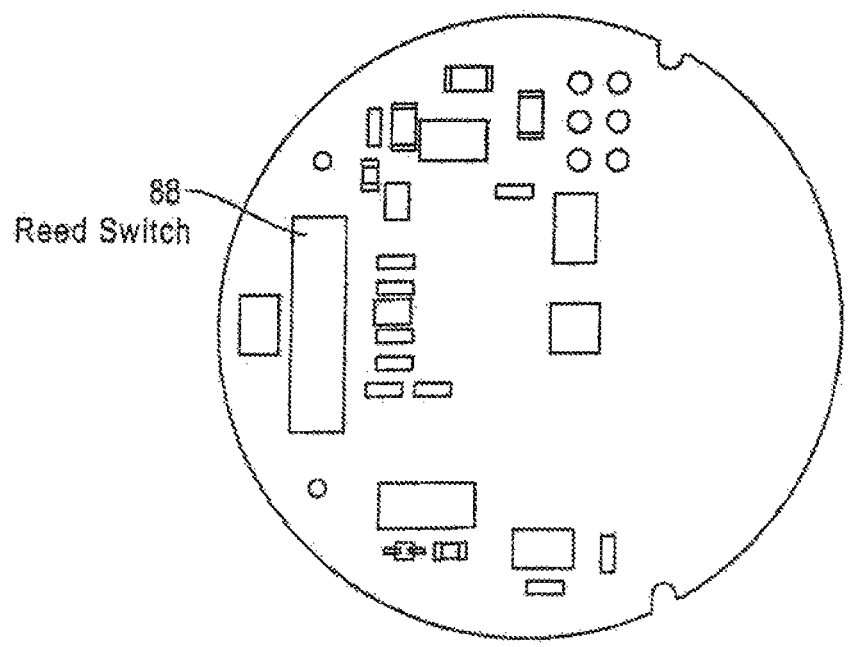
FIGS. 2(b) and 2(c) illustrate front and back surfaces of a board from the FIG. 2(a) motion/movement/gesture detection device with a reed switch and an accelerator.
Figure 2C:
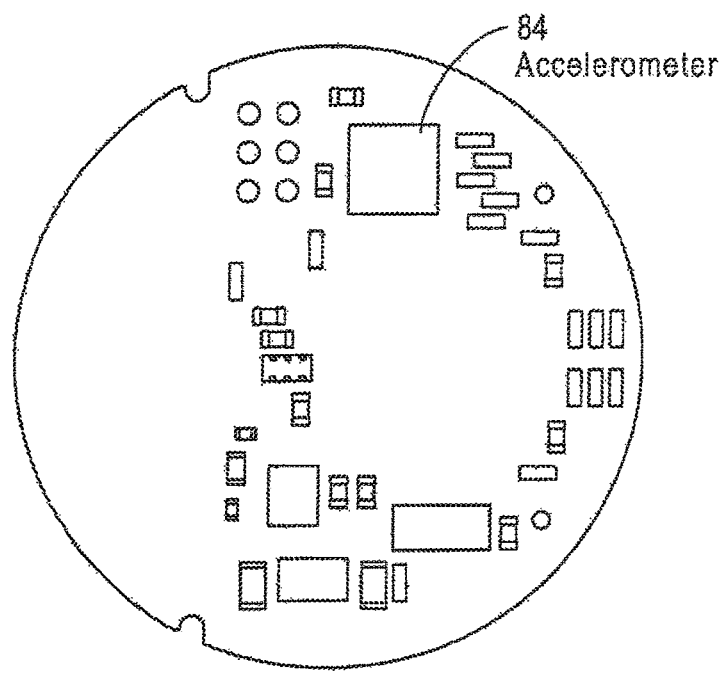

In one embodiment, illustrated in FIGS. 2(b) and 2(c) the motion/movement/gesture detection device 42 is provided that is located external to a monitor device 10 that includes one or more sensors. In one embodiment the motion/movement/gesture detection device 42 includes: an RF transmitter (BLE/ANT) 82, motion/movement/gesture detection detector 84; a central processing unit (CPU) 86, an RGB LED 88 and a reed switch 90. As a non-limiting example, motion/movement/gesture detection device 42 is attached to a pillow, bed cover, bed sheet, bedspread, and the like, in close enough proximity to the person being monitored that monitor device can detect signals from motion/movement/gesture detection device 42, and can be in the same room or a different room where the monitored person is.

In one embodiment the motion/movement/gesture detection device 42 is configured to detect motion, movement and the like, of a person over a certain threshold. When motion is detected, it wakes up the CPU 86 which processes the data emitted by the motion/movement/gesture detection device 42. The CPU 86 can optionally encrypt the data. The CPU 86 can broadcast the data collected through the RF transmitter.

In one embodiment the motion/movement/gesture detection device 42 is a position sensing device that is an accelerometer 84 which detects motion, movement/gesture and the like, of a person. As a non-limiting example, the accelerometer 84 provides a voltage output that is proportional to a detected acceleration. Suitable accelerometers are disclosed in, U.S. Pat. No. 8,347,720, U.S. Pat. No. 8,544,326, U.S. Pat. No. 8,542,189, U.S. Pat. No. 8,522,596. EP0486657B1, EP 2428774 A1, incorporated herein by reference. In one embodiment the accelerometer reports X, Y, and X axis information.

In certain embodiments other motion/movement gesture sensing devices 42 can be utilized including but not limited to: position sensing devices including but not limited to, optical encoders, magnetic encoders, mechanical encoders, Hall Effect sensors, potentiometers, contacts with ticks and the like.

The motion/movement/gesture detection device 84 provides one or more outputs. In one embodiment the output is a single value that detects the most interesting motion of the person within a defined time period. As a non-limiting example, this can be 60 seconds. The interesting motion is defined as that which provides the most information relative to movement/motion/gesture, and the like, of the person, that is different from a normal pattern of movement/motion/gesture and the like, that are not common occurrences of the person's movement/motion and gesture.

The motion/movement/gesture detection device 42 communicates with the monitor device 10 over the ANT protocol. The data collected by the motion/movement/gesture detection device 42 can be is encrypted before being broadcasted. Any motion/movement/gesture detection device can 42 safely connect to any monitor device to transmit data.

In one embodiment the monitor device 10 can also communicate with the motion/movement/gesture detection device 42 to exchange configuration information.

The monitor device 10 communicates with a Cloud System 110. The monitor device uploads data to the Cloud System at some interval controlled by the Cloud System 110. In one embodiment the data uploaded contains information collected from all sensors that are included in the monitor device, including but not limited to, temperature, humidity, particulates, sound, light, proximity, motion/movement/gesture detection device data, as well as system information including the monitor device's unique identifier (mac address), remaining storage capacity, system logs, and the like. To verify integrity and authenticity of the data, a cryptographic hash is included in the data.

In one embodiment monitor device receives commands and data from the Cloud System after each upload. As non-limiting examples the commands can include but are not limited to: light commands (color, pattern, duration); sound commands (sound, pattern, duration); personalized data which again as a non-limiting example can include ideal temperature, humidity, particulate level and the like; and custom configuration for algorithms running on monitor device.

Values generated by the monitor device elements, e.g., sensors and other elements in the monitor device, are collected over a selected time period. As a non-limiting example, this time period can be one minute. Data is also accumulated from the motion/movement/gesture detection device. The combination of the motion/movement/gesture detection device and the monitor device data and the combination of the two is then synchronized at a server. As a non-limiting example, the server can be at the Cloud System 110. Following the synchronization the server communicates instructions to the monitor device.

In one embodiment a person's mobile device communicates with monitor device over Bluetooth Low Energy (BLE). As non-limiting examples, the mobile device can send command information directed to one or more of: securely sharing Wife credentials; activating sensors, including but not limited to light, sound and the like; exchanges system state information; communicates maintenance operations; and the like.

In one embodiment mobile devices communicate securely to the Cloud System through mobile applications. As non-limiting examples these applications provide the ability to create an account, authenticate, access the data uploaded by monitor device, and perform other actions (set alarm, and the like) that are not typical of the environment where the client is.

In one embodiment the Cloud System pushes information to mobile devices when notification is needed.

In one embodiment monitor device performs audio classification and similarity detection to identify sounds and extra sound characteristics on the most interesting sounds that are not common occurrences.

In one embodiment algorithms are used to detect start, end, duration and quality of sleep activity. In one embodiment additional algorithms are used to detect motion events caused by another motion/movement/gesture detection device user sharing a same bed.

In one embodiment the Cloud System includes three subsystems which can communicate asynchronously. This can include one or more of a: (i) synchronization system that is responsible for receiving data uploaded by monitor device, verifying authenticity and integrity of the data uploaded, sending commands to monitor device 10. The data received is then queued for processing; (ii) processing service which is responsible for data analysis, persistence and transformation, visualization; and a presentation service for presenting data to the authenticated users.

In one embodiment the motion/movement/gesture detection device 42 analyzes motion data collected in real-time by an accelerometer. An algorithm processes the data and extract the most statistically interesting readings. At a predefined interval, the data collected is broadcasted to a monitor device.

In one embodiment the motion/movement/gesture detection device 42 is a three axis accelerometer. As a non-limiting example, the three axis accelerometer is modeled as $$zk=ak+gk+bk+vA;k$$

Where zk is the sensor output at time k, ak corresponds to the accelerations due to linear and rotational movement, bk is the o_set of the sensor, and vA; k is the observed noise.

Figure 3:
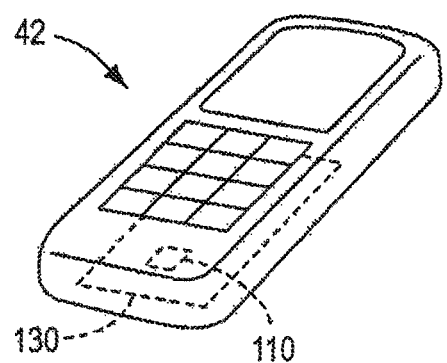
FIG. 3 is an image of an electronic device that contains an internal accelerometer.

In one embodiment of the present invention, illustrated in FIG. 3, the motion/movement/gesture detection device 42 includes an accelerometer 110 generally mounted on a circuit board 130 within the motion/movement/gesture detection device 42. The accelerometer 110 may be a single axis accelerometer (x axis), a dual axis accelerometer (x, y axes) or a tri-axis accelerometer (x, y, z axes). The electronic device may have multiple accelerometers that each measure 1, 2 or 3 axes of acceleration. The accelerometer 110 continuously measures acceleration producing a temporal acceleration signal. The temporal acceleration signal may contain more than one separate signal. For example, the temporal acceleration signal may include 3 separate acceleration signals, i.e. one for each axis. In certain embodiments, the accelerometer includes circuitry to determine if a tap and or shake have occurred by taking the derivative of the acceleration signal. In some embodiments, the accelerometer includes a computation module for comparing the derivative values to a threshold to determine if a tap and or shake have occurred. In other embodiments, the accelerometer outputs a temporal acceleration signal and the computation module takes the first derivative of the acceleration signal produce a plurality of derivative values. The computation module can then compare the first derivative values to a predetermined threshold value that is stored in a memory of the computation module to determine if a tap and or shake have occurred.

Figure 4:
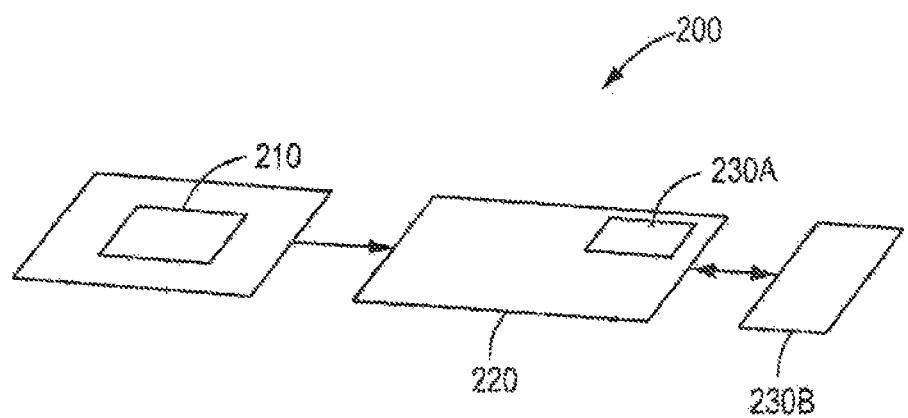
FIG. 4 illustrates one embodiment of a tap and or shake detection system.

FIG. 4 shows a first embodiment of the tap and or shake detection system 200 that includes a computation module 220 and the accelerometer 210. The accelerometer output signal is received by a computation module 220 that is electrically coupled to the accelerometer 210 and that is running (executing/interpreting) software code. It should be understood by one of ordinary skill in the art that the software code could be implemented in hardware, for example as an ASIC chip or in an FPGA or a combination of hardware and software code. The computation module running the software receives as input the data from the accelerometer and takes the derivative of the signal. For example, the accelerometer may produce digital output values for a given axis that are sampled at a predetermined rate. The derivative of the acceleration values or "jerk" can be determined by subtracting the N and N−1 sampled values. The acceleration values may be stored in memory 230A, 230B either internal to or external to the computation module 220 during the calculation of the derivative of acceleration.

Other methods/algorithms may also be used for determining the derivative of the acceleration. The jerk value can then be compared to a threshold. The threshold can be fixed or user-adjustable. If the jerk value exceeds the threshold then a tap and or shake is detected. In some embodiments, two threshold values may be present: a first threshold value for tap and or shakes about the measured axis in a positive direction and a second threshold for tap and or shakes about the axis in a negative direction. It should be recognized by one of ordinary skill in the art that the absolute value of the accelerometer output values could be taken and a single threshold could be employed for accelerations in both a positive and negative direction along an axis. When a tap and or shake have been detected, the computation unit can then forward a signal or data indicative of a tap and or shake as an input for another application/process. The application/process may use the detection of a tap and or shake as an input signal to perform an operation. For example, a tap and or shake may indicate that a device should be activated or deactivated (on/off). Thus, the tap and or shake detection input causes a program operating on the device to take a specific action. Other uses for tap and or shake detection include causing a cellular telephone to stop audible ringing when a tap and or shake is detected or causing a recording device to begin recording. These examples should not be viewed as limiting the scope of the invention and are exemplary only.

Figure 5:
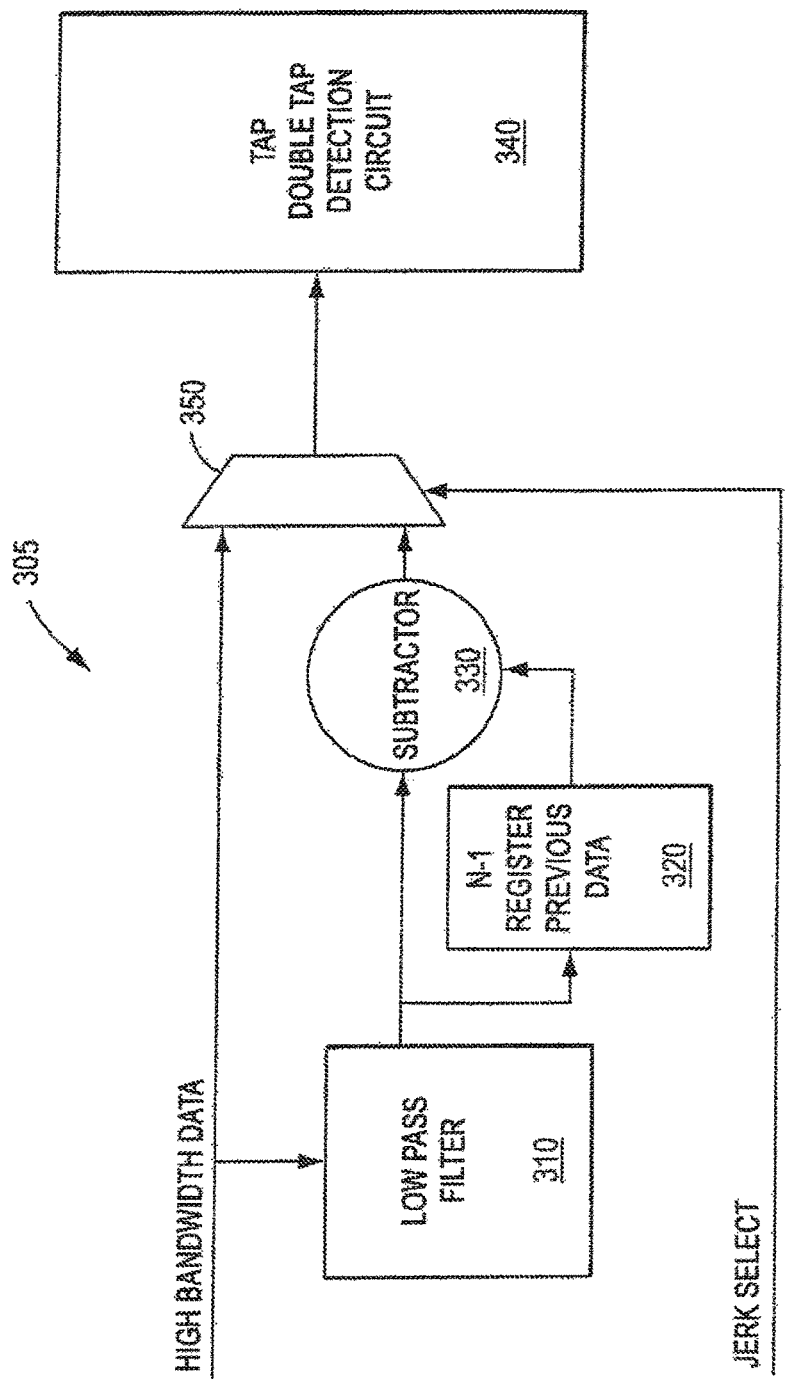
FIG. 5 illustrates another embodiment of a tap and or shake detection system that includes a subtraction circuit.

FIG. 5 shows a second embodiment of the tap and or shake detection system that uses a buffer for storing a temporal acceleration value along with a subtraction circuit. This embodiment can be used to retrofit an electronic device that already has a tap and or shake detection algorithm without needing to alter the algorithm. For purposes of this discussion, it will be assumed that the high bandwidth acceleration data is for a single axis. The acceleration data may include data from a multi-axis accelerometer.

The circuit shows high bandwidth data 300 from an accelerometer unit being used as input to the tap and or shake detection system 305. The high-bandwidth data 300 is fed to a multiplexor 350 and also to a low pass filter 310. The high bandwidth data 300 from the accelerometer is low pass filtered in order to reduce the data rate, so that the data rate will be compatible with the other circuit elements of the tap and or shake detection system 305. Therefore, the low pass filter is an optional circuit element if the data rate of the accelerometer is compatible with the other circuit elements. Once the acceleration data is filtered, the sampled data (N−1) is stored in a register 320. The next sampled data value (N) is passed to the subtraction circuit 330 along with the sampled value that is stored in the register (N−1) 320. As the N−1 data is moved to the subtraction circuit 330, the N data value replaces the N−1 value in the register 320. Not shown in the figure is a clock circuit that provides timing signals to the low pass filter 310, the register 320, and the subtraction circuit 330. The clock circuit determines the rate at which data is sampled and passed through the circuit elements. If the accelerometer samples at a different rate than the clock rate, the low pass filter can be used to make the accelerometer's output data compatible with the clock rate. The subtraction circuit 330 subtracts the N−1 value from the N value and outputs the resultant value. The resultant value is passed to the tap and or shakes detection circuit 340 when the jerk select command to the multiplexor is active. The acceleration data may also be passed directly to the tap and or shake detection circuit when there is no jerk select command. In certain embodiments of the invention, the accelerometer unit along with the register, subtraction circuit, and multiplexor are contained within the accelerometer package.

The tap and or shake detection circuit 340 may be a computation module with associated memory that stores the threshold jerk values within the memory. The tap and or shake detection circuit may be either internal to the accelerometer packaging or external to the accelerometer packaging. For example, in a cell phone that includes one or more processors, a processor can implement the functions of a computation module. The computation module 340 compares the resultant jerk value to the one or more threshold jerk values. In one embodiment, there is a positive and a negative threshold jerk value. If the resultant value exceeds the threshold for a tap and or shake in a positive direction or is below the threshold for a tap and or shake in a negative direction, the tap and or shake detection circuit indicates that a tap and or shake has occurred. The tap and or shake identification can be used as a signal to cause an action to be taken in a process or application. For example, if the electronic device is a cell phone and a tap and or shake are detected, the tap and or shake may cause the cell phone to mute its ringer.

In other embodiments, the computation module determines if a tap and or shake occurs and then can store this information along with timing information. When a second tap and or shake occurs, the computation module can compare the time between tap and or shakes to determine if a double tap and or shake has occurred. Thus, a temporal threshold between tap and or shakes would be indicative of a double tap and or shake. This determination could be similar to the double tap and or shake algorithms that are used for computer input devices. For example, a double click of a computer mouse is often required to cause execution of a certain routine within a computer program. Thus, the double tap and or shake could be used in a similar fashion.

Figure 6:
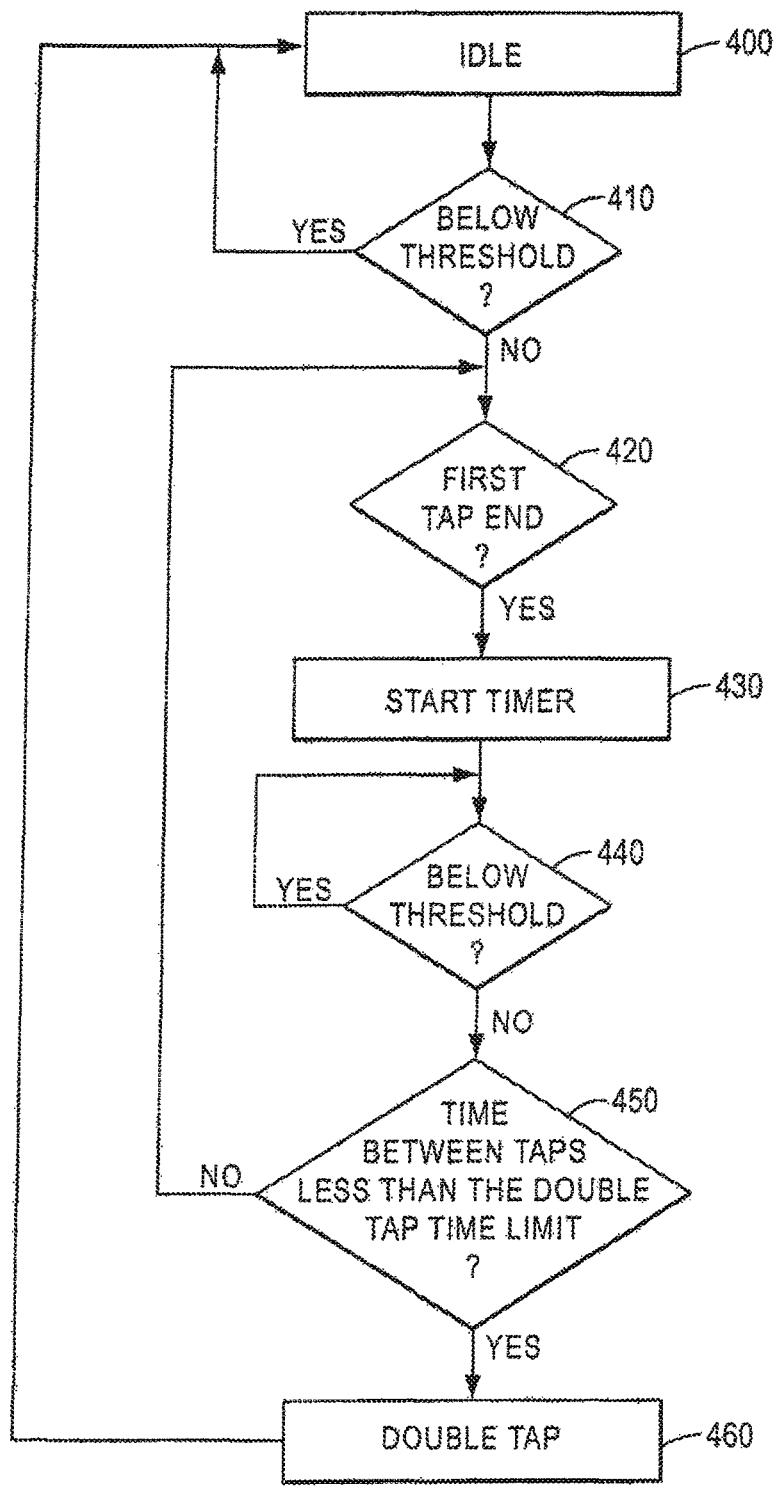
FIG. 6 illustrates one embodiment of a flow chart that shows a method for detecting when a double tap and or shake has occurred.

FIG. 6 shows a flow chart for determining if a double tap and or shake have occurred. The system is initially at idle and the acceleration derivative values (jerk values) are below the threshold value 400. Each jerk value is compared to a threshold value 410. When the threshold value is exceeded, a first click or tap and or shake are identified. The system waits either a predetermined length of time or determines when the jerk value goes below the threshold to signify that the first tap and or shake have ended 420. A timer then starts and measures the time from the end of the first tap and or shake and the system waits for a second tap and or shake 430. The system checks each jerk value to see if the jerk value has exceeded the threshold 440. If the jerk value does not exceed the threshold the system waits. When the threshold is exceeded, the system determines the time between tap and or shakes and compares the time between tap and or shakes to a double tap and or shake limit 440. If the time between tap and or shakes is less than the double tap and or shake time limit, a double tap and or shake is recognized 450. If a double tap and or shake is not recognized, the present tap and or shake becomes the first tap and or shake and the system waits for the end of the first tap and or shake. When a second tap and or shake occurs, an identifier of the second tap and or shake i.e. a data signal, flag or memory location is changed and this information may be provided as input to a process or program. Additionally, when a double tap and or shake have been monitored, the methodology loops back to the beginning and waits for a new tap and or shake.

Figure 7:
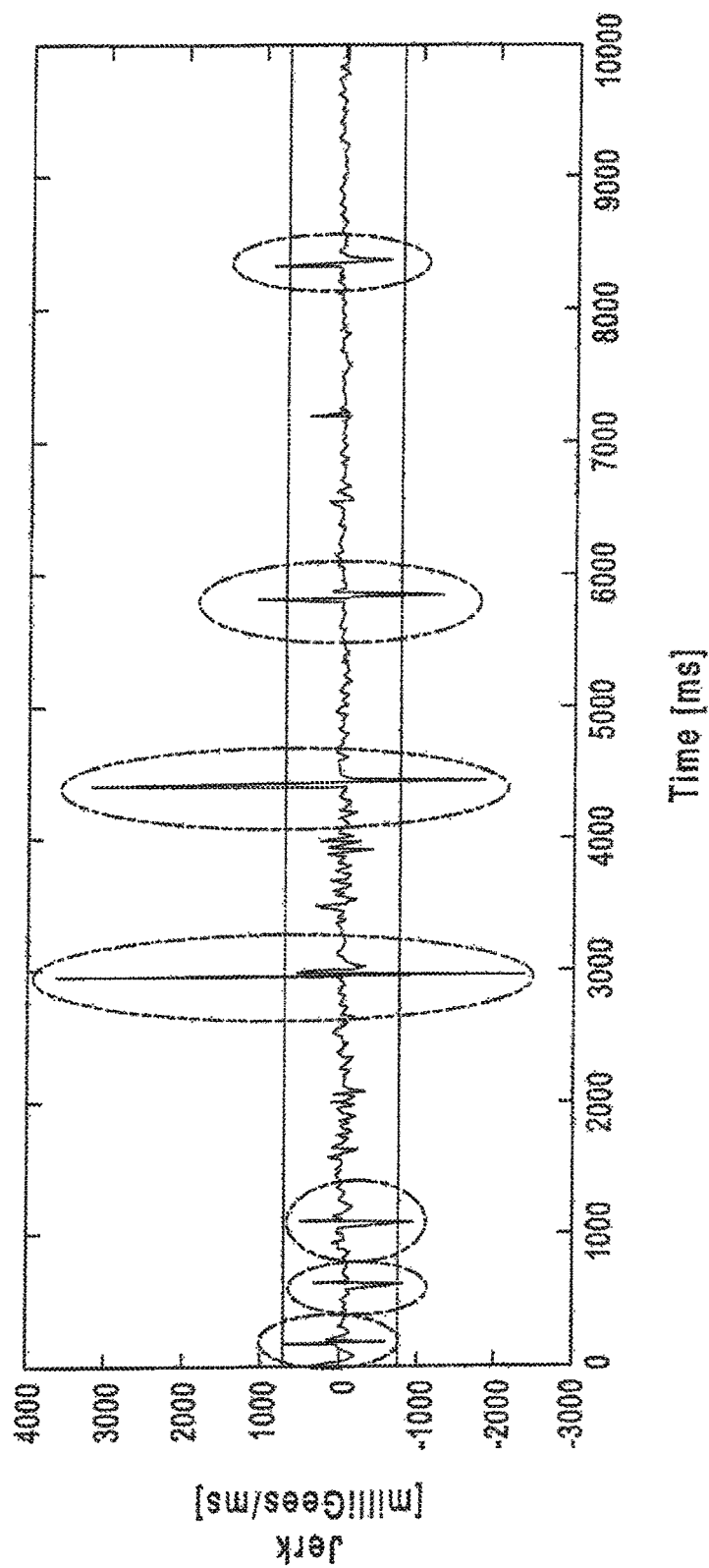
FIG. 7 is a graph that shows a derivative of acceleration with respect to time and includes thresholds for determining when a tap and or shake have occurred.

FIG. 7 shows a graph of the derivative of acceleration data ("jerk") with respect to time for the same series of accelerations as shown in FIG. 3. FIG. 5 provides a more accurate indication of tap and or shakes. FIG. 3 shows both false positive tap and or shake readings along with true negative readings. Thus, the acceleration measurement will not register some tap and or shakes and will also cause tap and or shakes to be registered when no tap and or shake was present. False positive readings occur, for example, when a user has a cell phone in his pocket and keys or other objects strike the cell phone due to movement of the user. These false readings are caused mainly because of the noise floor. By taking the derivative of the acceleration signal, the noise floor is lowered and the tap and or shake signals become more pronounced. Thus, false positive identifications of tap and or shakes are reduced with a lower noise floor. By requiring double tap and or shakes the number of false positives is reduced even further.

Audio

Figure 8:
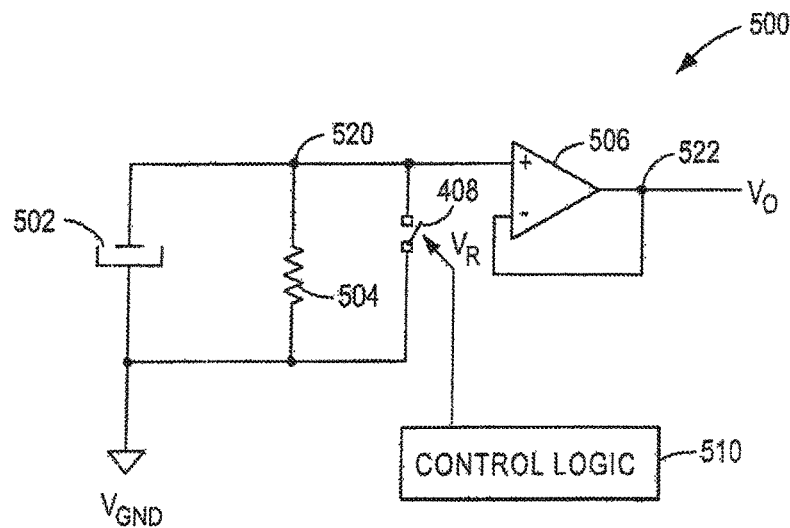
FIG. 8 illustrates one embodiment of a block diagram for a microphone circuit that can be used.

FIG. 8 is a block diagram of a microphone circuit 500 in one embodiment. In one embodiment, the microphone circuit 500 includes a transducer 502, a biasing resistor 504, a pre-amplifier 506, a switch circuit 508, and control logic 510. The transducer 502 is coupled between a ground VGND and a node 520. The transducer 502 converts a sound into a voltage signal and outputs the voltage signal to the node 520. The biasing resistor 504 is coupled between the node 520 and the ground VGND and biases the node 520 with a DC voltage level of the ground voltage VGND. The pre-amplifier 506 receives the voltage signal output by the transducer 502 at the node 520 and amplifies the voltage signal to obtain an output signal Vo at a node 522. In one embodiment, the pre-amplifier 506 is a unity gain buffer.

The pre-amplifier 506 requires power supplied by a biasing voltage for amplifying the voltage signal output by the transducer 502. The switch circuit 508 is coupled between the node 520 and the ground voltage VGND. The switch circuit 508 therefore controls whether the voltage of the node 520 is set to the ground voltage VGND. When the microphone circuit 500 is reset, the control logic 510 enables a resetting signal VR to switch on the switch circuit 508, and the node 520 is therefore directly coupled to the ground VGND. When the microphone circuit 500 is reset, a biasing voltage VDD is applied to the pre-amplifier 506, and the voltage at the node 520 tends to have a temporary voltage increase. However, because the switch circuit 508 couples the node 520 the ground VGND, the voltage of the node 520 is kept at the ground voltage VGND and prevented from increasing, thus avoiding generation of the popping noise during the reset period. After a voltage status of the pre-amplifier 506 is stable at time T1, the control logic 510 switches off the switch circuit 508. The node 520 is therefore decoupled from the ground VGND, allowing the voltage signal generated by the transducer 502 to be passed to the pre-amplifier 506. Thus, the switch circuit 508 clamps the voltage of the node 520 to the ground voltage during the reset period, in which the biasing voltage VDD is just applied to the pre-amplifier 506.

Figure 12A:
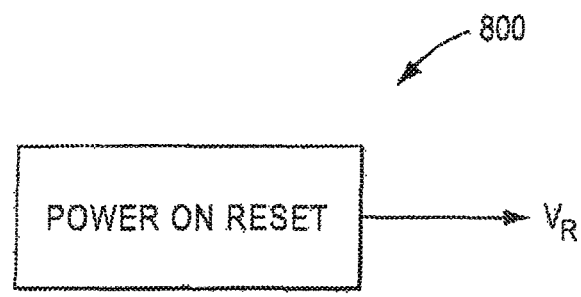
FIG. 12($a$) illustrates an embodiment of a control logic that can be used with the FIG. 4 embodiment.
Figure 12B:
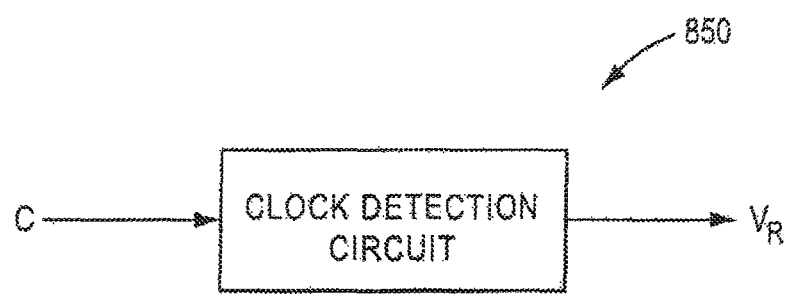

Referring to FIG. 12(*a*), an embodiment of control logic 510 is shown. In the embodiment, the control logic 510 is a power-on-reset circuit 800. The power-on-reset circuit 800 detects the power level of a biasing voltage of the pre-amplifier 506. When the power level of the biasing voltage of the pre-amplifier 506 is lower than a threshold, the power-on-reset circuit 800 enables the resetting signal VR to switch on the switch circuit 508, thus coupling the node 520 to the ground VGND to avoid generation of a popping noise. Referring to FIG. 12(*b*), another embodiment of control logic 510 of FIG. 8 is shown. In the embodiment, the control logic 510 is a clock detection circuit 850. The clock detection circuit 850 detects a clock signal C frequency for operating the microphone circuit 500. When the frequency of the clock signal C is lower than a threshold, the clock detection circuit 850 enables the resetting signal VR to switch on the switch circuit 508, thus coupling the node 520 to the ground VGND to avoid generation of a popping noise.

Figure 9:
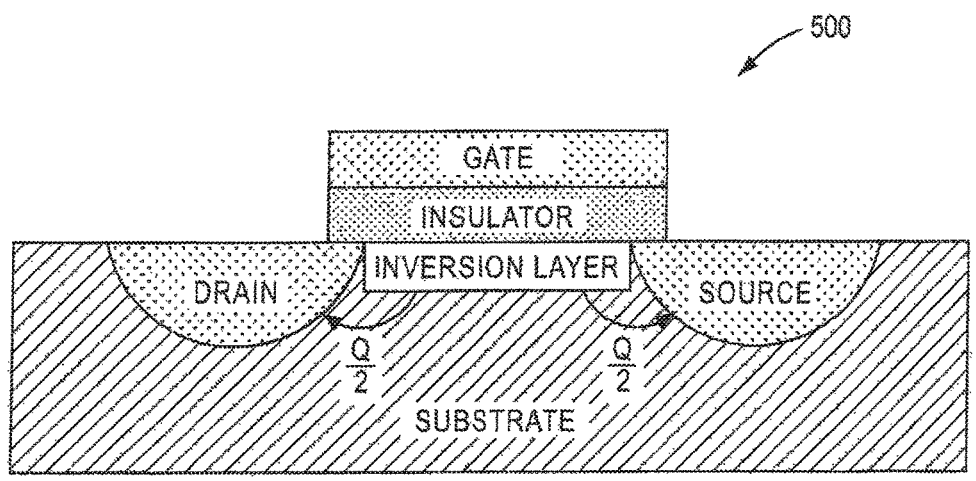
FIG. 9 is a cross-section view of an NMOS transistor.

In one embodiment, the switch circuit 508 is an NMOS transistor coupled between the node 520 and the ground VGND. The NMOS transistor has a gate coupled to the resetting voltage VR generated by the control logic 510. If the switch circuit 508 is an NMOS transistor, a noise is generated with a sound level less than that of the original popping noise when the control logic 510 switches off the switch circuit 508. Referring to FIG. 9, a cross-section view of an NMOS transistor 500 is shown. The NMOS transistor 500 has a gate on a substrate, and a source and a drain in the substrate. The gate, source, and drain are respectively coupled to the resetting signal VR, the ground voltage VGND, and the node 520. When the control logic 510 enables the resetting voltage VR to turn on the NMOS transistor 500, a charge amount Q is attracted by the gate voltage to form an inversion layer beneath the insulator. When the control logic 510 disables the resetting signal VR, the inversion layer vanishes, and a charge amount of Q/2 flows to the drain and source of the NMOS transistor 500, inducing a temporary voltage change at the node 520 and producing a noise.

Assume that the NMOS transistor 500 has a width of 1 µm, a length of 0.35 µm, and the resetting voltage is 1.8V, then the sheet capacitance of the gate oxide is 5 fF/µm2. The gate capacitance of the NMOS transistor 500 is therefore equal to (5 fF/µm2×1 µm×0.35 µm)=1.75 fF, and the charge Q stored in the inversion layer is therefore equal to (1.75 fF×1.8V)=3.15 fC. The drain of the NMOS transistor 500 has capacitance of (5 pF+200 fF)=5.2 pF, and the temporary voltage change at the node 520 is therefore equal to (3.15 fC/5.2 pF)=0.6 mV. With the NMOS switch 500, the node 520 of the microphone circuit 500 has a temporary voltage change of 0.6 mV instead of a popping noise of 64 mV during a reset period. The temporary voltage change of 0.6 mV, however, still produces an audible sound with a 63 dB sound pressure level. Thus, two more embodiments of the switch circuit 508 are introduced to solve the problem.

Figure 10:
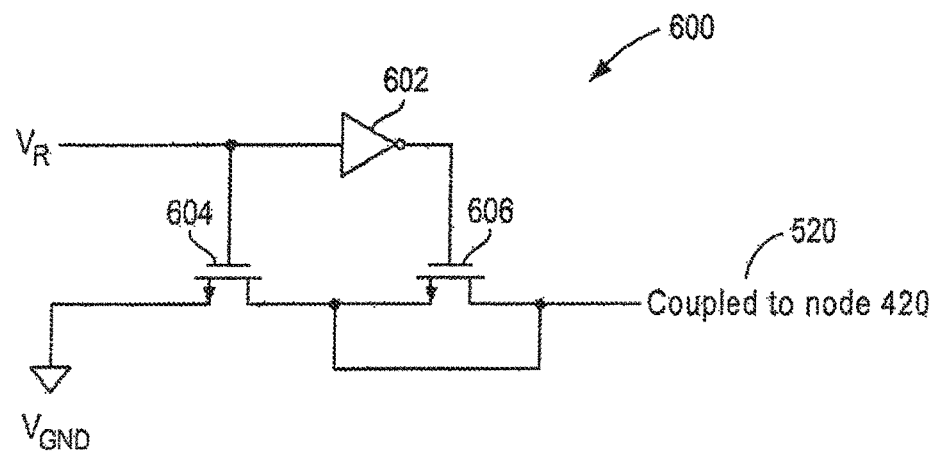
FIG. 10 is a block diagram of an embodiment of a switch circuit according to the invention.

Referring to FIG. 10, a block diagram of an embodiment of a switch circuit 600 is shown. The switch circuit 600 can include an inverter 602 and NMOS transistors 604 and 606, wherein a size of the NMOS transistor 606 is equal to a half of that of the NMOS transistor 604. When the control logic 510 enables the resetting signal VR, the NMOS transistor 604 is turned on to couple the node 520 to the ground voltage VGND, and the NMOS transistor 606 is turned off. When the control logic 510 disables the resetting signal VR, the NMOS transistor 604 is turned off to decouple the node 520 from the ground voltage VGND, and the NMOS transistor 606 is turned on. Charges originally stored in an inversion layer of the NMOS transistor 604 therefore flow from a drain of the NMOS transistor 604 to a source of the NMOS transistor 606 and are then absorbed by an inversion layer of the NMOS transistor 606, preventing the aforementioned problem of temporary voltage change of the node 520.

Figure 11:
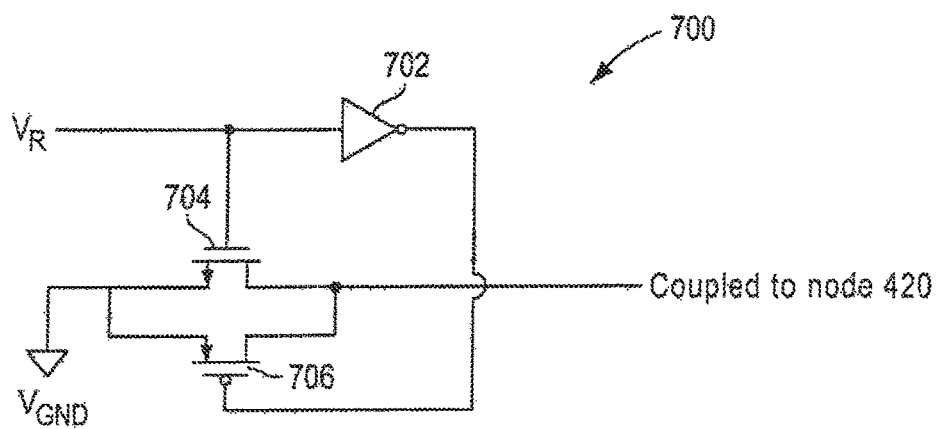
FIG. 11 is a block diagram of another embodiment of a switch circuit according to the invention.

Referring to FIG. 11, a block diagram of another embodiment of a switch circuit 700 according to the invention is shown. The switch circuit 700 comprises an inverter 702, an NMOS transistor 704, and a PMOS transistor 706, wherein a size of the NMOS transistor 704 is equal to that of the PMOS transistor 706. When the control logic 510 enables the resetting signal VR, the NMOS transistor 704 is turned on to couple the node 520 to the ground voltage VGND, and the PMOS transistor 706 is turned off. When the control logic 510 disables the resetting signal VR, the NMOS transistor 704 is turned off to decouple the node 520 from the ground voltage VGND, and the PMOS transistor 706 is turned on. Charges originally stored in an inversion layer of the NMOS transistor 704 therefore flow from a drain of the NMOS transistor 704 to a drain of the PMOS transistor 706 and are then absorbed by an inversion layer of the PMOS transistor 706, preventing the aforementioned problem of temporary voltage change of the node 520.

Gesture

Figure 13:
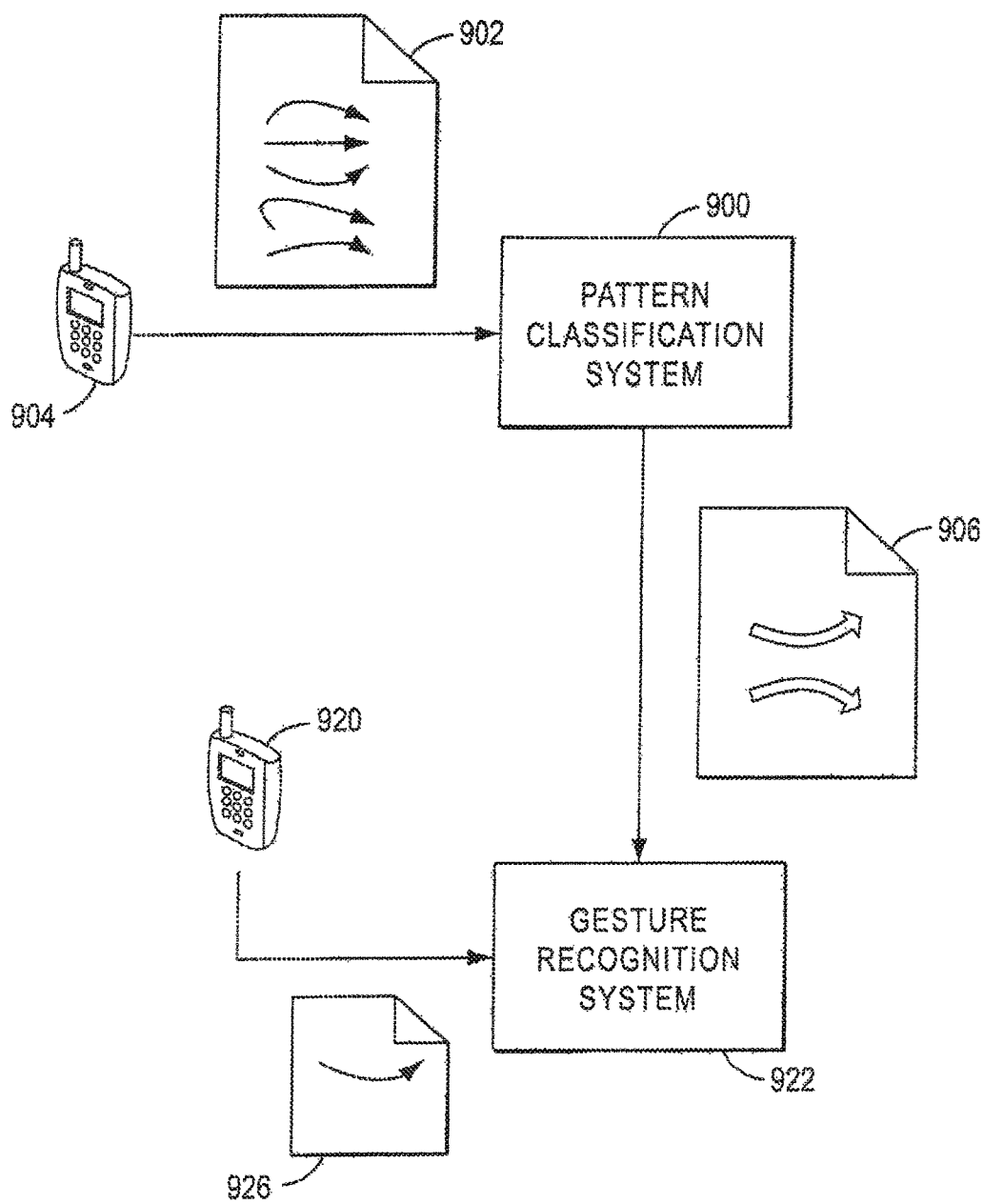
FIG. 13 is a diagram that provides an overview of motion pattern classification and gesture creation and recognition.

FIG. 13 is a diagram that provides an overview of motion pattern classification and gesture recognition. Motion pattern classification system 900 is a system including one or more computers programmed to generate one or more motion patterns from empirical data. Motion pattern classification system 900 can receive motion samples 902 as training data from at least one motion/movement/gesture detection device 904. Each of the motion samples 902 can include a time series of readings of a motion sensor of motion/movement/gesture detection device 904.

Motion pattern classification system 900 can process the received motion samples 902 and generate one or more motion patterns 906. Each of the motion patterns 906 can include a series of motion vectors. Each motion vector can include linear acceleration values, angular rate values, or both, on three axes of a Cartesian coordinate frame (e.g., X, Y, Z or pitch, yaw, roll). Each motion vector can be associated with a timestamp. Each motion pattern 906 can serve as a prototype to which motions are compared such that a gesture can be recognized. Motion pattern classification system 900 can send motion patterns 906 to motion/movement/gesture detection device 920 for gesture recognition.

Mobile device 920 can include, or be coupled to, gesture recognition system 922. Gesture recognition system 922 is a component of motion/movement/gesture detection device 920 that includes hardware, software, or both that are configured to identify a gesture based on motion patterns 906. Mobile device 920 can move (e.g., from a location A to a location B) and change orientations (e.g., from a face-up orientation on a table to an upright orientation near a face) following motion path 924. When motion/movement/gesture detection device 920 moves, a motion sensor of motion/movement/gesture detection device 920 can provide a series of sensor readings 926 (e.g., acceleration readings or angular rate readings). Gesture recognition system 922 can receive sensor readings 926 and filter sensor readings 926. Gesture recognition system 922 can compare the filtered sensor readings 926 with the motion patterns 906. If a match is found, motion/movement/gesture detection device 920 can determine that a gesture is recognized. Based on the recognized gesture, motion/movement/gesture detection device can perform a task associated with the motion patterns 906 (e.g., turning off a display screen of motion/movement/gesture detection device 920).

Figure 14:
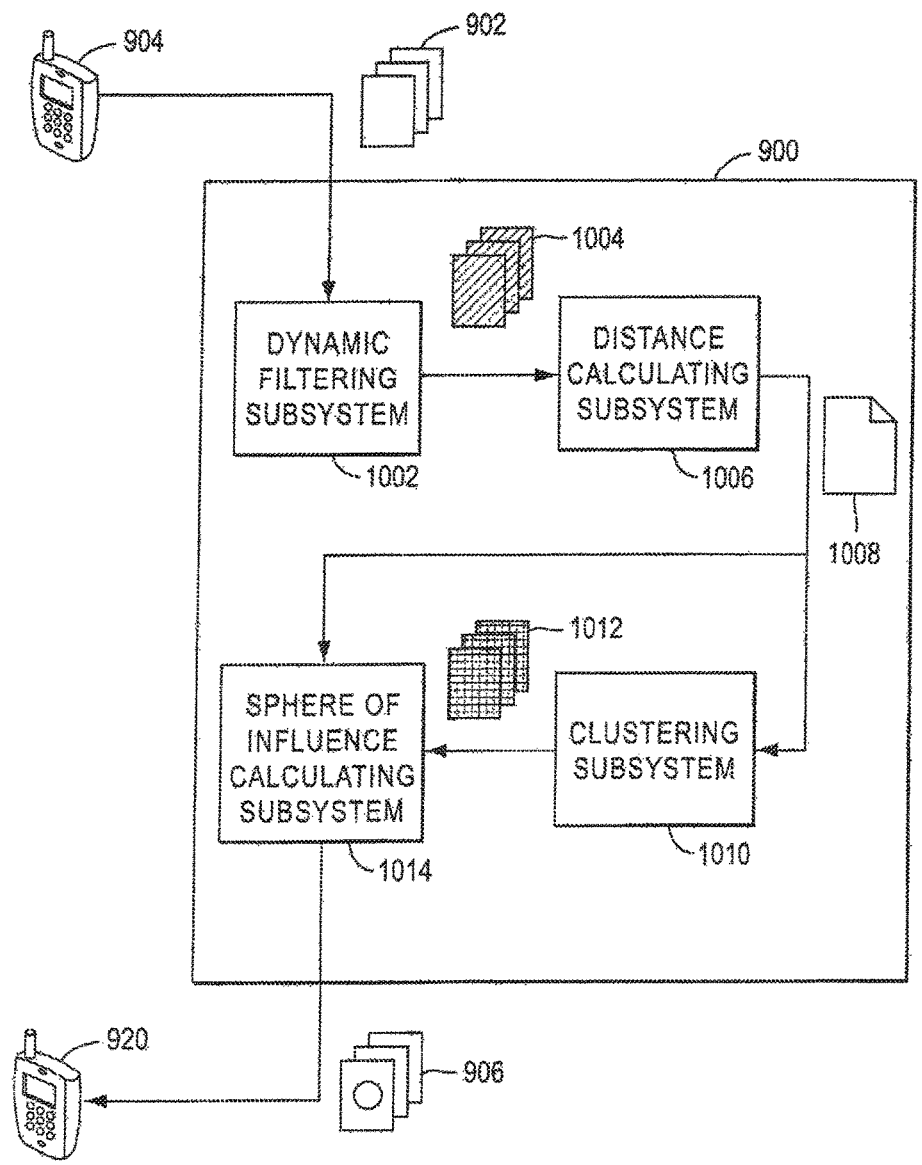
FIG. 14 is a block diagram of an exemplary system configured to perform operations of motion pattern classification.

FIG. 14 is a block diagram of an exemplary system configured to perform operations of motion pattern classification. Motion pattern classification system 900 can receive motion samples 902 from motion/movement/gesture detection device 904, generates prototype motion patterns 906 based on motion samples 902, and send prototype motion patterns 906 to motion/movement/gesture detection device 920.

Mobile device 904 is a device configured to gather motion samples 902. An application program executing on motion/movement/gesture detection device 904 can provide for display a user interface requesting a user to perform a specified physical gesture with motion/movement/gesture detection device 904 one or more times. The specified gesture can be, for example, a gesture of picking up motion/movement/gesture detection device 904 from a table or a pocket and putting motion/movement/gesture detection device 904 near a human face. The gesture can be performed in various ways (e.g., left-handed or right-handed). The user interface is configured to prompt the user to label a movement each time the user completes the movement. The label can be positive, indicating the user acknowledges that the just-completed movement is a way of performing the gesture. The label can be negative, indicating that the user specifies that the just-completed movement is not a way of performing the gesture. Mobile device 904 can record a series of motion sensor readings during the movement. Mobile device 904 can designate the recorded series of motion sensor readings, including those labeled as positive or negative, as motion samples 902. The portions of motion samples 902 that are labeled negative can be used as controls for tuning the motion patterns 906. Motion samples 902 can include multiple files, each file corresponding to a motion example and a series of motion sensor readings. Content of each file can include triplets of motion sensor readings (3 axes of sensed acceleration), each triplet being associated with a timestamp and a label. The label can include a text string or a value that designates the motion sample as a positive sample or a negative sample.

Motion pattern classification system 900 can include dynamic filtering subsystem 1002. Dynamic filtering subsystem 1002 is a component of motion pattern classification system 900 that is configured to generate normalized motion samples (also referred to as motion features) 1004 based on motion samples 902. Dynamic filtering subsystem 1002 can high-pass filter each of motion samples 902. High-pass filtering of motion samples 902 can include reducing a dimensionality of the motion example and compressing the motion sample in time such that each of motion samples 902 has a similar length in time. Further details of the operations of dynamic filtering subsystem 1002 will be described below in reference to FIG. 15.

Motion pattern classification system 900 can include distance calculating subsystem 1006. Distance calculating subsystem 1006 is a component of motion pattern classification system 100 that is configured to calculate a distance between each pair of motion features 1004. Distance calculating subsystem 1006 can generate a D-path matrix 1008 of distances. The distance between a pair of motion features 1004 can be a value that indicates a similarity between two motion features. Further details of the operations of calculating a distance between a pair of motion features 1004 and of the D-path matrix 1008 will be described below in reference to FIG. 16.

Figure 17:
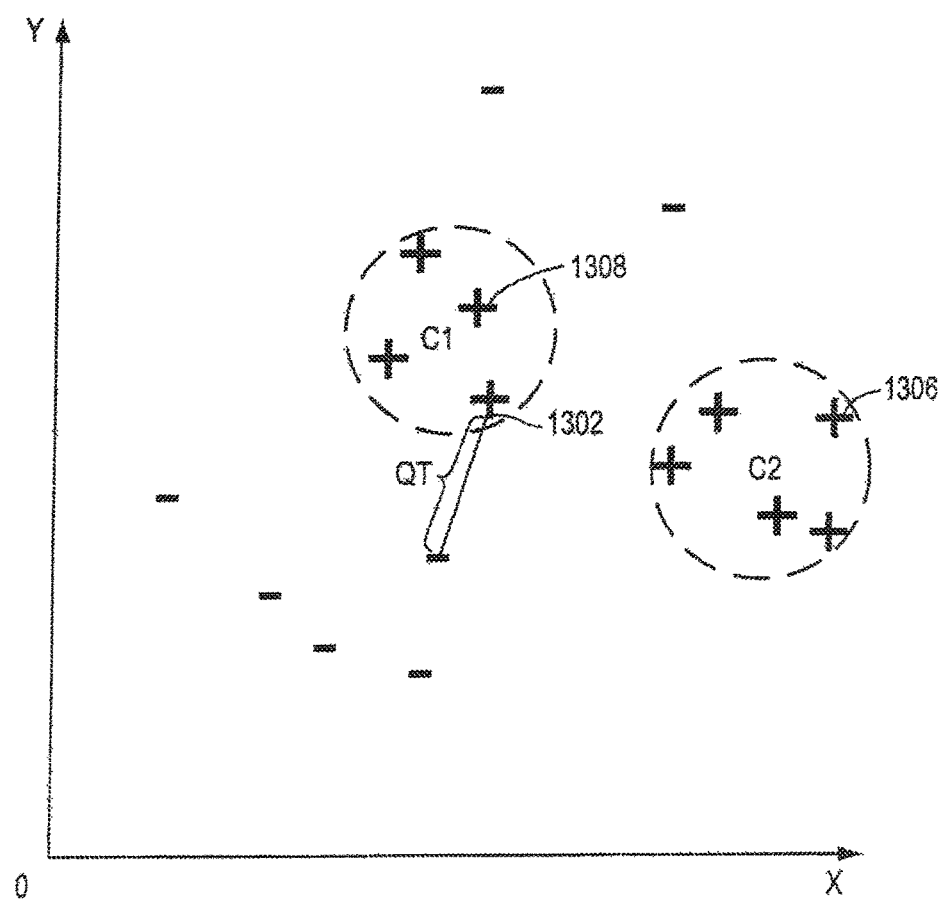
FIG. 17 is a diagram illustrating exemplary clustering techniques of motion pattern classification.

Motion pattern classification system 900 can include clustering subsystem 1010. Clustering subsystem 1010 is a component of motion pattern classification system 900 that is configured to generate one or more raw motion patterns 1012 based on the D-path matrix 1008 from the distance calculating system 1006. Each of the raw motion patterns 1012 can include a time series of motion vectors. The time series of motion vectors can represent a cluster of motion features 1004. The cluster can include one or more motion features 1004 that clustering subsystem 1010 determines to be sufficiently similar such that they can be treated as a class of motions. Further details of operations of clustering subsystem 1010 will be described below in reference to FIG. 17.

Motion pattern classification system 900 can include sphere-of-influence (SOI) calculating subsystem 1014. SOI calculating subsystem 1014 is a component of the motion pattern classification system 900 configured to generate one or more motion patterns 906 based on the raw motion patterns 1012 and the D-path matrix 1008. Each of the motion patterns 906 can include a raw motion pattern 1012 associated with an SOT. The SOI of a motion pattern is a value or a series of values that can indicate a tolerance or error margin of the motion pattern. A gesture recognition system can determine that a series of motion sensor readings match a motion pattern if the gesture recognition system determines that a distance between the series of motion sensor readings and the motion pattern is smaller than the SOI of the motion pattern. Further details of the operations of SOI calculating subsystem 1014 will be described below in reference FIGS. 18(*a*)-(*c*). The motion pattern classification system 900 can send the motion patterns 906 to device 920 to be used by device 920 to perform pattern-based gesture recognition.

Figure 15:
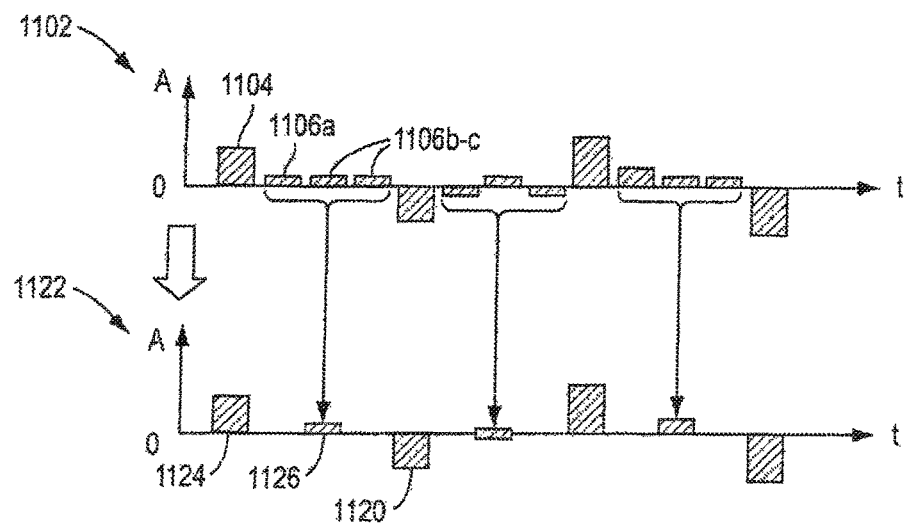
FIG. 15 is a diagram illustrating exemplary operations of dynamic filtering of motion example data.

FIG. 15 is a diagram illustrating exemplary operations of dynamic filtering motion sample data. Motion example 1102 can be one of the motion samples 902 (as described above in reference to FIGS. 13-14). Motion sample 1102 can include a time series of motion sensor readings 1104, 1106 *a-c*, 1108, etc. Each motion sensor reading is shown in one dimension ("A") for simplicity. Each motion sensor reading can include three acceleration values, one on each axis in a three dimensional space.

Dynamic filtering subsystem 1002 (as described in reference to FIG. 14) can receive motion sample 1102 and generate motion feature 1122. Motion feature 1122 can be one of the motion features 1004. Motion feature 1122 can include one or more motion vectors 1124, 1126, 1128, etc. To generate the motion feature 1122, dynamic filtering subsystem 1002 can reduce the motion sample 1102 in the time dimension. In some implementations, dynamic filtering subsystem 1002 can apply a filtering threshold to motion sample 1102. The filtering threshold can be a specified acceleration value. If a motion sensor reading 1108 exceeds the filtering threshold on at least one axis (e.g., axis X), dynamic filtering subsystem 1002 can process a series of one or more motion sensor readings 1106 *a-c* that precede the motion sensor reading 1108 in time. Processing the motion sensor readings 1106 *a-c* can include generating motion vector 1126 for replacing motion sensor readings 1106 *a-c*. Dynamic filtering subsystem 1002 can generate motion vector 1126 by calculating an average of motion sensor readings 1106 *a-c*. In a three-dimensional space, motion vector 1126 can include an average value on each of multiple axes. Thus, dynamic filtering subsystem 1002 can create motion feature 1122 that has fewer data points in the time series.

In some implementations, dynamic filtering subsystem 1002 can remove the timestamps of the motion samples such that motion feature 1122 includes an ordered series of motion vectors. The order of the series can implicitly indicate a time sequence. Dynamic filtering subsystem 1002 can preserve the labels associated with motion sample 1102. Accordingly, each motion vector in motion feature 1122 can be associated with a label.

Figure 16:
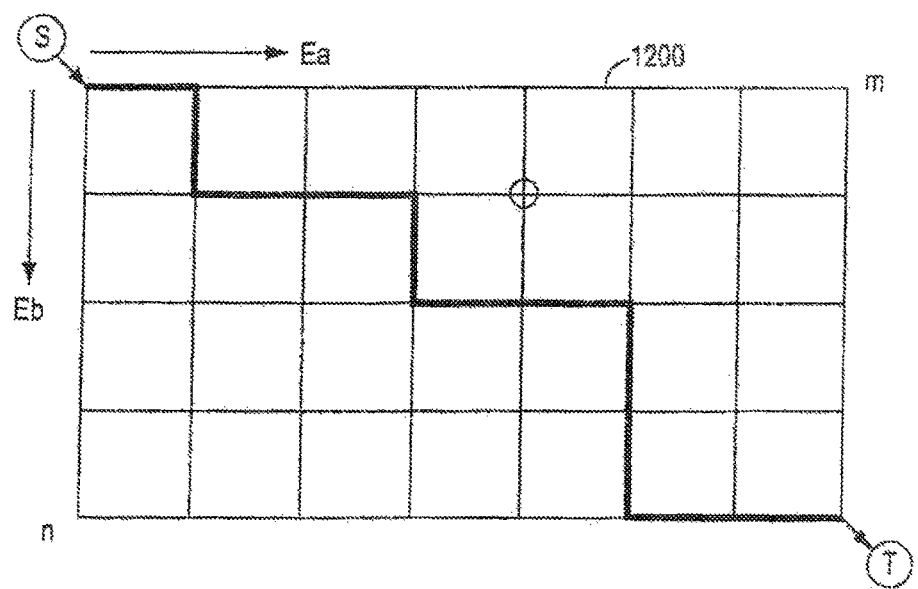
FIG. 16 is a diagram illustrating exemplary dynamic time warp techniques used in distance calculating operations of motion pattern classification.

FIG. 16 is a diagram illustrating exemplary dynamic time warp techniques used in distance calculating operations of motion pattern classification. Distance calculating subsystem 1006 (as described in reference to FIG. 14) can apply dynamic time warp techniques to calculate a distance between a first motion feature (e.g., Ea) and a second motion feature (e.g., Eb). The distance between Ea and Eb will be designated as D(Ea, Eb).

In the example shown, Ea includes a time series of m accelerometer readings r (a, 1) through r (a, m). Eb includes a time series of n accelerometer readings r (b, 1) through r (b, n). In some implementations, the distance calculating subsystem 1006 calculates the distance D(Ea, Eb) by employing a directed graph 1200. Directed graph 1200 can include m×n nodes. Each node can be associated with a cost. The cost of a node (i, j) can be determined based on a distance between accelerometer readings r(a, i) and r(b, j). For example, node 1202 can be associated with a distance between accelerometer readings r(a, 5) of Ea and accelerometer readings r(b, 2) of Eb. The distance can be a Euclidean distance, a Manhattan distance, or any other distance between two values in an n-dimensional space (e.g., a three-dimensional space).

Distance calculating subsystem 1006 can add a directed edge from a node (i, j) to a node (i, j+1) and from the node (i, j) to a node (i+1, j). The directed edges thus can form a grid, in which, in this example, multiple paths can lead from the node (1, 1) to the node (m, n).

Distance calculating subsystem 1006 can add, to directed graph 1200, a source node S and a directed edge from S to node (1, 1), and target node T and a directed edge from node (m, n) to T. Distance calculating subsystem 1006 can determine a shortest path (e.g., the path marked in bold lines) between S and T, and designate the cost of the shortest path as the distance between motion features Ea and Eb.

When distance calculating subsystem 1006 receives y of motion features E1 . . . Ey, distance calculating subsystem 1006 can create a y-by-y matrix, an element of which is a distance between two motion features. For example, element (a, b) of the y-by-y matrix is the distance D(Ea, Eb) between motion features Ea and Eb. Distance calculating subsystem 1006 can designate the y-by-y matrix as D-path matrix 1008 as described above in reference to FIG. 14.

Figure 20:
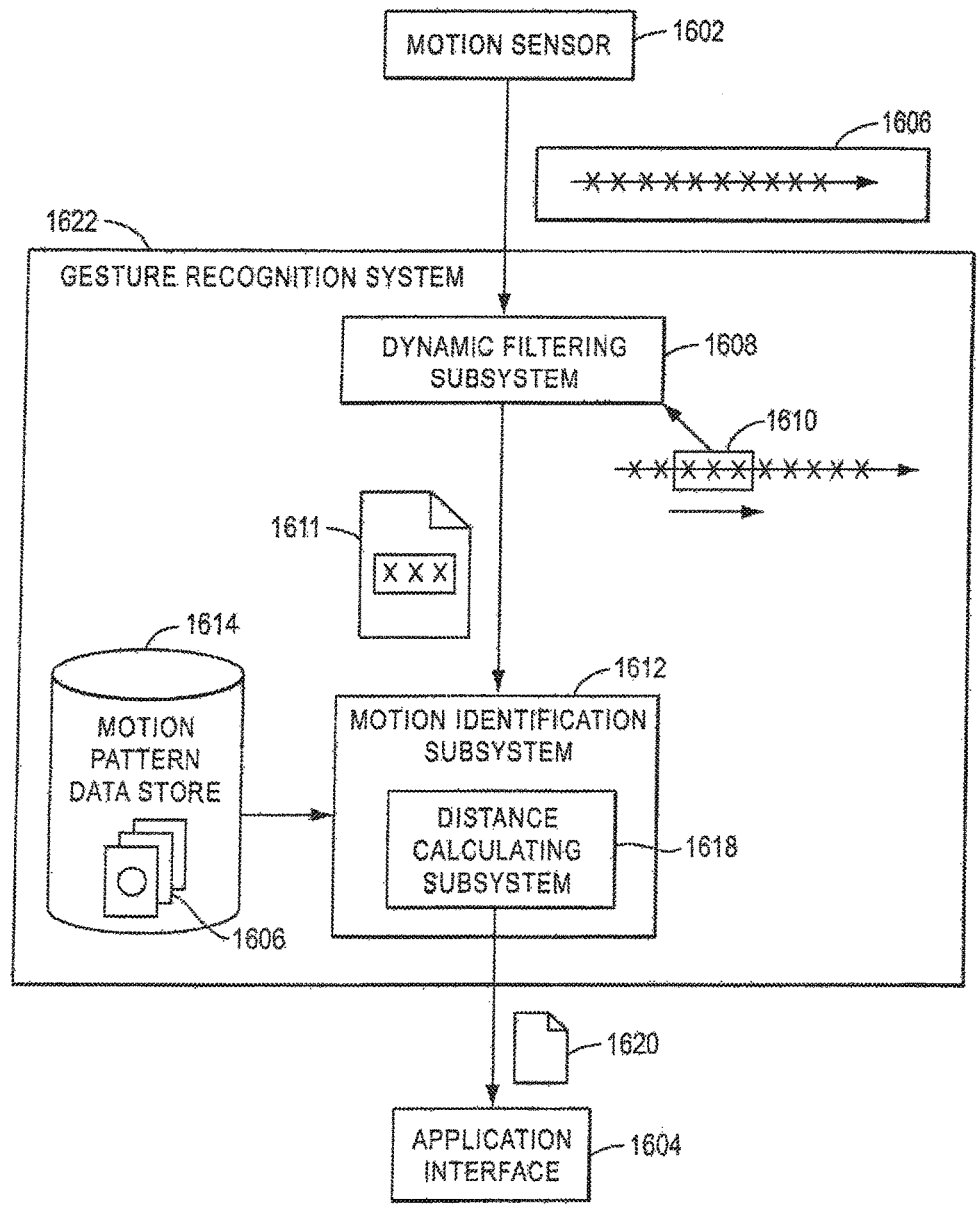
FIG. 20 is a block diagram illustrating an exemplary system configured to perform operations of gesture creation and recognition.

FIG. 20 is a diagram illustrating exemplary clustering techniques of motion pattern classification. The diagram is shown in a two-dimensional space for illustrative purposes. In some implementations, the clustering techniques are performed in a three-dimensional space. Clustering subsystem 1006 (as described in reference to FIG. 14) can apply quality threshold techniques to create exemplary clusters of motions C1 and C2.

Clustering subsystem 1006 can analyze D-path matrix 1008 as described above in references to FIG. 14 and FIG. 16 and the motion features 1004 as described above in reference to FIG. 14. Clustering subsystem 1006 can identify a first class of motion features 1004 having a first label (e.g., those labeled as "positive") and a second class of motion features 1004 having a second label (e.g., those labeled as "negative"). From D-path matrix 1008, clustering subsystem 1006 can identify a specified distance (e.g., a minimum distance) between a first class motion feature (e.g., "positive" motion feature 1302) and a second class motion feature (e.g., "negative" motion feature 1304). The system can designate this distance as Dmin(EL1, EL2), where L1 is a first label, and L2 is a second label. The specified distance can include the minimum distance adjusted by a factor (e.g., a multiplier k) for controlling the size of each cluster. Clustering subsystem 1006 can designate the specified distance (e.g., kDmin(EL1, EL2)) as a quality threshold.

Clustering subsystem 1006 can select a first class motion feature E1 (e.g., "positive" motion feature 1302) to add to a first cluster C1. Clustering subsystem 1006 can then identify a second first class motion feature E2 whose distance to E1 is less than the quality threshold, and add E2 to the first cluster C1. Clustering subsystem 1006 can iteratively add first class motion features to the first cluster C1 until all first class motion features whose distances to E1 are each less than the quality threshold has been added to the first cluster C1.

Clustering subsystem 1006 can remove the first class motion features in C1 from further clustering operations and select another first class motion feature E2 (e.g., "positive" motion feature 1306) to add to a second cluster C2. Clustering subsystem 1006 can iteratively add first class motion features to the second cluster C2 until all first class motion features whose distances to E2 are each less than the quality threshold have been added to the second cluster C2. Clustering subsystem 1006 can repeat the operations to create clusters C3, C4, and so on until all first class motion features are clustered.

Clustering subsystem 1006 can generate a representative series of motion vectors for each cluster. In some implementations, clustering subsystem 1006 can designate as the representative series of motion vectors a motion feature (e.g., motion feature 1308 illustrated in FIG. 17) that is closest to other motion samples in a cluster (e.g., cluster C1). Clustering subsystem 1006 can designate the representative series of motion vectors as a raw motion pattern (e.g., one of raw motion patterns 1012 as described above in reference to FIG. 14). To identify an example that is closest to other samples, clustering subsystem 1006 can calculate distances between pairs of motion features in cluster C1, and determine a reference distance for each motion sample. The reference distance for a motion sample can be maximum distance between the motion sample and another motion sample in the cluster. Clustering subsystem 1006 can identify motion feature 1308 in cluster C1 that has the minimum reference distance and designate motion feature 1308 as the motion pattern for cluster C1.

Figure 18A:
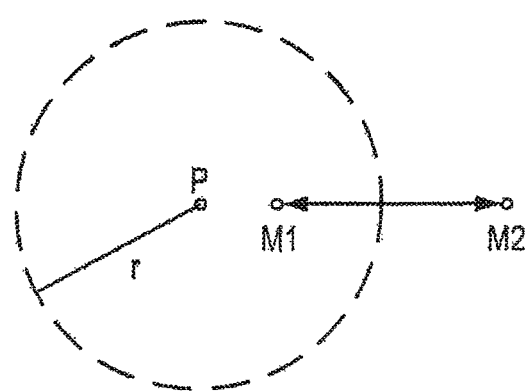
FIG. 18($a$)-($c$) are diagrams illustrating exemplary techniques of determining a sphere of influence of a motion pattern.
Figure 18B:
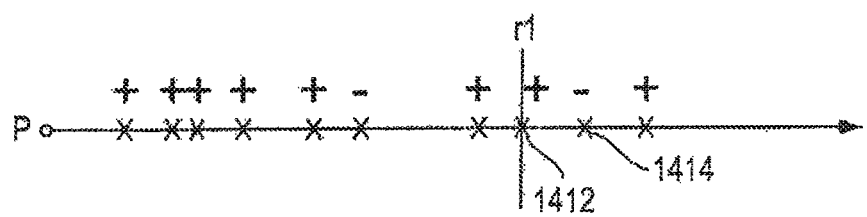
Figure 18C:
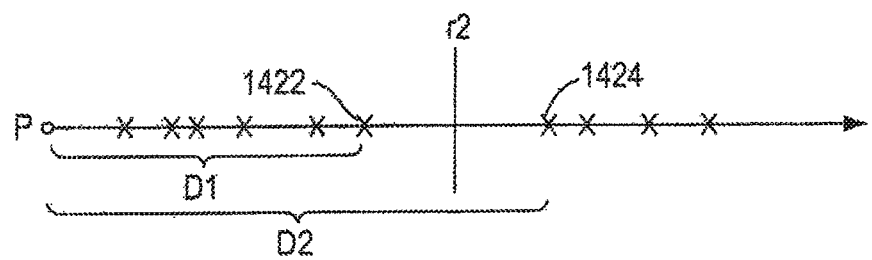

FIGS. 18(*a*)-(*c*) are diagrams illustrating techniques for determining a sphere of influence of a motion pattern. FIG. 18(*a*) is an illustration of a SOI of a motion pattern P. The SOI has a radius r that can be used as a threshold. If a distance between a motion M1 and the motion pattern P does not exceed r, a gesture recognition system can determine that motion M1 matches motion P. The match can indicate that a gesture is recognized. If a distance between a motion M2 and the motion pattern P exceeds r, the gesture recognition system can determine that motion M2 does not match motion P.

FIG. 18B is an illustration of exemplary operations of SOI calculating subsystem 1014 (as described above in reference to FIG. 14) for calculating a radius r1 of a SOI of a raw motion pattern P based on classification. SOI calculating subsystem 1014 can rank motion features 1004 based on a distance between each of the motion features 1004 and a raw motion pattern P. SOI calculating subsystem 1014 can determine the radius r1 based on a classification threshold and a classification ratio, which will be described below.

The radius r1 can be associated with a classification ratio. The classification ratio can be a ratio between a number of first class motion samples (e.g., "positive" motion samples) within distance r1 from the raw motion pattern P and a total number of motion samples (e.g., both "positive" and "negative" motion samples) within distance r1 from the motion pattern P.

SOI calculating subsystem 1014 can specify a classification threshold and determine the radius r1 based on the classification threshold. SOI calculating subsystem 1014 can increase the radius r1 from an initial value (e.g., 0) incrementally according to the incremental distances between the ordered motion samples and the raw motion pattern P. If, after r1 reaches a value (e.g., a distance between motion feature 1012 and raw motion pattern P), a further increment of r1 to a next closest distance between a motion feature (e.g., motion feature 1414) and raw motion pattern P will cause the classification ratio to be less than the classification threshold, SOI calculating subsystem 1014 can designate the value of r1 as a classification radius of the ROI.

FIG. 18(*c*) is an illustration of exemplary operations of SOI calculating subsystem 1014 (as described above in reference to FIG. 14) for calculating a density radius r2 of a SOI of raw motion pattern P based on variance. SOI calculating subsystem 1014 can rank motion features 1004 based on a distance between each of the motion features 1004 and a motion pattern P. SOI calculating subsystem 1014 can determine the density radius r2 based on a variance threshold and a variance value, which will be described in further detail below.

The density radius r2 can be associated with a variance value. The variance value can indicate a variance of distance between each of the motion samples that are within distance r2 of the raw motion pattern P. SOI calculating subsystem 1014 can specify a variance threshold and determine the density radius r2 based on the variance threshold. SOI calculating subsystem 1014 can increase a measuring distance from an initial value (e.g., 0) incrementally according to the incremental distances between the ordered motion samples and the motion pattern P. If, after the measuring distance reaches a value (e.g., a distance between motion feature 1422 and raw motion pattern P), a further increment of measuring distance to a next closest distance between a motion feature (e.g., motion feature 1424) and the raw motion pattern P will cause the variance value to be greater than the variance threshold, SOI calculating subsystem 1014 can designate an average ((D1+D2)/2) of the distance D1 between motion feature 1422 and the motion pattern P and the distance D2 between motion feature 1424 and the motion pattern P as the density radius r2 of the SOI.

In some implementations, SOI calculating subsystem 1014 can select the smaller between the classification radius and the density radius of an SOI as the radius of the SOI. In some implementations, SOI calculating subsystem 1014 can designate a weighted average of the classification radius and the density radius of an SOI as the radius of the SOI.

Figure 19:
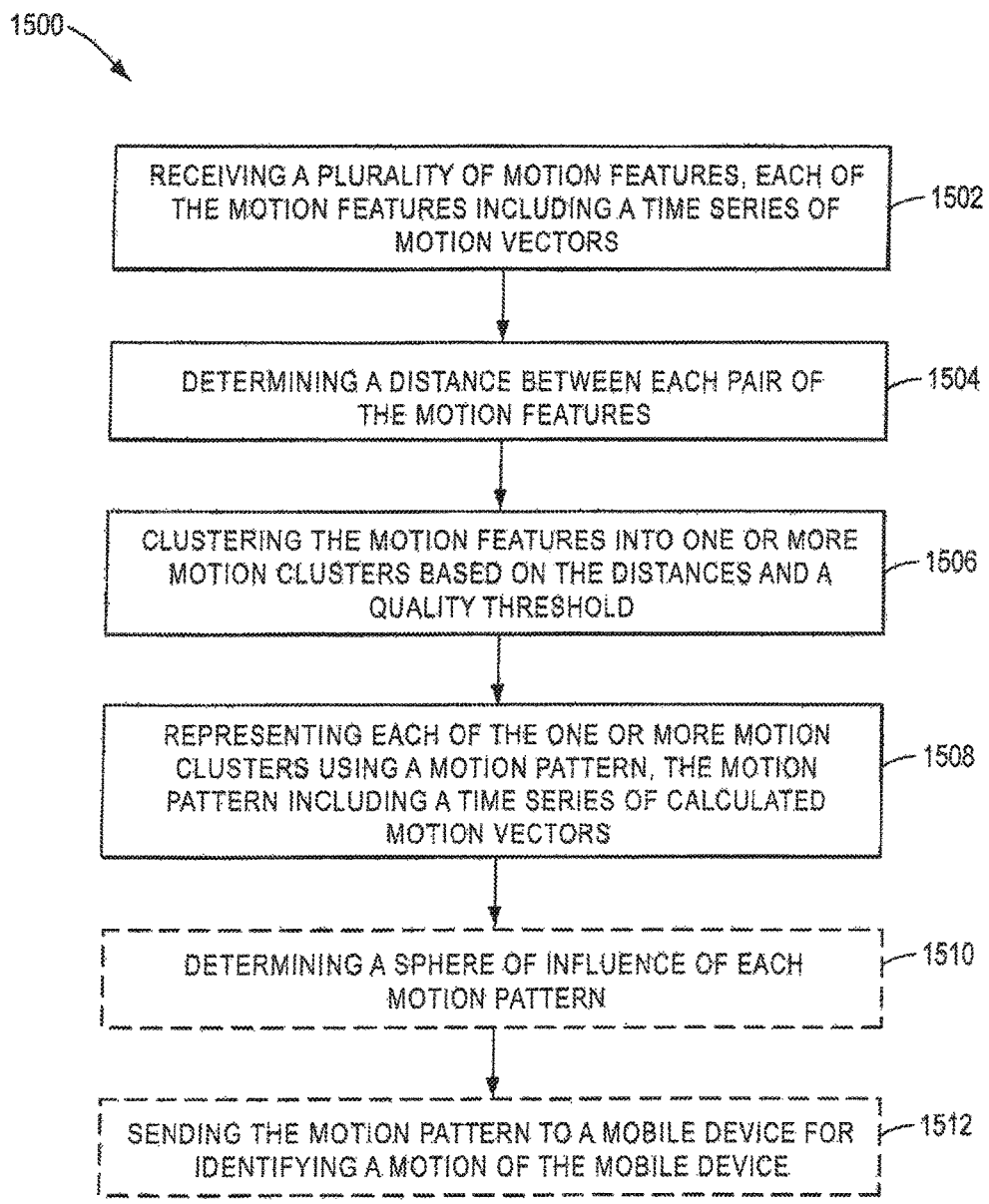
FIG. 19 is a flowchart illustrating an exemplary process of motion pattern classification.

FIG. 19 is a flowchart illustrating exemplary process 1500 of pattern-based gesture recognition. The process can be executed by a system including a motion/movement/gesture detection device.

The system can receive multiple motion patterns. Each of the motion patterns can include a time series of motion vectors. For clarity, the motion vectors in the motion patterns will be referred to as motion pattern vectors. Each of the motion patterns can be associated with an SOI. Each motion pattern vector can include a linear acceleration value, an angular rate value, or both, on each of multiple motion axes. In some implementations, each of the motion pattern vectors can include an angular rate value on each of pitch, roll, and yaw. Each of the motion patterns can include gyroscope data determined based on a gyroscope device of the motion/movement/gesture detection device, magnetometer data determined based on a magnetometer device of the motion/movement/gesture detection device, or gravimeter data from a gravimeter device of the motion/movement/gesture detection device. Each motion pattern vector can be associated with a motion pattern time. In some implementations, the motion pattern time is implied in the ordering of the motion pattern vectors.

The system can receive multiple motion sensor readings from a motion sensor built into or coupled with the system. The motion sensor readings can include multiple motion vectors, which will be referred to as motion reading vectors. Each motion reading vector can correspond to a timestamp, which can indicate a motion reading time. In some implementations, each motion reading vector can include an acceleration value on each of the axes as measured by the motion sensor, which includes an accelerometer. In some implementations, each motion reading vector can include a transformed acceleration value that is calculated based on one or more acceleration values as measured by the motion sensor. The transformation can include high-pass filtering, time-dimension compression, or other manipulations of the acceleration values. In some implementations, the motion reading time is implied in the ordering of the motion reading vectors.

The system can select, using a time window and from the motion sensor readings, a time series of motion reading vectors. The time window can include a specified time period and a beginning time. In some implementations, transforming the acceleration values can occur after the selection stage. The system can transform the selected time series of acceleration values.

The system can calculate a distance between the selected time series of motion reading vectors and each of the motion patterns. This distance will be referred to as a motion deviation distance. Calculating the motion deviation distance can include applying dynamic time warping based on the motion pattern times of the motion pattern and the motion reading times of the series of motion reading vectors. Calculating the motion deviation distance can include calculating a vector distance between (1) each motion reading vector in the selected time series of motion reading vectors, and (2) each motion pattern vector in the motion pattern. The system can then calculate the motion deviation distance based on each vector distance. Calculating the motion deviation distance based on each vector distance can include identifying a series of vector distances ordered according to the motion pattern times and the motion reading times (e.g., the identified shortest path described above with respect to FIG. 9B). The system can designate a measurement of the vector distances in the identified series as the motion deviation distance. The measurement can include at least one of a sum or a weighted sum of the vector distances in the identified series. The vector distances can include at least one of a Euclidean distance between a motion pattern vector and a motion reading vector or a Manhattan distance between a motion pattern vector and a motion reading vector.

The system can determine whether a match is found. Determining whether a match is found can include determining whether, according to a calculated motion deviation distance, the selected time series of motion reading vectors is located within the sphere of influence of a motion pattern (e.g., motion pattern P).

If a match is not found, the system slides the time window along a time dimension on the received motion sensor readings. Sliding the time window can include increasing the beginning time of the time window. The system can then perform operations 1504, 1506, 1508, and 1510 until a match is found, or until all the motion patterns have been compared against and no match is found.

If a match is found, a gesture is recognized. The system can designate the motion pattern P as a matching motion pattern. The system can perform (1014) a specified task based on the matching motion pattern. Performing the specific task can include at least one of: changing a configuration of a motion/movement/gesture detection device; providing a user interface for display, or removing a user interface from display on a motion/movement/gesture detection device; launching or terminating an application program on a motion/movement/gesture detection device; or initiating or terminating a communication between a motion/movement/gesture detection device and another device. Changing the configuration of the motion/movement/gesture detection device includes changing an input mode of the motion/movement/gesture detection device between a touch screen input mode and a voice input mode.

In some implementations, before performing the specified task, the system can apply confirmation operations to detect and eliminate false positives in matching. The confirmation operations can include examining a touch-screen input device or a proximity sensor of the motion/movement/gesture detection device. For example, if the gesture is "picking up the device," the device can confirm the gesture by examining proximity sensor readings to determine that the device is proximity to an object (e.g., a human face) at the end of the gesture.

FIG. 20 is a block diagram illustrating an exemplary system configured to perform operations of gesture recognition. The system can include motion sensor 1602, gesture recognition system, and application interface 1604. The system can be implemented on a mobile device.

Motion sensor 1602 can be a component of a mobile device that is configured to measure accelerations in multiple axes and produces motion sensor readings 1606 based on the measured accelerations. Motion sensor readings 1606 can include a time series of acceleration vectors.

Gesture recognition system can be configured to receive and process motion sensor readings 1606. Gesture recognition system 122 can include dynamic filtering subsystem 1608. Dynamic filtering subsystem 1608 is a component of the gesture recognition system that is configured to perform dynamic filtering on motion sensor readings 1606 in a manner similar to the operations of dynamic filtering subsystem. In addition, dynamic filtering subsystem 1608 can be configured to select a portion of motion sensor readings 1606 for further processing. The selection can be based on sliding time window 1610. Motion sensor 1602 can generate motion sensor readings 1606 continuously. Dynamic filtering subsystem 1608 can use the sliding time window 1610 to select segments of the continuous data, and generate normalized motion sensor readings 1611 based on the selected segments.

Gesture recognition system can include motion identification subsystem 1612. Motion identification subsystem 1612 is a component of gesture recognition system 1622 that is configured to determine whether normalized motion sensor readings 1611 match a known motion pattern. Motion identification subsystem 1612 can receive normalized motion sensor readings 1611, and access motion pattern data store 1614. Motion pattern data store 1614 includes a storage device that stores one or more motion patterns 106. Motion identification subsystem 1612 can compare the received normalized motion sensor readings 1611 with each of the stored motion patterns, and recognize a gesture based on the comparison.

Motion identification subsystem 1612 can include distance calculating subsystem 1618. Distance calculating subsystem 1618 is a component of motion identification subsystem 1612 that is configured to calculate a distance between normalized motion sensor readings 1611 and each of the motion patterns 106. If the distance between normalized motion sensor readings 1611 and a motion pattern P is within the radius of an SOI of the motion pattern P, motion identification subsystem 1612 can identify a match and recognize a gesture 1620. Further details of the operations of distance calculating subsystem 1618 will be described below in reference to FIGS. 21(*a*) and (*b*).

Motion identification subsystem 1612 can send the recognized gesture 1620 to application interface 1604. An application program or a system function of the mobile device can receive the gesture from application interface 1604 and perform a task (e.g., turning off a touch-input screen) in response.

Figure 21A:
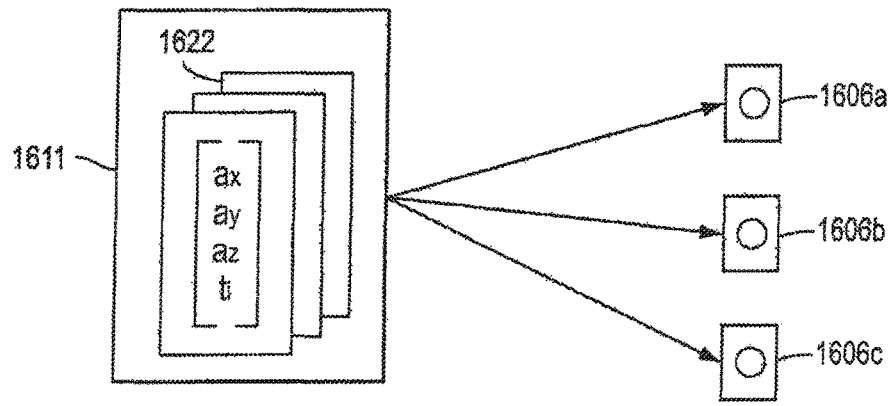
FIG. 21($a$)-($b$) are diagrams illustrating exemplary techniques of matching motion sensor readings to a motion pattern.
Figure 21B:
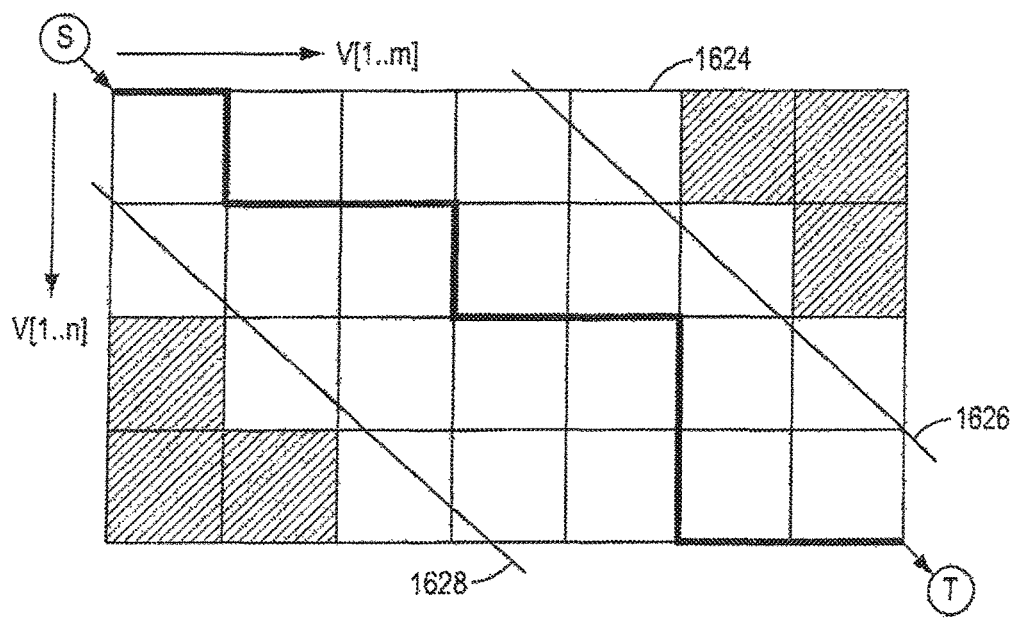

FIGS. 21(*a*) and (*b*) are diagrams illustrating techniques of matching motion sensor readings to a motion pattern. FIG. 21(*a*) illustrates an example data structure of normalized motion sensor readings 1611. Normalized motion sensor readings 1611 can include a series of motion vectors 1622. Each motion vector 1622 can include acceleration readings ax, ay, and az, for axes X, Y, and Z, respectively. In some implementations, each motion vector 1622 can be associated with a time ti, the time defining the time series. In some implementations, the normalized motion sensor readings 1611 designate the time dimension of the time series using an order of the motion vectors 1622. In these implementations, the time can be omitted.

Distance calculating subsystem 1618 (as described above in reference to FIG. 20) compares normalized motion sensor readings 1611 to each of the motion patterns 1606 *a*, 1606 *b*, and 1606 *c*. The operations of comparison are described in further detail below in reference to FIG. 21(*b*). A match between normalized motion sensor readings 1611 and any of the motion patterns 1606 *a*, 1606 *b*, and 1606 *c* can result in a recognition of a gesture.

FIG. 21(*b*) is a diagram illustrating distance calculating operations of distance calculating subsystem 1618. To perform the comparison, distance calculating subsystem 1618 can calculate a distance between the normalized motion sensor readings 1611, which can include readings R1, Rn, and a motion pattern (e.g., motion pattern 1606 *a*, 1606 *b*, or 1606 *c*), which can include motion vectors V1 . . . Vm. Distance calculating subsystem 1618 can calculate the distance using directed graph 1624 in operations similar to those described in reference to FIG. 20.

In some implementations, distance calculating subsystem 1618 can perform optimization on the comparing. Distance calculating subsystem 1618 can perform the optimization by applying comparison thresholds 1626 and 1628. Comparison thresholds 1626 and 1628 can define a series of vector pairs between which distance calculating subsystem 1618 performs a distance calculation. By applying comparison thresholds 1626 and 1628, distance calculating subsystem 1618 can exclude those calculations that are unlikely to yield a match. For example, a distance calculation between the first motion vector R1 in the normalized motion sensor readings 1611 and a last motion vector Vm of a motion pattern is unlikely to lead to a match, and therefore can be omitted from the calculations.

Distance calculating subsystem 1618 can determine a shortest path (e.g., the path marked in bold lines) in directed graph 1624, and designate the cost of the shortest path as a distance between normalized motion sensor readings 1611 and a motion pattern. Distance calculating subsystem 1618 can compare the distance with a SOI associated with the motion pattern. If the distance is less than the SOI, distance calculating subsystem 1618 can identify a match.

Figure 22:
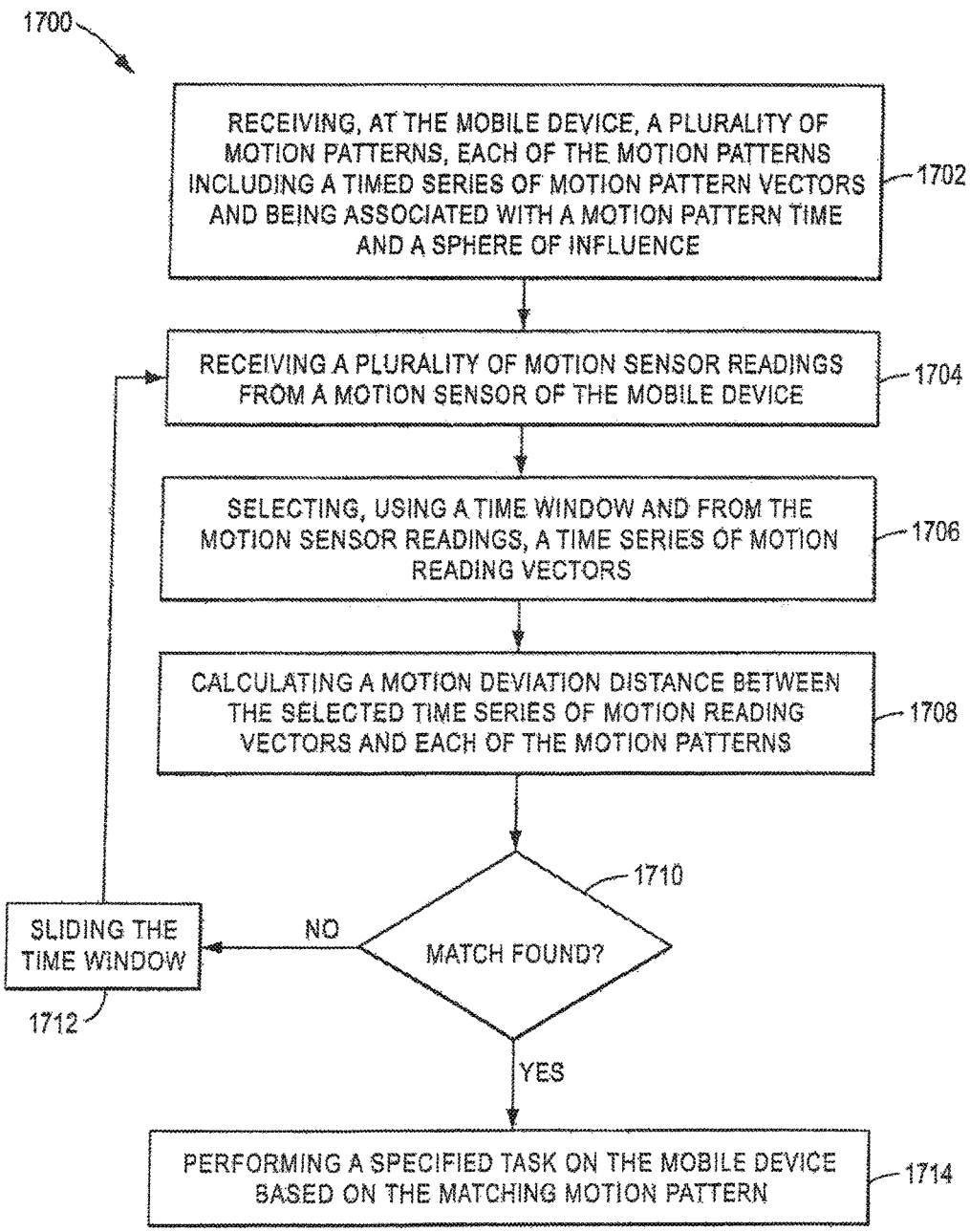
FIG. 22 is a flowchart illustrating an exemplary process of pattern-based gesture creation and recognition.

FIG. 22 is a flowchart illustrating exemplary process 1700 of pattern-based gesture recognition. The process can be executed by a system including a mobile device.

The system can receive (1702) multiple motion patterns. Each of the motion patterns can include a time series of motion vectors. For clarity, the motion vectors in the motion patterns will be referred to as motion pattern vectors. Each of the motion patterns can be associated with an SOI. Each motion pattern vector can include a linear acceleration value, an angular rate value, or both, on each of multiple motion axes. In some implementations, each of the motion pattern vectors can include an angular rate value on each of pitch, roll, and yaw. Each of the motion patterns can include gyroscope data determined based on a gyroscope device of the mobile device, magnetometer data determined based on a magnetometer device of the mobile device, or gravimeter data from a gravimeter device of the mobile device. Each motion pattern vector can be associated with a motion pattern time. In some implementations, the motion pattern time is implied in the ordering of the motion pattern vectors.

The system can receive (1704) multiple motion sensor readings from a motion sensor built into or coupled with the system. The motion sensor readings can include multiple motion vectors, which will be referred to as motion reading vectors. Each motion reading vector can correspond to a timestamp, which can indicate a motion reading time. In some implementations, each motion reading vector can include an acceleration value on each of the axes as measured by the motion sensor, which includes an accelerometer. In some implementations, each motion reading vector can include a transformed acceleration value that is calculated based on one or more acceleration values as measured by the motion sensor. The transformation can include high-pass filtering, time-dimension compression, or other manipulations of the acceleration values. In some implementations, the motion reading time is implied in the ordering of the motion reading vectors.

The system can select (1706), using a time window and from the motion sensor readings, a time series of motion reading vectors. The time window can include a specified time period and a beginning time. In some implementations, transforming the acceleration values can occur after the selection stage. The system can transform the selected time series of acceleration values.

The system can calculate (1708) a distance between the selected time series of motion reading vectors and each of the motion patterns. This distance will be referred to as a motion deviation distance. Calculating the motion deviation distance can include applying dynamic time warping based on the motion pattern times of the motion pattern and the motion reading times of the series of motion reading vectors. Calculating the motion deviation distance can include calculating a vector distance between (1) each motion reading vector in the selected time series of motion reading vectors, and (2) each motion pattern vector in the motion pattern. The system can then calculate the motion deviation distance based on each vector distance. Calculating the motion deviation distance based on each vector distance can include identifying a series of vector distances ordered according to the motion pattern times and the motion reading times (e.g., the identified shortest path described above with respect to FIG. 9B). The system can designate a measurement of the vector distances in the identified series as the motion deviation distance. The measurement can include at least one of a sum or a weighted sum of the vector distances in the identified series. The vector distances can include at least one of a Euclidean distance between a motion pattern vector and a motion reading vector or a Manhattan distance between a motion pattern vector and a motion reading vector.

The system can determine (1710) whether a match is found. Determining whether a match is found can include determining whether, according to a calculated motion deviation distance, the selected time series of motion reading vectors is located within the sphere of influence of a motion pattern (e.g., motion pattern P).

If a match is not found, the system slides (1712) the time window along a time dimension on the received motion sensor readings. Sliding the time window can include increasing the beginning time of the time window. The system can then perform operations 1704, 1706, 1708, and 1710 until a match is found, or until all the motion patterns have been compared against and no match is found.

If a match is found, a gesture is recognized. The system can designate the motion pattern P as a matching motion pattern. The system can perform (1714) a specified task based on the matching motion pattern. Performing the specific task can include at least one of: changing a configuration of a mobile device; providing a user interface for display, or removing a user interface from display on a mobile device; launching or terminating an application program on a mobile device; or initiating or terminating a communication between a mobile device and another device. Changing the configuration of the mobile device includes changing an input mode of the mobile device between a touch screen input mode and a voice input mode.

In some implementations, before performing the specified task, the system can apply confirmation operations to detect and eliminate false positives in matching. The confirmation operations can include examining a touch-screen input device or a proximity sensor of the mobile device. For example, if the gesture is "picking up the device," the device can confirm the gesture by examining proximity sensor readings to determine that the device is proximity to an object (e.g., a human face) at the end of the gesture.

Figure 23:
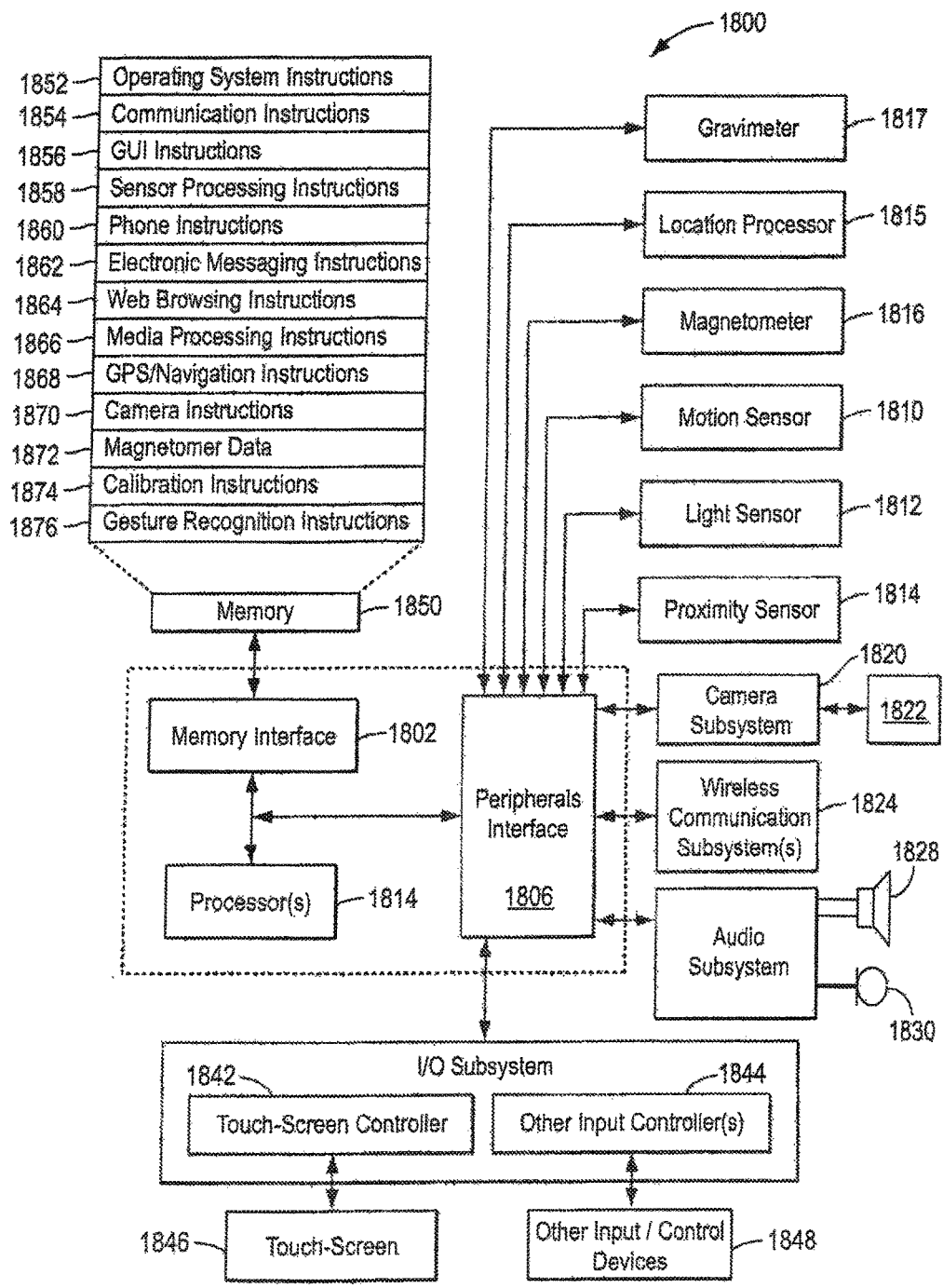
FIG. 23 is a block diagram illustrating exemplary device architecture of a monitoring system implementing the features and operations of pattern-based gesture creation and recognition.

FIG. 23 is a block diagram illustrating exemplary device architecture 1800 of a device implementing the features and operations of pattern-based gesture recognition. The device can include memory interface 1802, one or more data processors, image processors and/or processors 1804, and peripherals interface 1806. Memory interface 1802, one or more processors 1804 and/or peripherals interface 1806 can be separate components or can be integrated in one or more integrated circuits. Processors 1804 can include one or more application processors (APs) and one or more baseband processors (BPs). The application processors and baseband processors can be integrated in one single process chip. The various components in a motion/movement/gesture detection device, for example, can be coupled by one or more communication buses or signal lines.

Sensors, devices, and subsystems can be coupled to peripherals interface 1806 to facilitate multiple functionalities. For example, motion sensor 1810, light sensor 1812, and proximity sensor 1814 can be coupled to peripherals interface 1806 to facilitate orientation, lighting, and proximity functions of the motion/movement/gesture detection device. Location processor 1815 (e.g., GPS receiver) can be connected to peripherals interface 1806 to provide geo-positioning. Electronic magnetometer 1816 (e.g., an integrated circuit chip) can also be connected to peripherals interface 1806 to provide data that can be used to determine the direction of magnetic North. Thus, electronic magnetometer 1816 can be used as an electronic compass. Motion sensor 1810 can include one or more accelerometers configured to determine change of speed and direction of movement of the motion/movement/gesture detection device. Gravimeter 1817 can include one or more devices connected to peripherals interface 1806 and configured to measure a local gravitational field of Earth.

Camera subsystem 1820 and an optical sensor 1822, e.g., a charged coupled device (CCD) or a complementary metal-oxide semiconductor (CMOS) optical sensor, can be utilized to facilitate camera functions, such as recording photographs and video clips.

Communication functions can be facilitated through one or more wireless communication subsystems 1824, which can include radio frequency receivers and transmitters and/or optical (e.g., infrared) receivers and transmitters. The specific design and implementation of the communication subsystem 1824 can depend on the communication network (s) over which a motion/movement/gesture detection device is intended to operate. For example, a motion/movement/gesture detection device can include communication subsystems 1824 designed to operate over a CDMA system, a WiFi™ or WiMax™ network, and a Bluetooth™ network. In particular, the wireless communication subsystems 1824 can include hosting protocols such that the motion/movement/gesture detection device can be configured as a base station for other wireless devices.

Audio subsystem 1826 can be coupled to a speaker 1828 and a microphone 1830 to facilitate voice-enabled functions, ASR, such as voice recognition, voice replication, digital recording, and telephony functions I/O subsystem 1840 can include touch screen controller 1842 and/or other input controller(s) 1844. Touch-screen controller 1842 can be coupled to a touch screen 1846 or pad. Touch screen 1846 and touch screen controller 1842 can, for example, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with touch screen 1846.

Other input controller(s) 1844 can be coupled to other input/control devices 1848, such as one or more buttons, rocker switches, thumb-wheel, infrared port, USB port, and/or a pointer device such as a stylus. The one or more buttons (not shown) can include an up/down button for volume control of speaker 1828 and/or microphone 1830.

In one implementation, a pressing of the button for a first duration may disengage a lock of the touch screen 1846; and a pressing of the button for a second duration that is longer than the first duration may turn power to a motion/movement/gesture detection device on or off. The user may be able to customize a functionality of one or more of the buttons. The touch screen 1846 can, for example, also be used to implement virtual or soft buttons and/or a keyboard.

In some implementations, a motion/movement/gesture detection device can present recorded audio and/or video files, such as MP3, AAC, and MPEG files. In some implementations, a motion/movement/gesture detection device can include the functionality of an MP3 player, such as an iPod™. A motion/movement/gesture detection device may, therefore, include a pin connector that is compatible with the iPod. Other input/output and control devices can also be used.

Memory interface 1802 can be coupled to memory 1850. Memory 1850 can include high-speed random access memory and/or non-volatile memory, such as one or more magnetic disk storage devices, one or more optical storage devices, and/or flash memory (e.g., NAND, NOR). Memory 1850 can store operating system 1852, such as Darwin, RTXC, LINUX, UNIX, OS X, WINDOWS, or an embedded operating system such as VxWorks. Operating system 1852 may include instructions for handling basic system services and for performing hardware dependent tasks. In some implementations, operating system 1852 can include a kernel (e.g., UNIX kernel).

Memory 1850 may also store communication instructions 1854 to facilitate communicating with one or more additional devices, one or more computers and/or one or more servers. Memory 1850 may include graphical user interface instructions 1856 to facilitate graphic user interface processing; sensor processing instructions 1858 to facilitate sensor-related processing and functions; phone instructions 1860 to facilitate phone-related processes and functions; electronic messaging instructions 1862 to facilitate electronic-messaging related processes and functions; web browsing instructions 1864 to facilitate web browsing-related processes and functions; media processing instructions 1866 to facilitate media processing-related processes and functions; GPS/Navigation instructions 1868 to facilitate GPS and navigation-related processes and instructions; camera instructions 1870 to facilitate camera-related processes and functions; magnetometer data 1872 and calibration instructions 1874 to facilitate magnetometer calibration. The memory 1850 may also store other software instructions (not shown), such as security instructions, web video instructions to facilitate web video-related processes and functions, and/or web shopping instructions to facilitate web shopping-related processes and functions. In some implementations, the media processing instructions 1866 are divided into audio processing instructions and video processing instructions to facilitate audio processing-related processes and functions and video processing-related processes and functions, respectively. An activation record and International Mobile Equipment Identity (IMEI) or similar hardware identifier can also be stored in memory 1850. Memory 1850 can include gesture recognition instructions 1876. Gesture recognition instructions 1876 can be a computer program product that is configured to cause the motion/movement/gesture detection device to recognize one or more gestures using motion patterns, as described in reference to FIGS. 13-22.

Each of the above identified instructions and applications can correspond to a set of instructions for performing one or more functions described above. These instructions need not be implemented as separate software programs, procedures, or modules. Memory 1850 can include additional instructions or fewer instructions. Furthermore, various functions of the motion/movement/gesture detection device may be implemented in hardware and/or in software, including in one or more signal processing and/or application specific integrated circuits.

Exemplary Operating Environment

Figure 24:
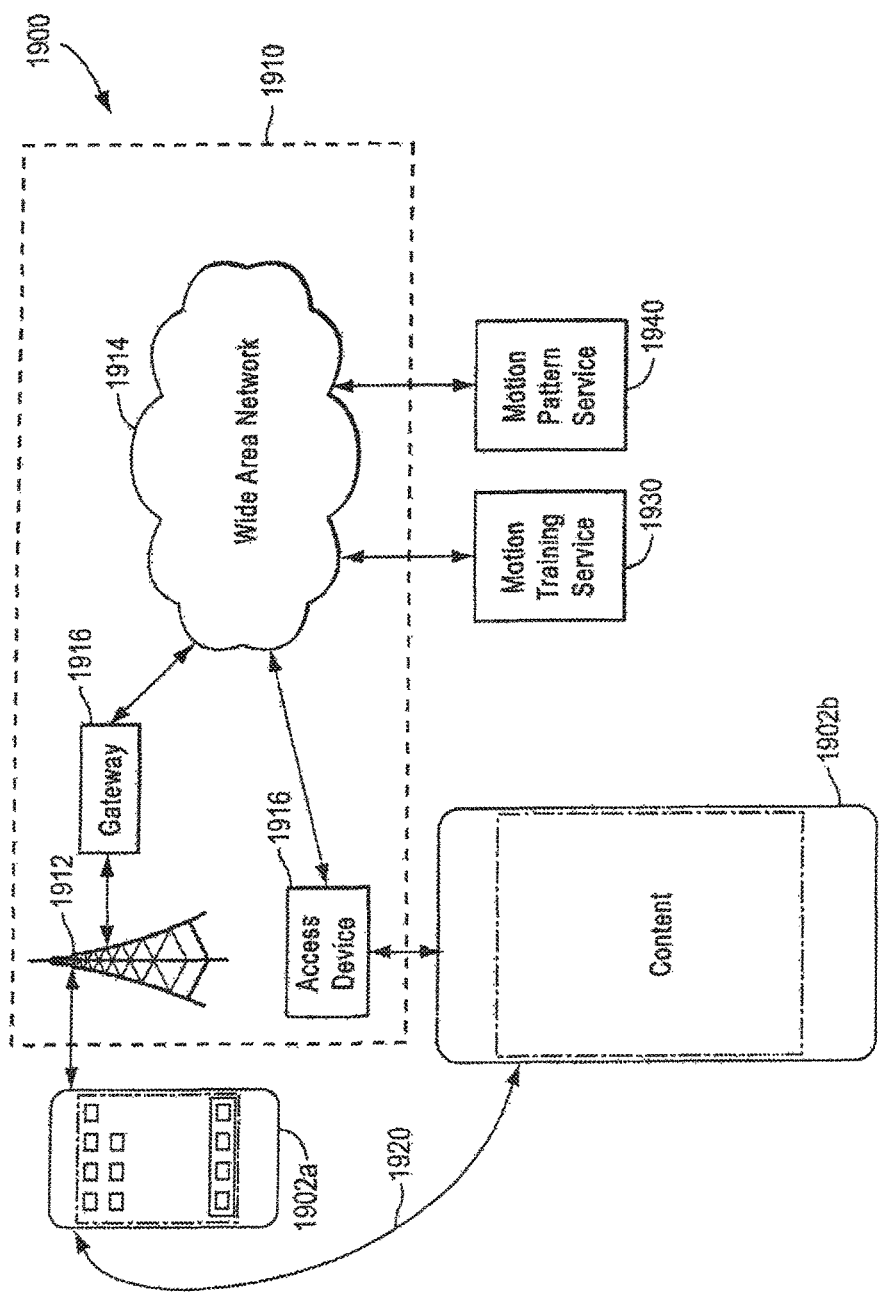
FIG. 24 is a block diagram of exemplary network operating environment for the monitoring systems implementing motion pattern classification and gesture creation and recognition techniques.

FIG. 24 is a block diagram of exemplary network operating environment 1900 for the motion/movement/gesture detection devices implementing motion pattern classification and gesture recognition techniques. Mobile devices 1902($a$) and 1902($b$) can, for example, communicate over one or more wired and/or wireless networks 1910 in data communication. For example, a wireless network 1912, e.g., a cellular network, can communicate with a wide area network (WAN) 1914, such as the Internet, by use of a gateway 1916. Likewise, an access device 1918, such as an 802.11g wireless access device, can provide communication access to the wide area network 1914.

In some implementations, both voice and data communications can be established over wireless network 1912 and the access device 1918. For example, motion/movement/gesture detection device 1902($a$) can place and receive phone calls (e.g., using voice over Internet Protocol (VoIP) protocols), send and receive e-mail messages (e.g., using Post Office Protocol 3 (POP3)), and retrieve electronic documents and/or streams, such as web pages, photographs, and videos, over wireless network 1912, gateway 1916, and wide area network 1914 (e.g., using Transmission Control Protocol/Internet Protocol (TCP/IP) or User Datagram Protocol (UDP)). Likewise, in some implementations, the motion/movement/gesture detection device 1902($b$) can place and receive phone calls, send and receive e-mail messages, and retrieve electronic documents over the access device 1918 and the wide area network 1914. In some implementations, motion/movement/gesture detection device 1902($a$) or 1902($b$) can be physically connected to the access device 1918 using one or more cables and the access device 1918 can be a personal computer. In this configuration, motion/movement/gesture detection device 1902($a$) or 1902($b$) can be referred to as a "tethered" device.

Mobile devices 1902($a$) and 1902($b$) can also establish communications by other means. For example, wireless motion/movement/gesture detection device 1902($a$) can communicate with other wireless devices, e.g., other motion/movement/gesture detection device s 1902($a$) or 1902($b$), cell phones, etc., over the wireless network 1912. Likewise, motion/movement/gesture detection device s 1902($a$) and 1902($b$) can establish peer-to-peer communications 1920, e.g., a personal area network, by use of one or more communication subsystems, such as the Bluetooth™ communication devices. Other communication protocols and topologies can also be implemented.

The motion/movement/gesture detection device 1902($a$) or 1902($b$) can, for example, communicate with one or more services 1930 and 1940 over the one or more wired and/or wireless networks. For example, one or more motion training services 1930 can be used to determine one or more motion patterns. Motion pattern service 1940 can provide the one or more one or more motion patterns to motion/movement/gesture detection device s 1902(*a*) and 1902(*b*) for recognizing gestures.

Mobile device 1902 (*a*) or 1902 (*b*) can also access other data and content over the one or more wired and/or wireless networks. For example, content publishers, such as news sites, Rally Simple Syndication (RSS) feeds, web sites, blogs, social networking sites, developer networks, etc., can be accessed by motion/movement/gesture detection device 1902(*a*) or 1902(*b*). Such access can be provided by invocation of a web browsing function or application (e.g., a browser) in response to a user touching, for example, a Web object.

Exemplary System Architecture

Figure 25:
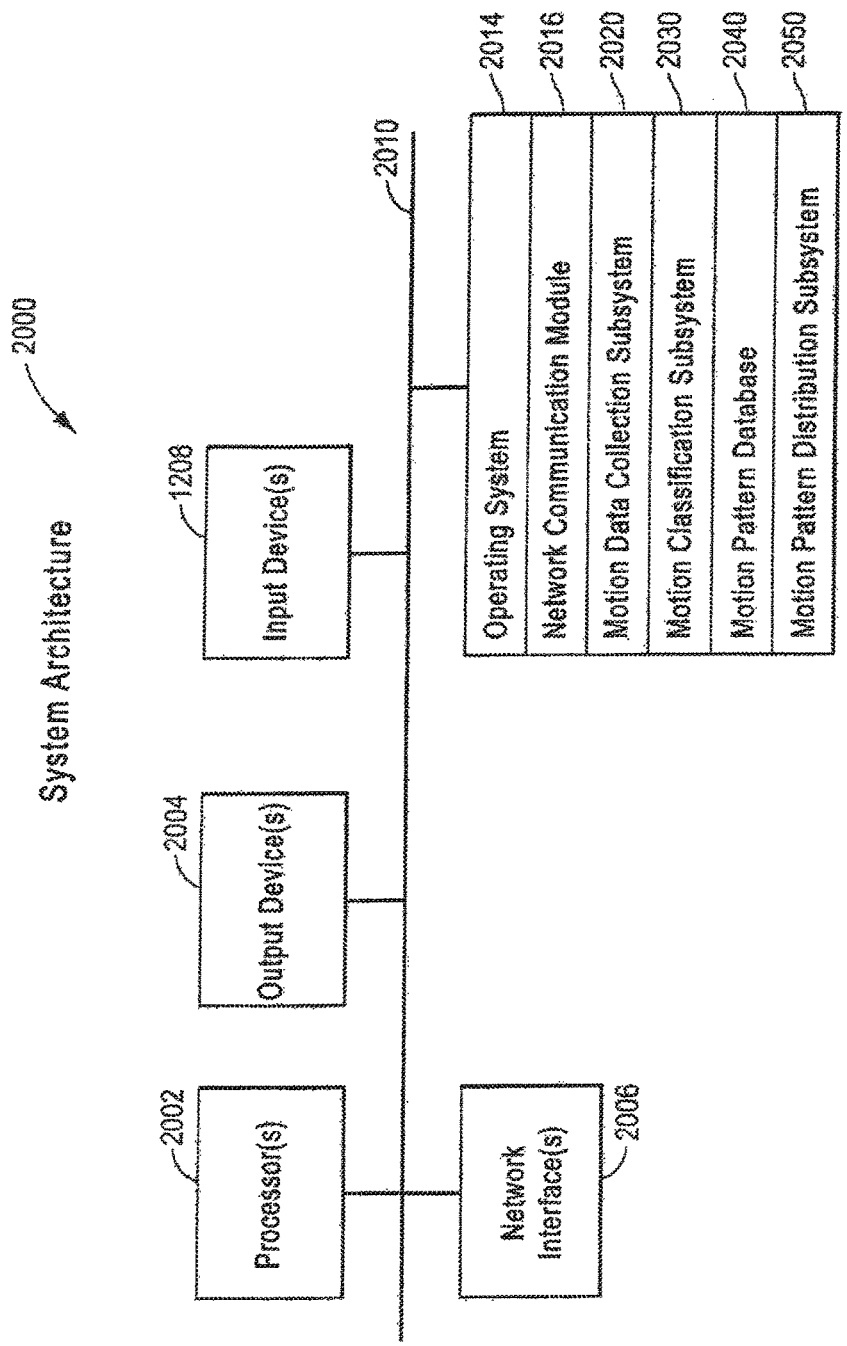
FIG. 25 is a block diagram of exemplary system architecture for implementing the features and operations of motion pattern classification and gesture creation and recognition.

FIG. 25 is a block diagram of exemplary system architecture for implementing the features and operations of motion pattern classification and gesture recognition. Other architectures are possible, including architectures with more or fewer components. In some implementations, architecture 2000 includes one or more processors 2002 (e.g., dual-core Intel® Xeon® Processors), one or more output devices 2004 (e.g., LCD), one or more network interfaces 2006, one or more input devices 2008 (e.g., mouse, keyboard, touch-sensitive display) and one or more computer-readable media 2012 (e.g., RAM, ROM, SDRAM, hard disk, optical disk, flash memory, etc.). These components can exchange communications and data over one or more communication channels 2010 (e.g., buses), which can utilize various hardware and software for facilitating the transfer of data and control signals between components.

The term "computer-readable medium" refers to any medium that participates in providing instructions to processor 2002 for execution, including without limitation, non-volatile media (e.g., optical or magnetic disks), volatile media (e.g., memory) and transmission media. Transmission media includes, without limitation, coaxial cables, copper wire and fiber optics.

Computer-readable medium 2012 can further include operating system 2014 (e.g., Mac OS® server, Windows® NT server), network communications module 2016, motion data collection subsystem 2020, motion classification subsystem 2030, motion pattern database 2040, and motion pattern distribution subsystem 2050. Motion data collection subsystem 2020 can be configured to receive motion samples from motion/movement/gesture detection device s. Motion classification subsystem 2030 can be configured to determine one or more motion patterns from the received motion samples. Motion pattern database 2040 can store the motion patterns. Motion pattern distribution subsystem 2050 can be configured to distribute the motion patterns to motion/movement/gesture detection device s. Operating system 2014 can be multi-user, multiprocessing, multitasking, multithreading, real time, etc. Operating system 2014 performs basic tasks, including but not limited to: recognizing input from and providing output to devices 2006, 2008; keeping track and managing files and directories on computer-readable media 2012 (e.g., memory or a storage device); controlling peripheral devices; and managing traffic on the one or more communication channels 2010. Network communications module 2016 includes various components for establishing and maintaining network connections (e.g., software for implementing communication protocols, such as TCP/IP, HTTP, etc.). Computer-readable medium 2012 can further include a database interface. The database interface can include interfaces to one or more databases on a file system. The databases can be organized under a hierarchical folder structure, the folders mapping to directories in the file system.

Architecture 2000 can be included in any device capable of hosting a database application program. Architecture 2000 can be implemented in a parallel processing or peer-to-peer infrastructure or on a single device with one or more processors. Software can include multiple software components or can be a single body of code.

The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., Objective-C, Java), including compiled or interpreted languages, and it can be deployed in any form, including as a stand-alone program or as a module, component, subroutine, a browser-based web application, or other unit suitable for use in a computing environment.

Suitable processors for the execution of a program of instructions include, by way of example, both general and special purpose microprocessors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network. The relationship of client and server arises by virtue of computer programs running on the respective computers and having a client-server relationship to each other.

Figure 26:
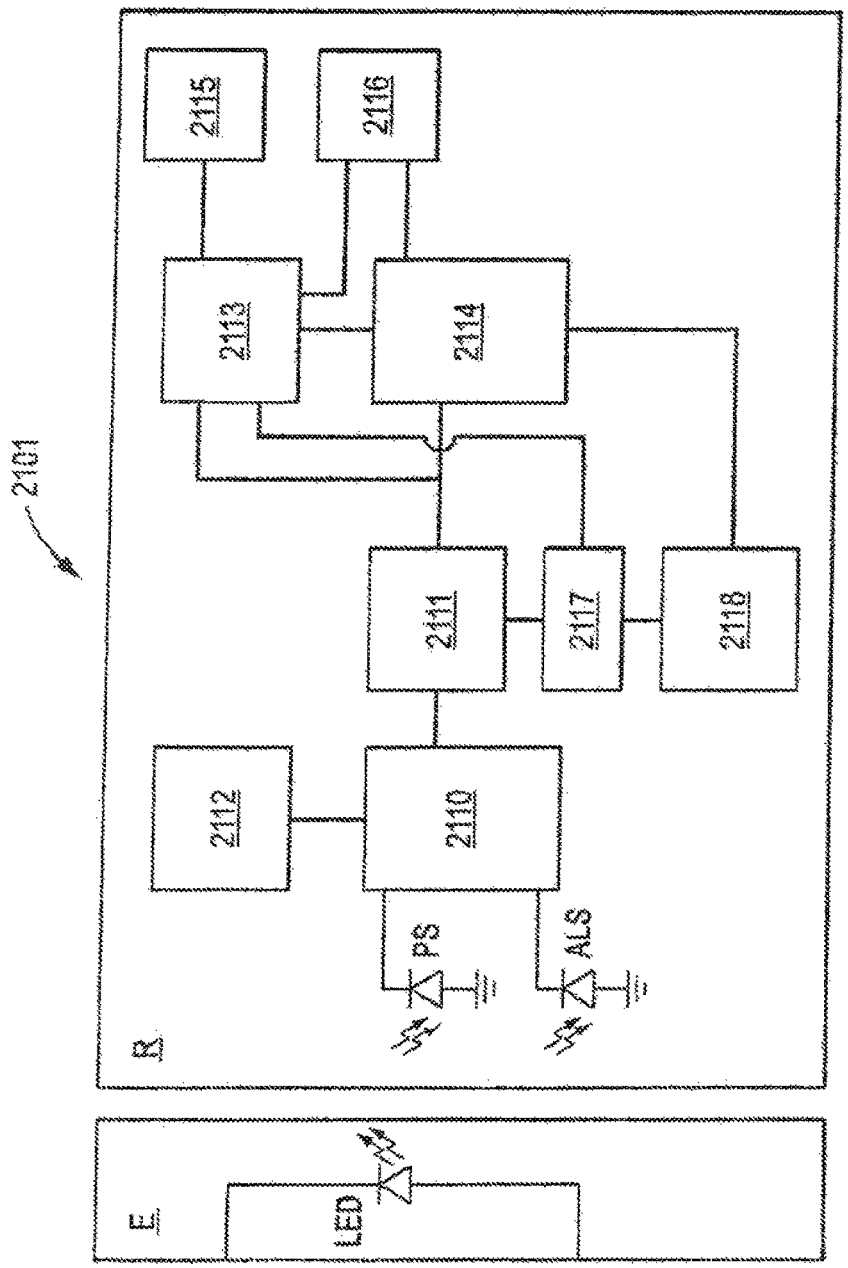
FIG. 26 illustrates a functional block diagram of a proximity sensor in an embodiment of the invention.

FIG. 26 illustrates a functional block diagram of a proximity sensor in one embodiment. As shown in FIG. 26, the proximity sensor 2101 includes a light emitter E and a light sensor R. The light emitter E includes a light-emitting diode LED used to emit lights. In one embodiment the light-emitting diode LED can be an infrared ray light-emitting diode (IR LED) used to emit infrared rays, but is not limited to this.

In one embodiment, the light sensor R can be an integrated circuit including at least one light sensing unit and a control circuit. In FIG. 26, the light sensor R includes a proximity sensing unit PS, an ambient light sensing unit ALS, a sensed light processing unit 2110, an analog/digital converter 2111, a temperature compensating unit 2112, a digital signal processing unit 2113, an inter-integrated circuit (I2C) interface 2114, a buffer 2115, a LED driver 2116, an oscillator 2117, and a reference value generator 2118. The proximity sensing unit PS and the ambient light sensing unit ALS are coupled to the sensed light processing unit 2110; the temperature compensating unit 2112 is coupled to the sensed light processing unit 2110; the analog/digital converter 2111 is coupled to the sensed light processing unit 2110, the digital signal processing unit 2113, the I2C interface 2114, and the oscillator 2117 respectively; the digital signal processing unit 2113 is coupled to the analog/digital converter 2111, the I2C interface 2114, the buffer 2115, the LED driver 2116, and the oscillator 2117 respectively; the I2C interface 2114 is coupled to the analog/digital converter 2111, the digital signal processing unit 2113, the LED driver 2116, and the reference value generator 2118 respectively; the oscillator 2117 is coupled to the analog/digital converter 2111, the digital signal processing unit 2113, and the reference value generator 2118 respectively; the reference value generator 2118 is coupled to the I2C interface 2114 and the oscillator 2117 respectively.

In this embodiment, the ambient light sensing unit ALS is used to sense an ambient light intensity around the proximity sensor 2111. The sensed light processing unit 2110 is used to process the light signal sensed by the ambient light sensing unit ALS and the proximity sensing unit PS and to perform temperature compensation according to the temperature compensating unit 2112. The LED driver 2116 is used to drive the light-emitting diode LED. The oscillator 2117 can be a quartz oscillator. The reference value generator 2118 is used to generate a default reference value.

The user can use the I2C interface 2114 to set digital signal processing parameters needed by the digital signal processing unit 2113. When the object is close to the light sensor R, the lights emitted from the light-emitting diode LED will be reflected to the proximity sensing unit PS by the object, and then the reflected lights will be processed by the sensed light processing unit 2110 and converted into digital light sensing signals by the analog/digital converter 2111. Then, the digital signal processing unit 2113 will determine whether the object is close to the light sensor R according to the digital light sensing signal.

If the result determined by the digital signal processing unit 2113 is yes, the buffer 2115 will output a proximity notification signal to inform the electronic apparatus including the proximity sensor 2111 that the object is close to the electronic apparatus, so that the electronic apparatus can immediately make corresponding action. For example, a smart phone with the proximity sensor 2111 will know that the face of the user is close to the smart phone according to the proximity notification signal; therefore, the smart phone will shut down the touch function of the touch monitor to avoid the touch monitor being carelessly touched by the face of the user.

However, the proximity sensor 2111 may have noise crosstalk problem due to poor packaging or mechanical design, which may cause the digital signal processing unit 2113 to make a misjudgment, and in turn causing the electronic apparatus, including the proximity sensor 2111, to malfunction. For example, if when the face of the user is not close to the smart phone, but the digital signal processing unit 2113 makes a misjudgment that an object is close to the smart phone, the smart phone will shut down the touch function of the touch monitor, and the user will not be able to user the touch function of the touch monitor. Therefore, the proximity sensor 2111 of this embodiment has three operation modes described as follows to solve the aforementioned malfunction problem.

Figure 27A:
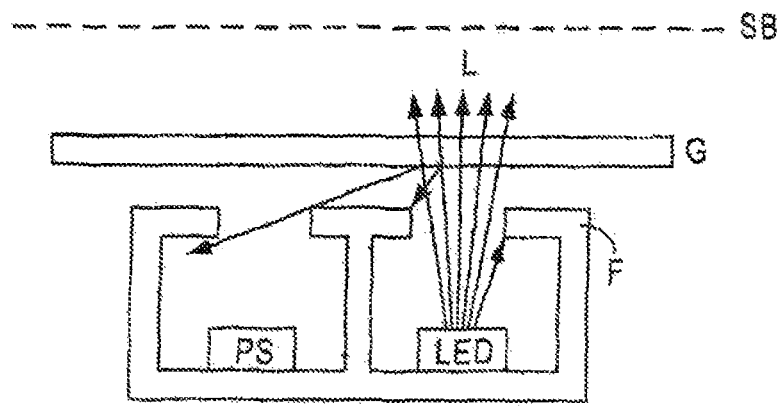
FIG. 27($a$) illustrates a schematic diagram of the proximity sensing unit sensing when the LED is active and emits lights under the condition that no object is close by to the proximity sensor of the electronic apparatus.
Figure 27B:
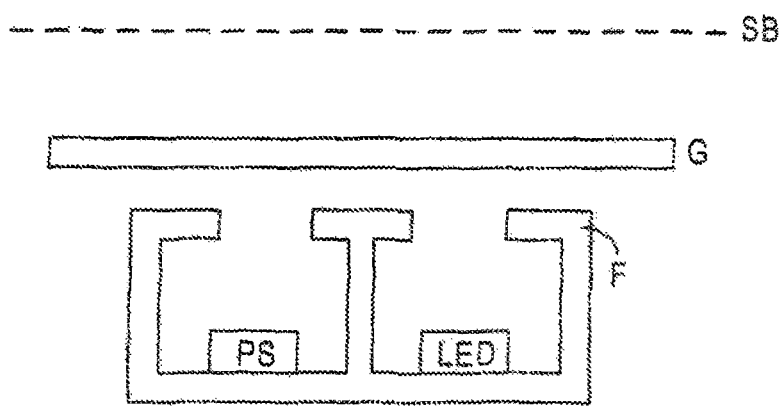
Figure 27C:
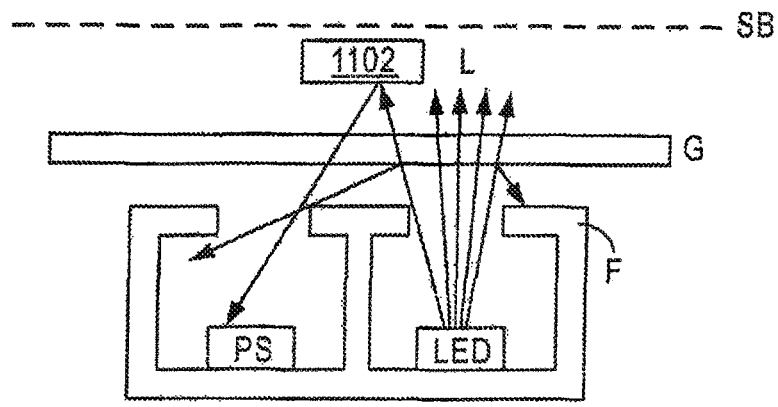
Figure 27D:
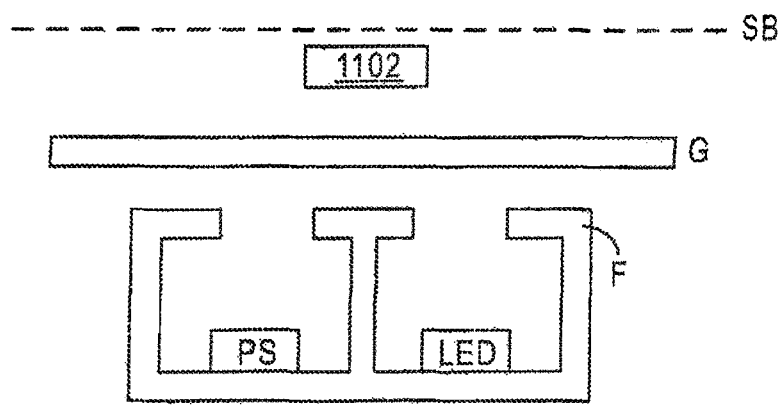
Figure 27E:
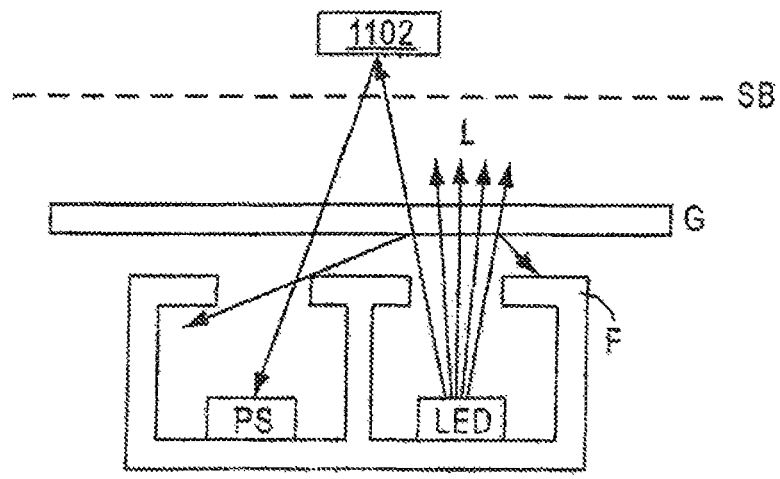
Figure 27F:
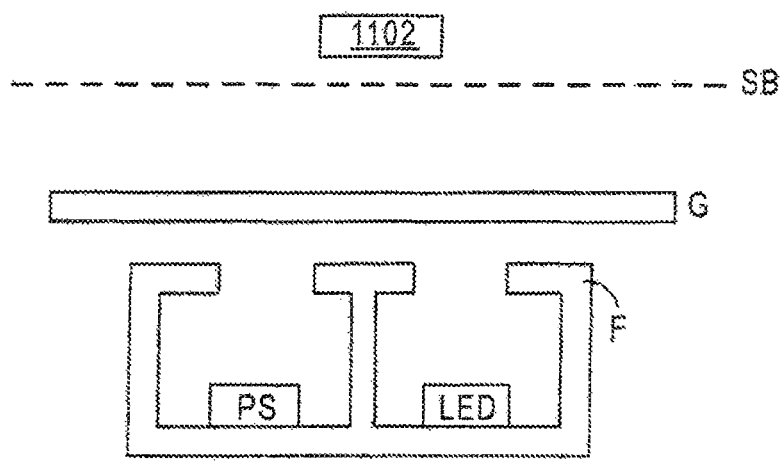

The first operation mode is a manual setting mode. After the electronic apparatus, including the proximity sensor 2111, is assembled as shown in FIGS. 27(a) and (b) under the condition that no object is close to the proximity sensor 2111 of the electronic apparatus, if the proximity sensing unit PS senses a first measured value C1 when the light-emitting diode LED is active and emits the light L (see FIG. 27(a) and senses a second measured value C2 when the light-emitting diode LED is inactive (see FIG. 27(b), since the second measured value C2 may include noise and the first measured value C1 may include noise and noise cross-talk (e.g., the portion reflected by the glass G), the digital signal processing unit 2113 can subtract the second measured value C2 from the first measured value C1 to obtain an initial noise cross-talk value CT under the condition that no object is close to the proximity sensor 2111 of the electronic apparatus, and store the initial noise cross-talk value CT in a register (not shown in the figure) through the I2C interface 2114. The initial noise cross-talk value CT can be used as a maximum threshold value of noise cross-talk in the system.

It should be noticed that since no object is close to the proximity sensor 2111 of the electronic apparatus at this time, the initial noise cross-talk value CT obtained by the digital signal processing unit 2113 should only include noise cross-talk values caused by the packaging and the mechanical portion of the system. Therefore, after the initial noise cross-talk value CT is obtained, whenever the proximity sensor 2111 tries to detect whether the object is close to the proximity sensor 2111, the digital signal processing unit 2113 needs to subtract the initial noise cross-talk value CT from the measured value to effectively reduce the effect of noise cross-talk.

The second operation mode is an automatic setting mode. Whenever the electronic apparatus, including the proximity sensor 2111, is active, the proximity sensor 2111 can obtain the initial noise cross-talk value CT by subtracting the second measured value C2 from the first measured value C1 as mentioned above, and the initial noise cross-talk value CT can be used as a standard to determine that the sensed value is noise, noise cross-talk, or light signal reflected by the object.\

As shown in FIG. 27(c) through FIG. 27(f), after the electronic apparatus including the proximity sensor 2111 is active, the object 2 may be close to the proximity sensor 2111 of the electronic apparatus, and the object 2 may be located in the detection range of the proximity sensor 2111. If the proximity sensing unit PS senses a third measured value C3 when the light-emitting diode LED is active and emits the light L and senses a fourth measured value C4 when the light-emitting diode LED is inactive. Since the fourth measured value C4 may include the noise, and the third measured value C3 may include the noise, the noise cross-talk, and the light signal reflected by the object 2, the digital signal processing unit 2113 can obtain a specific measured value M by subtracting the fourth measured value C4 from the third measured value C3, and the specific measured value M represents the noise cross-talk and the light signal reflected by the object 2.

Next, the digital signal processing unit 2113 determines whether the specific measured value M is larger than the initial noise cross-talk value CT. If the result determined by the digital signal processing unit 2113 is no, it means that the specific measured value M (the noise cross-talk and the light signal reflected by the object 2) at this time is smaller than the initial noise cross-talk value CT. Therefore, the proximity sensor 2111 needs to replace the initial noise cross-talk value CT stored in the register with the specific measured value M through the I2C interface 2114. Afterwards, when the proximity sensor 2111 detects whether any object is close to the proximity sensor 2111 again, the updated initial noise cross-talk value (the specific measured value M) will be used as a standard of determination.

If the result determined by the digital signal processing unit 2113 is yes, it means that the specific measured value M (the noise cross-talk and the light signal reflected by the object 2) at this time is larger than the initial noise cross-talk value CT. Therefore, it is unnecessary to update the initial noise cross-talk value CT stored in the register. Then, the digital signal processing unit 2113 will subtract the initial noise cross-talk value CT from the specific measured value M to obtain the reflection light signal value N of the object 2.

Afterwards, in order to determine whether the object 2 is located in the detection range of the proximity sensor 2111, that is to say, to determine whether the object 2 is close enough to the proximity sensor 2111, the digital signal processing unit 2113 compares the reflection light signal value N of the object 2 with a default value NO to determine whether the reflection light signal value N of the object 2 is larger than the default value NO. It should be noted that the default value NO is the object detecting threshold value detected by the proximity sensor 2111 when the object 2 is located at the boundary SB of the detection range of the proximity sensor 2111.

If the result determined by the digital signal processing unit 2113 is yes, that is to say, the reflection light signal value N of the object 2 is larger than the default value NO, it means that the strength of the light reflected by the object 2, reflecting the light of the light-emitting diode LED, is stronger than the strength of the light reflected by the object located at the boundary SB of the detection range of the proximity sensor 2111, also reflecting the light of the light-emitting diode LED. Therefore, the proximity sensor 2111 knows that the object 2 is located in the detection range of the proximity sensor 2111; that is say; the object 2 is close enough to the proximity sensor 2111, as shown in FIG. 27(*c*) and FIG. 27(*d*). At this time, the buffer 2115 will output a proximity notification signal to inform the electronic apparatus, including the proximity sensor 2111, that the object 2 is approaching, so that the electronic apparatus can immediately make corresponding actions. For example, the electronic apparatus can shut down the touch function of its touch monitor.

If the result determined by the digital signal processing unit 2113 is no, that is to say, the reflection light signal value N of the object 2 is not larger than the default value NO, it means that the strength of the light reflected by the object 2, reflecting the light of the light-emitting diode LED, is not stronger than the strength of the light reflected by the object located at the boundary SB of the detection range of the proximity sensor 2111, reflecting the light of the light-emitting diode LED. Therefore, the proximity sensor 2111 knows that the object 2 is not located in the detection range of the proximity sensor 2111; that is to say, the object 2 is not close enough to the proximity sensor 2111, as shown in FIGS. 27(*e*) and 27(*f*). Therefore, the buffer 2115 will not output the proximity notification signal to inform the electronic apparatus, including the proximity sensor 2111, that the object 2 is approaching, and the electronic apparatus will not make corresponding actions such as shutting down the touch function of its touch monitor.

The third operation mode is a selection setting mode. The user can use the I2C interface 2114 to set a control bit for the user to freely choose between the manual setting mode and the automatic setting mode to reduce the effect of the noise crosstalk.

Figure 28:
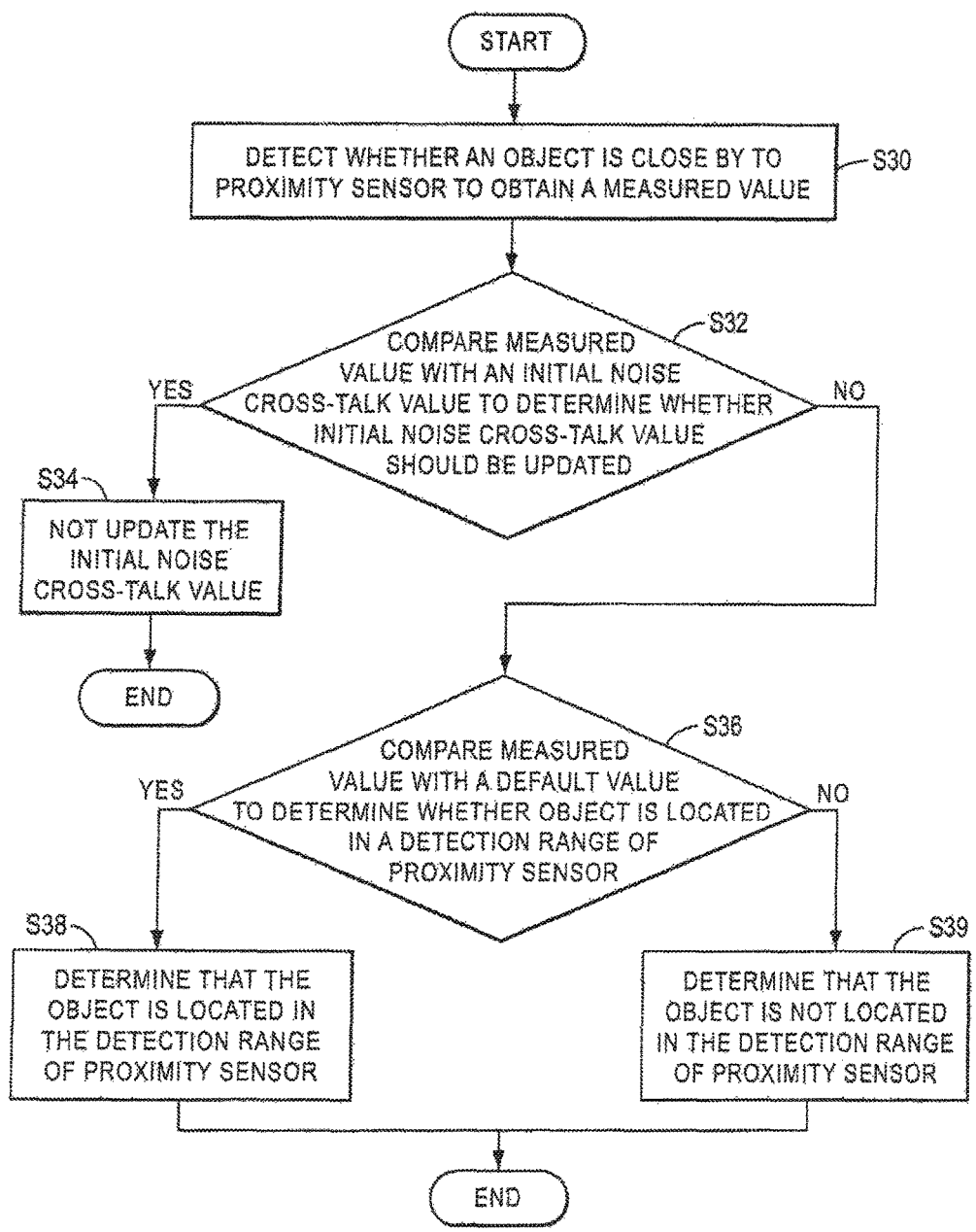
FIG. 28 illustrates a flowchart of the proximity sensor operating method in another embodiment of the invention.

Another preferred embodiment of the invention is a proximity sensor operating method. FIG. 28 illustrates a flowchart of the proximity sensor operating method in this embodiment.

As shown in FIG. 28, in the step S30, the method detects whether an object is close by to the proximity sensor to obtain a measured value. Then, in the step S32, the method compares the measured value with an initial noise cross-talk value to determine whether the initial noise cross-talk value should be updated. Wherein, the initial noise cross-talk value is obtained by the proximity sensor operated under the manual setting mode. Under the manual setting mode, the proximity sensor obtains a first measured value when the light emitter is active and a second measured value when the light emitter is inactive, and subtracts the second measured value from the first measured value to obtain an initial noise cross-talk value.

If the result determined by the step S32 is yes, the method will perform the step S34, not to update the initial noise cross-talk value. If the result determined by the step S32 is no, the method will perform the step S36 to compare the measured value with a default value to determine whether the object is located in a detection range of the proximity sensor. Wherein, the default value is the object detecting threshold value detected by the proximity sensor when the object is located at the boundary of the detection range of the proximity sensor.

If the result determined by the step S36 is yes, the method will perform the step S38 to determine that the object is located in the detection range of the proximity sensor. If the result determined by the step S36 is no, the method will perform the step S39 to determine that the object is not located in the detection range of the proximity sensor.

Figure 29A:
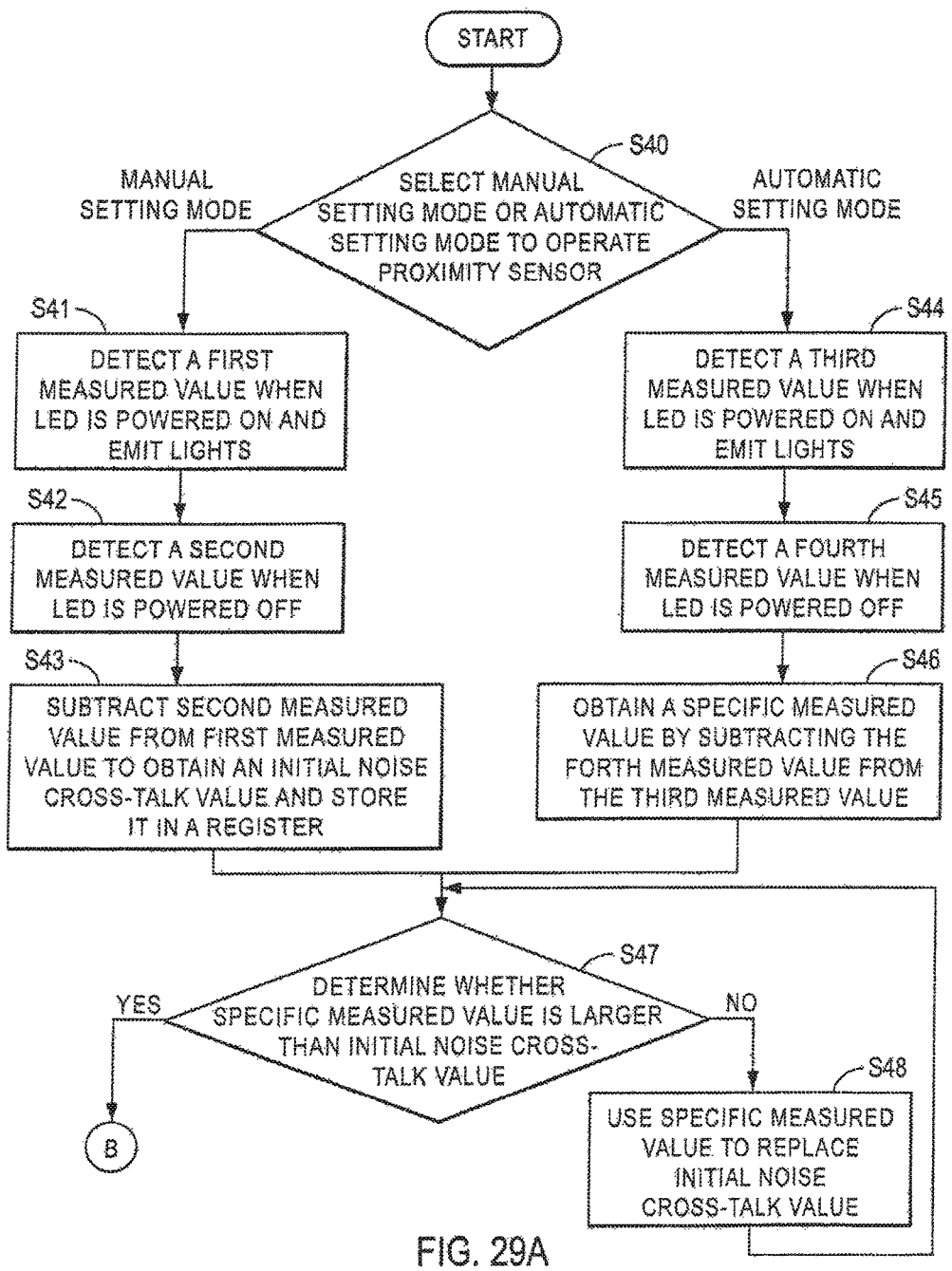
FIGS. 29($a$) and ($b$) illustrate flowcharts of the proximity sensor operating method in another embodiment of the invention.
Figure 29B:
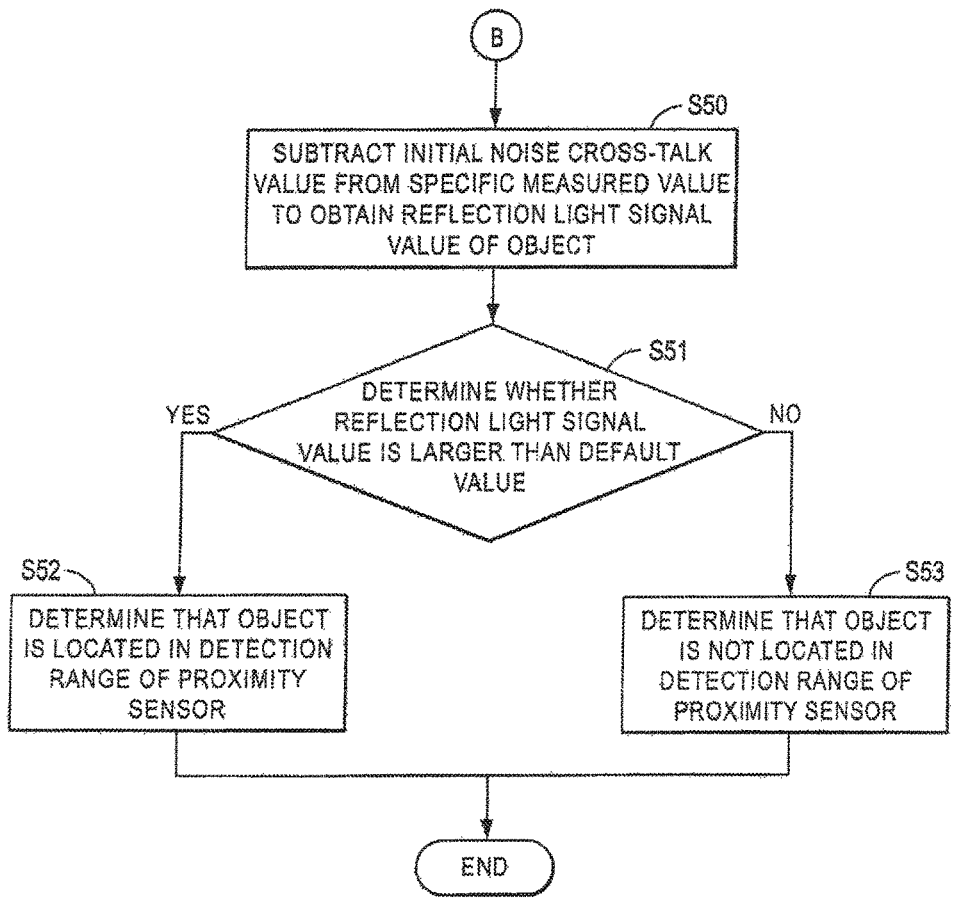

FIGS. 29(*a*) and (*b*) illustrate flowcharts of the proximity sensor operating method in another embodiment. As shown in FIGS. 29(*a*) and (*b*), in the step S40, the method selects either the manual setting mode or the automatic setting mode to operate the proximity sensor. If the manual setting mode is selected, under the condition that no object is close by to the proximity sensor of the electronic apparatus, the method performs the step S41 to detect a first measured value C1 when the LED is active and emit lights and the step S42 to detect a second measured value C2 when the LED is inactive.

Since the second measured value C2 may include noise and the first measured value C1 may include noise and noise cross-talk, in the step S43, the method subtracts the second measured value C2 from the first measured value C1 to obtain an initial noise cross-talk value CT and store the initial noise cross-talk value CT in a register, and the initial noise cross-talk value CT is used as a maximum threshold value of noise cross-talk in the system.

If the automatic setting mode is used, after the electronic apparatus, including the proximity sensor, is active, the object may be close to the proximity sensor of the electronic apparatus. The method performs the step S44 to detect a third measured value C3 when the LED is active and emit lights and the step S45 to detect a fourth measured value C4 when the LED is inactive. Since the fourth measured value C4 may include the noise, and the third measured value C3 may include the noise, the noise cross-talk, and the light signal reflected by the object. Therefore, in the step S46, the method obtains a specific measured value M by subtracting the fourth measured value C4 from the third measured value C3, and the specific measured value M represents the noise cross-talk and the light signal reflected by the object.

In step S47 the method determines whether the specific measured value M is larger than the initial noise cross-talk value CT. If the result determined by the step S47 is no, it means that the specific measured value M (the noise cross-talk and the light signal reflected by the object 2) at this time is smaller than the initial noise cross-talk value CT. Therefore, in the step S48, the method uses the specific measured value M to replace the initial noise cross-talk value CT; so that the specific measured value M can be used as an updated initial noise cross-talk value. Later, when the method performs the step S47 again, the updated initial noise cross-talk value (the specific measured value M) will be used to compare with another specific measured value M' obtained by the method performing the step S46 again to determine whether the specific measured value M' is larger than the updated initial noise cross-talk value (the specific measured value M).

If the result determined by the step S47 is yes, it means that the specific measured value M (the noise cross-talk and the light signal reflected by the object) at this time is larger than the initial noise cross-talk value CT. Therefore, it is unnecessary to update the initial noise cross-talk value CT stored in the register. In the step S50, the method will subtract the initial noise cross-talk value CT from the specific measured value M to obtain the reflection light signal value N of the object.

Afterwards, in order to determine whether the object is located in the detection range of the proximity sensor; that is to say, to determine whether the object is close enough to the proximity sensor, in the step S51, the method will compare the reflection light signal value N of the object with a default value NO to determine whether the reflection light signal value N of the object is larger than the default value NO. It should be noted that the default value NO is the object detecting threshold value detected by the proximity sensor when the object is located at the boundary of the detection range of the proximity sensor.

If the result determined by the step S51 is yes, that is to say, the reflection light signal value N of the object is larger than the default value NO, it means that the strength of the reflected light generated by the object reflecting the light of the LED is stronger than the strength of the reflected light generated by the strength of the reflected light generated by the object located at the boundary of the detection range of the proximity sensor reflecting the light of the LED. Therefore, in the step S52, the method determines that the object is located in the detection range of the proximity sensor; that is say, the object is close enough to the proximity sensor. At this time, the proximity sensor will output a proximity notification signal to inform the electronic apparatus that the object is approaching, so that the electronic apparatus can immediately make corresponding action.

If the result determined by the step S51 is no, that is to say, the reflection light signal value N of the object is not larger than the default value NO, it means that the strength of the light reflected by the object, reflecting the light of the LED, is not stronger than the strength of the light reflected by the object located at the boundary of the detection range of the proximity sensor, also reflecting the light of the LED. Therefore, in the step S53, the method determines that the object is not located in the detection range of the proximity sensor; that is to say, the object is not close enough to the proximity sensor. Therefore, the buffer will not output the proximity notification signal to inform the electronic apparatus that the object is approaching.

Particle Detection

Figure 30:
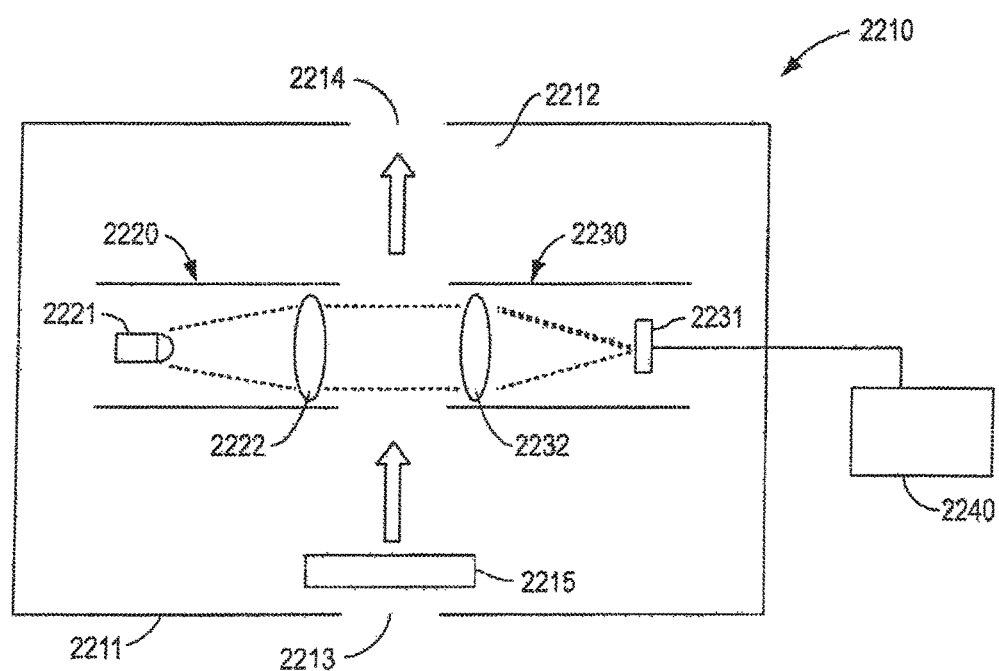
FIG. 30 is a schematic view showing a configuration of a particle detection apparatus of a first embodiment according to the present invention.

FIG. 30 is a schematic view showing a configuration of a particle detector according in one embodiment. An apparatus 2210 has a chamber 2212 surrounded by a wall 2211, and the chamber 2212 has an inlet 2213 for taking air from the outside and an outlet 2214 for discharging air. In order to take air and generate airflow at a particle detection position as later described, an airflow generating/controlling device 2215 is provided on the inner side of the inlet 2213. Even when the airflow generating/controlling device 2215 is not turned on, air can flow between the inlet 2213 and outlet 2214.

As the airflow generating/controlling device 2215, a small fan is typically used. However, in order to generate airflow in a rising direction opposite to the gravity, an air heating device such as a heater may be used. Air entered from the inlet 2213 into the chamber 2212 passes through the inside of the chamber 2212 and is guided to the outlet 2214. Though not shown, airflow guide means having, for example, a cylindrical shape may be provided between the inlet 2213 and the outlet 2214. Further, a filter may be installed at a prior stage to the airflow generating/controlling device 2215 to prevent the entry of particles having a size greater than target fine particles.

The apparatus 2210 also includes means for detecting a particle. That means includes a light source 2220 and a detection device 2230. In this embodiment, the light source 2220 and the detection device 2230 are arranged horizontally in an opposing manner. This allows the detection device 2230 to directly receive light from the light source 2220, and the light source 2220 and the detection device 2230 are configured to pass the airflow generated by the airflow generating/controlling device 2215 between them.

The light source 2220 is composed of a light-emitting element 2221 and an optical system 2222 including a lens. The light-emitting element 2221 may be typically composed of a semiconductor light-emitting element such as a laser diode or a light-emitting diode capable of emitting coherent light. If the degree of sensitivity is not pursued, other light-emitting element may be used. However, a light-emitting element capable of emitting light with a certain degree of directional characteristics is desired from the viewpoint of device design.

On the other hand, the detection device 2230 is composed of a photodetector 2231 and an optical system 2232 including a lens. As the photodetector 2231, an image sensor such as a CMOS image sensor or a CCD image sensor may be used. The photodetector 2231 is configured so as to output a detection signal to an external analyzer 2240.

Light emitted from the light emitting-element 2221 passes through the optical system 2222, and is illuminated to a gas to be measured. In one embodiment, light emitted from the light emitting-element 21 is substantially collimated by the optical system 2222. The light passing through the gas in the measurement area is collected by the optical system 2232 in the detection device 2230, and detected as an image by an image sensor 31. The image sensor 31 outputs a signal of the image to the analyzer 2240.

Optical dimensions of the lens in the optical system 2222, such as a focal length, can be determined based on a radiation angle of light from the light-emitting element 2221 and a diameter of fine particles to be measured. Specifically, it is necessary to select a focal length of the lens so that a light flux has a diameter several times larger than the size of the fine particles to be measured. For example, in measuring fine particles having a size of approximately 100 micrometers, it is necessary to illuminate light in such a way that the light has a diameter of not less than several hundred micrometers, so as to keep the sensitivity of the entire system. However, if light is illuminated to a large area, the power of transmitted light to be detected decreases, resulting in a degraded signal/noise ratio. Therefore, optimization may be necessary.

Figure 31:
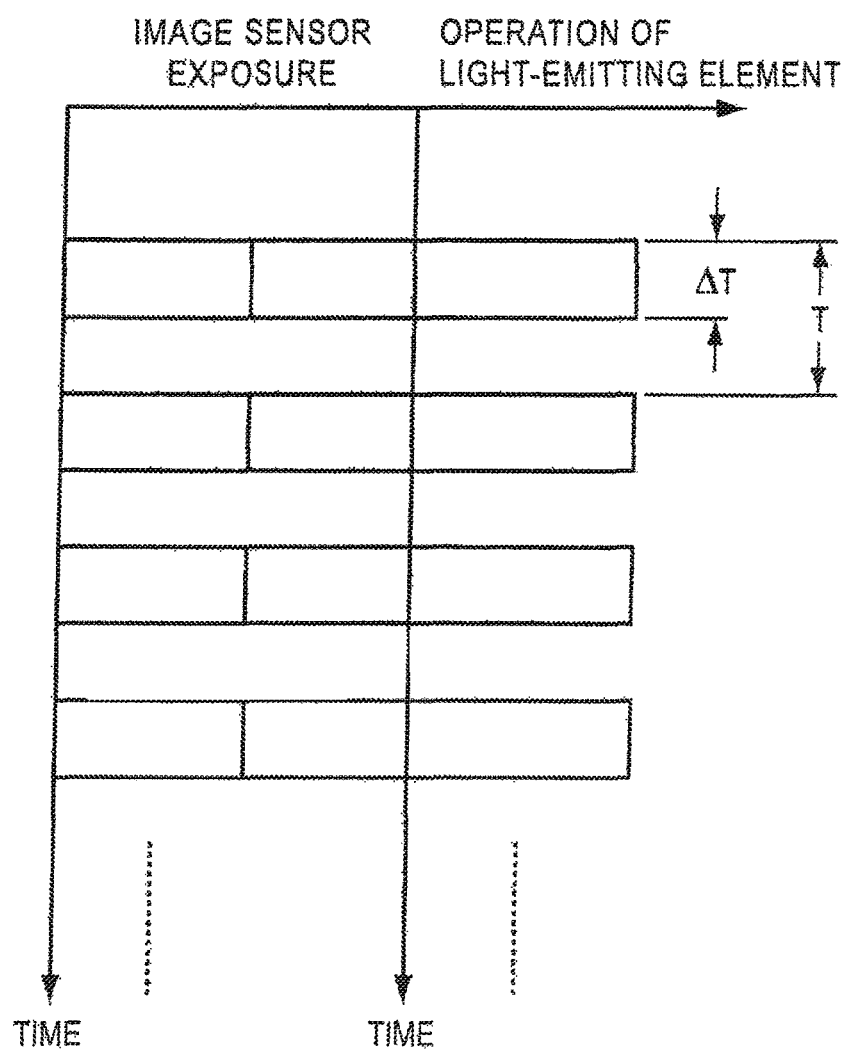
FIG. 31 is a time chart showing the timing of the operation of the light emitting-element and the exposure of the image sensor.

FIG. 31 is a time chart showing the timing of the operation of the light emitting-element and the exposure of the image sensor. The light emitting-element 2221 such as a laser diode is made to generate light pulses rather than continuous light (CW) for the purpose of reducing power consumption. The cycle (T) of a light pulse and a time period ($\Delta T$) for illumination are properly selected from the moving speed of fine particles to be measured. If the cycle T is too long, problems may arise that, for example, fine particles themselves may not be detected or a captured image becomes blurred. If the cycle T is too short, the light application time $\Delta T$ is also short and thus there is a drawback that the signal/noise ratio is degraded.

In FIG. 30, the exposure time of the image sensor 2231 is the same as that of the light emitting-element 2221. This period is optimized by taking into consideration the signal/noise ratio of the entire system. The number of pixels of the image sensor mainly depends upon the size of fine particles to be measured. If the size of fine particles to be measured is from 1 micrometer to 100 micrometers, the number of pixels may be approximately 10,000.

Hereafter, an algorithm for detecting smoke particles, dust and pollen will be described. This method is not limited to the present embodiment, any may be applied to apparatus according to second and third embodiments described later.

Here, an output taken by the image sensor along x-axis (i-th) and y-axis (j-th) is indicated as V (i,j). Depending on the configuration of a focal length of a lens, there may be a difference in an output of the image sensor per pixel. Therefore, calibration is carried out at the beginning to adjust all of the pixels so that offset and sensitivity fall within a certain range. This adjustment may be carried out by hardware means or software means. In the following description, V (i,j) is an output value after the adjustment is carried out.

First, a state without the presence of obstacles, such as smoke particles, dust and pollen, is considered. In this case, transmitted light is detected directly by the image sensor without scattering, and thus its output V_non (i,j) has a very small variance σ_non for the entire pixels.

When any of fine particles such as smoke particles, dust or pollen is entered, light is scattered thereby, resulting in a reduction in an amount of transmitted light. This enables to detect the fine particles. A predetermined value V_noise is set by taking into accounts the stability of LD inside the detection apparatus, shot noises which may occur in the image sensor, noises in amplifier circuitry, and thermal noises. If this value is exceeded, it is determined that a signal is supplied. While the fine particles may be introduced by generating airflow, natural diffusion or natural introduction of particles may be utilized without generating the airflow.

When it is determined that a signal is supplied, smoke particles, dust and pollen are distinguished in accordance with the following procedure.

1. When it is determined that a signal is supplied to all of the pixels, that is determined to be attributable to smoke particles.

In other words, when $$V(i,j) < V\_\text{non} - V\_\text{detect-1}$$

is valid for all of the pixels, smoke particles are identified. Here, V_detect-1 is a constant threshold larger than V_noise. Even if very large particles are introduced, the signal is detected in all of the pixels. However, as stated previously, in this case, such particles are removed in advance by a filter. Further, a concentration of the smoke is identified depending on an intensity of the signal.

2. When part of pixels has responded, dust or pollen is identified. Binarization is carried out to identify a portion shielded by fine particles. FIG. 28 is a view schematically showing such binarization. For example, if a dust has a size and shape as shown in (a), that is identified by binarization as an image as shown in (b). V_detect-2 are used as a parameter for performing the binarization, and pixels that output a signal exceeding this threshold V_detect-2 are counted. The count number is proportional to a light-shielding cross-sectional area by the fine particles, with respect to the incident light. On the basis of the counted pixel number, fine particles of 20 micrometers or less or 50 micrometers or more are identified as dust.

3. When the result of the above size measurement of the fine particles indicates that the particles are determined to have a size from 20 micrometer to 50 micrometer, it is possible that the particles are pollen. Therefore, in such a case, determination by a further method is necessary. In general, since dust is lighter than pollen, dust has a higher moving speed in airflow than pollen. Therefore, the moving speed of floating particles is calculated. When the moving speed of the particles is at a predetermined level or higher, those particles are determined to be dust, and otherwise they are determined to be pollen. When the airflow is not rising and the fine particles flow from top to down, the particles having a higher moving speed is considered pollen and slow particles are considered dust.

The speed value is obtained by taking two images at successive units of time, and calculating from a moving distance between the images and a frame time.

Figure 32A:
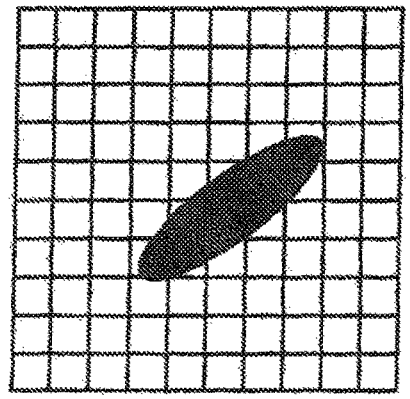
FIGS. 32($a$) and ($b$) are views showing schematized image information of a binarized particle image.
Figure 32B:
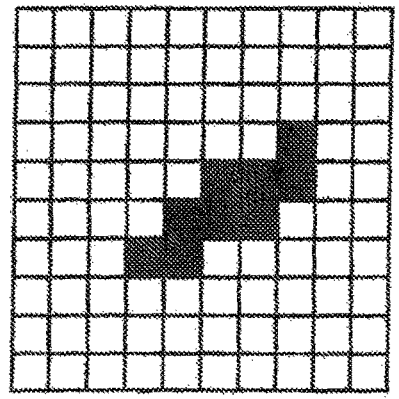

FIGS. 32(a) and (b) are views showing schematized image information of a binarized particle image.

Figure 33A:
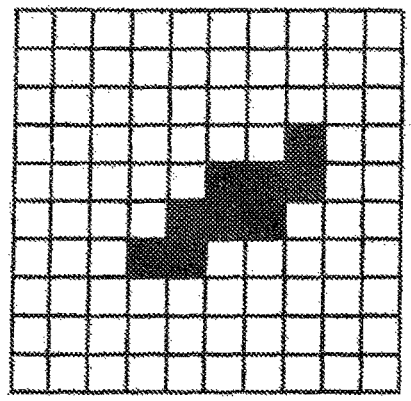
FIGS. 33($a$) and ($b$) are views showing temporal changes of a binarized image signal.
Figure 33B:
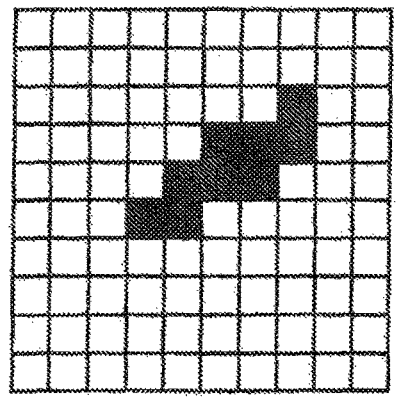

FIGS. 33(a) and (b) show temporal a change in a binarized image signal. In this example, it is recognized that a particle is moving upwardly. In order to recognize movement of particles from image information, a correlation value conventionally used in related technology can be utilized. As a result of determining the moving speed, when it is not lower than or not higher than a predetermined speed, the particles can be identified as dust or pollen, respectively.

In this description, detection of fine particles such as dust and pollen has been mainly described. However, by improving the analytical algorithm of the present apparatus, it is possible to produce a histogram of passing particles over a certain period in terms of size or weight of fine particles contained in an introduced gas. From this result, it is possible to analyze what types of fine particles exist in a room or in the open air.

Figure 35:
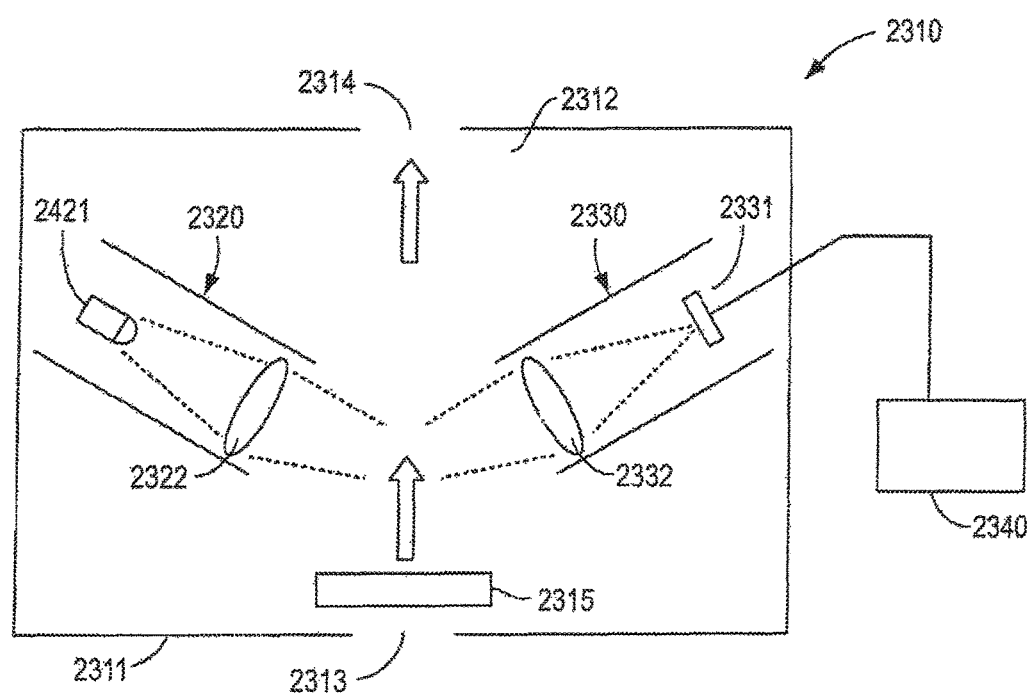
FIG. 35 is a schematic view showing a configuration of a particle detection apparatus in one embodiment.

FIG. 35 is a view describing a modified embodiment of the photodetector. In the aforementioned embodiment, the image sensor as a photodetector is provided with detection elements in the form of a matrix of approximately 100×100. However, a photodetector is not necessarily provided with a matrix of detection elements, and a photodetector having detection elements 51 disposed in a striped form may be used. That is, in this apparatus, when airflow is generated, the moving direction of fine particles is considered to run along a direction of the airflow. Therefore, detection of particles as in the foregoing embodiment is possible, by utilizing a photodetector 2250 having a striped configuration wherein elongated detection elements 2251 are extended in a direction perpendicular to the moving direction of the fine particles.

Figure 34A:
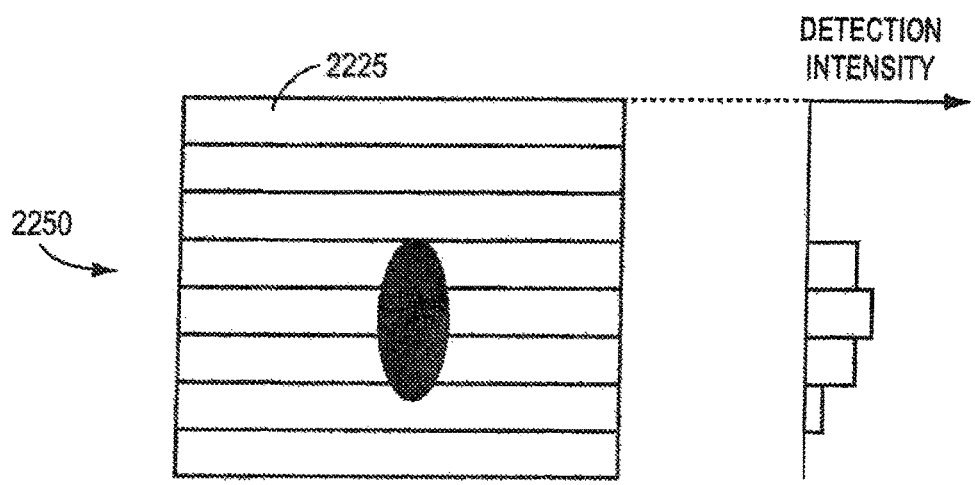
FIGS. 34($a$) and ($b$) are views showing a modified embodiment of a photodetector, which indicate particle detection at different times for each view. Each view shows a positional relation between the photodetector and the particle at left side and output values at right side.
Figure 34B:
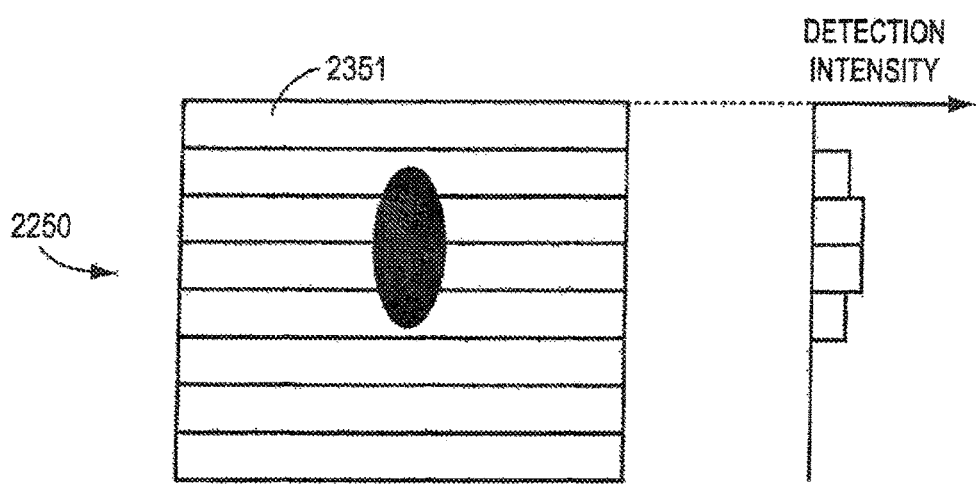

FIGS. 34(a) and (b) show particle detection at different times when the photodetector 50 is used. In each figure, a positional relation between the photodetector and a particle is shown on the left and output values are shown on the right. FIG. 34(a) shows an initial state and FIG. 34(b) show a state after a predetermined time period after the state of FIG. 34(a). Each of the detection elements 2251 constituting a stripe can output a signal which is substantially proportional to the area of an image. Therefore, by establishing and comparing the output values, the position of a particle at that time and a particle moving speed may be determined. For example, when data obtained from the individual stripe-shaped light detection elements 2251 is processed using a spatial filter as in a sensing device, the size and the moving speed of the fine particle can be easily obtained. In this case, however, there is a certain tradeoff between the particle size and the moving speed.

This method can reduce an amount of data to be processed, compared with a case wherein an image sensor in the form of a matrix is used, and therefore this method is advantageous in that data processing can be performed more easily and rapidly.

Figure 36:
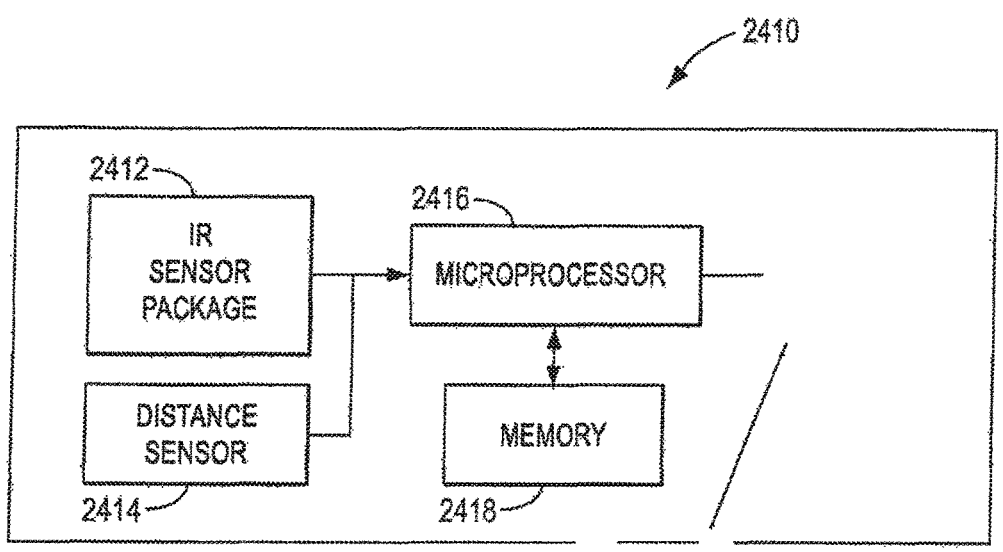
FIG. 36 is a block diagram representative of an embodiment of the present invention.

FIG. 36 is a schematic view showing the configuration of a particle detection apparatus according to a second embodiment of the present invention. In the first embodiment, a particle detection apparatus utilizing transmitted light was described. However, with a method of measuring reflected light or scattered light as described in FIG. 6, it is possible to detect smoke particles, dust and pollen. The description of operation of each component is omitted by attaching thereto a reference numeral which is greater by 100 than the numeral reference of a corresponding component shown in FIG. 30.

Regarding the positional relation between a light source 2320 and a detection device 2330, they are disposed on opposite sides of airflow, but they are not necessarily disposed in such a way. For example, the light source and the detection device may be disposed on the same side of the airflow, and in that case, light from the light source may be illuminated from either an upstream side or a downstream side of the airflow. Further, the light source and the detection device are disposed in a plane that is orthogonal to the airflow, and they may be disposed not linearly like that of FIG. 30, but in a tilted direction within the plane.

In the apparatus according to the first embodiment, as transmission light is always incident, it has to keep a certain level of an input range. As a result, measurements may not always be performed properly. In contrast, in accordance with the detection system of the second embodiment, a dynamic range of the image sensor of the apparatus can be utilized to advantage. Therefore, it is advantageously suitable for a high sensitive measurement of fine particles.

This apparatus is applicable to systems that detect fine particles including dust, pollen and smoke particles, such as an air cleaner, an air conditioner, a vacuum cleaner, an air fan, a fire alarm, a sensor for environmental measurement and a fine particle detection apparatus in a clean room.

Temperature Sensor

FIG. 36 is a block diagram illustrating an embodiment of the IR thermometer 2410. This embodiment includes an IR sensor package/assembly 2412, distance sensor 2414, a microprocessor 2416 and a memory 2418.

In one embodiment one or more sensors, which can be in an assembly 2412 includes a sensor. In one embodiment a sensor and a temperature sensor is provided. As a non-limiting example, the sensor can be an IR sensor. In one embodiment the sensor is an IR sensor. In one embodiment a temperature sensor senses the temperature of the sensor and/or the temperature of the ambient environment. The sensor is configured to capture thermal radiation emanating from a target object or target body part, e.g., a person's forehead, armpit, ear drum, etc., which is converted into an electrical temperature signal and communicated, along with a signal regarding the temperature of the sensor as measured by the temperature sensor, to microprocessor 2416, as is known in the art. Distance sensor 2414 is configured to emit radiation from IR thermometer 2410 and to capture at least a portion of the emitted radiation reflected from the target, which is converted into an electrical distance signal and communicated to microprocessor 2416. Microprocessor 2416 is configured to, among other things, determine a temperature value of the target based on the signal from sensor package/assembly 2412, determine an ambient environment or thermometer temperature, and to determine a distance value corresponding to the distance between thermometer 2410 and the target using a correlation routine based on the signal from distance sensor 2414 and the characteristics of the reflected radiation. In various embodiments, the temperature signal, distance signal, temperature value, distance value, or any combination thereof may be stored in memory 2418.

Memory 2418 includes therein predetermined compensation information. This predetermined compensation information may be empirically predetermined by performing clinical tests. These clinical tests may relate the detected temperature of a target (e.g., forehead), the distance of the thermometer from the target, as well as the actual temperature of the target and the ambient environment or thermometer temperature. These clinical tests may further relate the temperature of the target, either the detected temperature, the actual temperature, or both, to, e.g., an actual oral or oral-equivalent temperature. Accordingly, target temperatures of various persons having oral temperatures between, e.g., 94° Fahrenheit to 108° Fahrenheit, may be measured using a thermometer at various known distances from the targets, e.g., from 0 centimeters (i.e., thermometer contacts target) to 1 meter, in increments of, e.g., 1 centimeter, 5 centimeters, or 10 centimeters. In some embodiments, the range of distances corresponds to a range of distances over which thermometer 2410 may be operational. Additionally, these measurements may be conducted in environments having various ambient temperatures between, e.g., 60° Fahrenheit to 90° Fahrenheit. These data may be used to create compensation information, such as a look-up table or mathematical function, whereby a compensated temperature of the target may subsequently be determined from a measured distance value, e.g., using distance sensor 2414, a measured target temperature value, e.g., using IR sensor package or assembly 2412, and, in some embodiments, an ambient environment temperature value and/or thermometer temperature value. In other embodiments, data relating to actual oral or oral-equivalent temperatures may be further used to create the compensation information, whereby a compensated oral or compensated oral-equivalent temperature may be determined from a measured distance value, a measured target temperature value, and, in some embodiments, an ambient environment temperature value and/or thermometer temperature value.

For example, where d is defined as a distance between the target and thermometer 2410, the predetermined compensation information for obtaining a compensated temperature in degrees Fahrenheit may be a linear function or functions defined by the following relationships:

Compensated Temperature=Target Temperature+$A*d+B$

Or

Compensated Temperature=Target Temperature+$C*d+D$ {for $0<d\leq Y$}, and

Compensated Temperature=Target Temperature+$E*d+F$ {for $Y<d\leq Z$},

Where A, C, and E are coefficients having dimensions of Temperature/Length; B, D and F are coefficients having dimensions of Temperature; and Y and Z are distances from the target. Values of A, B, C, D, E, F, Y, and Z may be determined empirically from clinical tests. For purposes of illustration and not limitation, the following exemplary and approximate values for the coefficients and distances are provided: A=0.05, B=0.1, C=0.05, D=0.2, E=0.15, F=0.1, Y=15, and Z=30. However, as will be recognized by persons having ordinary skill in the art, other values for each coefficient and distance may be used depending on various design features and aspects of a thermometer 2410.

It is also possible for the mathematical function to be of a higher degree or order, for example, a mathematical function that is non-linear with respect to the measured distance to obtain the compensated temperature, such as the following quadratic equation:

Compensated Temperature=Target Temperature+$G*d2-H*d+L$

Where G, H, and L are coefficients determined from the clinical tests. For purposes of illustration and not limitation, the following exemplary and approximate values for the coefficients are provided: G=0.001, H=0.15, and L=0.1. However, as will be recognized by persons having ordinary skill in the art, other values for each coefficient may be used depending on various design features and aspects of thermometer 2410.

The compensation information may alternatively be provided as various offset values, whereby, for each distance increment or range of distances from the target surface, there is a corresponding offset value. In various embodiments, these offsets may be fixed for each of the distance increments or range of distances from the target surface. For example, in various embodiments, the offset value may be, e.g., any one of 0.1° F., 0.2° F., or 0.5° F. over a range of distances from the target surface such as 0 cm to 5 cm, 0 cm to 20 cm, or 5 cm to 30 cm. For example, in one embodiment, the offset value may be 0.0° F. from 0.0 cm to 0.1 cm, 0.1° F. from 0.1 cm to 3.0 cm, 0.2° F. from 3.0 cm to 15 cm, and 0.5° F. from 15.1 cm to 30 cm. Alternatively, the compensation information may be in the form of a single, e.g., "best-fit," offset value that may be used to determine a compensated temperature from any of the target temperatures over a distance range, either the entire distance range recited above or a portion thereof. For example, the "best-fit" offset value may be, e.g., any one of 0.1° F., 0.2° F., or 0.5° F. For example, in one embodiment, the offset value may be 0.1° F. over the distance range from 0.0 cm to 10 cm, and 0.0° F. for greater distances. In other embodiments, the offset value may be 0.1° F. over the distance range from 0.0 cm to 30 cm, and 0.0° F. for distances greater than 30 cm.

In other embodiments, the compensation information may be in the form of a look-up table, which may be devised from predetermined information collected during clinical tests, such as actual target temperature, measured target temperature, ambient environment and/or thermometer temperature, and distance measurements, such that, subsequently, a compensated temperature may be determined by identifying in the look-up table those values that best correspond to the measured distance and measured target-temperature values. In the event of an imperfect match between the measured values and the table values, the closest table values may be used, or, additional values interpolated from the table values may be used. In other embodiments, the compensation information may include a combination of more than one of the approaches (e.g., mathematical function, offset value, look-up table) described above Further, as noted above, the ambient environment temperature value and/or thermometer temperature value may be used in generating compensation information. It may be beneficial to include these values as factors in the compensation information because these values may increase the accuracy of a compensated temperature calculated based on the compensation information. For example, the above discussed mathematical functions may be modified based on ambient environment temperature and/or thermometer temperature. For example, a first "best fit" offset value (e.g., 0.1° F.) may be used when the ambient temperature is within a first range of temperatures (e.g., 60° F. to 75° F.), and a second "best fit" offset value (e.g., 0.2° F.) may be used when the ambient temperature is within a second range of temperatures (e.g., 75° F. and 90° F.).

Microprocessor 2416 is configured to use a temperature value corresponding to a target and a distance value corresponding to the distance between thermometer 2410 and the target to determine a compensated temperature using the predetermined compensation information stored in memory 2418. In some embodiments, Microprocessor 2416 may be further configured to use an ambient and/or thermometer temperature in this determination. In some embodiments, the predetermined compensation information may be based in part on ambient and/or thermometer temperature. In those embodiments where the predetermined compensation information includes predetermined information concerning oral or oral-equivalent temperatures, Microprocessor 2416 may be further configured to determine a compensated temperature corresponding to an oral or oral-equivalent temperature.

Microprocessor 2416 may further store one or more compensated temperature values in memory 2418. In various embodiments, the microprocessor is further configured to interpolate additional values from any values stored in a look-up table in memory 2418.

Figure 37:
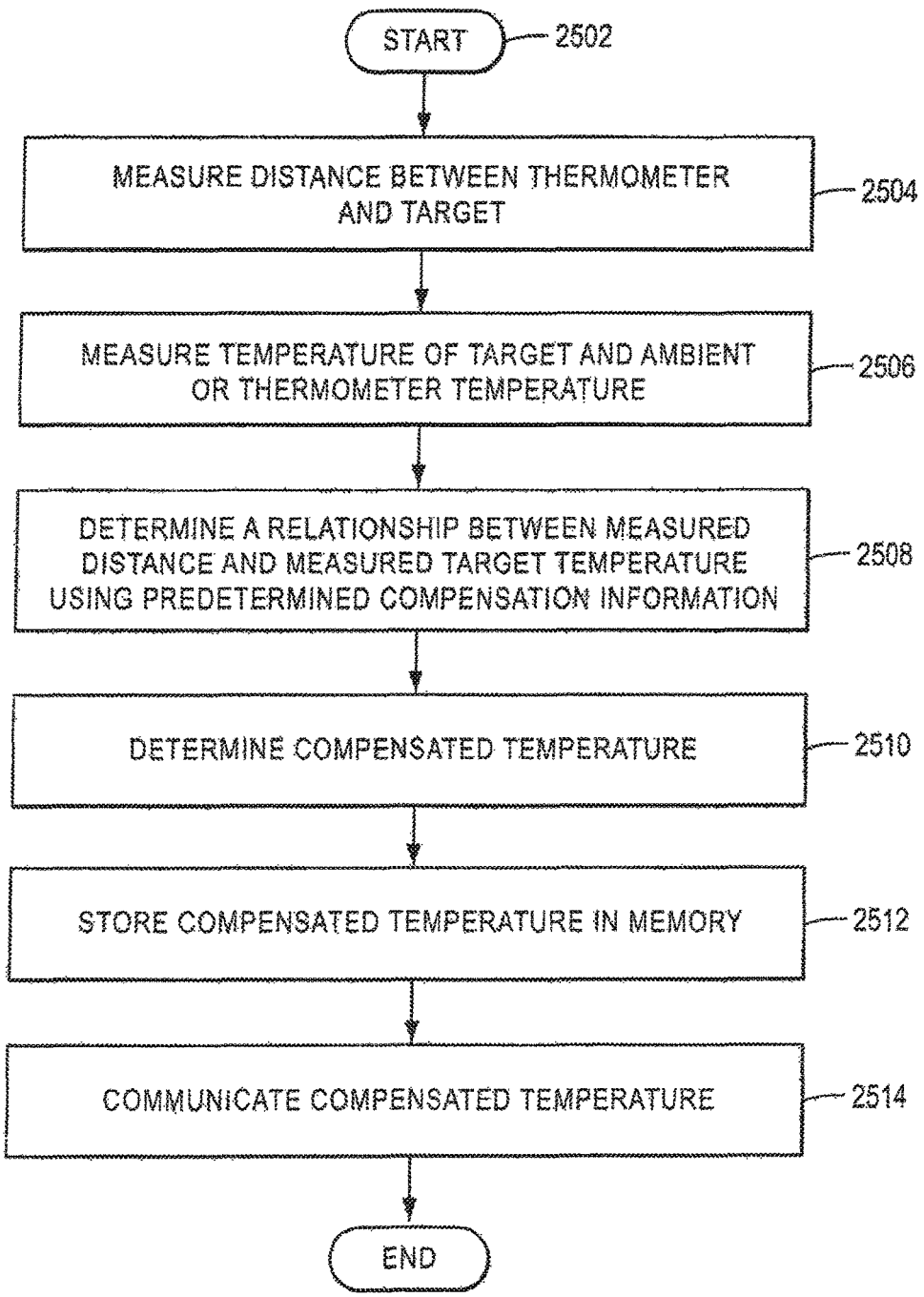
FIG. 37 is a flow chart showing the method for compensated temperature determination in accordance with an embodiment of the invention.
Figure 38A:
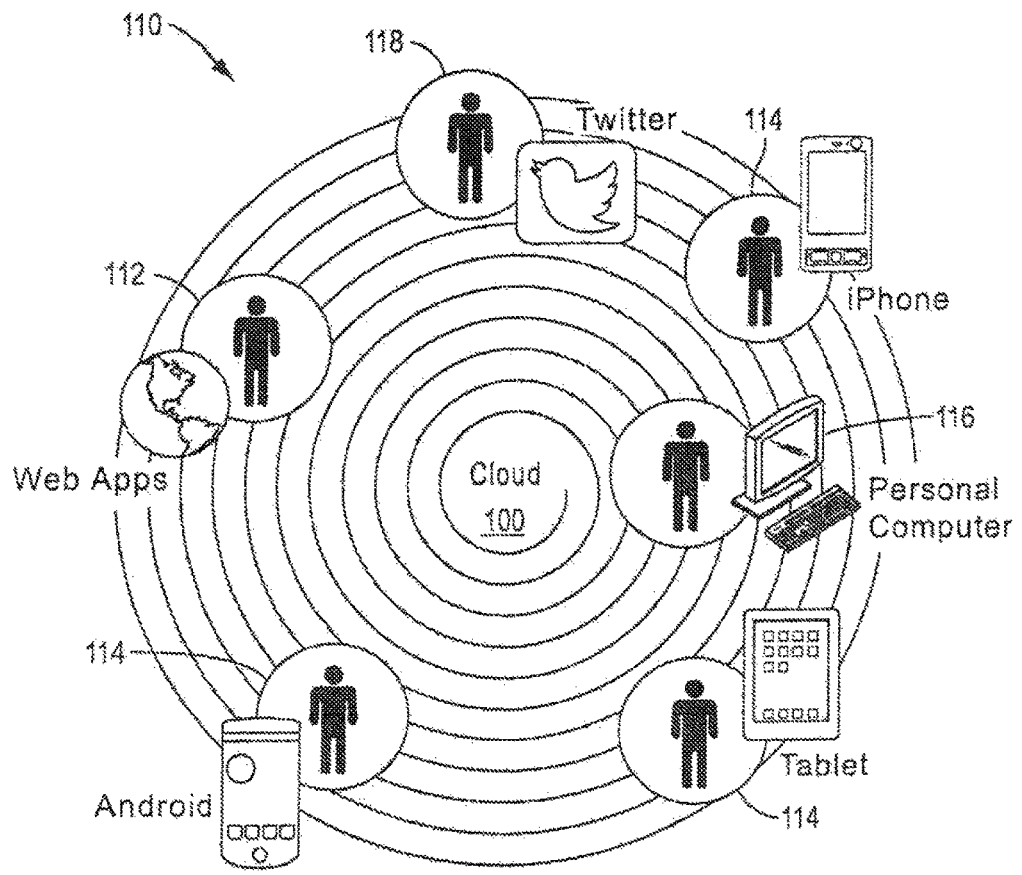
FIGS. 38($a$)-($e$) illustrate one embodiment of a Cloud Infrastructure that can be used with the present invention.
Figure 38B:
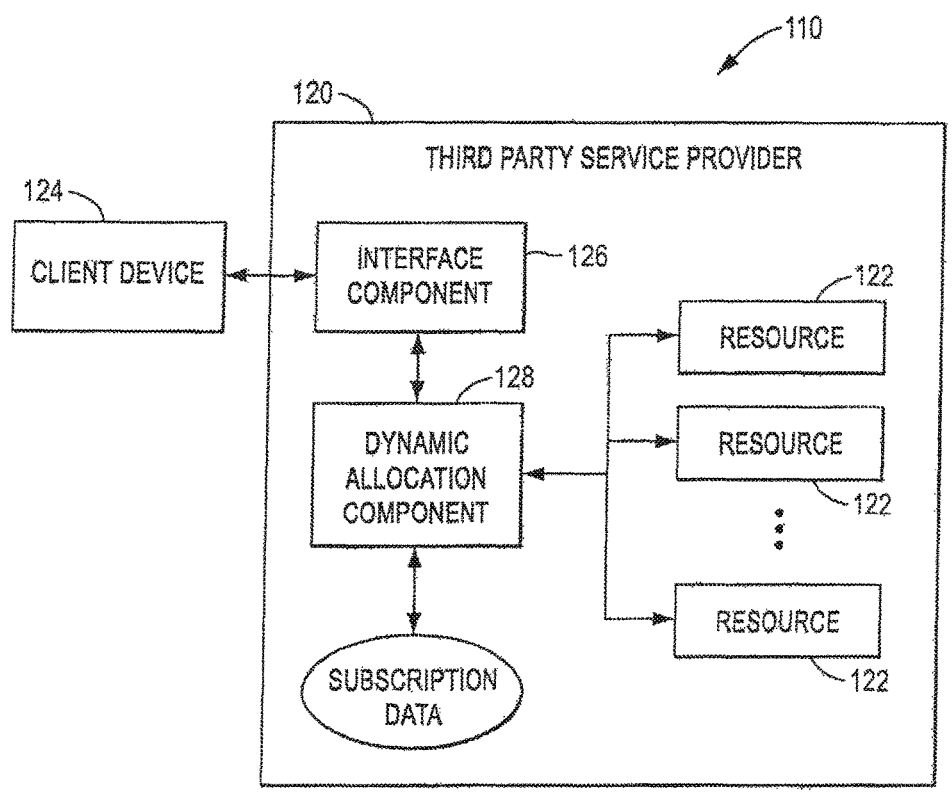
Figure 38C:
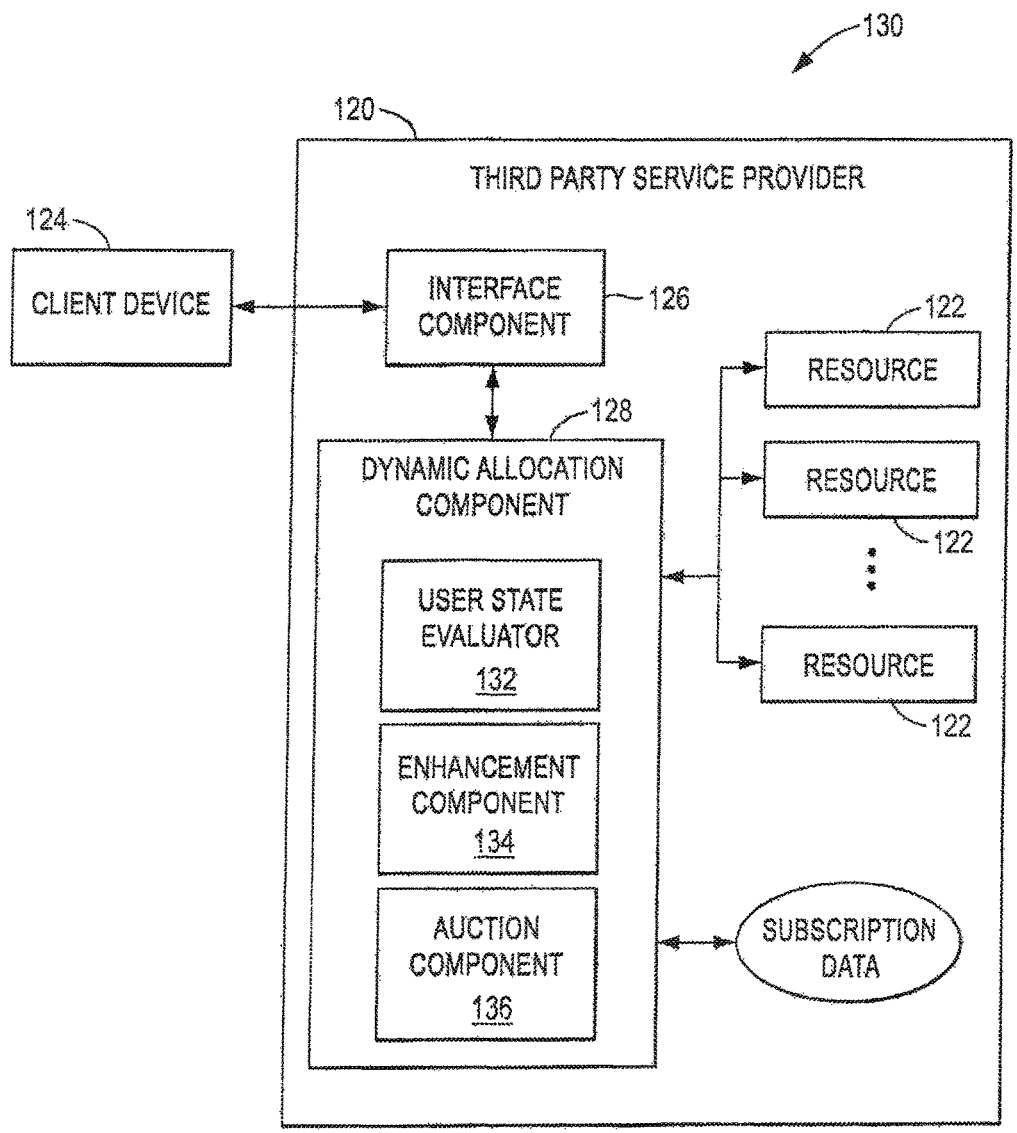
Figure 38D:
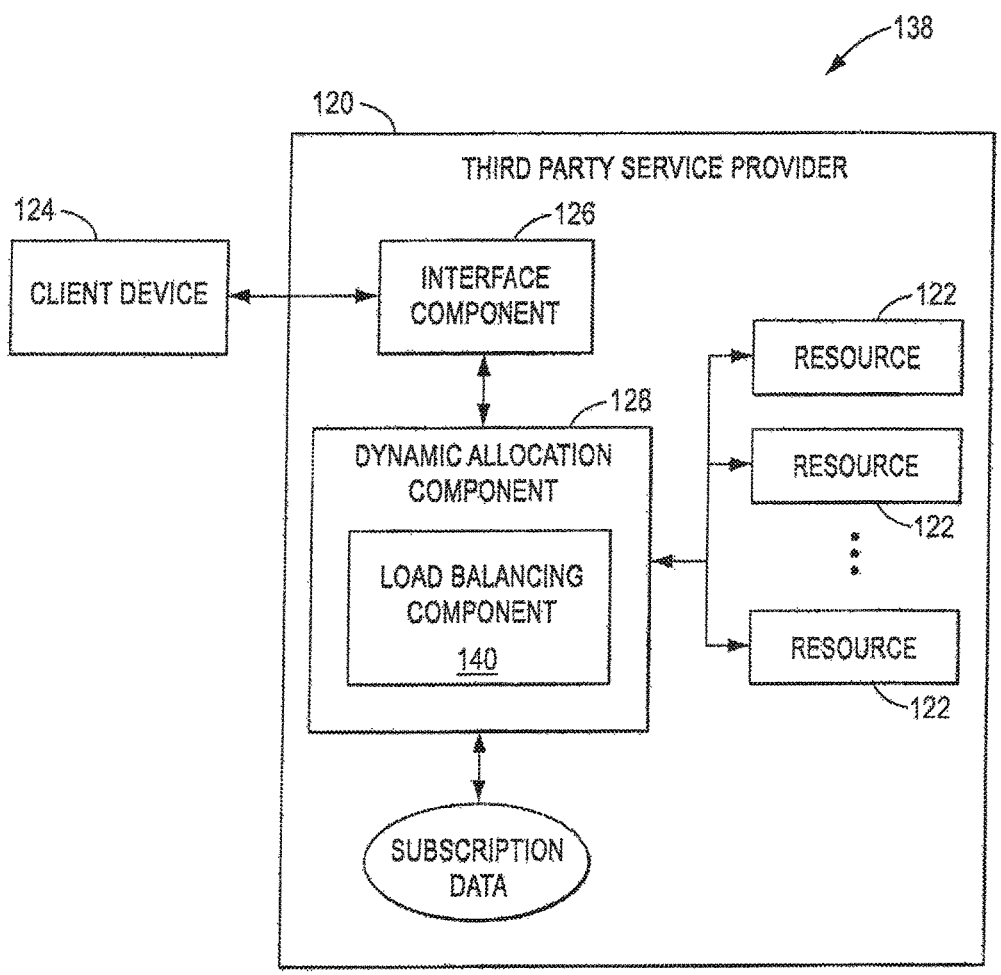
Figure 38E:
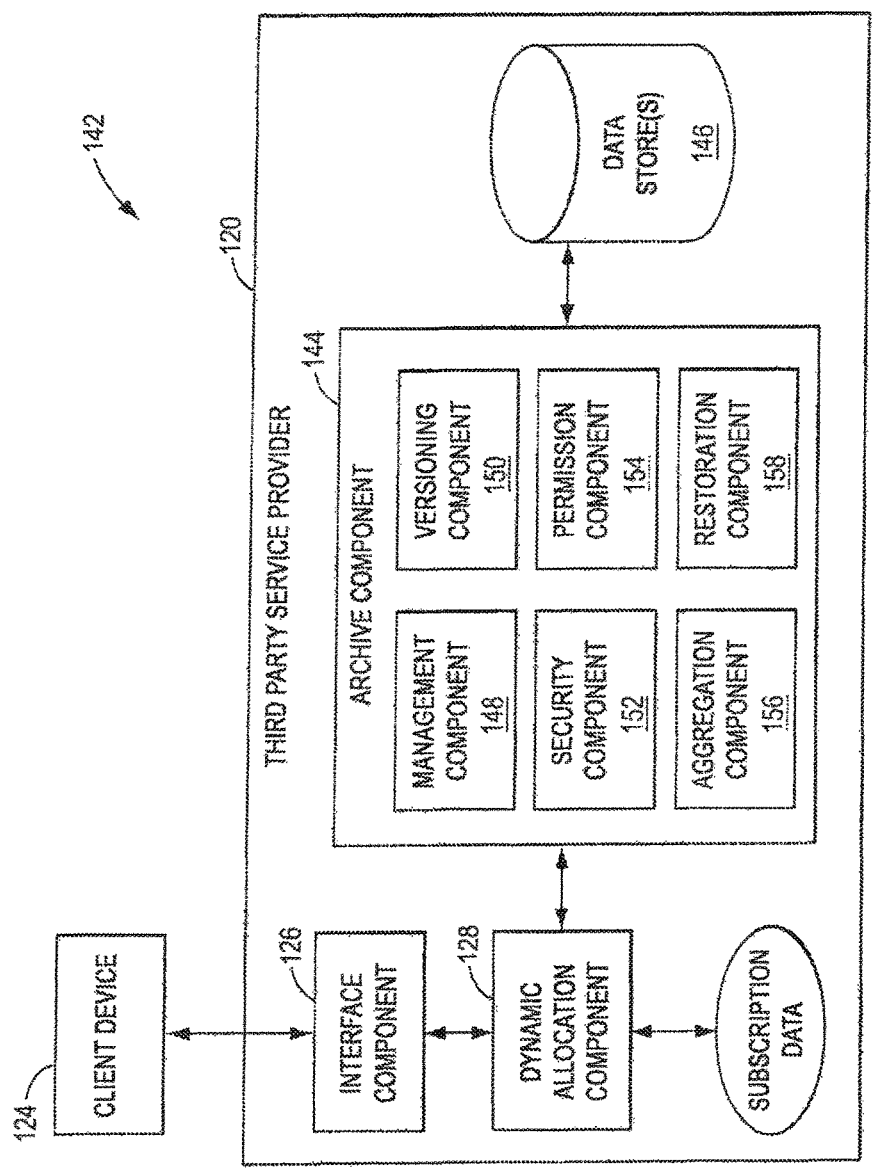

Referring to FIG. 37, the flow chart shows an embodiment of a method for determining a compensated temperature based on a measured temperature of a target on that person, e.g., that person's forehead. In step 2502, the process for determining the compensated temperature starts, e.g., by the user depressing a start button to, e.g., activate thermometer 2410. In step 2504, distance sensor 2414 is used to emit radiation and capture reflected radiation from a target to generate a distance signal, which is communicated to microprocessor 2416. Microprocessor 2416 determines a distance value from the distance signal, which microprocessor 2416 may store in memory 2418. In step 2506, sensor package/assembly 2412 is used to capture thermal radiation emanating from the target to generate a temperature signal, and, optionally, to capture an ambient and/or thermometer temperature, which are communicated to microprocessor 2416. Microprocessor 2416 determines a temperature value from the temperature signal, which microprocessor 2416 may store in memory 2418. In optional step 2508, which is performed when the predetermined compensation information includes a look-up table, microprocessor 2416 determines a relationship between the distance value and the temperature values using predetermined compensation information. In step 2510 microprocessor 16 determines a compensated temperature value based on the predetermined compensation information. In step 2512, microprocessor 2416 stores the compensated temperature in memory 2418. In step 2514, the compensated temperature value is communicated.

Humidity Sensor

Absolute humidity is the total amount of water vapor present in a given volume of air. It does not take temperature into consideration. Absolute humidity in the atmosphere ranges from near zero to roughly 30 grams per cubic meter when the air is saturated at 30° C.

Absolute humidity is the mass of the water vapor ($m_w$), divided by the volume of the air and water vapor mixture ($P_{net}$), which can be expressed as:

$$AH = \frac{m_w}{p_{net}}.$$

The absolute humidity changes as air temperature or pressure changes. This makes it unsuitable for chemical engineering calculations, e.g. for clothes dryers, where temperature can vary considerably. As a result, absolute humidity in chemical engineering may refer to mass of water vapor per unit mass of dry air, also known as the mass mixing ratio (see "specific humidity" below), which is better suited for heat and mass balance calculations. Mass of water per unit volume as in the equation above is also defined as volumetric humidity. Because of the potential confusion, British Standard BS 1339 (revised 2002) suggests avoiding the term "absolute humidity". Units should always be carefully checked. Many humidity charts are given in g/kg or kg/kg, but any mass units may be used.

The field concerned with the study of physical and thermodynamic properties of gas-vapor mixtures is named psychrometrics.

The relative humidity (ϕ) of an air-water mixture is defined as the ratio of the partial pressure of water vapor (H2O) ($e_w$) in the mixture to the saturated vapor pressure of water ($e^*_w$) at a given temperature. Thus the relative humidity of air is a function of both water content and temperature.

Relative humidity is normally expressed as a percentage and is calculated by using the following equation:[5]

$$\phi = \frac{e_w}{e^*_w} \times 100\%$$

Relative humidity is an important metric used in weather forecasts and reports, as it is an indicator of the likelihood of precipitation, dew, or fog. In hot summer weather, a rise in relative humidity increases the apparent temperature to humans (and other animals) by hindering the evaporation of perspiration from the skin. For example, according to the Heat Index, a relative humidity of 75% at 80.0° F. (26.7° C.) would feel like 83.6° F.±1.3° F. (28.7° C.±0.7° C.) at −44% relative humidity.

Specific humidity:

Specific humidity (or moisture content) is the ratio of water vapor mass ($m_v$) to the air parcel's total (i.e., including dry) mass ($m_a$) and is sometimes referred to as the humidity ratio.[8] Specific humidity is approximately equal to the "mixing ratio", which is defined as the ratio of the mass of water vapor in an air parcel to the mass of dry air for the same parcel.

Specific Humidity is defined as:

$$SH = \frac{m_v}{m_a}.$$

Specific humidity can be expressed in other ways including:

$$SH = \frac{0.622 p_{(H_2O)}}{p_{(dry\ air)}}$$

$$0.622 = \frac{MM_{H_2O}}{MM_{dry\ air}}$$

or:

$$SH = \frac{0.622 p_{(H_2O)}}{p - 0.378 * p_{(H_2O)}}.$$

Using this definition of specific humidity, the relative humidity can be expressed as $$\phi = \frac{SH * p}{(0.622 + 0.378 * SH) p^*_{(H_2O)}} \times 100$$

However, specific humidity is also defined as the ratio of water vapor to the total mass of the system (dry air plus water vapor). For example, the ASHRAE 2009 Handbook defines specific humidity as "the ratio of the mass of water vapor to total mass of the moist air sample".

Measurement

Various devices can be used to measure and regulate humidity. In one embodiment a psychrometer or hygrometer is used.

Figure 42:
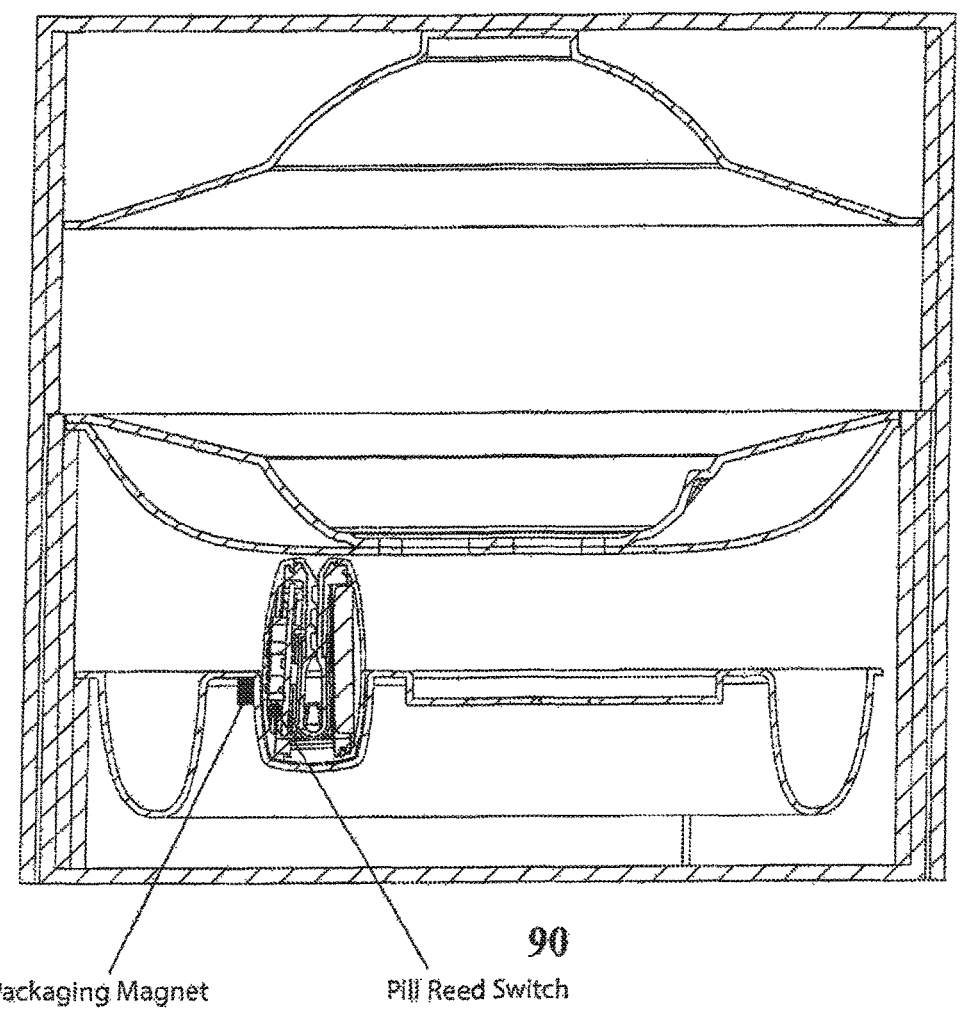
FIG. 42 illustrates one embodiment of a packaging for the motion detection device.

In one embodiment, illustrated in FIG. 42, a packaging is provided for the motion detection device 42 that includes a packaging magnet and the reed switch 90. The magnet activates the reed switch which keeps the motion detection device 42 in a low power mode. The low power mode preserves the motion detection device 42 battery life during storage and shipment. Once the user receives the packaging and removes the motion detection device 42 the reed switch 90 is deactivated (because it is no longer in close proximity to the magnet) and the motion detection device 42 is turned on. Simply removing the motion detection device 42 from its packaging is enough to deactivate the reed switch 90. No additional steps are needed. In one embodiment the distance between the packaging magnet and reed switch 90 is no greater than 2 mm, 1 mm, 0.5 mm, 0.4 mm, 0.3 mm, 0.2 mm, 0.1 mm and in a substantially adjacent relation. It can be as close as you want in transit. In one embodiment the packaging magnet has a Gauss. In one embodiment any kind of reed switch 90 can be used.

Figure 43:
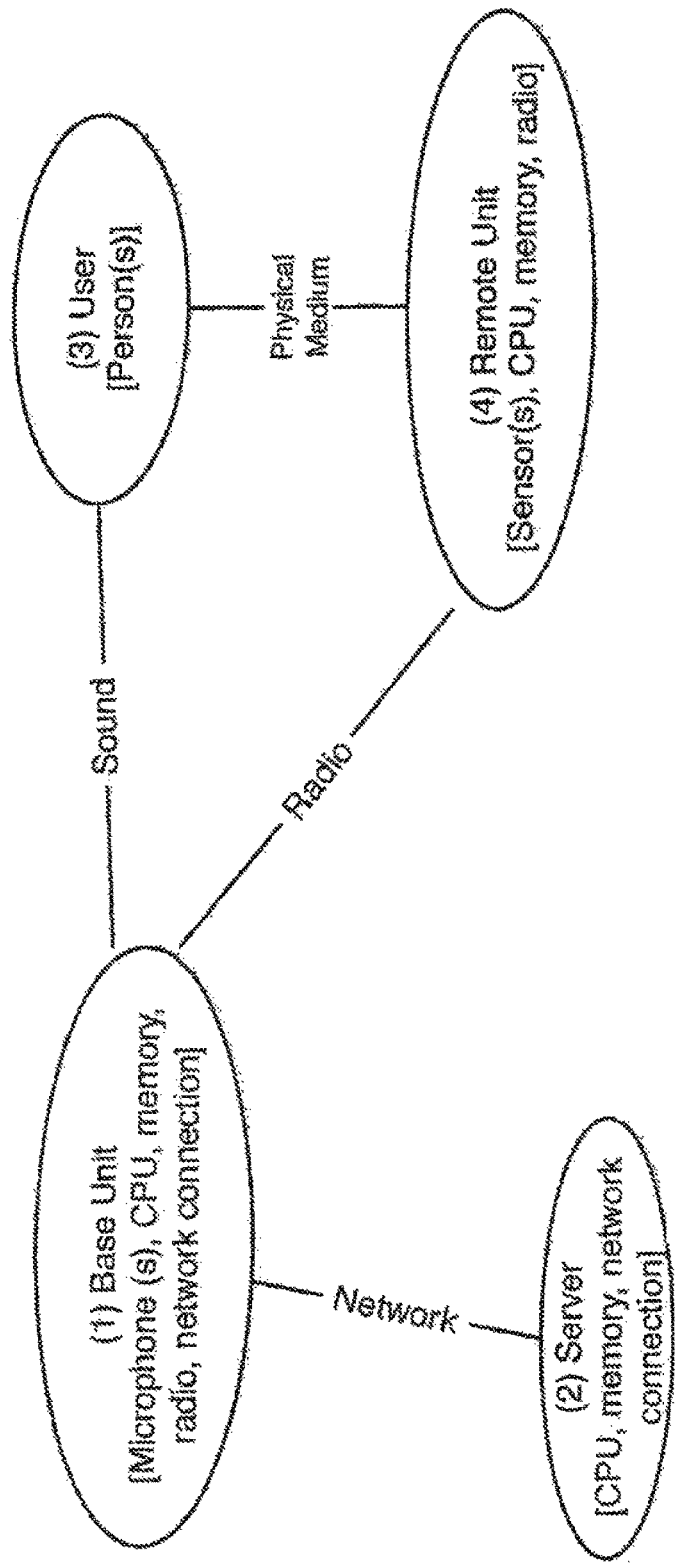
FIGS. 43 and 44 illustrate one embodiment of the present invention where recording the movement of the person by the motion detection device is not always preserved, and is halted in response to the sounds received from the room where the person is located.
Figure 44:
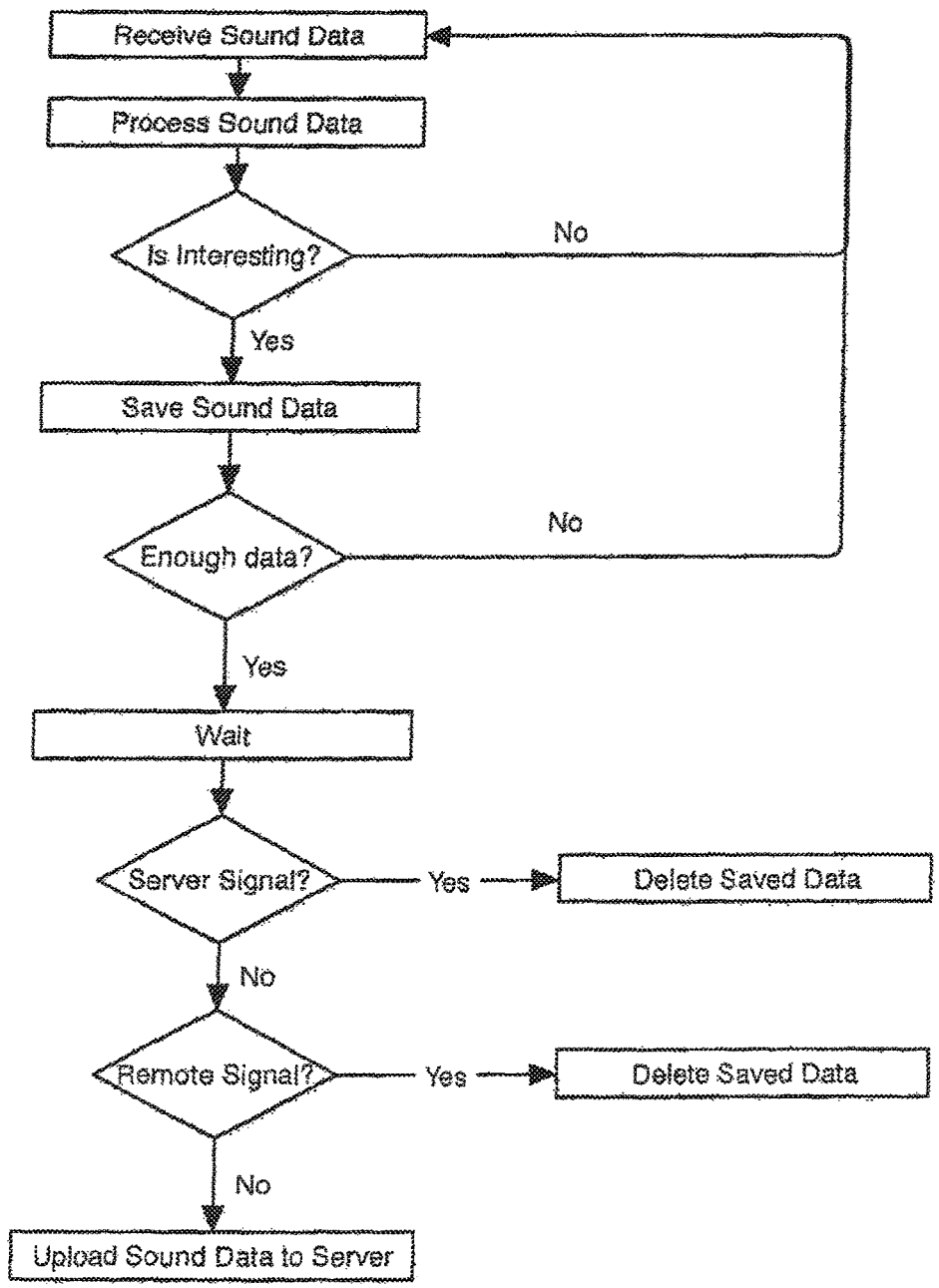

As illustrated in FIGS. 43 and 44, recording of the sound where at the location, preferably in a dwelling room environment, by monitoring device 42 is not always preserved. It is halted in response to motion sounds received from the person monitored. Recording via the microphone 18 is initiated but ceases in responses to signals received from the motion detection device 42 in order to provide privacy. The signals are low energy Bluetooth, the motion detection device 42, when it moves, or after it moves, it sends a signal to the monitoring device 42, which knows that the person moves and will cease recording. In one embodiment the system 10 has a database of classifications that provide for turn on and off in response to the signals. In one embodiment the system classifies the movement and determines desired to be preserved. The database can have a classifier to determine when to record and when not to for privacy concerns.

a. As a non-limiting example, one embodiment of a cloud system is illustrated in FIGS. 38(a)-38(e).

The cloud based system includes a third party service provider 120, that is provided by the methods used with the present invention, that can concurrently service requests from several clients without user perception of degraded computing performance as compared to conventional techniques where computational tasks can be performed upon a client or a server within a proprietary intranet. The third party service provider (e.g., "cloud") supports a collection of hardware and/or software resources. The hardware and/or software resources can be maintained by an off-premises party, and the resources can be accessed and utilized by identified users over Network Systems. Resources provided by the third party service provider can be centrally located and/or distributed at various geographic locations. For example, the third party service provider can include any number of data center machines that provide resources. The data center machines can be utilized for storing/retrieving data, effectuating computational tasks, rendering graphical outputs, routing data, and so forth.

In one embodiment, the third party service provider can provide any number of resources such as servers, CPU's, data storage services, computational services, word processing services, electronic mail services, presentation services, spreadsheet services, web syndication services (e.g., subscribing to a RSS feed), and any other services or applications that are conventionally associated with personal computers and/or local servers. Further, utilization of any number of third party service providers similar to the third party service provider is contemplated. According to an illustration, disparate third party service providers can be maintained by differing off-premise parties and a user can employ, concurrently, at different times, and the like, all or a subset of the third party service providers.

By leveraging resources supported by the third party service provider 120, limitations commonly encountered with respect to hardware associated with clients and servers within proprietary intranets can be mitigated. Off-premises parties, instead of users of clients or network administrators of servers within proprietary intranets, can maintain, troubleshoot, replace and update the hardware resources. Further, for example, lengthy downtimes can be mitigated by the third party service provider utilizing redundant resources; thus, if a subset of the resources are being updated or replaced, the remainder of the resources can be utilized to service requests from users. According to this example, the resources can be modular in nature, and thus, resources can be added, removed, tested, modified, etc. while the remainder of the resources can support servicing user requests. Moreover, hardware resources supported by the third party service provider can encounter fewer constraints with respect to storage, processing power, security, bandwidth, redundancy, graphical display rendering capabilities, etc. as compared to conventional hardware associated with clients and servers within proprietary intranets.

The cloud based system can include a client device that employs resources of the third party service provider. Although one client device is depicted, it is to be appreciated that the cloud based system can include any number of client devices similar to the client device, and the plurality of client devices can concurrently utilize supported resources. By way of illustration, the client device can be a desktop device (e.g., personal computer), motion/movement/gesture detection device, and the like. Further, the client device can be an embedded system that can be physically limited, and hence, it can be beneficial to leverage resources of the third party service provider.

Resources can be shared amongst a plurality of client devices subscribing to the third party service provider. According to an illustration, one of the resources can be at least one central processing unit (CPU), where CPU cycles can be employed to effectuate computational tasks requested by the client device. Pursuant to this illustration, the client device can be allocated a subset of an overall total number of CPU cycles, while the remainder of the CPU cycles can be allocated to disparate client device(s). Additionally or alternatively, the subset of the overall total number of CPU cycles allocated to the client device can vary over time. Further, a number of CPU cycles can be purchased by the user of the client device. In accordance with another example, the resources can include data store(s) that can be employed by the client device to retain data. The user employing the client device can have access to a portion of the data store(s) supported by the third party service provider, while access can be denied to remaining portions of the data store(s) (e.g., the data store(s) can selectively mask memory based upon user/device identity, permissions, and the like). It is contemplated that any additional types of resources can likewise be shared.

The third party service provider can further include an interface component that can receive input(s) from the client device and/or enable transferring a response to such input(s) to the client device (as well as perform similar communications with any disparate client devices). According to an example, the input(s) can be request(s), data, executable program(s), etc. For instance, request(s) from the client device can relate to effectuating a computational task, storing/retrieving data, rendering a user interface, and the like via employing one or more resources. Further, the interface component can obtain and/or transmit data over a network connection. According to an illustration, executable code can be received and/or sent by the interface component over the network connection. Pursuant to another example, a user (e.g. employing the client device) can issue commands via the interface component.

Moreover, the third party service provider includes a dynamic allocation component that apportions resources (e.g., hardware resource(s)) supported by the third party service provider to process and respond to the input(s) (e.g., request(s), data, executable program(s) and the like) obtained from the client device.

Although the interface component is depicted as being separate from the dynamic allocation component, it is contemplated that the dynamic allocation component can include the interface component or a portion thereof. The interface component can provide various adaptors, connectors, channels, communication paths, etc. to enable interaction with the dynamic allocation component.

Figure 39:
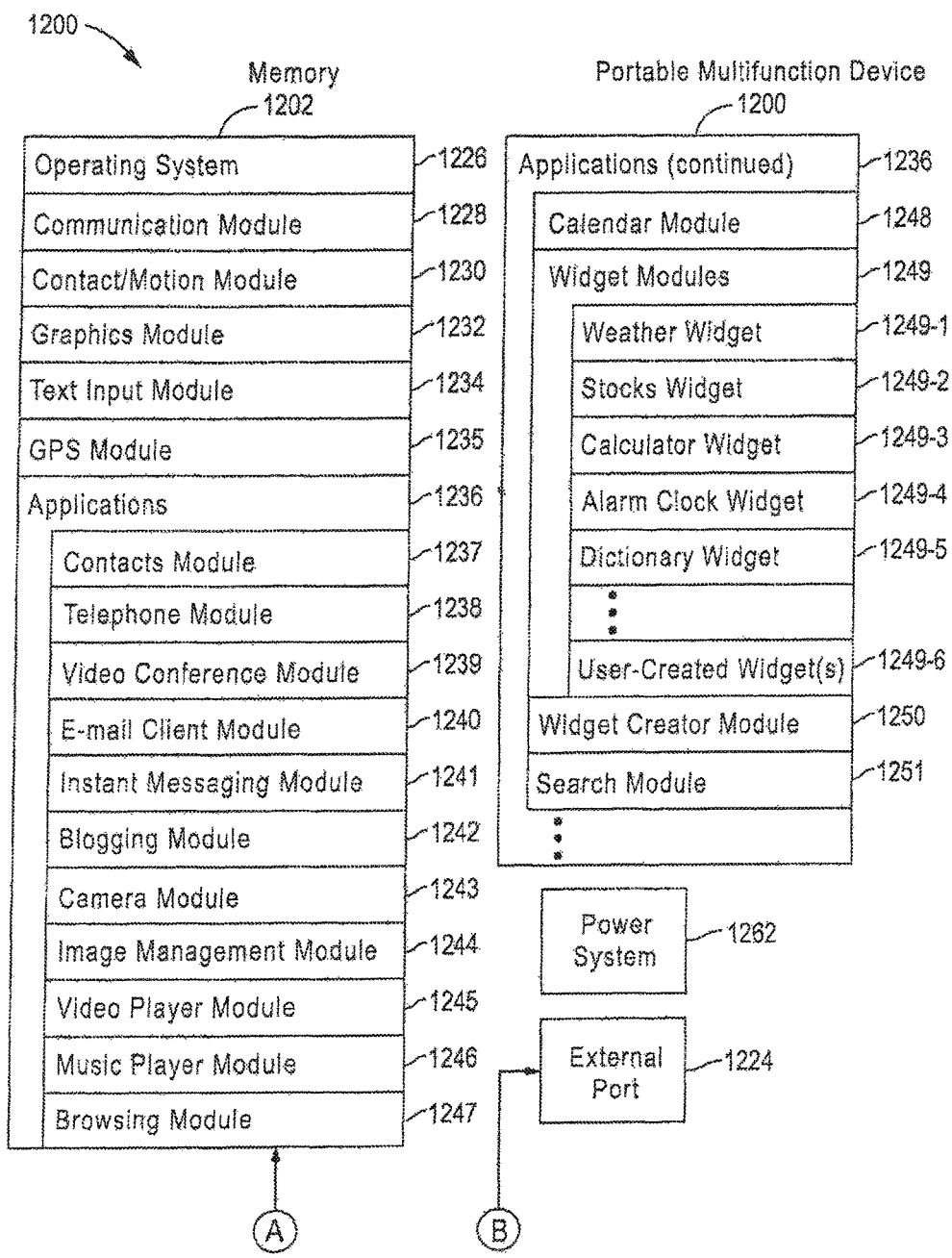
FIGS. 39-41 illustrate one embodiment of a mobile device that can be used with the present invention.
Figure 40:
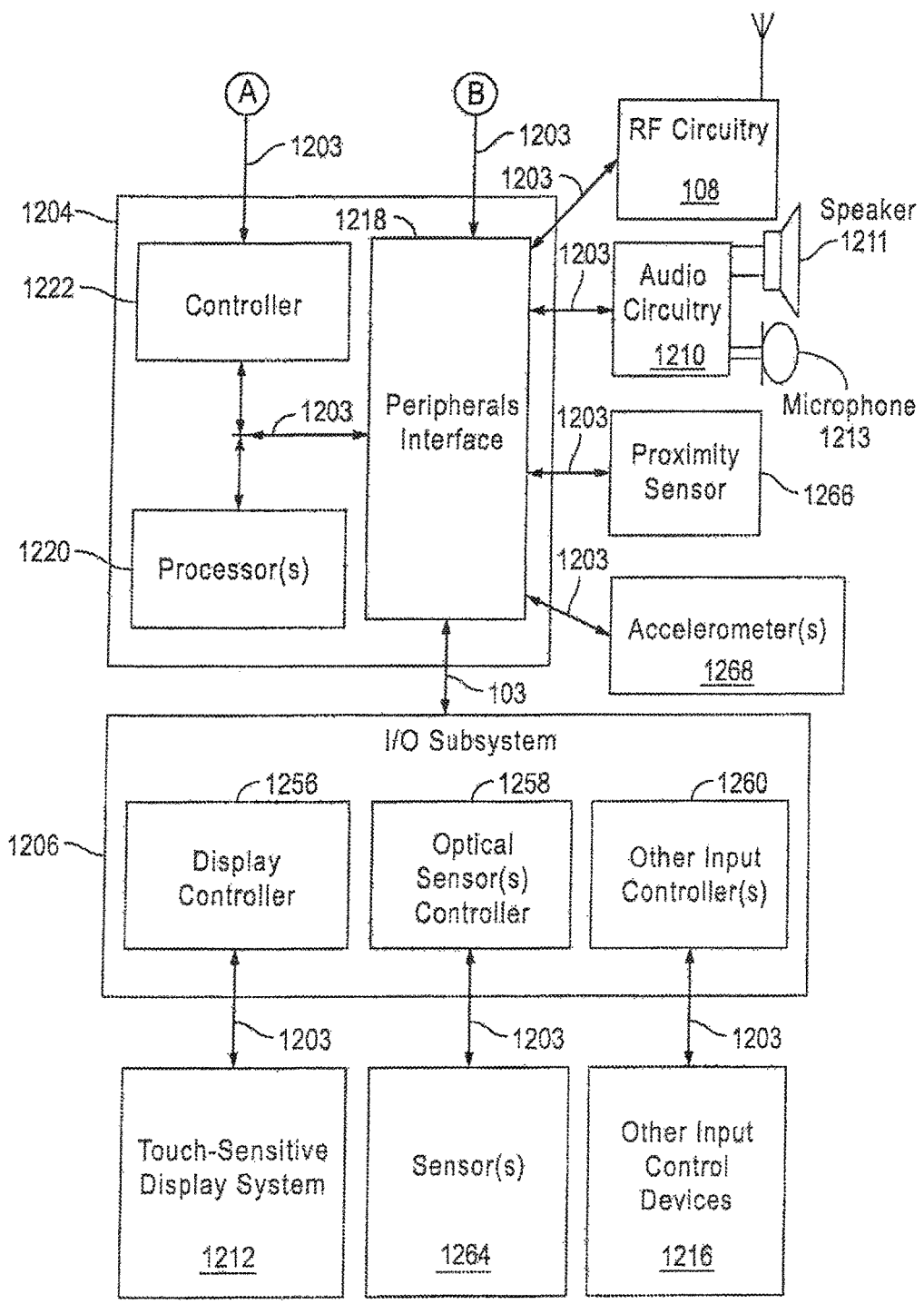
Figure 41:
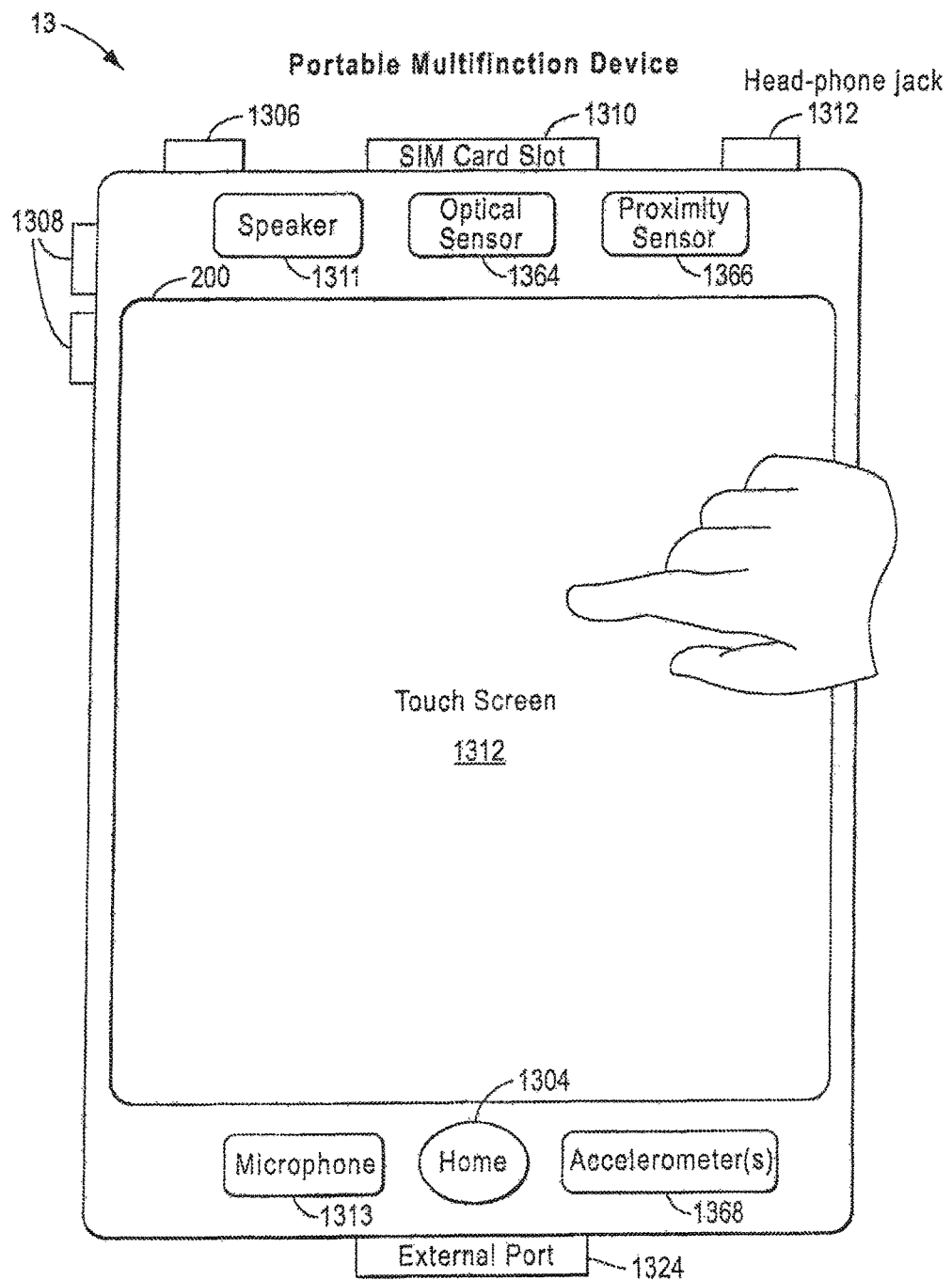

FIGS. 39-41 illustrate one embodiment of a mobile device that can be used with the present invention.

The mobile or computing device can include a display that can be a touch sensitive display. The touch-sensitive display is sometimes called a "touch screen" for convenience, and may also be known as or called a touch-sensitive display system. The mobile or computing device may include a memory (which may include one or more computer readable storage mediums), a memory controller, one or more processing units (CPU's), a peripherals interface, Network Systems circuitry, including but not limited to RF circuitry, audio circuitry, a speaker, a microphone, an input/output (I/O) subsystem, other input or control devices, and an external port. The mobile or computing device may include one or more optical sensors. These components may communicate over one or more communication buses or signal lines.

It should be appreciated that the mobile or computing device is only one example of a portable multifunction mobile or computing device, and that the mobile or computing device may have more or fewer components than shown, may combine two or more components, or a may have a different configuration or arrangement of the components. The various components may be implemented in hardware, software or a combination of hardware and software, including one or more signal processing and/or application specific integrated circuits.

Memory may include high-speed random access memory and may also include non-volatile memory, such as one or more magnetic disk storage devices, flash memory devices, or other non-volatile solid-state memory devices. Access to memory by other components of the mobile or computing device, such as the CPU and the peripherals interface, may be controlled by the memory controller.

The peripherals interface couples the input and output peripherals of the device to the CPU and memory. The one or more processors run or execute various software programs and/or sets of instructions stored in memory to perform various functions for the mobile or computing device and to process data.

In some embodiments, the peripherals interface, the CPU, and the memory controller may be implemented on a single chip, such as a chip. In some other embodiments, they may be implemented on separate chips.

The Network System circuitry receives and sends signals, including but not limited to RF, also called electromagnetic signals. The Network System circuitry converts electrical signals to/from electromagnetic signals and communicates with communications Network Systems and other communications devices via the electromagnetic signals. The Network Systems circuitry may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. The Network Systems circuitry may communicate with Network Systems and other devices by wireless communication.

The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), BLUETOOTH®, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this document.

The audio circuitry, the speaker, and the microphone provide an audio interface between a user and the mobile or computing device. The audio circuitry receives audio data from the peripherals interface, converts the audio data to an electrical signal, and transmits the electrical signal to the speaker. The speaker converts the electrical signal to human-audible sound waves. The audio circuitry also receives electrical signals converted by the microphone from sound waves. The audio circuitry converts the electrical signal to audio data and transmits the audio data to the peripherals interface for processing. Audio data may be retrieved from and/or transmitted to memory and/or the Network Systems circuitry by the peripherals interface. In some embodiments, the audio circuitry also includes a headset jack. The headset jack provides an interface between the audio circuitry and removable audio input/output peripherals, such as output-only headphones or a headset with both output (e.g., a headphone for one or both ears) and input (e.g., a microphone).

The I/O subsystem couples input/output peripherals on the mobile or computing device, such as the touch screen and other input/control devices, to the peripherals interface. The I/O subsystem may include a display controller and one or more input controllers for other input or control devices. The one or more input controllers receive/send electrical signals from/to other input or control devices. The other input/control devices may include physical buttons (e.g., push buttons, rocker buttons, etc.), dials, slider switches, and joysticks, click wheels, and so forth. In some alternate embodiments, input controller(s) may be coupled to any (or none) of the following: a keyboard, infrared port, USB port, and a pointer device such as a mouse. The one or more buttons may include an up/down button for volume control of the speaker and/or the microphone. The one or more buttons may include a push button. A quick press of the push button may disengage a lock of the touch screen or begin a process that uses gestures on the touch screen to unlock the device, as described in U.S. patent application Ser. No. 11/322,549, "Unlocking a Device by Performing Gestures on an Unlock Image," filed Dec. 23, 2005, which is hereby incorporated by reference in its entirety. A longer press of the push button may turn power to the mobile or computing device on or off. The user may be able to customize a functionality of one or more of the buttons. The touch screen is used to implement virtual or soft buttons and one or more soft keyboards.

The touch-sensitive touch screen provides an input interface and an output interface between the device and a user. The display controller receives and/or sends electrical signals from/to the touch screen. The touch screen displays visual output to the user. The visual output may include graphics, text, icons, video, and any combination thereof (collectively termed "graphics"). In some embodiments, some or all of the visual output may correspond to user-interface objects, further details of which are described below.

A touch screen has a touch-sensitive surface, sensor or set of sensors that accepts input from the user based on haptic and/or tactile contact. The touch screen and the display controller (along with any associated modules and/or sets of instructions in memory) detect contact (and any movement or breaking of the contact) on the touch screen and converts the detected contact into interaction with user-interface objects (e.g., one or more soft keys, icons, web pages or images) that are displayed on the touch screen. In an exemplary embodiment, a point of contact between a touch screen and the user corresponds to a finger of the user.

The touch screen may use LCD (liquid crystal display) technology, or LPD (light emitting polymer display) technology, although other display technologies may be used in other embodiments. The touch screen and the display controller may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with a touch screen.

A touch-sensitive display in some embodiments of the touch screen may be analogous to the multi-touch sensitive tablets described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in their entirety. However, a touch screen displays visual output from the portable mobile or computing device, whereas touch sensitive tablets do not provide visual output.

A touch-sensitive display in some embodiments of the touch screen may be as described in the following applications: (1) U.S. patent application Ser. No. 11/381,313, "Multipoint Touch Surface Controller," filed May 12, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

The touch screen may have a resolution in excess of 1000 dpi. In an exemplary embodiment, the touch screen has a resolution of approximately 1060 dpi. The user may make contact with the touch screen using any suitable object or appendage, such as a stylus, a finger, and so forth. In some embodiments, the user interface is designed to work primarily with finger-based contacts and facial expressions, which are much less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, the mobile or computing device may include a touchpad (not shown) for activating or deactivating particular functions. In some embodiments, the touchpad is a touch-sensitive area of the device that, unlike the touch screen, does not display visual output. The touchpad may be a touch-sensitive surface that is separate from the touch screen or an extension of the touch-sensitive surface formed by the touch screen.

In some embodiments, the mobile or computing device may include a physical or virtual click wheel as an input control device. A user may navigate among and interact with one or more graphical objects (henceforth referred to as icons) displayed in the touch screen by rotating the click wheel or by moving a point of contact with the click wheel (e.g., where the amount of movement of the point of contact is measured by its angular displacement with respect to a center point of the click wheel). The click wheel may also be used to select one or more of the displayed icons. For example, the user may press down on at least a portion of the click wheel or an associated button. User commands and navigation commands provided by the user via the click wheel may be processed by an input controller as well as one or more of the modules and/or sets of instructions in memory. For a virtual click wheel, the click wheel and click wheel controller may be part of the touch screen and the display controller, respectively. For a virtual click wheel, the click wheel may be either an opaque or semitransparent object that appears and disappears on the touch screen display in response to user interaction with the device. In some embodiments, a virtual click wheel is displayed on the touch screen of a portable multifunction device and operated by user contact with the touch screen.

The mobile or computing device also includes a power system for powering the various components. The power system may include a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

The mobile or computing device may also include one or more sensors, including not limited to optical sensors. In one embodiment an optical sensor is coupled to an optical sensor controller in I/O subsystem. The optical sensor may include charge-coupled device (CCD) or complementary metal-oxide semiconductor (CMOS) phototransistors. The optical sensor receives light from the environment, projected through one or more lens, and converts the light to data representing an image. In conjunction with an imaging module (also called a camera module); the optical sensor may capture still images or video. In some embodiments, an optical sensor is located on the back of the mobile or computing device, opposite the touch screen display on the front of the device, so that the touch screen display may be used as a viewfinder for either still and/or video image acquisition. In some embodiments, an optical sensor is located on the front of the device so that the user's image may be obtained for videoconferencing while the user views the other video conference participants on the touch screen display. In some embodiments, the position of the optical sensor can be changed by the user (e.g., by rotating the lens and the sensor in the device housing) so that a single optical sensor may be used along with the touch screen display for both video conferencing and still and/or video image acquisition.

The mobile or computing device may also include one or more proximity sensors. In one embodiment, the proximity sensor is coupled to the peripherals interface. Alternately, the proximity sensor may be coupled to an input controller in the I/O subsystem. The proximity sensor may perform as described in U.S. patent application Ser. No. 11/241,839, "Proximity Detector In Handheld Device," filed Sep. 30, 2005; Ser. No. 11/240,788, "Proximity Detector In Handheld Device," filed Sep. 30, 2005; Ser. No. 13/096,386, "Using Ambient Light Sensor To Augment Proximity Sensor Output"; Ser. No. 13/096,386, "Automated Response To And Sensing Of User Activity In Portable Devices," filed Oct. 24, 2006; and Ser. No. 11/638,251, "Methods And Systems For Automatic Configuration Of Peripherals," which are hereby incorporated by reference in their entirety. In some embodiments, the proximity sensor turns off and disables the touch screen when the multifunction device is placed near the user's ear (e.g., when the user is making a phone call). In some embodiments, the proximity sensor keeps the screen off when the device is in the user's pocket, purse, or other dark area to prevent unnecessary battery drainage when the device is a locked state.

In some embodiments, the software components stored in memory may include an operating system, a communication module (or set of instructions), a contact/motion module (or set of instructions), a graphics module (or set of instructions), a text input module (or set of instructions), a Global Positioning System (GPS) module (or set of instructions), and applications (or set of instructions).

The operating system (e.g., Darwin, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

The communication module facilitates communication with other devices over one or more external ports and also includes various software components for handling data received by the Network Systems circuitry and/or the external port. The external port (e.g., Universal Serial Bus (USB), FIREWIRE, etc.) is adapted for coupling directly to other devices or indirectly over Network System. In some embodiments, the external port is a multi-pin (e.g., 30-pin) connector that is the same as, or similar to and/or compatible with the 30-pin connector used on iPod (trademark of Apple Computer, Inc.) devices.

The contact/motion module may detect contact with the touch screen (in conjunction with the display controller) and other touch sensitive devices (e.g., a touchpad or physical click wheel). The contact/motion module includes various software components for performing various operations related to detection of contact, such as determining if contact has occurred, determining if there is movement of the contact and tracking the movement across the touch screen, and determining if the contact has been broken (i.e., if the contact has ceased). Determining movement of the point of contact may include determining speed (magnitude), velocity (magnitude and direction), and/or an acceleration (a change in magnitude and/or direction) of the point of contact. These operations may be applied to single contacts (e.g., one finger contacts) or to multiple simultaneous contacts (e.g., "multitouch"/multiple finger contacts). In some embodiments, the contact/motion module and the display controller also detect contact on a touchpad. In some embodiments, the contact/motion module and the controller detects contact on a click wheel.

Examples of other applications that may be stored in memory include other word processing applications, JAVA-enabled applications, encryption, digital rights management, voice recognition, and voice replication.

In conjunction with touch screen, display controller, contact module, graphics module, and text input module, a contacts module may be used to manage an address book or contact list, including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone, video conference, e-mail, or IM; and so forth.

In one embodiment system 10 is used to detect sleep disorders and psychiatric disorders that are closely interrelated. The system detects sleep disorders and sleep disturbances. These disorders are related to some degrees of mood disturbances and psychiatric disorders.

The detect sleep disorders are associated with a psychiatric pathology that can be primary or secondary.

A sleep disorder is judged to be primary in nature when no etiology can be identified or when, related to a mental disorder, it is sufficiently severe to warrant independent clinical attention. Such patients focus on their sleep disturbances and sublimate their psychiatric symptomatology (which may emerge only after a systematic questioning).

In one embodiment the sleep and sleep related data collected with system 10 relative to sleep disorders is used to provide analysis on the impact on treatment and the follow-up of patients.

As non-limiting examples system 10 is used to determine insomnia. This is then used to classify a plurality of categories of sleep disorders associated with mental disorders including but not limited to: (i) mental disorders producing insomnia; (ii) depression; and (iii) anxiety.

As a non-limiting example between 35% to 75% of depressed individuals have insomnia. As a non-limiting example system 10 is used to detect insomnia that includes but is not limited to: difficulties of initiating or maintaining sleep.

In one embodiment system 10 is used to detect polysomnographic abnormalities in sleep during a major depressive episode. In one embodiment system detects the precocious appearance of paradoxical sleep.

In one embodiment detected insomnia is an indicator of a precocious symptom of a manic episode. In one embodiment system 10 measures reduced total sleep time and sleep efficacy.

In one embodiment system 10 is used to detect various levels of insomnia which is indicative of different levels of anxiety disorders, panic disorders, posttraumatic stress disorders and the like.

As a non-limiting example system 10 measures: (i) REM sleep of patients; (ii) increases in sleep latency as compared to non-insomnia subjects; (iii) total sleep time; and (iv) a reduction in sleep efficiency.

In one embodiment system 10 records and analyzes nocturnal panic attacks. These attacks can occur between stages 2 and 3 as opposed to during nightmares (REM sleep) or night terrors (stage 4).

In one embodiment system 10 is used with schizophrenic patients to determine sleep changes. As non-limiting examples, system 10 determines: (i) a decline in sleep efficiency; sleep disruption; and (iii) a decline in the REM latency as observed also in major depressive episodes.

In one embodiment system 10 is used for monitoring sleep and slap activity of anorexic patients. As a non-limiting example, system 10 is used to determine when a person, an anorexic patient, has a diminution of total sleep time and an increase in the amount of time awake at night.

As a non-limiting example these changes are related to the severity of weight lost.

In one embodiment system 10 is used to determine personality disorders resulting from a detection of insomnia.

In one embodiment system 10 monitors sleep to detect hypersomnia. The consequences of excessive daytime sleepiness can lead to road accidents, work-related accidents and household accidents and the like.

Excessive daytime sleepiness can be a consequence of insomnia in depressed individuals as well as well for those with a bipolar disorder.

In one embodiment hypersomnia is related to anxiety disorders.

In one embodiment system 10 monitors sleep and sleep changes for schizophrenic patients. The process of withdrawal and apathy combined with leading questions about sleep change leads to changes in sleep as determined by system 10.

In one embodiment system 10 monitors sleep in order to detect a variety of psychiatric disorders including but not limited to: (i) continuous recurrent nightmares in response to antidepressant medications in depressed individuals; (ii) nightmares are also observed in schizophrenic patients and acute schizophrenic episodes are often preceded of a period of frequent nightmares; (iii) individuals with a posttraumatic stress disorder may also experience recurrent nightmares about the traumatic event; (iv) eating abnormalities; (v) violent behaviors during sleep, and the like.

In one embodiment a computer-based training program (CBT for CBT), a virtual reality therapy (VRT), and the like is used by system 10 and/or Cloud System 100. As non-limiting examples these can be used to focus on teaching basic coping skills, presenting examples of effective use of coping skills in a number of realistic situations in video form, and provide opportunities for patients to practice and review new skills while receiving substance abuse treatment.

In one embodiment computerized self-administered CBT (CCBT) is used via system 10 and/or Cloud System 110. In this embodiment patients can work at their own pace on their own schedule. Some of the advantages are reduced time, no need for travel, reduced costs, privacy/anonymity, and the like. As with any treatment, adherence is required for the treatment to exert its effect. Patients who do more CBT homework sessions have greater decreases in symptoms. In one embodiment human coaching, with or without a therapist, can be added to the computer-administered CBT treatments. In one embodiment computer-administered CBT is used with limited human contact with non-therapist coaches.

In one embodiment stepped care models of treatment are utilized using system 10 and/or Cloud System 110, matching the appropriate level of intervention, starting with the least restrictive and most effective, enhances treatment outcomes, controls healthcare costs, and helps allocate scarce mental health resources more effectively.

In one embodiment internet-based interventions are used with system 10 and/or Cloud System 110. These can be based on cognitive behavioral therapy, be therapist or non-therapist guided, be guided by third parties who are not therapists and the like.

Cognitive behavioral interventions are designed to reflect concepts from cognitive behavioral therapy (CBT), which examines the association among thoughts, feelings, and behaviors. In one embodiment cognitive behavioral intervention approaches help individuals to identify helpful and unhelpful behaviors, establish goals, and develop skills to solve problems and implement new behaviors to facilitate effective coping. Structured programs based on cognitive behavioral approaches may include activities such as education or relaxation training, may be provided in individual or group settings, and may be delivered in person, telephonically, or by other methods.

In one embodiment patients are assigned a case manager who coordinates all aspects of treatment in conjunction with a program psychiatrist who also provides medication management, in response to system 10 and/or Cloud System 110 provided information. In one embodiment a written treatment contract is provided that is reviewed weekly with a case manager. In one embodiment family interventions and support are also incorporated into the treatment and aftercare.

In one embodiment the patient learns to identify triggers and warning signs of their disorder, to utilize cognitive restructuring, to begin self scheduling and behavioral activation, and optionally to develop interpersonal communication. In one embodiment relapse prevention plans, crisis plans, transition plans for returning to work, school, and the like are developed and used.

In one embodiment system 10 and/or Cloud System 110 is used for self-assessment and behavioral coping. Self-assessment skills create a framework from which a patient can identify realistic priorities for treatment and begin to challenge maladaptive self-cognitions.

In one embodiment system 10 and/or Cloud System 110 provides CBT that focuses on specific problems, problem behaviors and problem thinking are identified, prioritized, and specifically addressed.

In one embodiment system 10 and/or Cloud System 110 provides CBT that is goal oriented. As a non-limiting example patients working with system 10 and/or their therapists are asked to define goals including but not limited to longer-term goals. As a non-limiting example system 10 and/or Cloud System can use structured learning experiences that teach patients to monitor and write down their negative thoughts and mental images. The goal is to recognize how those ideas affect their mood, behavior, and physical condition. In one embodiment patients are taught important coping skills, such as problem solving and scheduling pleasurable experiences.

As a non-limiting CBT patients are expected to take an active role in their learning, in the session and between sessions via system 10 and/or Cloud System 110. They are given homework assignments at each session—some of them graded in the beginning—and the assignment tasks are reviewed at the start of the next session.

As a non-limiting example CBT employs multiple strategies, including Socratic questioning, role playing, imagery, guided discovery, and behavioral experiments. In one embodiment system 10 and/or Cloud System 110 enables the patient to see itself and is then able to control the events that happen around it. This provides a capacity for introspection.

In one embodiment system 10 and/or Cloud System 110 is used for cognitive restructuring which refers to the process in CBT of identifying and changing inaccurate negative thoughts that contribute to the development of depression. This can be done with or without a therapist.

As a non-limiting example a patient can use system 10 and/or Cloud System 110 with CBT to learn to recognize negative thoughts and find a healthier way to view a situation. In one embodiment a goal for a patient is to discover the underlying assumptions out of which those thoughts arise and evaluate them. Once the inaccuracy of the assumption becomes evident, the patient can replace that perspective with a more accurate one.

In one embodiment a patient uses system 10 and/or Cloud System 110 for behavioral activation which aims to help patients engage more often in enjoyable activities and develop or enhance problem-solving skills.

As a non-limiting example inertia can be a problem for people with depression. One major symptom of depression can be loss of interest in things that were once found enjoyable. As a non-limiting example a person with depression stops doing things because he or she thinks it's not worth the effort.

In one embodiment system 10 and/or Cloud System 110 can be used for patient to help the patient schedule enjoyable experiences, often with other people who can reinforce the enjoyment. Part of the process is looking at obstacles to taking part in that experience and deciding how to get past those obstacles by breaking the process down into smaller steps.

In one embodiment patients are encouraged to keep a record of the experience, noting how he or she felt and what the specific circumstances were. If it didn't go as planned, the patient is encouraged to explore why and what might be done to change it. By taking action that moves toward a positive solution and goal, the patient moves farther from the paralyzing inaction that locks him or her inside their disorder.

In one embodiment with anxiety disorders, situations are perceived as more dangerous than they really are. System 10 and/or Cloud System 110 can be used by the patient to challenge its negative thoughts. This can involve questioning the evidence for frightening thoughts, analyzing unhelpful beliefs, and testing out the reality of negative predictions. Strategies for challenging negative thoughts include conducting experiments, weighing the pros and cons of worrying or avoiding the thing you fear, and determining the realistic chances that what you're anxious about will actually happen. This allows the patient to replace negative thoughts with new thoughts that are more accurate and positive.

In one embodiment a patient can learn via system 10 and/or Cloud System 110 learning skills, coping skills, relaxation techniques to counteract anxiety, depression, panic and the like.

In one embodiment System 10 and/or Cloud System 110 is used for the diagnosis of insomnia and/or treatment of insomnia.

In various embodiments a diagnosis of insomnia can be based on the following: (i) A primarily diagnosis from the person experiencing sleep issues, as well as family/caregiver complaints through one or more clinical interview. However it is known that people are often inaccurate in reporting their own sleep latency and periods of wakefulness during the night; (ii) Medical histories and physical examinations can be used to establish comorbid syndromes; (iii) sleep diaries are utilized to document sleep/wake cycles; and (iv) system 10 and/or cloud system 110 are used to document sleep/wake cycles.

In one embodiment in response to system 10 and/or cloud system 110 determinations and/or measure of a person's sleep/wake cycles, the monitored person can receive a sleep therapy worksheet. The monitored person can be advised as follows: (i) Do not stay in bed awake for more than 15-20 minutes, or upset, frustrated, or even just alert; and (ii) Do not compensate for a bad night. Do not turn in early, stay in bed later, or nap. Remember that if you sleep poorly tonight, tomorrow night you are likely to sleep better.

In one embodiment the monitored person is notified by system 10 and/or cloud system 110 of personal triggers for bad sleep including but not limited to: (i) traveling to a different time zone; (ii) certain stresses, such as job, family stress and the like, can cause insomnia; (iii) there are states, including but not limited to depression and anxiety that can cause or increase the chances of insomnia; and (iv) bad habits, including but not limited to working close to bed time and/or working late can be a factor relative to sleep disorders and insomnia.

In one embodiment a determination is made to see if the monitored person suffers from sleep apnea (from movement, breathing, snoring)

As a non-limiting example, this can be determined from: (i) a person's response to questions about their sleep quality, alertness, which can be as matching those questions to clinical benchmarks; (ii) comparisons of a person's movement and sound measurements over a long period of time to those of the population; (ii) comparisons of a person's movement and sound measurements to those of known sleep apniacs. For the preceding, system 10, motion detection device 42 and cloud system 110 are used.

In one embodiment system 10, motion detection device 42 is used with CBT. In one embodiment system 10, motion detection device 42 and cloud system 110 are used along with: a person's response to questions about their sleep quality, alertness, anxiety, depression and the like; comparisons of a person's question responses, sleep habits (latency, consistency of bed time, consistency of wake time) with those of a population over a selected period of time; comparisons of a person's measured sleep habits to those of known insomniacs, and the like.

In one embodiment system 10, motion detection device 42 and cloud system 110 are used for measurement and/or analysis along for determining: changes to a person's sleep habits, including but not limited to a waking time becomes more and more frequently inconsistent, and inconsistency lasts for a long period of time; changes to a person's answers to questions regarding sleep quality and alertness; changes to a person's engagement with the app.

In one embodiment system 10 is utilized for anomaly detection and monitoring of sleep to for insomnia and other sleep related disorders. System 10, motion detection device 42 and cloud system 110 automates parts of the reaction aspect of CBT, which as a non-limiting example can be in an app. In one embodiment system 10, motion detection device 42 and cloud system 110, with or without an app is utilized for persons who keep a sleep diary and track their own sleep anomalies. System 10, motion detection device 42 and cloud system 110 can be used is utilized with a person's sleep diary.

In one embodiment system 10, motion detection device 42 and cloud system 110, with or without an app, are used for the all or some of the following: (i) A person has experienced a higher than normal sleep latency. System 10, motion detection device 42 and cloud system 110 can be used to provide a message regarding relaxation tools and/or reschedule worry-times to earlier in the day; (ii) A person has experienced greater than normal agitated sleep. The person can then be sent a message: Did you have a stressful week? Use relaxation tools. Reschedule worry-times to earlier in the day; and (iii) a person has stayed up longer than usual in the bedroom. The person can then be sent messages: Did you have a lot of work, anxiety and the like. Use relaxation tools. You should return to good sleep habits. (iv) A person went to bed much earlier than usual but woke up at the same time. The following messages can be sent: Please keep consistent habits. Sleep the same duration. If there is no change in sleep this can be an indication of depression. (v) The person went to bed earlier than usual and woke up earlier as well. A message can be sent to keep consistent habits. (vi) A person has not gone to bed for a day but system 10, device 42 and system 110 provide this data. The person can be sending messages such as, Have you gone on a trip, and the like. Remember time-zone adjustment tips. (vii) A person has returned home after a trip. A message to remember time-zone adjustment can be sent. (viii) A person had higher than normal fluctuations in waking time/sleeping time. The person can be reminded of maintaining consistent habits, the use of relaxation techniques depending on the cause, and the like. (ix) A person had lower than normal interactions as determined by system 10, device 42 and system 110. A reminder can be sent to be mindful of sleep. The person can be asked if it is now feeling comfortable with their sleep habits. (x) A person has experienced a change in average particulate levels during a certain time period, e.g., a day, week, and the like. The person can be asked about the cause, and suggestions made relative to improvements. (XI) A person has experienced a spike in particulates sometime today. A timestamp of the spike can be provided. A question as to the cause can be sent. (XII) A person has experienced a change in environmental factor temperature before bed. (XIII) A person has experienced a spike in temperature sometime today. (XIV) A person has experienced a change in humidity. (XV) A person has experienced a spike in sound during a time of day which has not occurred before. (XVI) A person has experienced a change in light levels.

Figure 45:
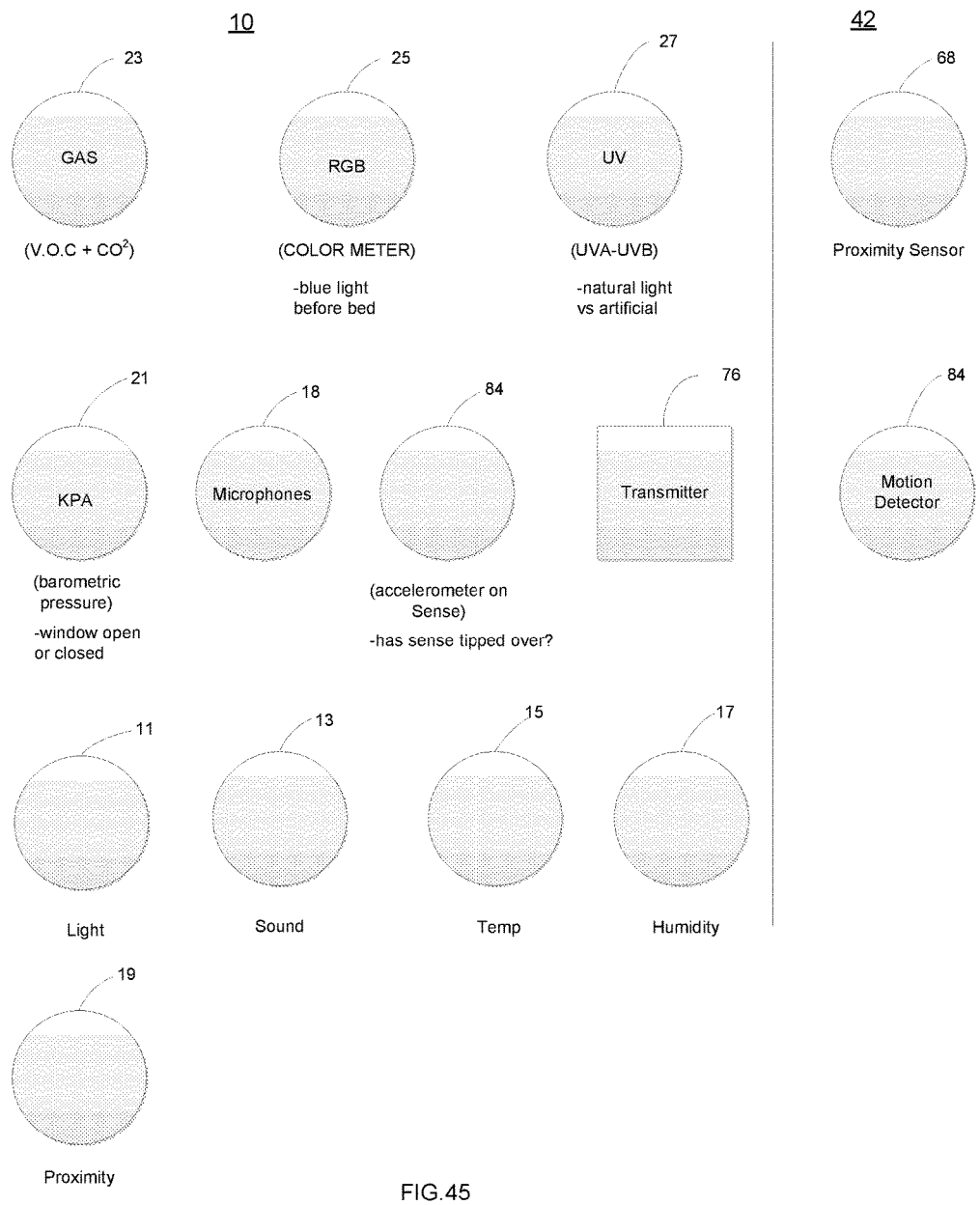
FIG. 45 illustrates one embodiment of a monitoring apparatus of the present invention.

In one embodiment, illustrated in FIG. 45, monitoring device 10 includes all or some of the elements of the monitoring device 10 illustrated in FIGS. 1(a)-1(d) as well as additional elements.

As illustrated in FIG. 45 monitoring device 10 can include includes light, sound temperature and humidity sensors, 11, 13, 15 and 17 respectively. A proximity sensor 19 can be included. A barometric pressure sensor 21 can also be included. As a non-limiting example the barometric pressure sensor 21 can be used to detect any change in pressure in the vicinity of the person being monitored. This can include but is not limited is a window being opened or closed. Monitoring device 10 can also include a motion/movement, gesture detection device such as motion/movement, gesture detection device 84 which can be an accelerometer and the like. In this embodiment the motion/movement, gesture detection device 84 provides additional motion information about motion activity at the bed.

In one embodiment monitoring device 10 includes a gas sensor 23. As a non-limiting example gas sensor 23 can be used to measure VOC's, CO2 and the like in the vicinity of the person being monitored, e.g., the room. A color meter or sensor 25 can be included. As a non-limiting example the color meter 25 provides information about the color of light in the vicinity of the person being monitored, such as in the room where the person being monitored is being monitored. A UV sensor 27 can be included. As a non-limiting example the UV sensor 27 provides information relative to the quality of light in the vicinity of the person being monitored. This can include whether or not the light is natural or artificial. The color temperature and the UV spectrum can be determined with the color sensor 25 and the UV sensor 27.

In one embodiment the monitoring device 10 includes a plurality of microphones 18. As a non-limiting example four microphones 18 can be provided. The one or more microphones 18 can provide for noise cancellation, echo cancellation as well as determine where a sound comes from. Transmitter 76 is also included In one embodiment the motion/movement/gesture/detection device 42 can include all of the elements of the motion/movement/gesture/detection device 42 set forth above as well as additional elements. In one embodiment, illustrated in FIG. 45, a proximity sensor 68 is included that provides information relative to the location of the person being monitored. As a non-limiting example this can be utilized to determine if the person being monitored is in bed, has left the bed, is moving about, and the like. As a non-limiting example the proximity sensor provides allows for a distinction be made to determine if motion is caused by the person being monitored or some other reason such as if motion of anything that can be located near or at the bed where the monitored position is located. As a non-limiting example, the proximity sensor provides information relative to the person being monitored actually being in the bed or not.

As non-limiting examples, the user monitoring device 10 can be used to monitor sleep, monitor the environment, as previously mentioned, used as a personal assistant and the like. In one embodiment the user's respiration is detected, and/or measured without a physical contact to the user. As a non-limiting example, this can be achieved with radar. The radar or other motion detection device can be non-contact. As a non-limiting example, the radar is used for chest movements, back movement and any other body movement which indicates user breathing.

In one embodiment, alerts are provide to the user monitored including but not limited to: visual, light, sound, e-mail, messaging, with the use of a display and the like. In one embodiment a display is provide near the user monitored to provide light, sounds, and the like that are pleasing to the user. In one embodiment a subscription is paid.

In one embodiment user monitoring device 10 has voice interaction that can be a voice service. As a non-limiting example the voice service (VS) is an intelligent and scalable cloud service that adds voice commands to any connected product using microphone 18 and/or speaker module 20 (hereafter collectively "microphone 18). As a non-limiting example the VS users are able to talk to their VS enabled products, play music, answer questions, get news and local information, and control home products, control electronic devices and more.

Voice interaction can be achieved by a variety of different systems and methods. In one embodiment voice interaction uses speech recognition which is an inter-disciplinary subfield of computational linguistics that incorporates knowledge and research in the linguistics, computer science, and electrical engineering fields to develop methodologies and technologies that enables the recognition and translation of spoken language into text by computers and computerized devices such as those categorized as smart technologies and robotics. It is also known as "automatic speech recognition" (ASR), "computer speech recognition", or just "speech to text" (STT).

In one embodiment of speech recognition "training" (also called "enrollment") is used where an individual speaker reads text or isolated vocabulary into a system. The system analyzes the person's specific voice and uses it to fine-tune the recognition of that person's speech, resulting in increased accuracy. As a non-limiting example speech recognition applications include voice user interfaces such as voice commands, call routing, domotic appliance control, search, simple data entry, preparation of structured documents speech-to-text processing, and the like.

In one embodiment Hidden Markov Models (HMMs) are used and can be combined with feed forward artificial neural networks. In one embodiment a deep learning method called Long short term memory (LSTM) is used. In one embodiment deep feed forward (non-recurrent) networks are used. In one embodiment language modeling is used As non-limiting examples a speech recognition systems can be used that is based on Hidden Markov Models. This provides statistical models that output a sequence of symbols or quantities.

In one embodiment a large-vocabulary system is used that is context dependent for phonemes. As a non-limiting example it can use dependency for the phonemes and cepstral normalization to normalize for different speaker and recording conditions In one embodiment a Viterbi algorithm is used to find a best path, and can use dynamically created combination hidden Markov model, which includes both the acoustic and language model information. This can be combined statically beforehand.

HMM's and neural networks can be utilized. As non-limiting examples LSTM Recurrent Neural Networks (RNNs) and Time Delay Neural Networks (TDNN's) can be used.

In one embodiment Deep Neural Networks and DenoisingAutoencoders are used.

In one embodiment neural networks are utilized as a pre-processing for the HMM based recognition.

In one embodiment a deep feed forward neural network (DNN) is used with multiple hidden layers of units between the input and output layers.

In one embodiment a Long short term memory (LSTM) recurrent neural network is used.

In one embodiment scaling up/out and speedup DNN training and decoding is used as follows; (i) sequence discriminative training of DNNs; (ii) feature processing by deep models with solid understanding of the underlying mechanisms; (iii) adaptation of DNNs and of related deep models; (iv) multi-task and transfer learning by DNNs and related deep models; (v) convolution neural networks; (vi) a recurrent neural network and its rich LSTM variants Other types of deep models including tensor-based models and integrated deep generative/discriminative models.

In one embodiment microphone 18 provides voice-enabled activities and or actives by the user. As a non-limiting example the microphone 18 can include a plurality of microphones, e.g., a microphone array, including but not limited to four microphones. In one embodiment the microphone 18 responds to a user's speaking an activating word that wakes the microphone 18. The selected word can be used by all, or can be individualized. The microphone 18 can be used for voice interaction, music playback, making to-do lists, setting alarms, streaming podcasts, playing audiobooks, providing weather, traffic and other real time information, to control one or more mobile devices, one or more smart devices using a home automation hub.

As a non-limiting example in a default mode the microphone 18 continuously listens to all speech, monitoring for the activating word to be spoken. In one embodiment the microphone 18 can have manual and voice-activated remote control which can be used in lieu of the activating word. In one embodiment the microphone 18's microphones can be manually disabled by pressing a mute button to turn off the audio processing circuit.

In one embodiment the microphone 18 uses a Wi-Fi internet connection. In one embodiment microphone's 18 voice recognition capability is based on acoustic modeling, language modeling and the like.

In one embodiment microphone 18 has access to skills built with 3rd-party developed voice experiences that add to the capabilities of any wireless speaker device and/or voice enabled device. As non-limiting examples, such skills can include but are not limited to: play music, answer general questions, set an alarm, order items, pay for items and the like, as set forth hereafter. Skills can be added to increase the capabilities available to the user. In one embodiment microphone 18 has access to a collection of self-service APIs, tools, documentation and code samples that make it fast and easy for any developer to add skills to microphone 18. As non-limiting examples cloud-controlled lighting and thermostat devices can be controlled used the microphone 18. In one embodiment all of the code runs in the cloud and not on a user device. In another embodiment, a user device can be utilized.

In one embodiment microphone 18's natural lifelike voices result from speech-unit selection technology. As a non-limiting example high speech accuracy is achieved through sophisticated natural language processing (NLP) algorithms built into a microphone 18's text-to-speech (TTS) engine.

In one embodiment microphone 18 functionality periodically evolves as new software releases are produced. As a non-limiting example the microphone 18 provides dual-band Wi-Fi 802.11a/b/g/n and Bluetooth 4.0.

In one embodiment microphone 18 is voice controlled at the speaker device, however, a mic-enabled remote control can be used. An action button at monitoring device 10 can be provided for setup by a user in a new location, and a mute button allows the microphones 18 to be turned off. As a non-limiting example microphone 18 devices can have rotation to increase or decrease the speaker volume, be plugged in to operate, and/or use batteries.

In one embodiment microphone 18 provides for private conversations in the user's home, or other non-verbal indications that can identify who is present in the home and who is not. As a non-limiting example this can be based on audible cues such as footstep-cadence or radio/television programming, and the like. As a non-limiting example microphone 18 only streams recordings from the user's home when the activating word activates the device, though the microphone 18 is capable of streaming voice recordings at all times, and can always be listening to detect if a user has uttered the word.

In one embodiment microphone 18 uses past voice recordings the user has sent to the cloud to improve response to future questions the user may pose. To address privacy concerns, the user can delete voice recordings that are currently associated with the user's account.

In one embodiment voice commands include but are not limited to: setting/editing alarms, dismissing alarms, snoozing alarms, sleep sounds, room conditions and the like.

Non-limiting examples of voice commands can include the following:

"Go to a selected web site."
"Instruct one or more connected products or services".
"Search for X"
"Open e-mail"
"Take a picture."
"Record a video."
"Remind me to call or contact a person"
"Remind me to buy an item"
"Set an alarm for a selected time"
"Create a calendar event"
"Where's my package?"
"Note to self: remember to buy X"
"What's the tip for X dollars?"
"Text a person:
"Send an email to a person:
"Listen to voicemail."
"Find a person's number."
"When is a person's birthday?"
"Post something"
"Listen to X"
"Play: X"
"What's this song?"
"Play some music."
"Watch a movie"
"What movies are playing tonight?"
"Where is a movie playing?"
"Show me pictures of a location"
"Navigate to a destination"
"Biking directions to a destination"
"Find a selected tourist site"
"Where is a selected tourist site"
"Where's the nearest type of shop, store or restaurant"
"Show me the menu of a restaurant"
"Call a selected restaurant"
"Show me my flights."
"Where is my hotel?"
"What are some attractions in a selected city"
"What time is it at a selected city or location"
"What's the weather in a selected location on a selected time period"
"Conduct research about anything"
"How do you say selected words in another language"
"What does a selected word or term mean"
"What's a selected company stock price?"
"What is a selected company trading at?"
"What's selected amount of ounces in pounds"
"Perform a mathematical computation"
"When is sunset?"
"Did a sports team win today?"
"How did a sports team do?"
"Wake me up at [alarmTime]"
"Set an [Alarm/Smart Alarm] for [alarmTime] (on) [alarmDate]."
"Set a repeating [Alarm/Smart Alarm] for [alarmTime] (on) [dayOfWeek]s
"Dismiss", "stop.", "off.", "turn off my alarm"
"Snooze"
"Play Sleep Sounds"
"Play [sleepSoundName]"
"Play [sleepSoundName] for [sleepSoundDuration] on sleepSoundVolume]"
"Stop"
"Stop sleep sound"
"What are my bedroom conditions?"

As further non-limiting examples voice interaction can be used for various control functions. Non-limiting examples of control functions are listed above and can also include: voice control over devices, such as large appliances, (e.g., ovens, refrigerators, dishwashers, washers and dryers), small appliances (e.g., toasters, thermostats, coffee makers, microwave ovens), media devices (stereos, televisions, digital video recorders, digital video players), as well as doors, lights, curtains, and the like. However, the uses for voice control are many and these examples are not be considered as limiting.

In one embodiment monitoring system 10 includes an app or mobile device 210 has an app that allows users to control and manage their products from anywhere. In one embodiment monitoring device is a mobile device 210.

In one embodiment monitoring device 10 integrates with a third party voice platform. In one embodiment monitoring device 10 includes personal assistant capability of the monitored person, as well as for a third party in communication with the monitored person.

Figure 46:
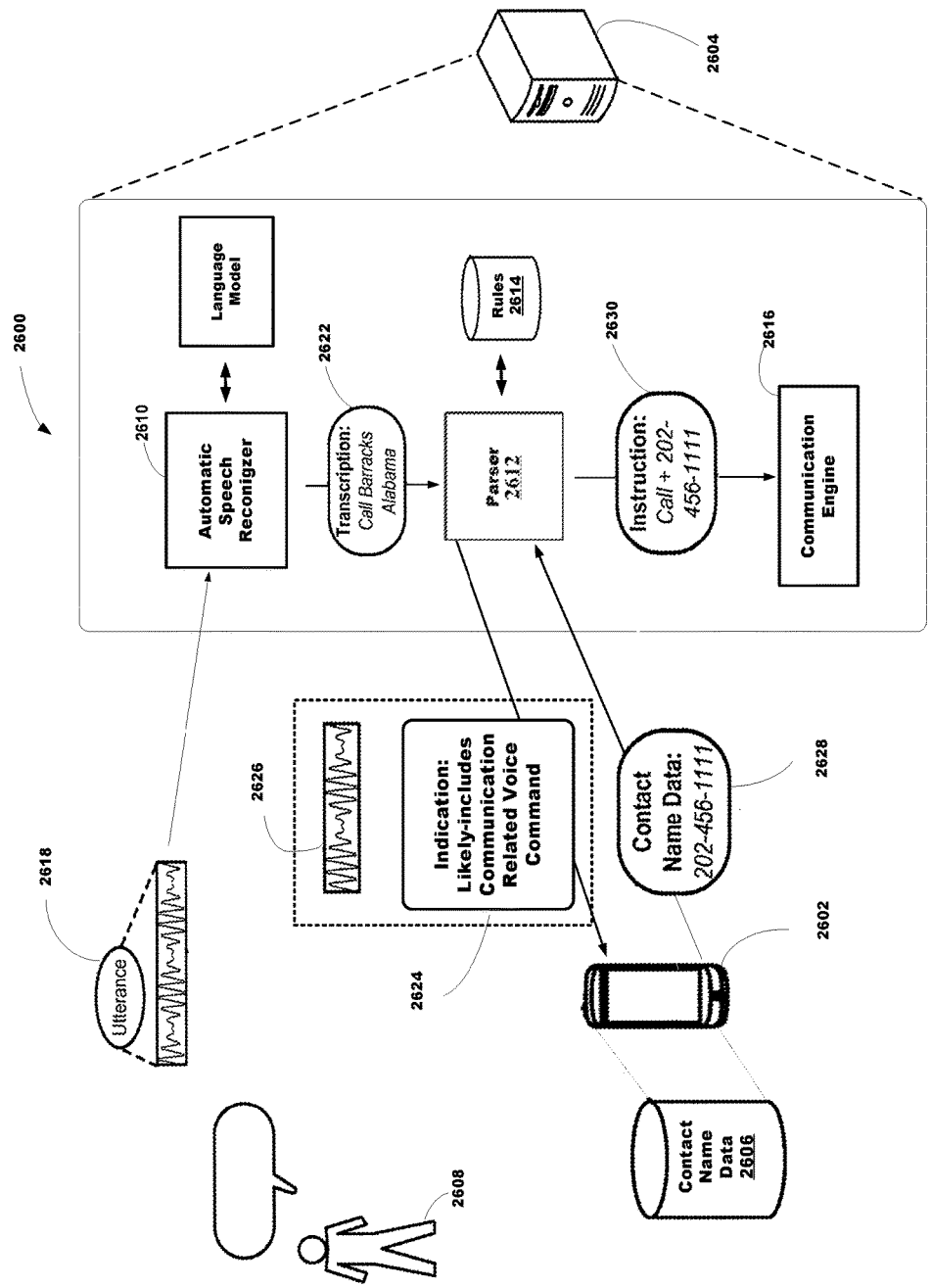
FIG. 46 illustrates one embodiment of a voice recognition system for identifying voice commands.

In one embodiment, illustrated in FIG. 46, illustrates a speech recognition system 2600 for initiating communication based on identifying a voice command. In one embodiment the commands are sent from monitoring device 10 to server, e.g., the cloud server. In one embodiment monitoring device 10 is a mobile device 210. In one embodiment monitoring device 10 and server is in communication with a contact name database 2606 coupled to the cloud based server. In one embodiment the server is coupled to an automatic speech recognizer (ASR) 2610, a parser 2612, a rules database 2614, and a communication engine 2616. The server computing system 2604 is in communication with monitoring device 10 over Network Systems.

In one embodiment monitoring device 10 receives one or more commands by the user, such as those set forth above.

In one embodiment the monitoring device 10 transmits audio data, e.g., the waveform data 2620, corresponds to the utterance 118 to the ASR 110. For example, the monitoring device 10 provides audio data corresponding to the utterance 2618 of the information requested by the command to the ASR 2610 over Network System.

In some embodiments, the ASR 2610 receives the audio data, e.g., the waveform data 2620, corresponding to the utterance 2618 from the monitoring device 10. As a non-limiting example, the ASR 2610 receives the audio data corresponding to the utterance 2618 of the information requested from the command.

In one embodiment, ASR 2610 obtains a transcription of the utterance 2618 using a first language model. As a non-limiting example ASR 2610 processes the utterance 2618 by applying the utterance 2618 to a first language model 2624 to generate a transcription 2622 of the utterance 2618. In one embodiment the first language model 2624 is a "general" or "generic" language model trained on one or more natural languages, e.g., the first language model 2624 is not specific to the user 2608, but is utilized by a general population of users accessing the server computing system 2604.

In one embodiment the ASR 2610 applies the utterance 2618 of the information from the requested command to the first language model 2624 to generate the transcription 2622 of the command.

In one embodiment the ASR 2610 provides the transcription 2622 to the parser 2612. In one embodiment the parser 2612 determines that the transcription 2622 of the utterance 2618 probably includes a voice command.

In one embodiment the parser 2612 uses the rules database 2614 in determining whether the transcription 2622 of the utterance 2618 includes a voice command, or is associated with a voice command. In one embodiment the parser 2612 compares some or all of the transcription 2622 of the utterance 2618 to the rules of the rules database 2614. In response to comparing the transcription 2622 of the utterance 118 to the rules of the rules database 2614, the parser 2612 determines whether the transcription 2622 of the utterance 2618 satisfies at least one rule of the rules database 2614, or matches a text pattern associated with a rule.

In one embodiment, the server computing system 2604 can transmit a portion of the received audio data to monitoring device 10. As a non-limiting example the server computing system 2604 extracts a portion of the received audio data as a waveform 2626.

In one embodiment in response to receiving the indication 2624 from the server computing system 2604, the monitoring device 10 applies a representation of the audio data corresponding to the utterance, e.g., the waveform 2626, to a different, second language model. In the illustrated example, in response to receiving the indication 2624, the monitoring device 10 applies the waveform 2626 to the different, second language model to identify data 2628 that references a contact. In one embodiment monitoring device 10 applies the waveform 2626 to the different, second language model to obtain a transcription of the utterance 2618 that corresponds to the waveform 2626.

By applying the waveform 2626 to a language model, the monitoring device 10 identifies data 2628 that references a contact that is associated with the user 2608. As a non-limiting example monitoring device 10 processes the waveform 2626 according to the second, different language model to identify the data 2628 referencing a contact. As a non-limiting example the monitoring device 10 is in communication with a contact name database 2606. The monitoring device 10 determines that the waveform 2626 "matches," based on the different, second language model, at least one of the contact names stored by the contact name database 2606. As a non-limiting example the contact name database 2606 stores mappings between contact names and an output of the language model.

In one embodiment based on the transcription of the information retrieved from the commend that corresponds to the waveform 2626, the monitoring device 10 identifies a mapping stored by the contact name database 2606 between the transcription of a command and the data 2628. As a non-limiting example in the event of a command to call somebody the data 2628 of a phone number associated with that person is identified.

In one embodiment monitoring device 10 transmits the data 2628 referencing the contact to the server 104, e.g., over Network Systems.

In one embodiment a server computing device 2602, and specifically, the parser 2612, receives the data 2628 referencing the contact. As a non-limiting example the parser 2612 receives the phone number that is associated with the contact corresponding to user's command.

In one embodiment the parser 2612 causes the voice command to be performed using the data 2628 referencing the contact. As a non-limiting example the parser 2612 generates an instruction 2630 that is transmitted to communication engine 2616. The communication engine 2616 causes the voice command to be performed. As a non-limiting example the voice command is performed by monitoring device 10 the server computing system 2604, or a combination of both. In one embodiment the instruction is further based on a portion of a transcription 2622 of the utterance 2618 and the data 2628 referencing the contact.

Figure 47:
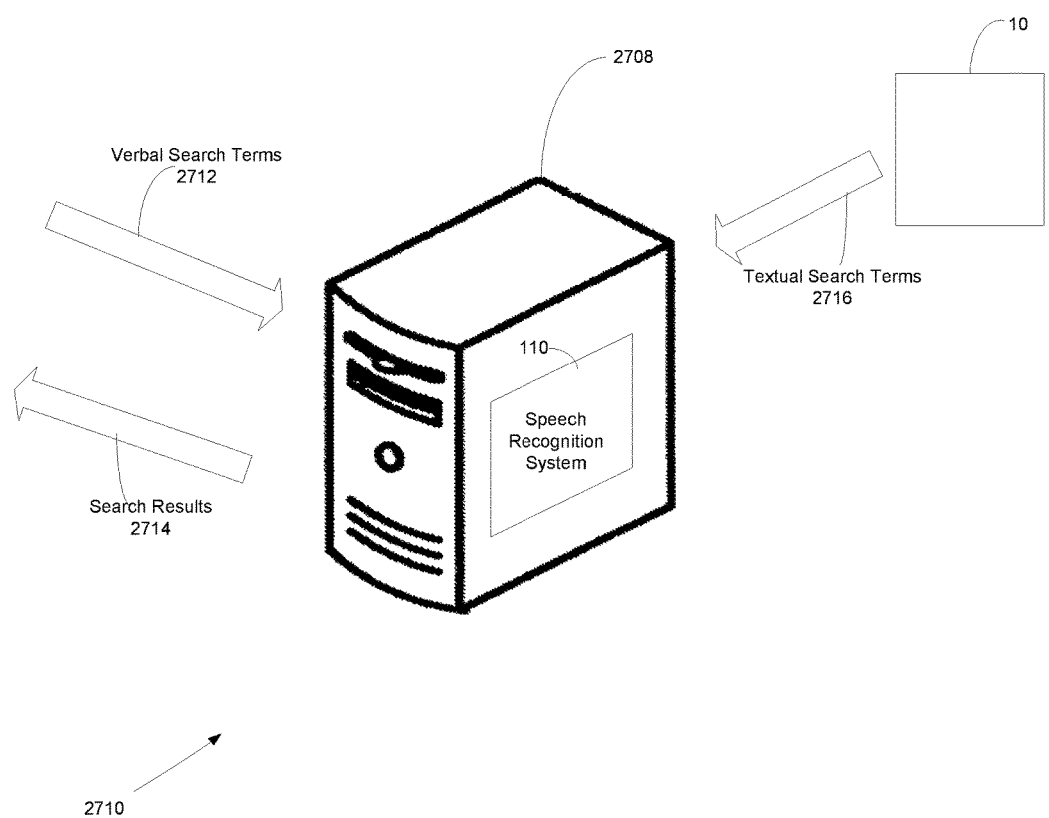
FIG. 47 shows a data entry system able to perform speech recognition on data received from remote audio or text entering devices according to one implementation.

Referring now to FIG. 47 a speech recognition system 2710 receives verbal search terms from a command and uses a language model to access the updated entries for the word and recognize the associated text. In one embodiment a cloud based search server 2708 retrieves the requested data relative to the information requested by the user based on the search terms that have been translated from verbal search terms to text, collects the search results 2714, and transmits the search results, which as a non-limiting example can be monitoring device 10. In one embodiment monitoring device can play a voice, which can be synthesized, through an audio speaker that speaks the results to the user.

In one embodiment monitoring device 10, in FIG. 47, can have networking capabilities and is shown sending textual search terms (commands) 2716 to the search server 2708. The entered textual search terms, which may include one or more portions of sound, can be added to an available dictionary terms for speech recognition system 2710.

As a non-limiting example a probability value may be assigned to the complete terms or the portions of sound based on a chronological receipt of the terms or sounds by the search server 2708 or number of times the terms are received by search server 2708. Popular search terms may be assigned higher probabilities of occurrence and assigned more prominence for a particular time period. In addition, the search may also return data to the device to update probabilities for the concurrence of the words. In particular, other terms associated with a search can have their probabilities increased if the terms themselves already exist in the dictionary. Also, they may be added to the dictionary when they otherwise would not have been in the dictionary. Additionally, a dictionary entry may be changed independently of the others and may have separate probabilities associated with the occurrence of each word.

As non-limiting examples speech recognition system 2710 can utilize language models (grammar) and acoustic models. In one embodiment language models may be rule-based, statistical models, or both. As a non-limiting example a rule based language model has a set of explicit rules describing a limited set of word strings that a user is likely to say in a defined context.

In one embodiment a statistical language model is utilized that is not limited to a predefined set of word strings, and instead represents what word strings occur in a more variable language setting. As a non-limiting example a search entry can be variable because any number of words or phrases may be entered. As a non-limiting example a statistical model uses probabilities associated with the words and phrases to determine which words and phrases are more likely to have been spoken. The probabilities may be constructed using a training set of data to generate probabilities for word occurrence. The larger and more representative the training data set, the more likely it will predict new data, thereby providing more accurate recognition of verbal input.

Language models may also assign categories, or meanings, to strings of words in order to simplify word recognition tasks. For example, a language model may use slot-filling to create a language model that organizes words into slots based on categories. The term "slot" refers to the specific category, or meaning, to which a term or phrase belongs. The system has a slot for each meaningful item of information and attempts to "fill" values from an inputted string of words into the slots. For example, in a travel application, slots could consist of origin, destination, date or time. Incoming information that can be associated with a particular slot could be put into that slot. For example, the slots may indicate that a destination and a date exist.

In one embodiment acoustic models represent the expected sounds associated with the phonemes and words a recognition system must identify. A phoneme is the smallest unit a sound can be broken into, e.g., the sounds "d" and "t" in the words "bid" and "bit." Acoustic models can be used to transcribe uncaptioned video or to recognize spoken queries. It may be challenging to transcribe uncaptioned video or spoken queries because of the limitations of current acoustic models. For instance, this may be because new spoken words and phrases are not in the acoustic language model and also because of the challenging nature of broadcast speech (e.g., possible background music or sounds, spontaneous speech on wide-ranging topics).

Figure 48:
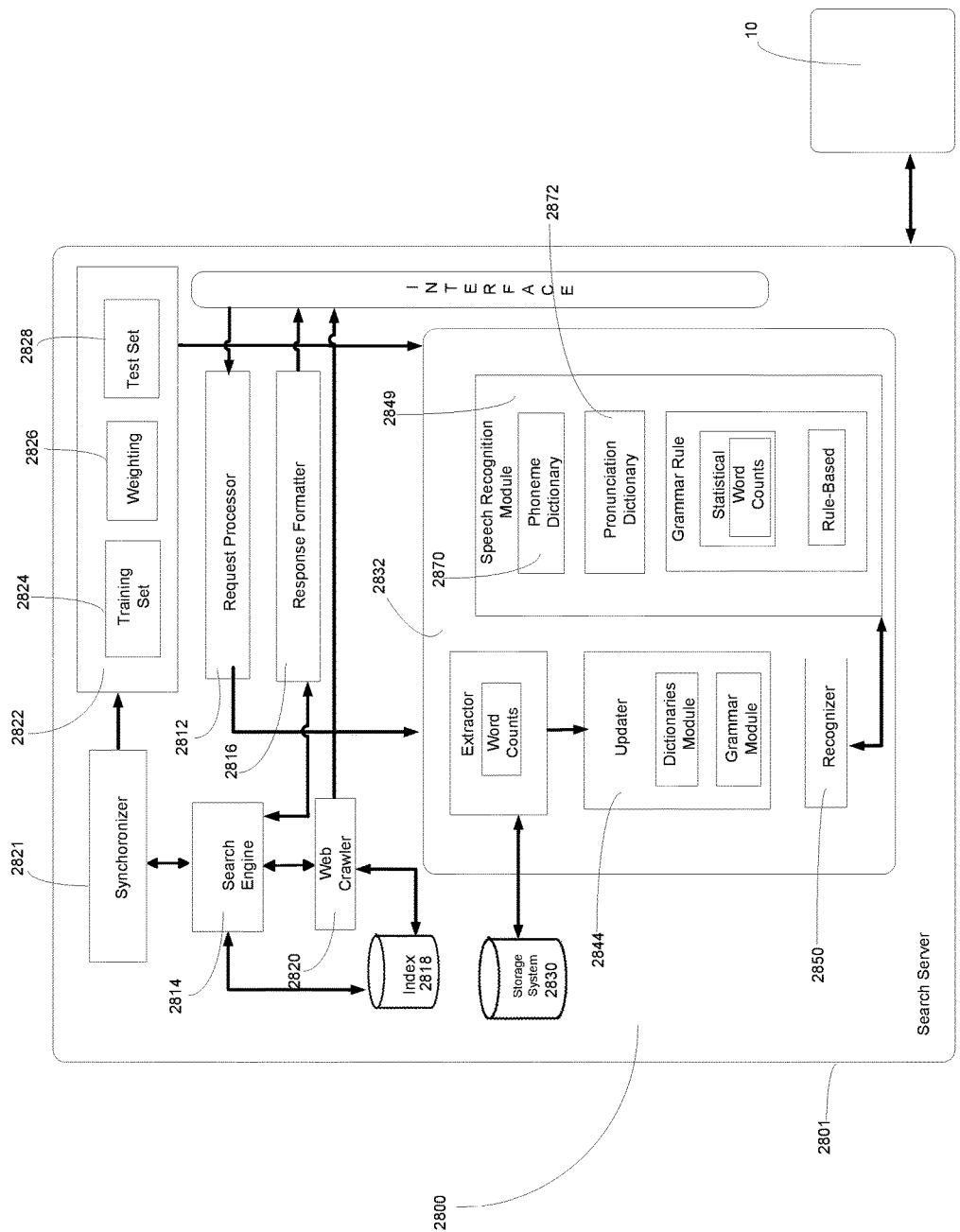
FIG. 48 is a schematic diagram of a search server using a speech recognition system to identify, update and distribute information for a data entry dictionary according to one implementation.

Referring to FIG. 48 one embodiment of a search server 2801 using a speech recognition system 2832 is shown to identify, update and distribute information for a data entry dictionary according to one implementation. System 2800 can be one implementation of system 2700 shown in FIG. 47. In one embodiment system 2800 is implemented as part of a Network System search provider's general system. The system 2800 can be equipped to obtain information about the occurrence and concurrence of terms from various sources. In one embodiment system 2800 also obtains information about the pronunciation of words and phonemes, which include one or more portions of sound, from verbal input associated with textual input. Both types of obtained information are used to generate dictionary information. Such sources could include, for example, audio or transcript data received from a television transmitter, data related to an individual (such as outgoing messages stored in a Sent Items box), data entered verbally or textually into a wireless communication device, or data about search terms entered recently by users of an Internet search service.

The system 2800 can include an interface 2802 to allow communications in a variety of ways.

Commands and requests received from monitoring devices 10 may be provided to request processor 2812, which may interpret a request, associate it with predefined acceptable requests, and pass it on, such as in the form of a command to another component of search server system 2800 to perform a particular action. As a non-limiting example, where the request includes a search request, the request processor 2812 may cause a search engine 2814 to generate search results corresponding to the search request. In one embodiment search engine 2814 can use data retrieval and search techniques like those used by the Google PageRank™ system. The results generated by the search engine client 2814 can be provided back to the original requester using a response formatter 2816. The response formatter 2816 carries out necessary formatting on the results.

Search engine 2814 can use a number of other components for its operation. As a non-limiting example the search engine 2814 can refer to an index 2818 of web sites instead of searching the web sites themselves each time a request is made, so as to make the searching much more efficient. The index 2818 can be populated using information collected and formatted by a web crawler 2820, which may continuously scan potential information sources for changing information. Search engine 2814 may also use a synchronizer 2821 to ensure received data updates system 2800 with the latest language model available.

In addition to search results, system 2800 can use the dictionary generator module 2844 to provide users with updated dictionary information, which may include user-specific information. As a non-limiting example updater module 2844 can operate by extracting relevant concurrence data or information from previous search terms, generating occurrence data for the information, and organizing the information in a manner that can be transmitted to a remote device which can be monitoring device 10.

In one embodiment dictionary generator 2822 uses the components in FIG. 48. As a non-limiting example this can include a training set 2824, weightings 2826, and a test set 2828. In one embodiment the training set 2824 is a set of audio recordings and associated transcripts used to generate pronunciation and sound entries in a pronunciation dictionary 2872 and a phoneme dictionary 2870, respectively. Audio recordings can be associated or synched with the associated transcript text using a synchronizer 2821, and the dictionary generator 2822 can create preliminary dictionary entries based on the synchronized audio recordings and transcripts. In one embodiment, the sounds that are extracted from an audio recording correspond to one or more letters from the transcript that is associated and synchronized with the audio recording. The dictionary generator 2822 uses these extracted components to generate the dictionary entries.

In one embodiment, the weightings include factors, or coefficients, that indicate when the voice recognition system 2800 received a word associated with the weightings. The factors can cause the voice recognition system 2800 to favor words that were received more recently over words that were received in the past. As a non-limiting example the dictionary generator 2822 can access system storage 2830 as necessary. In one embodiment system storage 2830 can be one or more storage locations for files needed to operate voice recognition system 2800.

In one embodiment speech recognition system 2800 uses an extractor to analyze word counts 2842 from the entered search term(s) and an updater 2844 with dictionary 2846 and grammar modules 2848 to access the current speech recognition model 2849. In one embodiment speech recognition model 2849 can use a recognizer 2850 to interpret verbal search terms.

Figure 49:
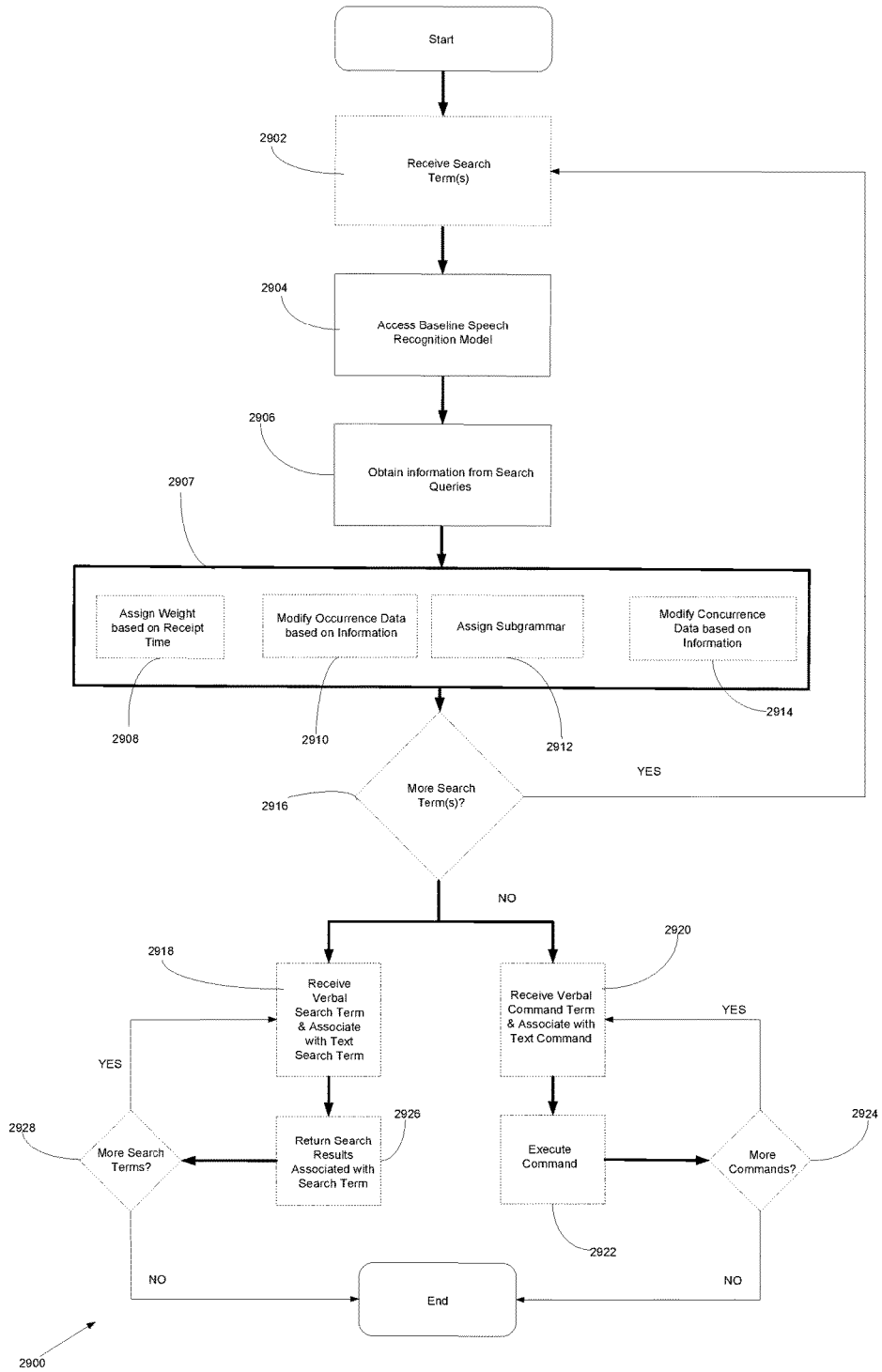
FIG. 49 is a flow chart showing exemplary steps for adding data to a speech recognition statistical model.

In one embodiment, the recognizer 2850 determines a context for the verbal search terms In one embodiment illustrated in FIG. 49 exemplary steps are used for adding data to a speech recognition system. The chart shows an embodiment in which a system updates a statistical speech recognition model based on user entered terms. The user entered terms may be accepted into the system as they are entered, or the terms may already reside in system storage. At step 2902, search terms may be received wirelessly or accessed from system storage. The search terms may be textual input or verbal input. At step 2904, the baseline speech recognition model is accessed to determine the existence of the search terms in the current dictionary. In step 2906, the system obtains information from previous search queries in an attempt to find a match for the search terms entered. The system may determine to split the terms and continue analysis separately for each entered term or the system may determine multiple strings of terms belong together and continue to step 2907 with all terms intact.

In step 2907, four optional steps are introduced. Optional step 2908 may assign a weighting value to the term(s) based on receipt time into the system. Optional step 2910 may modify existing dictionary occurrence data based on the new information entered. Optional step 2912 may assign a sub-grammar to the new information. Optional step 2914 may modify existing dictionary concurrence data based on the new information entered. One, all, or none of steps 2908, 2910, 2912 and 2914 could be executed.

Once the search terms have been analyzed for occurrence, existence and weightings, step 2916 verifies no further search terms remain. If more search terms exist, the process begins again in step 2902. If a certain number of search terms have not been received, the system continues to analyze the entered search term(s). Alternatively, the system may continually update the dictionary entries.

The speech recognition system determines whether or not the data is a verbal search term in step 2918 or a verbal system command in step 2920.

In one embodiment monitoring device 10 may receive the terms and transfer them to a speech recognition system. The speech recognition system may decide this is a system command and associate the verbal command with a text command on the monitoring device 10 as shown in step 2920. In the example above, the speech recognition system would allow a monitoring device 10 to make the phone call to "Cameron," where the translated verbal search term is associated with a telephone number, thereby executing the call command in step 2922. However, the speech recognition system may determine the received verbal term is a search and attempt to associate the verbal search term with a test search term as shown in step 2918. If the entry "call Cameron" is determined not to be a system command, the speech recognition system attempts to match the term with using dictionary entries derived from daily news broadcasts and text search terms.

In one embodiment once a textual term is associated with the spoken verbal search, the text term may be transmitted to the search server 201. The search server 201 may generate search results using the text search term, and, the results are returned to the monitoring device 10 in step 2926. The system checks for additional verbal search terms in step 2928. If no further system commands or search terms exist, the processing for the entered data ends.

Figure 50:
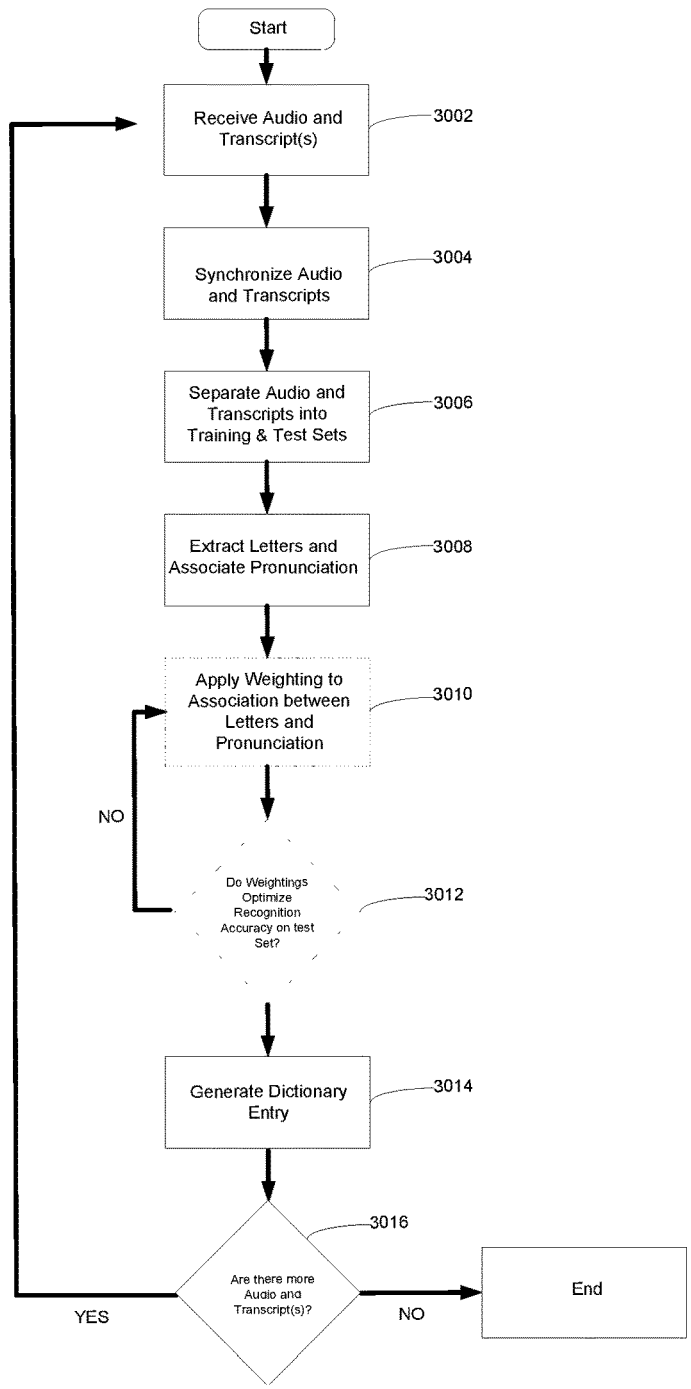
FIG. 50 is a flow chart showing exemplary steps for adding data to a pronunciation model.

In one embodiment, illustrated in FIG. 50, exemplary steps are utilized for adding data to a pronunciation model. The data for updating acoustic models may include captioned video. The data may be used to update acoustic models used for spoken search queries since new or current words previously not in the acoustic model are often provided from new captioned video broadcasts. The flow chart shows an embodiment in which a system updates a pronunciation model based on received audio or transcript information.

In step 3002, audio or transcript information is received wirelessly or accessed from system storage. The information may be textual input, audio input, video input, or any combination thereof. In step 3004, synchronizing the audio and transcript information is performed. This ensures the audio information "matches" the associated transcript for the audio. Any piece of audio information or transcript information may be divided into training and test data for the system. The training data is analyzed to generate probability values for the acoustic model. As shown in step 3008, this analysis may include extracting letters to associate pronunciation of words. A weighting system is introduced to appropriately balance the new data with the old data. In step 3010, the associations between letters and pronunciations are weighted.

In step 3012, verification is performed on the test set to determine if weightings optimize recognition accuracy on the test set. The system may associate several weights with the corresponding preliminary dictionary entry in an attempt to maximize recognition accuracy when the dictionary entries are accessed to interpret the test set of audio recordings. The system then selects the weighting that optimizes recognition accuracy on the test set. If the weightings optimize recognition accuracy on the test set, a dictionary entry can be generated in step 3014. If the weights cannot optimize recognition, step 3010 is repeated. When a dictionary term is generated, monitoring device 10 executes, in step 3016, operations to determine if more audio transcripts are available. If more audio or transcripts exist, the process returns to step 3002. If no more audio or transcript information is available, the process terminates.

For purposes of the present invention an "activity", can be a data construct describing a thing to do, which a user can associate with a user's "activity-assistant account." In an example embodiment, an activity is defined at least in part by one or more singular, global activity parameters. For example, global parameters for a given activity may include: (a) a title or text description (e.g., "get brunch at Boogaloo's restaurant"), (b) data indicating the location that is associated with the activity (e.g., the latitude/longitude and/or the address of Boogaloo's restaurant), (c) data indicating one or more user "moods" that may be indicative of the activity being more or less well-suited for a given user (e.g., "fun", "social", "cerebral", "productive", "ambitious", etc.), (d) data indicating time constraints on the activity (e.g., the hours Boogaloo's restaurant is open and/or the hours during which Boogaloo's restaurant serves brunch), and/or (e) any other data that may be directly or indirectly interpreted to affect the importance of a given activity to a given user. Further, an activity can be doable at multiple locations (e.g., "Eat a hamburger" or "Go river rafting").

Generally, an activity is a user-defined construct, and thus the global parameters that define each activity may vary. In particular, a given activity may or may not include all of the above-mentioned global activity parameters. For example, a user may create an activity that is not tied to any particular location (e.g., "do homework for math class"), and thus choose not to provide a location. Furthermore, as activities are flexible and dynamic constructs, it should be understood that the above-mentioned examples of global parameters are not limiting. It is also possible that an activity may be generated by a computing system without any initial user input (or alternatively, generated based on some user-provided input).

Once an activity is created, however, its global parameters apply to all users who add the activity. Thus, in effect, there is a single copy of each activity and its global parameters that is common all users that have access to the activity. It should be understood, however, that global parameters can still be flexible and dynamic; changing over time in relation to the activity. For example, a "popularity" parameter may be defined for an activity that is updated on an ongoing basis to reflect the number of users that have added the activity.

To further allow for customization of activities to a particular user, "user-specific" parameters, which vary between users, may be defined for an activity. Accordingly, while the global parameters of an activity are the same for all users, each user that adds an activity may customize their user-specific parameters for the activity. For instance, user-specific parameters may be used to specify: (a) plans regarding the activity (e.g., "I want to do it", "I want to do it again, but not for a few weeks," "I must do it before Dec. 25," "I never want to do it again," etc.), (b) the user's history regarding that scheme (e.g., I went there with Lauren on November 4 and again with Ryan on November 28), (c) personal time constraints based on user preferences (e.g., preference of brunch early on Sunday so she has time to digest before her yoga class at noon or preference of brunch around noon because he usually stays out late on the weekends), and/or (d) any other personal preferences related to, and "overrides" or modifications of, the global parameters (e.g., "I like to go to Boogaloo's restaurant when I'm depressed because it cheers me up," "I like to go to Boogaloo's restaurant when I have friends in town," etc.).

In a further aspect, an activity may be designated as a "public" or "private" activity. Depending on how a given activity is defined, this designation may be made by setting a global parameter when the activity is created (and thus apply to all users who add the activity), and/or may be made via a user-specific parameter that is settable by each user who adds an activity.

An activity that is designated as "public" via a global parameter may be viewable (and thus addable) to all users, whereas an activity that is designated as "private" via a global parameter may only be viewable to the creator of the activity. In an example embodiment, a global parameter may be set to designate an activity as a "private shared" activity, in which case the activity may only be viewable by the author and the users the author specifies. Further, the fact that a given activity is designated as "public," "private," or "private shared" via a global parameter may be interpreted as a signal relevant to the importance of the activity to a certain user.

When an activity is designated as "private" via a user-specific parameter, other users are generally not notified that the user has added the activity. And when an activity is designated as "public" via a user-specific parameter, other users may be notified and/or is able to see that the user has added the activity. Further, when an activity is designated as "public" via a user-specific parameter, the user may be able to define which other users can view and/or which other users should be notified that they have added the activity.

In an example embodiment, an "voice activated digital assistant", and/or activity module, is provided, which is configured to evaluate the relative importance of activities to a particular user so that activities can be presented on the voice activated digital assistant user interface in a logical manner. In particular, the voice activated digital assistant may score an activity based not only on the characteristics of the activity itself, but also based on data that is indicative of the user's "context" (e.g., the user's, interests, intents, moods, experiences, associations with other users, etc.). With the support of the voice activated digital assistant, the voice activated digital assistant user interface may therefore provide users with a dynamic and flexible mechanism for deciding what activities they might enjoy, and how they would like to spend their time.

In order to quantify the importance of a particular activity for a particular user, the voice activated digital assistant may identify and/or determine any number of "signals" that may be directly or indirectly relevant to the importance of an activity to the particular user. From the perspective of the voice activated digital assistant, signals may take the form of information provided by global parameters and user-specific parameters taken individually or information determined by evaluating interactions between global parameters, user-specific parameters, and/or other data sources. The voice activated digital assistant may evaluate the signals for a particular user in combination with a particular activity, the voice activated digital assistant may quantify the importance of the particular activity for the particular user (e.g., by assigning a "score" to the activity).

To provide some examples of such signals, they may include but are not limited to: (a) the level of similarity between user's mood and activity mood, (b) the level of similarity between the user's context (as indicated by user-specific signals and/or user-specific parameters indicating, for example, whether the user is on a desktop computer/mobile phone, on-line/off-line, talking on the phone, driving, walking, etc.) and corresponding activity context requirements and/or restrictions (as indicated by global parameters of the activity), (c) distance between user's location and activity location (if available), (d) appropriateness of current weather at user's location and/or activity's location for the activity (e.g., rainy, sunny, snowy, etc.), (e) user-designated priority for the activity, (f) user-designated due date (or next due date, if recurring), (f) snooze history or pattern for the activity, (g) amount of time required for the activity, (h) progress or status of the activity (done, active, in-progress, etc.), (i) ownership of the activity (e.g., whether the owner is the particular user in question or another user), (j) whether the user received a heads-up, (k) popularity of the activity (e.g., number of comments on an activity, or the number of people who have commented, copied, liked, shared, done, or followed the activity), (l) similarity between user query string and activity text (for search/suggest), (m) similarity between user query string and names or e-mails of other users in the activity (for search/suggest), (n) similarity between user query string and activity comment text (for search/suggest), and (o) whether the user indicated another user with whom to participate in the activity with.

Supported with this intelligence from the voice activated digital assistant, the voice activated digital assistant user interface may present activities that a particular user has associated with their account in a logical order that is based at least in part upon the relative importance of the activities to the user. In particular, the voice activated digital assistant may evaluate the signals for each activity in a user's activity list (e.g., each activity that has been added by the user) and assign a score to the activity. The voice activated digital assistant can then rank the activities in the user's activity list according to their respectively determined score, and relay this information to the voice activated digital assistant user interface so that it can adjust the displayed activity list accordingly.

Further, the intelligence of the voice activated digital assistant may be utilized to provide "suggested" activities that are tailored to the particular user's preferences, tendencies, location, time table, associated other users, and/or mood at a given point in time. In particular, the voice activated digital assistant may initiate an activity search that takes into account the scores of activities when ranking the search results, and these search results may be presented to the user via the voice activated digital assistant user interface. In a similar manner, the voice activated digital assistant may support an "activity search" feature of the voice activated digital assistant user interface. This feature may allow the user to enter text and initiate an activity search on the text, the results of which factor in the relative scores of activities as assessed by the voice activated digital assistant.

In some examples, when a certain available activity exceeds a certain relevance threshold for a user's current context, the voice activated digital assistant sends a "push" notification (or "alert") to a given user's computing device (e.g., mobile phone, etc.). By way of example, the user has indicated that the user needs to buy a mother's day present via a given activity, the user is passing a location where this activity can be done, and the current date is the day before mother's day. This example would utilize the scoring function as in the above described activity list, but an activity would have to pass a higher threshold in order to generate a notification.

According to an example embodiment, a user interface is provided that allows for intuitive user interaction with such activities. This user interface may be generally referred to herein as an "voice activated digital assistant user interface." A user typically accesses the voice activated digital assistant user interface by logging in to a user's activity-assistant account. According to an example embodiment, the voice activated digital assistant user interface displays graphical representations of activities to a user in a logical manner that varies according to the interests, intents, associations with other users, and moods of the user. Via the voice activated digital assistant user interface, the user may view activities they have added to a personal "activity list," view suggested activities, create and add new activities to their activity list, and/or add/delete existing activities (e.g., those created by other users) to/from their activity list, among other functions.

Figure 51:
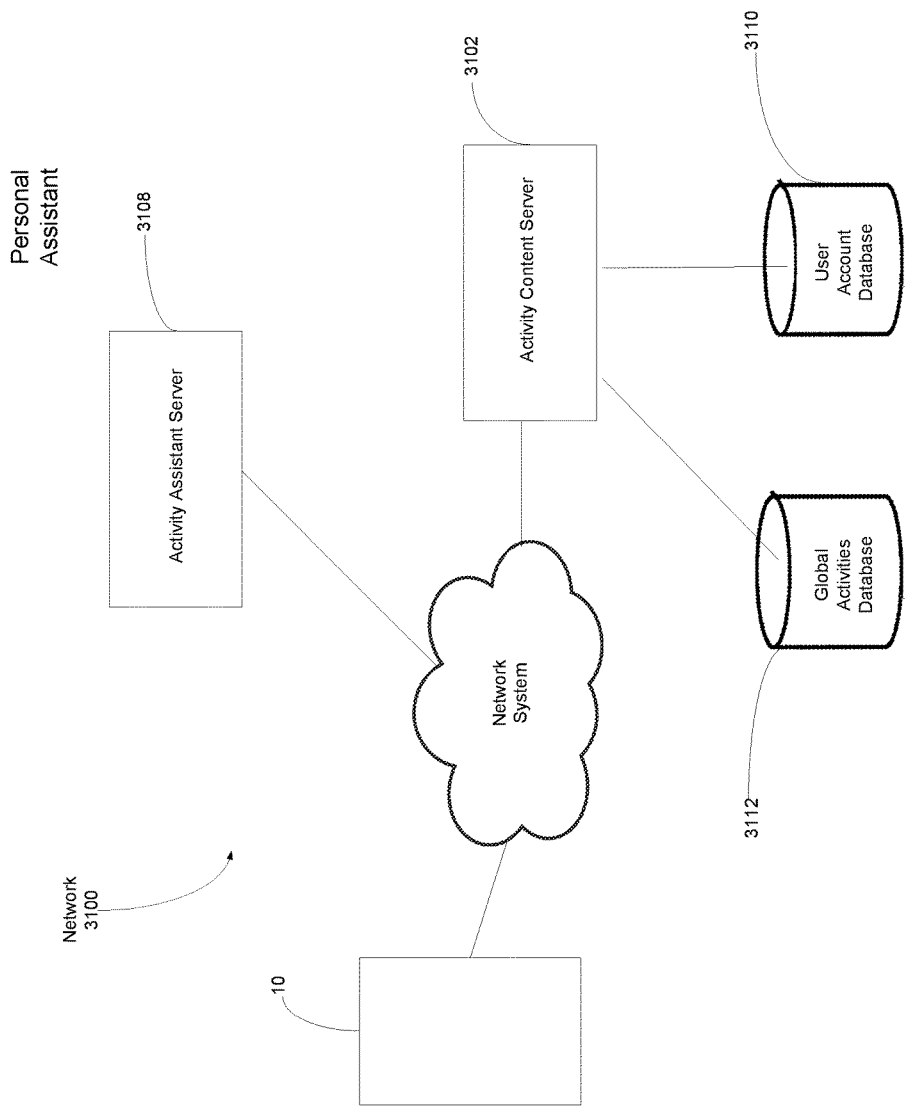
FIG. 51 depicts a network in accordance with an example embodiment.

Turning to the figures, FIG. 51 illustrates one embodiment of an voice activated digital assistant network ("network"). In one embodiment network 3100, voice activated digital assistant server 3108 and possibly activity content server 3102 are configured to communicate, via a network 3106, with client devices 3104 *a*, 3104 *b*, and 3104 *c*. As shown in FIG. 51, client devices can include a personal computer 3104 *a*, a telephone 3104 *b*, and a smart-phone 3104 *c*. More generally, the client devices 3104 *a*, 3104 *b*, and 3104 *c* (or any additional client devices) can be any sort of computing device, such as an ordinary laptop computer, desktop computer, network terminal, wireless communication device (e.g., a cell phone or smart phone), and so on.

The network 3106 is Network System which can correspond to a local area network, a wide area network, a corporate intranet, the public Internet, combinations thereof, or any other type of network(s) configured to provide communication between networked computing devices. Activity content server 3102 can provide content to client device 3104 *a*-3104 *c* and/or voice activated digital assistant server 3108. The content can include, but is not limited to, web pages, hypertext, scripts, binary data such as compiled software, images, audio, and/or video. The content can include compressed and/or uncompressed content and/or encrypted and/or unencrypted content. Other types of content are possible as well.

In an alternative arrangement, voice activated digital assistant server 3108 and activity content server 3102 can be co-located and/or combined as a common server. Further, it also possible that voice activated digital assistant server 3108 and/or activity content server 3102 can be accessible via a network separate from the network 3106. Yet further, although FIG. 51 only shows three client devices, voice activated digital assistant server 3108 and/or activity content server 3102 can serve any number of client devices (from a single client device to hundreds, thousands, or even more client devices).

Global activity database 3112 typically includes activity data that defines a plurality of activities. In particular, the activity data for each activity may include one or more global activity parameters that collectively define the global context for the activity. Further, user-account database 3110 may include data for users' activity accounts. This data may include, for a given one of the accounts, data indicating user-specific parameters and signals. Further, for a given activity account, the data may include an indication of which activities, if any, are associated with the account (e.g., the activities that a user has added to their activity list).

According to an example embodiment, voice activated digital assistant server 3108 embodies the "voice activated digital assistant" and thus is configured to provide the activity-assistant functionality described herein. In particular, voice activated digital assistant server 3108 may be configured to identify signals relating to the importance of a particular activity to a particular user (e.g., relating to a given user-activity pair), so that activities can be logically displayed to a user, suggested to a user, and/or searched for a user via an voice activated digital assistant user interface.

In some embodiments, activity-assistant functionality described herein may also be performed by software on the device such as, but not limited to, devices 3104 *a*, 3104 *b*, and 3104 *c* as shown in FIG. 51. For example, the client software running on the device such as, but not limited to, devices 3104 *a*, 3104 *b*, and 3104 *c* as shown in FIG. 51 may perform all or some portion of the ranking functionality and/or provide more advanced assistance, e.g. by providing a latitude/longitude and/or map for an address entered by the user via an voice activated digital assistant user interface and/or by directly communicating with an voice activated digital assistant processing system.

The voice activated digital assistant server 3108 may acquire the data from which signals are determined, and/or data directly providing signals, from a number of different data sources. For example, activity content server 3102 may provide voice activated digital assistant server 3108 with access to global activity database 3112 and user-account database 3110. Thus, when evaluating the importance of a particular activity to a particular user, voice activated digital assistant server 3108 may retrieve the global parameters of the activity from global activity database 3112, as well as user-specific parameters from user-account database 110.

Figure 52A:
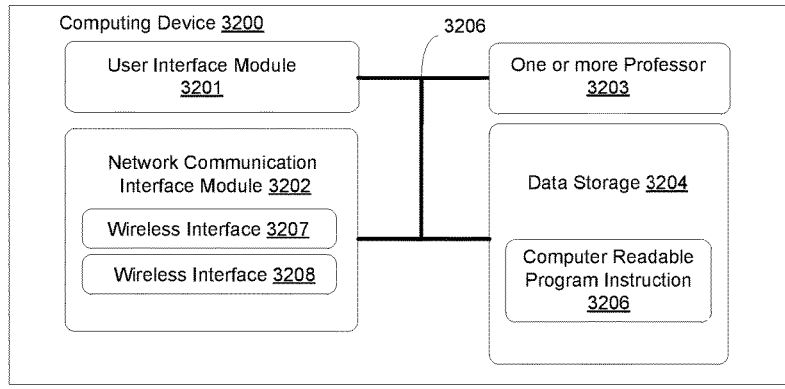
FIG. 52A is a block diagram of a computing device in accordance with an example embodiment.

FIG. 52(*a*) is a block diagram of a computing device in accordance with an example embodiment. Computing device 3200 can be configured to perform one or more functions of client devices 3104 *a*, 3104 *b*, and 3104 *c*, voice activated digital assistant server 3108, and/or activity content server 3102. The computing device 3200 can include a user interface module 3201, a network-communication interface module 3202, one or more processors 3203, and/or data storage 3204, all of which can be linked together via a system bus, network, or other connection mechanism 3205.

The user interface module 3201 can be operable to send data to and/or receive data from external user input/output devices. For example, the user interface module 3201 can be configured to send/receive data to/from user input devices such as a keyboard, a keypad, a touch screen, a computer mouse, a track ball, a joystick, a microphone, and/or other similar devices, now known or later developed. The user interface module 3201 can also be configured to provide output to user display devices, such as one or more cathode ray tubes (CRT), liquid crystal displays (LCD), light emitting diodes (LEDs), displays using digital light processing (DLP) technology, printers, light bulbs, and/or other similar devices, now known or later developed. The user interface module 3201 can also be configured to receive audible input(s) via the microphone (or similar audio input device) and/or generate audible output(s), such as a speaker, speaker jack, audio output port, audio output device, earphones, and/or other similar devices, now known or later developed.

The network-communications interface module 3202 can include one or more wireless interfaces 3207 and/or wireline interfaces 3208 that are configurable to communicate via Network System, such as the network 3106 shown in FIG. 41. The wireless interfaces 3207 can include one or more wireless transceivers, such as a Bluetooth transceiver, a Wi-Fi transceiver perhaps operating in accordance with an IEEE 802.11 standard (e.g., 802.11a, 802.11b, 802.11g), a WiMAX transceiver perhaps operating in accordance with an IEEE 802.16 standard, and/or other types of wireless transceivers configurable to communicate via a wireless network. The wireline interfaces 3208 can include one or more wireline transceivers, such as an Ethernet transceiver, a Universal Serial Bus (USB) transceiver, or similar transceiver configurable to communicate via a wire, a twisted pair of wires, a coaxial cable, an optical link, a fiber-optic link, or other physical connection to a wireline network.

In some embodiments, the network communications interface module 3202 can be configured to provide reliable, secured, compressed, and/or authenticated communications. For each communication described herein, information for ensuring reliable communications (e.g., guaranteed message delivery) can be provided, perhaps as part of a message header and/or footer (e.g., packet/message sequencing information, encapsulation header(s) and/or footer(s), size/time information, and transmission verification information such as cyclic redundancy check (CRC) and/or parity check values). Communications can be compressed and decompressed using one or more compression and/or decompression algorithms and/or protocols such as, but not limited to, one or more lossless data compression algorithms and/or one or more lossy data compression algorithms. Communications can be made secure (e.g., be encoded or encrypted) and/or decrypted/decoded using one or more cryptographic protocols and/or algorithms, such as, but not limited to, DES, AES, RSA, Diffie-Hellman, and/or DSA. Other cryptographic protocols and/or algorithms can be used as well or in addition to those listed herein to secure (and then decrypt/decode) communications.

The one or more processors 3203 can include one or more general purpose processors and/or one or more special purpose processors (e.g., digital signal processors, application specific integrated circuits, etc.). The one or more processors 3203 can be configured to execute computer-readable program instructions 3206 that are contained in the data storage 3204 and/or other instructions as described herein.

The data storage 3204 can include one or more computer-readable storage media that can be read or accessed by at least one of the processors 3203. The one or more computer-readable storage media can include volatile and/or non-volatile storage components, such as optical, magnetic, organic or other memory or disc storage, which can be integrated in whole or in part with at least one of the one or more processors 3203. In some embodiments, the data storage 3204 can be implemented using a single physical device (e.g., one optical, magnetic, organic or other memory or disc storage unit), while in other embodiments, the data storage 3204 can be implemented using two or more physical devices.

Computer-readable storage media associated with data storage 3204 and/or other computer-readable media described herein can also include non-transitory computer-readable media such as computer-readable media that stores data for short periods of time like register memory, processor cache, and random access memory (RAM). Computer-readable storage media associated with data storage 3204 and/or other computer-readable media described herein can also include non-transitory computer readable media that stores program code and/or data for longer periods of time, such as secondary or persistent long term storage, like read only memory (ROM), optical or magnetic disks, compact-disc read only memory (CD-ROM), for example. Computer-readable storage media associated with data storage 3204 and/or other computer-readable media described herein can also be any other volatile or non-volatile storage systems. Computer-readable storage media associated with data storage 3204 and/or other computer-readable media described herein can be considered computer readable storage media for example, or a tangible storage device.

The data storage 3204 can include computer-readable program instructions 3206 and perhaps additional data. In some embodiments, the data storage 3204 can additionally include storage required to perform at least part of the herein-described techniques, methods (e.g., methods 700 and 800), and/or at least part of the functionality of the herein-described devices and networks.

Figure 52B:
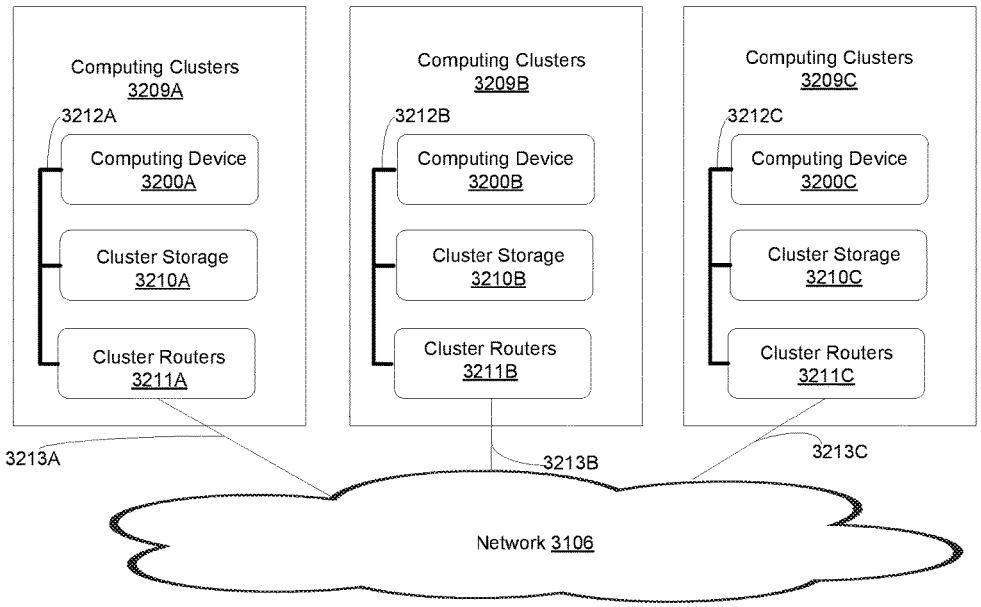
FIG. 52B depicts a network with computing clusters in accordance with an example embodiment.

FIG. 52(b) depicts a network with computing clusters in accordance with an example embodiment. In FIG. 52(b), functions of voice activated digital assistant server 108 and/or activity content server 3110 can be distributed among three computing clusters 3209 a, 3209 b, and 3208 c. The computing cluster 3209 a can include one or more computing devices 3200 a, cluster storage arrays 3210 a, and cluster routers 3211 a connected by local cluster network 3212 a. Similarly, computing cluster 3209 b can include one or more computing devices 3200 b, cluster storage arrays 3210 b, and cluster routers 3211 b connected by local cluster network 3212 b. Likewise, computing cluster 3209 c can include one or more computing devices 3200 c, cluster storage arrays 3210 c, and cluster routers 3211 c connected by a local cluster network 3212 c.

In some embodiments, each of computing clusters 3209 a, 3209 b, and 3209 c can have an equal number of computing devices, an equal number of cluster storage arrays, and an equal number of cluster routers. In other embodiments, however, some or all of computing clusters 3209 a, 3209 b, and 3209 c can have different numbers of computing devices, different numbers of cluster storage arrays, and/or different numbers of cluster routers. The number of computing devices, cluster storage arrays, and cluster routers in each computing cluster can depend on the computing task or tasks assigned to each computing cluster.

In computing cluster 3209 a, for example, computing devices 3200 a can be configured to perform various computing tasks of activity content server 3102. In one embodiment, the various functionalities of activity content server 3102 can be distributed among one or more of the computing devices 3200 a. For example, some of these computing devices can be configured to provide part or all of a first set of content while the remaining computing devices can provide part or all of a second set of content. Still other computing devices of the computing cluster 3209 a can be configured to communicate with voice activated digital assistant server 108. Computing devices 3200 b and 3200 c in computing clusters 3209 b and 3209 c can be configured the same or similarly to the computing devices 3200 a in computing cluster 3209 a.

On the other hand, in some embodiments, computing devices 3200 a, 3200 b, and 3200 c each can be configured to perform different functions. For example, computing devices 3200 a and 3200 b can be configured to perform one or more functions of activity content server 3102, and the computing devices 3200 c can be configured to perform one or more functions of voice activated digital assistant server 3108.

Cluster storage arrays 3210 a, 3210 b, and 3210 c of computing clusters 3209 a, 3209 b, and 3209 c can be data storage arrays that include disk array controllers configured to manage read and write access to groups of hard disk drives. The disk array controllers, alone or in conjunction with their respective computing devices, can also be configured to manage backup or redundant copies of the data stored in the cluster storage arrays to protect against disk drive or other cluster storage array failures and/or network failures that prevent one or more computing devices from accessing one or more cluster storage arrays.

Similar to the manner in which the functions of voice activated digital assistant server 108 and/or activity content server 3102 can be distributed across computing devices 3200 a, 3200 b, and 3200 c of respective computing clusters 3209 a, 3209 b, and 3209 c, various active portions and/or backup/redundant portions of these components can be distributed across cluster storage arrays 3210 a, 3210 b, and 3210 c. For example, some cluster storage arrays can be configured to store data for voice activated digital assistant server 3108, while other cluster storage arrays can store data for activity content server 3102. Additionally, some cluster storage arrays can be configured to store backup versions of data stored in other cluster storage arrays.

The cluster routers 3211 a, 3211 b, and 3211 c in the computing clusters 3209 a, 3209 b, and 3209 c can include networking equipment configured to provide internal and external communications for the computing clusters. For example, the cluster routers 3211 a in the computing cluster 3209 a can include one or more internet switching and/or routing devices configured to provide (i) local area network communications between the computing devices 200 a and the cluster storage arrays 3201 a via the local cluster network 3212 a, and/or (ii) wide area network communications between the computing cluster 3209 a and the computing clusters 3209 b and 3209 c via the wide area network connection 3213 a to the network 3106. The cluster routers 3211 b and 3211 c can include network equipment similar to the cluster routers 3211 a, and the cluster routers 3211 b and 3211 c can perform similar networking functions for the computing clusters 3209 b and 3209 b that the cluster routers 3211 a perform for the computing cluster 3209 a.

In some embodiments, computing tasks and stored data associated with voice activated digital assistant server 108 and/or activity content server 3102 can be distributed across the computing devices 3200 a, 3200 b, and 3200 c based at least in part on the processing requirements for functions of voice activated digital assistant server 3108 and/or user account server 3102, the processing capabilities of the computing devices 3200 a, 3200 b, and 3200 c, the latency of the local cluster networks 3212 a, 3212 b, and 3212 c and/or of the wide area network connections 3213 a, 3213 b, and 3213 c, and/or other factors that can contribute to the cost, speed, fault-tolerance, resiliency, efficiency, and/or other design goals of the overall system architecture.

Additionally, the configuration of the cluster routers 3211 a, 3211 b, and 3211 c can be based at least in part on the data communication requirements of the computing devices and cluster storage arrays, the data communications capabilities of the network equipment in the cluster routers 3211 a, 3211 b, and 3211 c, the latency and throughput of the local cluster networks 3212 a, 3212 b, 3212 c, the latency, throughput, and cost of the wide area network connections 3213 a, 3213 b, and 3213 c, and/or other factors that can contribute to the cost, speed, fault-tolerance, resiliency, efficiency and/or other design goals of the system architecture.

Figure 54:
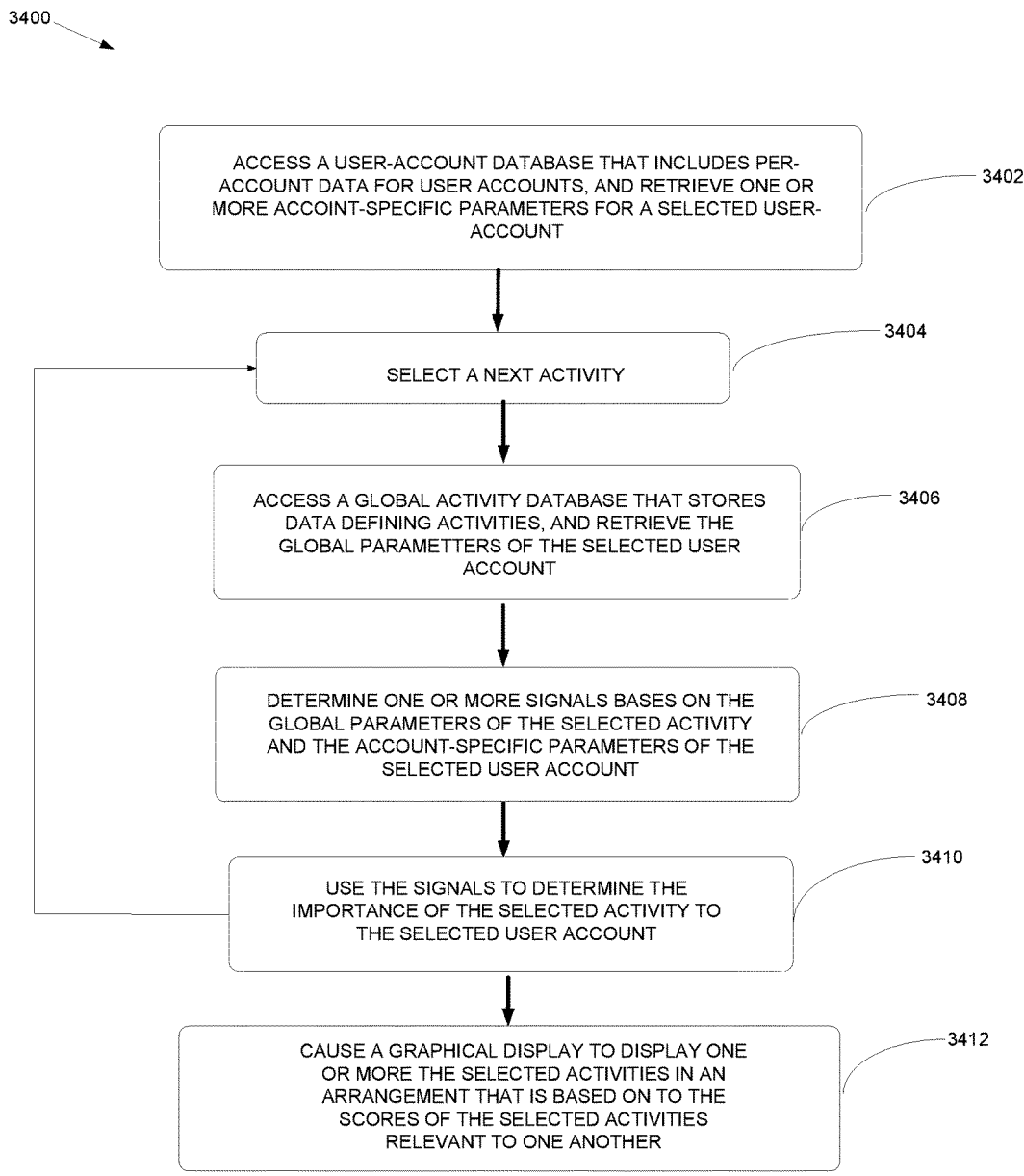
FIG. 54 is flow chart illustrating a method according to an example embodiment

FIG. 54 is a block diagram illustrating features of a user interface, according to an example embodiment that is with monitoring device 10. In particular, activity-assistant user interface 3300 may be displayed via monitoring device 10, and may allow a user to interact with an voice activated digital assistant. While only one screen of the activity-assistant user interface 3300 is shown, it should be understood that the activity-assistant user interface may include other screens, which provide additional functionality, without departing from the scope of the invention. As shown, activity-assistant user interface 3300 includes a personalized activity panel 3302, an activity feed 3304 that displays activities that have been added, done, and/or recently updated by friends of the user (or members of the user's social graph and/or social network), a search/add bar 3306, and a context panel 3308. Further, context panel 3308 includes a number of input mechanisms 3310 A-C via which a user can input context signals.

The context panel 3308 provides an interactive mechanism for users to provide context signal data that describes a "user context" (e.g. to provide signals indicative of the user's intent, interest, mood, state-of-mind, experience, perception, associations with other users, etc.). In the illustrated example, input mechanism 3310A on the left of context panel 3308 allows a user to signal their mood (e.g., "up for anything", "lazy", "productive", "social", etc.). The input mechanism 3310B in the center of context panel 3308 allows a user to signal a location (e.g., "current location", "home", "work", "stadium", etc.). Further, input mechanism 3310C on the right of context panel 3308 allows a user to signal a time or timeframe (e.g., "now", "tomorrow", "tonight", "next Wednesday morning", "2:00 AM CST", "9:00 PM EST on Saturday", etc.). Other input mechanisms are possible as well.

While the context information provided via the input mechanisms of the context panel 3308 may be referred to as "signals" from the user, it should be understood that, programmatically, this information may take the form of user-specific parameters that are associated with the user's activity account. As such, the data provided via input mechanisms 3310 A-C may be stored in a user-account database. For example, referring back to FIG. 1, data from input mechanisms 3310 A-C may be stored as user-specific parameters in user-account database 110. It is also possible that voice activated digital assistant server 108 may be fed data or may pull data directly from input mechanisms 3310 in real-time.

The context signal data acquired from the context panel 3308 (e.g., user-specific parameters related to "user context") may be combined by the voice activated digital assistant (e.g., activity-assistant server 108 and/or activity content server 102) with global parameters of a given activity, other user-specific parameters, and/or data from other sources, in order to derive signals indicative of activity-importance of the given activity to the user. In this context, the "signals" are the information relative to the importance of the activity that is derived from the data (e.g., the user-specific parameters, global parameters, etc.). As such, the voice activated digital assistant may interpret a user-parameter as a signal in and of itself.

For instance, the user's mood (provided via input mechanism 3310A) may be interpreted as a signal that makes any number of activities more or less important for the user. As a specific example, if the user's mood is "lazy", the activity "watching a movie" may become more important than it otherwise would be (as global parameters may indicate that "lazy" is a mood associated with the "watching a movie"

activity). On the other hand, the activity "go to the gym" may become less important than it otherwise would be (as global parameters of "watching a movie" do not typically include "lazy" as an associated mood, or may in fact indicate that "lazy" is a mood that is likely incompatible with this activity).

The voice activated digital assistant may also derive more complex signals by evaluating the relationships and/or interactions between user-specific parameters, global parameters, and/or other data items. To provide an example, a user may have provided a "love being outdoors" signal, which may be stored in the user's account as a user-specific parameter (note that a user interface input mechanism not shown on the screen 3300, but is contemplated as being available). At a given point in time, the user also may have set their mood to "active" via input mechanism 3310A, set their location to "current location" via input mechanism 3310B, and set their time to "tomorrow afternoon". The voice activated digital assistant may interpret this data as including a signal that the user would like to do something active tomorrow afternoon at the same place they are currently located.

Further, the voice activated digital assistant may use other data sources to determine other relevant signals, such as the weather forecast for the next day at the user's current location or the location that the user will likely be at the next day. Tomorrow afternoon's weather forecast may thus be a signal, which can be combined with the signal derived from the user-specific parameters to provide a more-refined signal that, for example, outdoor fitness or sporting activities near the user's location should always be favored over indoor fitness or sporting activities near the user's location, unless the tomorrow afternoon's forecast is for rain, in which case the amount by which outdoor activities are favored over indoor activities may be reduced (or indoor activities may actually be favored). For instance, combining all of this information, the voice activated digital assistant may increase the importance of active outdoor activities (e.g., "go for a run", "play flag football", etc.) to a greater extent when the forecast is for sunny weather, than when the forecast is for rain or snow.

The voice activated digital assistant may apply signal-based techniques, such as those described herein, to assess activity-importance for a number of activities and the importance of these activities relative to one another. This technique may be employed to provide the user with various functions that are tailored to the user's context.

For example, personalized activity panel 3302 may display intelligently selected and ordered activities from a pool of activities including the activities a user has added to their account and suggested activities that have been selected for a user. For example, a number of suggested activities may be determined based on factors such as user preferences, signals from the context panel, and global parameters of potential activities, activities that have been added and/or done by friends of the user, and/or activities that have been added and/or done by the user in the past, among others. These suggested activities may then be combined with the activities a user has already added to create a pool of potential activities for the personalized activity panel 3302. Then, to determine which specific activities to display in personalized activity panel 3302, the voice activated digital assistant may quantify the importance of each activity (e.g., by evaluating signals for each activity), so that the activities that are most important to the user are displayed.

Note that personalized activity panel 3302 may visually differentiate between activities that a user has already added to their account, and suggested activities. For example, the "Watch Movie" activity is displayed with a dark background and white text to indicate that it is a suggested activity (and that the user may thus wish to add it), whereas the other activities listed in personalized activity panel 3302 all have a white background with black text, thus indicating that the user has already added these activities.

Further, the evaluation of importance may also be applied in the process of determining which activities should be displayed in the activity feed 3304 (and possibly the order in which those activities are displayed). In particular, a certain number of the most recently-added and updated activities may be evaluated based on signals such as those described above, and the most important of the recent activities may be displayed (possibly in the order of importance. Alternatively, it should be understood that activity feed 3304 may simply display activities in a time-wise manner as they are added/updated/completed, without adjusting based on the user's context. In a similar manner, search results (not shown) for an activity search via search/add bar 3306 may be displayed based at least in part on importance of the activities located in the search, or may simply be displayed in an order according to one of the many well-known search techniques.

Figure 53A:
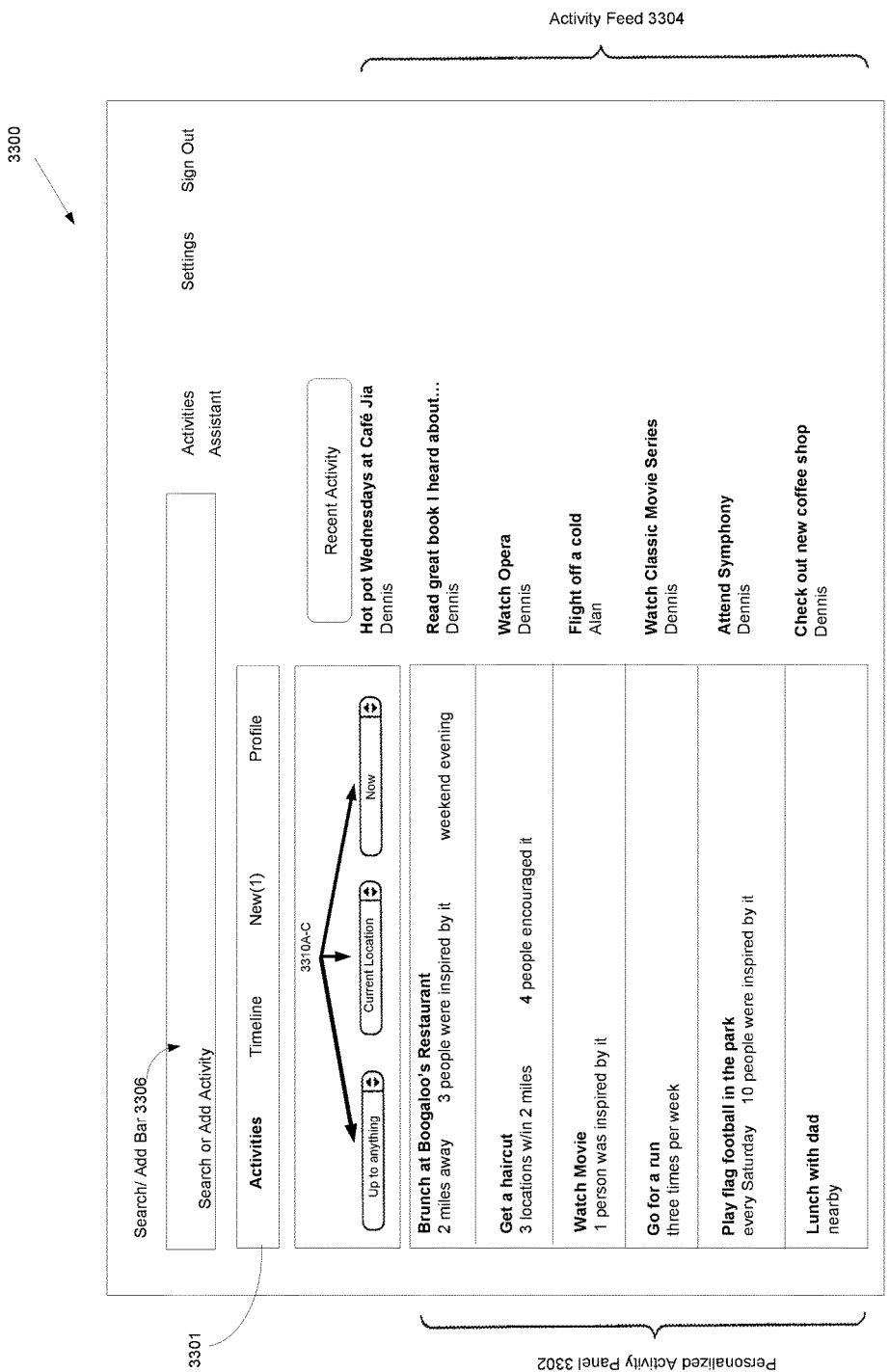
FIG. 53A is a block diagram illustrating features of a user interface, according to an example embodiment.
Figure 53B:
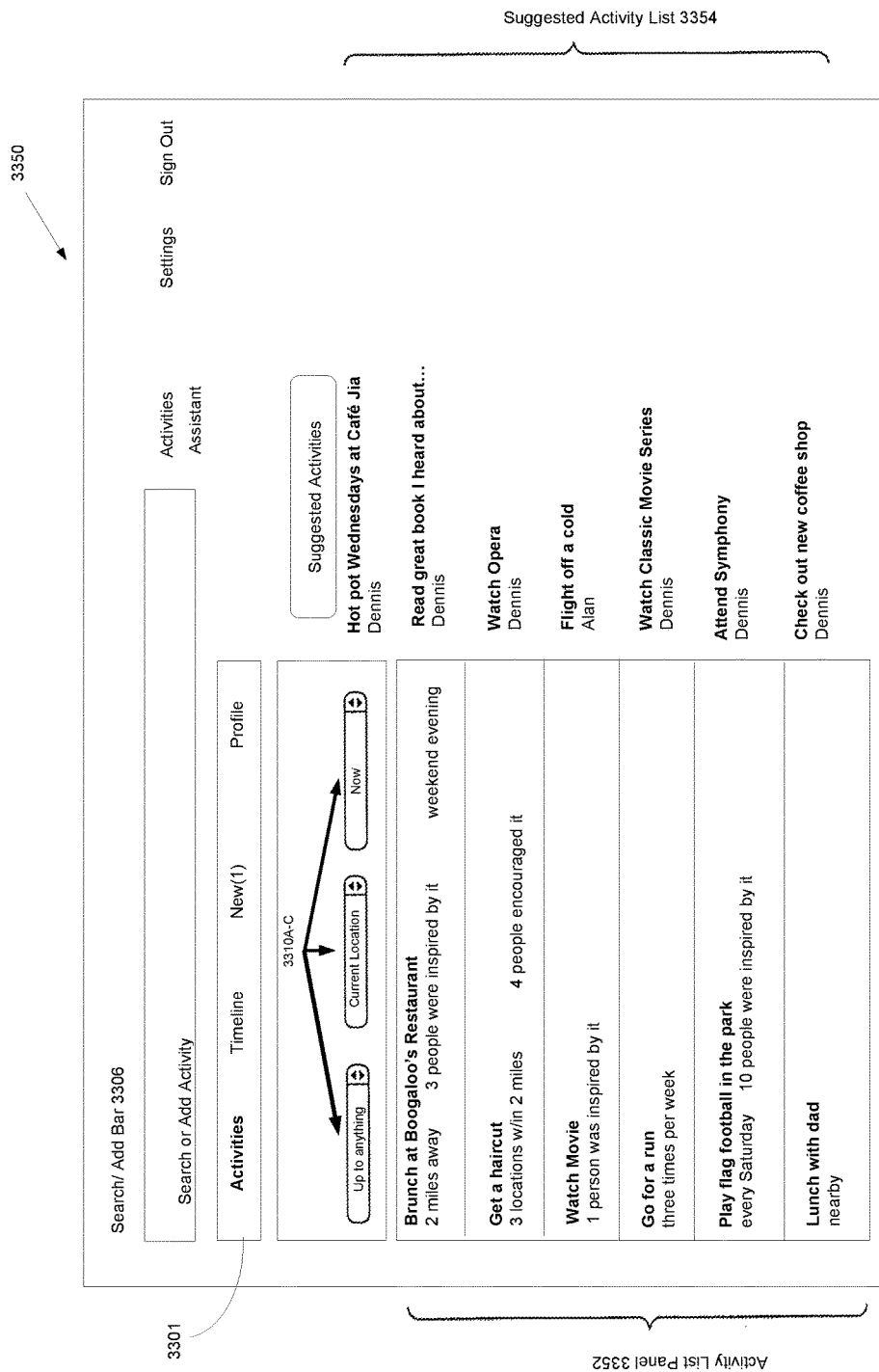
FIG. 53B is another block diagram illustrating features of a user interface, according to an example embodiment.

FIG. 53(*b*) is another block diagram illustrating features of a user interface, according to an example embodiment. As a non-limiting example FIG. 53(*b*) illustrates an alternative activity-assistant user interface 3350, which may be displayed via a client device once a user has logged in to their activity-assistant account. Activity-assistant user interface 3350 includes some of the same UI elements as activity-assistant user interface 3300 of FIG. 53(*a*) (e.g., search/add bar 3306 and context panel 3308 including a number of input mechanisms 3310 A-C). However, activity-assistant user interface 3350 includes an activity list 3352 and a suggested activity list 3354.

In this embodiment, activity list 3352 may include only activities that a user has added to their account. Thus, by evaluating signals for each activity a user has added to their account, the voice activated digital assistant can determine which activities should be displayed in activity list 3352 (and the order in which those activities should be displayed).

Furthermore, suggested activity list 3354 may display only suggested activities (which have not yet been added by the user.) Accordingly, the importance of specific activities may also be a factor in the process of determining which activities should be displayed in the suggested activity list 3354 (and the order of those activities).

FIG. 54 is flow chart illustrating a method according to an example embodiment. In particular, method 3400 may be carried out by an voice activated digital assistant in order to facilitate dynamic and flexible and activities. For example, voice activated digital assistant server 108 and/or user account server 3102 of FIG. 51 carries out a method such as method 3400 to facilitate dynamic user interaction with activities via an interface such as the activity-assistant user interfaces of FIGS. 53(*a*) and 53(*b*) in some embodiments.

More specifically, method 3400 involves the voice activated digital assistant accessing a user-account database and retrieving the one or more account-specific parameters of a selected user account, as shown by block 3402. The voice activated digital assistant then selects a next activity, as shown by block 3404, and accesses a global activity database to retrieve the global parameters of a selected activity, as shown by block 3406. Then, for the combination of the selected user account and the selected activity, the voice activated digital assistant determines one or more signals based at least in part on the global parameters of the selected activity and the account-specific parameters of the selected user account, as shown by block 3408. Also as shown by block 3408, each signal provides an indication as to the importance of the selected activity to the selected user account. Accordingly, the voice activated digital assistant can then use the determined signals as a basis for determining the importance of the selected activity for the selected user, as shown by block 3410. The voice activated digital assistant then causes a graphical display to display one or more of the selected activities in an arrangement that is based at least in part on to the importance of the selected activities relevant to one another in some configurations.

With respect to any or all of the block diagrams and flow charts in the figures as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or message may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or non-volatile storage systems. A computer readable medium may be considered a computer readable storage medium, for example, or a tangible storage device.

It should be understood that for situations in which the systems and methods discussed herein collect personal information about users, the users may be provided with an opportunity to opt in/out of programs or features that may collect personal information (e.g., information about a user's preferences or a user's contributions to social content providers). In addition, certain data may be anonymized in one or more ways before it is stored or used, so that personally identifiable information is removed. For example, a user's identity may be anonymized so that the no personally identifiable information can be determined for the user and so that any identified user preferences or user interactions are generalized (for example, generalized based on user demographics) rather than associated with a particular user.

Moreover, a block that represents one or more information transmissions may correspond to information transmissions between software and/or hardware modules in the same physical device. However, other information transmissions may be between software modules and/or hardware modules in different physical devices.

The foregoing description of various embodiments of the claimed user matter has been provided for the purposes of illustration and description. It is not intended to be exhaustive or to limit the claimed user matter to the precise forms disclosed. Many modifications and variations will be apparent to the practitioner skilled in the art. Particularly, while the concept "component" is used in the embodiments of the systems and methods described above, it will be evident that such concept can be interchangeably used with equivalent concepts such as, class, method, type, interface, module, object model, and other suitable concepts. Embodiments were chosen and described in order to best describe the principles of the invention and its practical application, thereby enabling others skilled in the relevant art to understand the claimed user matter, the various embodiments and with various modifications that are suited to the particular use contemplated.

What is claimed is:

1. A system, comprising:
a user monitoring device including a transmitter and one or more sensors, the one or more sensors configured to provide environmental data in response to detecting at least one of a light quality, a sound quality, a temperature quality, or a humidity proximate the user monitoring device,
a motion detection sensor configured to detect movement information associated with a user of the motion detection sensor; and
a monitoring system in communication with the user monitoring device and the motion detection sensor, the monitoring system including a user database and at least one processor enabled to analyze the movement information in light of the environmental data received from the user monitoring device to determine state information for the user, the state information relating to at least one of user sleep state, user sleep behavior, or user respiration information.

2. The system of claim 1, wherein the one or more sensors comprises a proximity sensor at the user monitoring device.

3. The system of claim 1, wherein the one or more sensors comprises a barometric pressure sensor at the user monitoring device.

4. The system of claim 3, wherein the barometric pressure sensor is configured to detect changes in pressure within a receiving vicinity of the user monitoring device.

5. The system of claim 1, wherein the one or more sensors comprises a motion detection apparatus at the user monitoring device.

6. The system of claim 5, wherein the motion detection apparatus at the user monitoring device provides additional motion information about motion activity within a receiving vicinity of the user monitoring device.

7. The system of claim 1, wherein the one or more sensors comprises a gas sensor at the user monitoring device.

8. The system of claim 7, wherein the gas sensor is configured to measure one or more of:
a VOC and $CO_2$ within a receiving vicinity of the user monitoring device.

9. The system of claim 1, wherein the one or more sensors comprises a color meter or sensor at the user monitoring device.

10. The system of claim 9, wherein the color meter or sensor is configured to determine a type of light within a receiving vicinity of the user monitoring device.

11. The system of claim 10, wherein the type of light includes fluorescent and incandescent.

12. The system of claim 9, wherein the color meter or sensor is configured to provide information about a color of light within a receiving vicinity of the user monitoring device.

13. The system of claim 1, wherein the one or more sensors comprises a UV sensor at the user monitoring device.

14. The system of claim 13, wherein the UV sensor is configured to provide information relative to a quality of light within a receiving vicinity of the user monitoring device.

15. The system of claim 13, wherein the UV sensor is configured to determine light within a receiving vicinity of the user monitoring device being monitored is natural or artificial.

16. The system of claim 13, wherein the UV sensor is configured to a UV spectrum.

17. The system of claim 1, wherein the system includes a plurality of microphones.

18. The system of claim 17, wherein the plurality of microphones provides for at least partial noise cancellation.

19. The system of claim 17, wherein the plurality of microphones is provides for at least partial echo cancellation.

20. The system of claim 17, wherein the plurality of microphones is configured to determine a direction for which a sound comes from.

21. A system, comprising:
   a user monitoring device including a transmitter and one or more sensors, the one or more sensors configured to provide environmental data in response to detecting at least one of a light quality, a sound quality, a temperature quality, or a humidity proximate the user monitoring device,
   a motion detection sensor configured to detect movement information associated with a user of the motion detection sensor; and
   a monitoring system in communication with the user monitoring device and the motion detection sensor, the monitoring system including a user database and at least one processor enabled to analyze the movement information in light of the environmental data received from the user monitoring device to determine state information for the user, the state information relating to at least one of user sleep state, user sleep behavior, or user respiration information; and
   a voice recognition system at the monitoring system or at the user monitoring device configured to analyze audio data captured using one or more microphones of the user monitoring device.

22. The system of claim 21, further comprising:
   an voice activated digital assistant at the monitoring system or included with the user monitoring device.

23. A user monitoring system, comprising:
   at least one processor; and
   memory storing instructions that, when executed by the at least one processor, cause the user monitoring system to:
      receive environmental data from an environmental monitoring device, the environmental data relating to at least one or a light quality, a sound quality, a temperature quality, or a humidity proximate the environmental monitoring device;
      receive movement data captured by a detection sensor, the movement data corresponding to an identified user proximate the detection sensor; and
      analyze the movement data in light of the environmental data received from the environmental monitoring device to determine state information for the identified user, the state information relating to at least one of user sleep state, user sleep behavior, or user respiration information for the identified user.

* * * * *